US012630820B2

(12) United States Patent
Becker et al.

(10) Patent No.: US 12,630,820 B2
(45) Date of Patent: May 19, 2026

(54) COMPOSITIONS AND METHODS FOR IMMUNOTHERAPY

(71) Applicant: Intellia Therapeutics, Inc., Cambridge, MA (US)

(72) Inventors: Amy Melissa Becker, Lexington, MA (US); Surbhi Goel, Winchester, MA (US); Sarah Beth Hesse, Arlington, MA (US); Troy Aaron Luster, Norfolk, MA (US); Birgit Schultes, Arlington, MA (US); Stephanie A. Yazinski, Lynnfield, MA (US); Pooja Vinay, St. Louis, MO (US)

(73) Assignee: Intellia Therapeutics, Inc., Cambridge, MA (US)

(*) Notice: Subject to any disclaimer, the term of this patent is extended or adjusted under 35 U.S.C. 154(b) by 1375 days.

(21) Appl. No.: 17/231,556

(22) Filed: Apr. 15, 2021

(65) Prior Publication Data

US 2021/0340530 A1 Nov. 4, 2021

Related U.S. Application Data

(63) Continuation of application No. PCT/US2019/056399, filed on Oct. 15, 2019.

(60) Provisional application No. 62/747,037, filed on Oct. 17, 2018, provisional application No. 62/746,522, filed on Oct. 16, 2018.

(51) Int. Cl.

*C12N 15/11* (2006.01)
*C07K 14/725* (2006.01)
*C12N 9/22* (2006.01)

(52) U.S. Cl.

CPC ........ *C12N 15/111* (2013.01); *C07K 14/7051* (2013.01); *C12N 9/22* (2013.01); *C12N 2310/20* (2017.05); *C12N 2320/30* (2013.01)

(58) Field of Classification Search

CPC .... C12N 15/111; C12N 9/22; C12N 2310/20; C12N 2320/30; C12N 2750/14143; C12N 15/1138; C12N 15/907; C12N 2310/315; C12N 2310/321; C12N 2310/322; C07K 14/7051; C07K 14/705; A61K 48/0058; A61P 35/00

See application file for complete search history.

(56) References Cited

U.S. PATENT DOCUMENTS 5,378,825 A 1/1995 Cook et al.
5,585,481 A 12/1996 Arnold, Jr. et al.
8,889,356 B2 11/2014 Zhang
9,023,649 B2 5/2015 Mali et al.
9,890,393 B2 * 2/2018 Duchateau ........... C12N 5/0636
10,934,336 B2 * 3/2021 Zhao .................... C07K 14/705
2014/0186958 A1 7/2014 Zhang
2015/0166980 A1 6/2015 Liu et al.
2016/0083449 A1 3/2016 Schmitt et al.
2016/0312198 A1 10/2016 Joung et al.
2016/0312199 A1 10/2016 Joung et al.
2017/0114334 A1 4/2017 May et al.
2017/0175128 A1 6/2017 Welstead et al.
2020/0216805 A1 7/2020 Yuan et al.
2021/0017249 A1 1/2021 Sather et al.
2021/0137978 A1 * 5/2021 Maus ..................... A61K 40/31

FOREIGN PATENT DOCUMENTS

CN 106191062 A 12/2016
CN 107723275 A 2/2018
CN 107746831 A 3/2018
CN 107828730 A 3/2018
CN 108138183 A 6/2018
EP 3309248 B1 4/2018
EP 3686275 A1 7/2020
EP 3699268 A1 8/2020
JP 2016525888 A 9/2016
JP 2017535261 A 11/2017
WO 1993013121 A1 7/1993
WO 1995032305 11/1995
WO 2014136086 9/2014
WO 2014153470 A2 9/2014
WO 2014191128 A1 12/2014
WO 2015095340 6/2015
WO 2015136001 A1 9/2015
WO 2015161276 A2 10/2015
WO 2016069282 A1 5/2016
WO 2016069283 A1 5/2016
WO 2016073964 A1 5/2016
WO 2016073966 A1 5/2016
WO 2016154596 A1 9/2016
WO 2016160721 A1 10/2016
WO 2016161273 A1 10/2016
WO 2017062451 A1 4/2017

(Continued)

OTHER PUBLICATIONS

Provasi, E., Genovese, P., Lombardo, A. et al. Editing T cell specificity towards leukemia by zinc finger nucleases and lentiviral gene transfer. Nat Med 18, 807â815 (2012). (Year: 2012).*
Jiangtao Ren, Xiaojun Liu, Chongyun Fang, Shuguang Jiang, Carl H. June, Yangbing Zhao; Multiplex Genome Editing to Generate Universal CAR T Cells Resistant to PD1 Inhibition. Clin Cancer Res May 1, 2017; 23 (9): 2255â2266. (Year: 2017).*
Clarke et al. Enhanced bacterial immunity and mammalian genome editing via RNA polymerase-mediated dislodging of Cas9 from double strand DNA breaks. Mol Cell. Jul. 5, 2018;71(1):42-55.e8. (Year: 2018).*

(Continued)

*Primary Examiner* — Brian Whiteman
*Assistant Examiner* — Amanda M Zahorik
(74) *Attorney, Agent, or Firm* — McNeill PLLC

(57) ABSTRACT

Compositions and methods for editing, e.g., altering a DNA sequence, within the TRBC1, TRBC2 and/or TRAC genes are provided. Compositions and methods for immunotherapy are provided, for example.

30 Claims, 40 Drawing Sheets

Specification includes a Sequence Listing.

(56) References Cited

FOREIGN PATENT DOCUMENTS

| | | | |
|---|---|---|---|
| WO | 2017070429 | A1 | 4/2017 |
| WO | 2017093969 | A1 | 6/2017 |
| WO | 2017106528 | A2 | 6/2017 |
| WO | 2017112944 | A1 | 6/2017 |
| WO | 2017136794 | A1 | 8/2017 |
| WO | 2017152015 | A1 | 9/2017 |
| WO | 2017173054 | | 10/2017 |
| WO | 2017180989 | A2 | 10/2017 |
| WO | 2017193107 | A2 | 11/2017 |
| WO | 2018073393 | A2 | 4/2018 |
| WO | 2018107028 | A1 | 6/2018 |
| WO | 2018115887 | A1 | 6/2018 |
| WO | 2018132479 | A1 | 7/2018 |
| WO | 2018191490 | A1 | 10/2018 |
| WO | 2018197492 | A1 | 11/2018 |
| WO | 2019052577 | A1 | 3/2019 |
| WO | 2019067992 | A1 | 4/2019 |
| WO | 2019070541 | A1 | 4/2019 |
| WO | 2019086007 | A1 | 5/2019 |
| WO | 2019089610 | A1 | 5/2019 |
| WO | 2019097305 | A2 | 5/2019 |
| WO | 2019195491 | A1 | 10/2019 |
| WO | 2019195492 | A1 | 10/2019 |

OTHER PUBLICATIONS

Abbas, Yazan M et al. "Structure of human IFIT1 with capped RNA reveals adaptable mRNA binding and mechanisms for sensing N1 and N2 ribose 2'-O methylations." Proceedings of the National Academy of Sciences of the United States of America vol. 114, 11 (2017): E2106-E2115.

Adams et al., "The Biochemistry of the Nucleic Acids", ed., 11th ed., 1992.

Cameron et al., "Mapping the genomic landscape of CRISPR-Cas9 cleavage", Nature Methods. 6, 600-606; 2017.

Dunbar et al., "ANARCI: antigen receptor numbering and receptor classification," Bioinformatics. Jan. 15, 2016; 32(2):298-300.

Eyquem, J. et al. "Targeting a CAR to the TRAC locus with CRISPR/Cas9 enhances tumor rejection" Nature, vol. 543, No. 7643 (Feb. 22, 2017) pp. 113-117.

Gilbert et al., "CRISPR-mediated modular RNA-guided regulation of transcription in eukaryotes," Cell 154:442-51 (2013).

Guo, P X, and B Moss., "Interaction and mutual stabilization of the two subunits of vaccinia virus mRNA capping enzyme coexpressed in *Escherichia coli*." Proceedings of the National Academy of Sciences of the United States of America vol. 87, 11 (1990): 4023-7.

International Search Report and Written Opinion issued in PCT. US2019/056399 dated Apr. 1, 2020.

Kabat et al., "Sequences of Proteins of Immunological Interest", U.S. Dept. of Health and Human Services, Public Health Service, National Institutes of Health, 1991.

Katibah, George E et al. "Broad and adaptable RNA structure recognition by the human interferon-induced tetratricopeptide repeat protein IFIT5." Proceedings of the National Academy of Sciences of the United States of America vol. 111,33 (2014): 12025-30.

Makarova et al., "An updated evolutionary classification of CRISPR-Cas systems" Nat Rev Microbiol, 13(11):722-36 (2015).

Makarova et al. "Evolution and classification of the CRISPR-Cas systems." Nature reviews. Microbiology vol. 9,6 (2011): 467-77.

Mali et al., "CAS9 transcriptional activators for target specificity screening and paired nickases for cooperative genome engineering," Nat. Biotechnol. 31:833-8 (2013).

Mao, X. and Shuman, S. (1994) "Intrinsic RNA (Guanine-7) Methyltransferase Activity of the Vaccinia Virus Capping Enzyme D1 Subunit Is Stimulated by the D12 Subunit", J. Biol. Chem. 269, 24472-24479.

Perez-Pinera et al., "RNA-guided gene activation by CRISPR-Cas9-based transcription factors," Nat. Methods 10:973-6 (2013).

Qi et al., "Repurposing CRISPR as an RNA-guided platform for sequence-specific control of gene expression," Cell 152:1173-83 (2013).

Shmakov et al., "Discovery and Functional Characterization of Diverse Class 2 CRISPR-Cas Systems" Molecular Cell, 60:385-397 (2015).

Stepinski et al., (2001) "Synthesis and properties of mRNAs containing the novel 'anti-reverse' cap analogs 7-methyl (3'-O-methyl)GpppG and 7-methyl(3'deoxy)GpppG," RNA 7: 1486-1495.

Vester and Wengel, 2004, "LNA (locked nucleic acid): high-affinity targeting of complementary RNA and DNA" Biochemistry 43(42):13233-41.

Zetsche et al., "Cpf1 is a Single RNA-Guided Endonuclease of a Class 2 CRISPR-Cas System," Cell, (2015) 163, 3:759-771.

Georgiadis et al., "Long Terminal Repeat CRISPR-CAR-Coupled "Universal" T Cells Mediate Potent Anti-leukemic Effects," Molecular Therapy, vol. 26, No. 5, pp. 1215-1227 (Mar. 6, 2018).

* cited by examiner

AV16-TCR-H

AV15-TCR-G

COMPOSITIONS AND METHODS FOR IMMUNOTHERAPY

The present application is a Continuation of International Application No. PCT/US2019/056399, filed Oct. 15, 2019, which claims the benefit of priority to U.S. Provisional Patent Application Nos 62/746,522, filed Oct. 16, 2018, and 62/747,037, filed Oct. 17, 2018, all of which are incorporated herein by reference.

The instant application contains a Sequence Listing which has been submitted electronically in ASCII format and is hereby incorporated by reference in its entirety. The ASCII copy, created on Sep. 25, 2025, is named 2025-09-25_01155-0026-00US_ST25.txt and is 299,475 bytes in size.

CRISPRs (Clustered Regularly Interspaced Short Palindromic Repeats) evolved in bacteria as an adaptive immune system to defend against viral attack. Upon exposure to a virus, short segments of viral DNA are integrated into the CRISPR locus of the bacterial genome. RNA is transcribed from a portion of the CRISPR locus that includes the viral sequence. That RNA, which contains sequence complementary to the viral genome, mediates targeting of a Cas9 protein to the sequence in the viral genome. The Cas9 protein cleaves and thereby restricts the viral target.

Recently, the CRISPR/Cas system has been adapted for genome editing in eukaryotic cells. The introduction of site-specific single strand breaks (SSBs) or double strand breaks (DSBs) allows for target sequence alteration through, for example, non-homologous end-joining (NHEJ) or homology-directed repair (HDR).

Eyquem et al. (2017) *Nature* 543(7643):113-117 report that targeting a chimeric antigen receptor (CAR) to the locus of the TRAC gene with a CRISPR-Cas9 system enhances tumor rejection. In addition, such targeting to the TRAC locus averts tonic CAR signaling and establishes effective internalization and re-expression of the CAR following single or repeated exposure to antigen, thus delaying effector T-cell differentiation and exhaustion. Nonetheless, existing approaches may produce T cells with less than desired activity against the intended target (including, but not limited to, producing T cells that express a CAR from the TRAC locus and an endogenous TRBC gene product that can interact with the CAR and provide T cells with undesired reactivity). Thus, there is a need for improved compositions and methods for immunotherapy.

Accordingly, the following embodiments are provided. In some embodiments, the present invention provides compositions and methods using a guide RNA with an RNA-guided DNA binding agent such as the CRISPR/Cas system to substantially reduce or knockout expression of the TRBC and/or TRAC genes, thereby substantially reducing or eliminating the production of the native alpha and/or beta subunits of the T-cell receptor, also called TCR.

SUMMARY

The inventions described herein relate to compositions and methods for engineered T cell therapies (e.g., immunooncology and for reducing autoimmunity), for example, cells modified at specific target sequences in their genome, including as modified by introduction of CRISPR systems that include gRNA molecules which target said target sequences, and methods of making and using therefor. For example, the present disclosure relates to and provides gRNA molecules, CRISPR systems, cells, and methods useful for genome editing of cells, e.g. T cells, e.g. T cells engineered to lack endogenous T-cell receptor expression, e.g. T cells suitable for further engineering to insert a coding sequence of interest, e.g. T cells further engineered to express a T-cell receptor, such as a modified or mutant T-cell receptor, and useful for immunotherapy.

In a first aspect, the invention provides a gRNA molecule including a tracrRNA and crRNA, wherein the crRNA includes a targeting domain that binds to a target sequence of a T cell. In an embodiment, the targeting domain is complementary with a target sequence of a T cell. The T cell may be an autologous or allogeneic T cell. The T cell may be a $CD3^+$, $CD4^+$, and/or $CD8^+$ T cell.

The invention is as provided in the claims and further embodiments are set out below.

The invention provides a method of altering a DNA sequence within the TRBC1 and/or TRBC2 gene, comprising delivering a composition to a cell, wherein the composition comprises:

- (a) a guide RNA comprising a sequence chosen from:
  - i. a guide sequence selected from SEQ ID NOs: 1-89;
  - ii. at least 17, 18, 19, or 20 contiguous nucleotides of a sequence selected from SEQ ID NOs: 1-89;
  - iii. a guide sequence that is at least 99%, 98%, 97%, 96%, 95%, 94%, 93%, 92%, 91%, or 90% identical to a sequence selected from SEQ ID NOs: 1-89;
  - iv. a guide sequence comprising any one of SEQ ID NOs: 1-24; and
  - v. a guide sequence comprising any one of SEQ ID NOs: 1-6; or
- (b) a nucleic acid encoding a guide RNA of (a); and optionally
- (c) an RNA-guided DNA binding agent or a nucleic acid encoding an RNA-guided DNA binding agent.

The invention additionally provides a method of altering a DNA sequence, comprising delivering a composition to a cell, wherein the composition comprises:

- (a) a guide RNA comprising a sequence chosen from:
  - i. a sequence that comprises 15 consecutive nucleotides ±10 nucleotides of a genomic coordinate listed in any of Tables 1 and/or 3 for SEQ ID NOs: 1-89 and 179-184;
  - ii. at least 17, 18, 19, or 20 contiguous nucleotides of a sequence from (i);
  - iii. a guide sequence that is at least 99%, 98%, 97%, 96%, 95%, 94%, 93%, 92%, 91%, or 90% identical to a sequence selected from (i);
- (b) a nucleic acid encoding a guide RNA of (a); and optionally
- (c) an RNA-guided DNA binding agent or a nucleic acid encoding an RNA-guided DNA binding agent.

The invention additionally also provides a method of reducing the expression of the TRBC1 and/or TRBC2 gene comprising delivering a composition to a cell, wherein the composition comprises:

- (a) a guide RNA comprising a sequence chosen from:
  - i) a guide sequence selected from SEQ ID NOs: 1-89;
  - ii) at least 17, 18, 19, or 20 contiguous nucleotides of a sequence selected from SEQ ID NOs: 1-89;
  - iii) a guide sequence that is at least 99%, 98%, 97%, 96%, 95%, 94%, 93%, 92%, 91%, or 90% identical to a sequence selected from SEQ ID NOs: 1-89;
  - iv) a guide sequence comprising any one of SEQ ID NOs: 1-24; and
  - v) a guide sequence comprising any one of SEQ ID NOs: 1-6; or (b) a nucleic acid encoding a guide RNA of (a); and optionally (c) an RNA-guided DNA binding agent or a nucleic acid encoding an RNA-guided DNA binding agent.

The invention additionally provides a method of immunotherapy comprising administering a composition to a subject, an autologous cell thereof, and/or an allogeneic cell, wherein the composition comprises:

(a) a guide RNA comprising a sequence chosen from:

i) a guide sequence selected from SEQ ID NOs: 1-89;

ii) at least 17, 18, 19, or 20 contiguous nucleotides of a sequence selected from SEQ ID NOs: 1-89;

iii) a guide sequence that is at least 99%, 98%, 97%, 96%, 95%, 94%, 93%, 92%, 91%, or 90% identical to a sequence selected from SEQ ID NOs: 1-89;

iv) a guide sequence comprising any one of SEQ ID NOs: 1-24; and v) a guide sequence comprising any one of SEQ ID NOs: 1-6; or (b) a nucleic acid encoding a guide RNA of (a); and optionally (c) an RNA-guided DNA binding agent or nucleic acid encoding an RNA-guided DNA binding agent.

The invention additionally also provides method of altering a DNA sequence within the TRAC gene, comprising delivering a composition to a cell, wherein the composition comprises:

(a) a guide RNA comprising a sequence chosen from:

i) a guide sequence selected from SEQ ID NOs: 90-178, 185, and 213-218;

ii) at least 17, 18, 19, or 20 contiguous nucleotides of a sequence selected from SEQ ID NOs: 90-178, 185, and 213-218;

iii) a guide sequence that is at least 99%, 98%, 97%, 96%, 95%, 94%, 93%, 92%, 91%, or 90% identical to a sequence selected from SEQ ID NOs: 90-178, 185, and 213-218;

iv) a guide sequence comprising any one of SEQ ID NOs: 90-113 and 213-218; and v) a guide sequence comprising any one of SEQ ID NOs: 90-95; or (b) a nucleic acid encoding a guide RNA of (a); and optionally (c) an RNA-guided DNA binding agent or a nucleic acid encoding an RNA-guided DNA binding agent.

The invention additionally provides a method of reducing the expression of the TRAC gene comprising delivering a composition to a cell, wherein the composition comprises:

(a) a guide RNA comprising a sequence chosen from:

i) a guide sequence selected from SEQ ID NOs: 90-178, 185, and 213-218;

ii) at least 17, 18, 19, or 20 contiguous nucleotides of a sequence selected from SEQ ID NOs: 90-178, 185, and 213-218;

iii) a guide sequence that is at least 99%, 98%, 97%, 96%, 95%, 94%, 93%, 92%, 91%, or 90% identical to a sequence selected from SEQ ID NOs: 90-178, 185, and 213-218;

iv) a guide sequence comprising any one of SEQ ID NOs: 90-113 and 213-218; and v) a guide sequence comprising any one of SEQ ID NOs: 90-95; or (b) a nucleic acid encoding a guide RNA of (a); and optionally (c) an RNA-guided DNA binding agent or a nucleic acid encoding an RNA-guided DNA binding agent.

The invention additionally also provides method of immunotherapy comprising administering a composition to a subject, an autologous cell thereof, and/or an allogeneic cell, wherein the composition comprises:

(a) a guide RNA comprising a sequence chosen from:

i) a guide sequence selected from SEQ ID NOs: 90-178, 185, and 213-218;

ii) at least 17, 18, 19, or 20 contiguous nucleotides of a sequence selected from SEQ ID NOs: 90-178, 185, and 213-218;

iii) a guide sequence that is at least 99%, 98%, 97%, 96%, 95%, 94%, 93%, 92%, 91%, or 90% identical to a sequence selected from SEQ ID NOs: 90-178, 185, and 213-218;

iv) a guide sequence comprising any one of SEQ ID NOs: 90-113 and 213-218; and v) a guide sequence comprising any one of SEQ ID NOs: 90-95; or (b) a nucleic acid encoding a guide RNA of (a.); and optionally (c) an RNA-guided DNA binding agent or nucleic acid encoding an RNA-guided DNA binding agent.

The invention additionally provides a method of altering a DNA sequence, comprising delivering a composition to a cell, wherein the composition comprises:

(a) a guide RNA comprising a sequence chosen from:

i. a sequence that comprises 15 consecutive nucleotides ±10 nucleotides of a genomic coordinate listed in any of Tables 2 and/or 3 for SEQ ID NOs: 90-218;

ii. at least 17, 18, 19, or 20 contiguous nucleotides of a sequence from (i);

iii. a guide sequence that is at least 99%, 98%, 97%, 96%, 95%, 94%, 93%, 92%, 91%, or 90% identical to a sequence selected from (i);

(b) a nucleic acid encoding a guide RNA of (a); and optionally (c) an RNA-guided DNA binding agent or a nucleic acid encoding an RNA-guided DNA binding agent.

The invention additionally also provides a method of altering a DNA sequence within the TRBC1, TRBC2 and/or TRAC genes, comprising delivering to a cell a first guide RNA, a second guide RNA and optionally an RNA-guided DNA binding agent or a nucleic acid encoding an RNA-guided DNA binding agent, wherein the first guide RNA comprises a sequence chosen from:

i) a guide sequence selected from SEQ ID NOs: 1-89;

ii) at least 17, 18, 19, or 20 contiguous nucleotides of a sequence selected from SEQ ID NOs: 1-89;

iii) a guide sequence that is at least 99%, 98%, 97%, 96%, 95%, 94%, 93%, 92%, 91%, or 90% identical to a sequence selected from SEQ ID NOs: 1-89;

iv) a guide sequence comprising any one of SEQ ID NOs: 1-24; and v) a guide sequence comprising any one of SEQ ID NOs: 1-6, and wherein the second guide RNA comprises a sequence chosen from:

i. a guide sequence selected from SEQ ID NOs: 90-178, 185, and 213-218;

ii. at least 17, 18, 19, or 20 contiguous nucleotides of a sequence selected from SEQ ID NOs: 90-178, 185, and 213-218;

iii. a guide sequence that is at least 99%, 98%, 97%, 96%, 95%, 94%, 93%, 92%, 91%, or 90% identical to a sequence selected from SEQ ID NOs: 90-178, 185, and 213-218;

iv. a guide sequence comprising any one of SEQ ID NOs: 90-113 and 213-218; and v. a guide sequence comprising any one of SEQ ID NOs: 90-95.

The invention additionally also provides a method of reducing the expression of the TRBC1, TRBC2 and/or TRAC genes, comprising delivering to a cell a first guide RNA, a second guide RNA and optionally an RNA-guided DNA binding agent or a nucleic acid encoding an RNA-guided DNA binding agent, wherein the first guide RNA comprises a sequence chosen from:

i) a guide sequence selected from SEQ ID NOs: 1-89;
ii) at least 17, 18, 19, or 20 contiguous nucleotides of a sequence selected from SEQ ID NOs: 1-89;
iii) a guide sequence that is at least 99%, 98%, 97%, 96%, 95%, 94%, 93%, 92%, 91%, or 90% identical to a sequence selected from SEQ ID NOs: 1-89;
iv) a guide sequence comprising any one of SEQ ID NOs: 1-24; and
v) a guide sequence comprising any one of SEQ ID NOs: 1-6, and wherein the second guide RNA comprises a sequence chosen from:

i) a guide sequence selected from SEQ ID NOs: 90-178, 185, and 213-218;
ii) at least 17, 18, 19, or 20 contiguous nucleotides of a sequence selected from SEQ ID NOs: 90-178, 185, and 213-218;
iii) a guide sequence that is at least 99%, 98%, 97%, 96%, 95%, 94%, 93%, 92%, 91%, or 90% identical to a sequence selected from SEQ ID NOs: 90-178, 185, and 213-218;
iv) a guide sequence comprising any one of SEQ ID NOs: 90-113 and 213-218; and
v) a guide sequence comprising any one of SEQ ID NOs: 90-95.

The invention additionally provides a method of immunotherapy comprising administering a composition to a subject, an autologous cell thereof, or an allogeneic cell, wherein the composition comprises: a first guide RNA, a second guide RNA, and optionally an RNA-guided DNA binding agent or a nucleic acid encoding an RNA-guided DNA binding agent, wherein the first guide RNA comprises a sequence chosen from:

i) a guide sequence selected from SEQ ID NOs: 1-89;
ii) at least 17, 18, 19, or 20 contiguous nucleotides of a sequence selected from SEQ ID NOs: 1-89;
iii) a guide sequence that is at least 99%, 98%, 97%, 96%, 95%, 94%, 93%, 92%, 91%, or 90% identical to a sequence selected from SEQ ID NOs: 1-89;
iv) a guide sequence comprising any one of SEQ ID NOs: 1-24; and
v) a guide sequence comprising any one of SEQ ID NOs: 1-6, and wherein the second guide RNA comprises a sequence chosen from:

i. a guide sequence selected from SEQ ID NOs: 90-178, 185, and 213-218;
ii. at least 17, 18, 19, or 20 contiguous nucleotides of a sequence selected from SEQ ID NOs: 90-178, 185, and 213-218;
iii. a guide sequence that is at least 99%, 98%, 97%, 96%, 95%, 94%, 93%, 92%, 91%, or 90% identical to a sequence selected from SEQ ID NOs: 90-178, 185, and 213-218;
iv. a guide sequence comprising any one of SEQ ID NOs: 90-113 and 213-218; and
v. a guide sequence comprising any one of SEQ ID NOs: 90-95.

Without wishing to be bound by theory, the use of a double TRAC/TRBC mutant, e.g., a knockout mutant is in some embodiments advantageous in the context of the present invention as a greater proportion of the engineered/introduced TCR reaches the cell surface.

In some embodiments, a TRBC knockout in combination with a TRAC knock-in of an exogenous TCR in an engineered cell is advantageous in yielding greater activity of the exogenous TCR in an engineered cell.

In some embodiments, a TRBC knockout in combination with a TRAC knock-in of an exogenous TCR in an engineered cell is advantageous in yielding greater selectivity of the exogenous TCR in an engineered cell.

In addition, in some embodiments, a TRBC knockout in combination with a TRAC knockin of an exogenous TCR in an engineered cell may be advantageous in yielding greater cell killing, e.g., as measured by a caspase assay.

In some embodiments, a TRBC knockout in combination with a TRAC knock-in of an exogenous TCR in an engineered cell is advantageous in yielding greater IFN-gamma secretion, e.g., in response to an inducing peptide (e.g. Wilms' tumor gene (WT1) antigen).

Furthermore, in some embodiments, a double TRAC/TRBC knockout with the TCR is advantageous in yielding greater IFN-gamma secretion, e.g., in CD4+ cells.

In addition, advantageously in some embodiments, the interferon response (IFNγ and/or TNFα) is increased in edited cells wherein transcription of an inserted donor construct is promoted by an endogenous promoter of the TRAC.

Furthermore, in some embodiments, a double TRAC/TRBC knockout with these particular TCR is advantageous in yielding greater IFN-γ secretion in CD4+ cells. Not wishing to be bound by theory, in some embodiments, it is rarer to observe such activity in CD4+ cells, which are not usually strongly linked with reactivity to peptides presented on HLA Class I.

In addition, in some embodiments, a double TRAC/TRBC knockout with these particular TCR is advantageous in yielding a greater response in CD4+ cells, e.g., in a degranulation assay. Again, not wishing to be bound by theory, in some embodiments, it is rarer to observe such activity in CD4+ cells, which are not usually strongly linked with reactivity to peptides presented on HLA Class I.

In addition, in some embodiments, a double TRAC/TRBC knockout mutant is advantageous in yielding a lesser degree of alloreactivity than the TRAC single knockout mutant, e.g., when tested in a mixed lymphocyte reaction.

The invention additionally provides a method of expressing a heterologous immunological receptor via in locus insertion at the TRAC locus, comprising delivering to a cell a first guide RNA, a second guide RNA and an RNA-guided DNA binding agent or a nucleic acid encoding an RNA-guided DNA binding agent, wherein the first guide RNA comprises a sequence chosen from:

i) a guide sequence selected from SEQ ID NOs: 1-89;
ii) at least 17, 18, 19, or 20 contiguous nucleotides of a sequence selected from SEQ ID NOs: 1-89;
iii) a guide sequence that is at least 99%, 98%, 97%, 96%, 95%, 94%, 93%, 92%, 91%, or 90% identical to a sequence selected from SEQ ID NOs: 1-89;
iv) a guide sequence comprising any one of SEQ ID NOs: 1, 2, 3, 5, 6; and
v) a guide sequence comprising any one of SEQ ID NOs: 2, 3, 5, 6, and wherein the second guide RNA comprises a sequence chosen from:

i) a guide sequence selected from SEQ ID NOs: 90, 95, 97, 98, 185, 214, 218;

ii) at least 17, 18, 19, or 20 contiguous nucleotides of a sequence selected from SEQ ID NOs: 90, 95, 97, 98, 185, 214, and 218;

iii) a guide sequence that is at least 99%, 98%, 97%, 96%, 95%, 94%, 93%, 92%, 91%, or 90% identical to a sequence selected from SEQ ID NOs: 90, 95, 97, 98, 185, 214, and 218;

iv) a guide sequence comprising any one of SEQ ID NOs: 90, 95, 97, 185, and 214;

v) a guide sequence comprising any one of SEQ ID NOs: 90, 95, and 185; and vi) a guide sequence comprising SEQ ID NO: 90 or 214.

A single cleavage and/or editing event may allow the "knock out" of the endogenous TRAC gene. As a further advantage, if a template is introduced or supplied during the editing process an exogenous polypeptide of interest may be inserted into the target locus of the editing event. This advantage flows particularly from the use of guide RNAs with the following SEQ ID NOs: 90, 95, 97, 185, 203, 204, 205, 206, 210, 211, and/or 214. These guide RNAs may also be introduced in concert with a gRNA targeting the locus or loci of the TRBC genes.

The first guide RNA may comprise the sequence of SEQ ID NO: 2 and the second guide RNA comprises the sequence of SEQ ID NO: 90.

The first guide RNA may comprise the sequence of SEQ ID NO: 180 and the second guide RNA may comprise the sequence of SEQ ID NO: 186.

The first guide RNA may comprise the sequence of any one of SEQ ID NOs: 1, 2, 3, 5, 6, and the second guide RNA may comprise the sequence of SEQ ID NO: 90.

The first guide RNA may comprise the sequence of any one of SEQ ID NOs: 1, 2, 3, 5, 6, and the second guide RNA may comprise the sequence of SEQ ID NO: 214.

The first guide RNA, the second guide RNA and the RNA-guided DNA binding agent or the nucleic acid encoding an RNA-guided DNA binding agent may be introduced or administered at substantially the same time.

The DNA sequences within the TRBC1, TRBC2 and/or TRAC genes may be altered simultaneously.

An RNA-guided DNA binding agent or nucleic acid encoding an RNA-guided DNA binding agent may be introduced or administered as a part of methods of modification.

The methods may further comprise:

(a) inducing a double-stranded break (DSB) within the TRBC1, TRBC2 and/or TRAC genes in a cell and/or subject; or (b) inducing a single-stranded break (SSB) within the TRBC1, TRBC2 and/or TRAC genes in a cell and/or a subject; or (c) reducing the expression of the TRBC1, TRBC2 and/or TRAC genes in a cell and/or subject.

The methods may further comprise introducing a nucleic acid sequence encoding a polypeptide of interest, optionally wherein:

(a) the one or more polypeptides of interest comprise a receptor;

(b) the one or more polypeptides of interest comprise an immunological receptor;

(c) the one or more polypeptides of interest comprise a T-cell receptor, further optionally wherein the T-cell receptor recognizes a cancer antigen;

(d) the one or more polypeptides of interest comprise a WT1-specific T-cell receptor, wherein the T-cell receptor recognizes WT1 or a fragment thereof;

(e) the one or more polypeptides of interest comprise a chimeric antigen receptor, further optionally wherein the chimeric antigen receptor recognizes a cancer antigen; or (f) the one or more polypeptides of interest comprise a WT1-specific chimeric antigen receptor, wherein the chimeric antigen receptor recognizes WT1 or a fragment thereof.

The methods may further comprise:

a. introducing a TCR α chain and a TCR β chain;

b. introducing one or more nucleic acid sequences that encode a TCR α chain and a TCR β chain;

c. introducing a WT1-specific TCR α chain and β chain;

d. introducing one or more nucleic acid sequences that encode a WT1-specific TCR α chain and β chain;

e. introducing a first TCR sequence selected from: (i) SEQ ID NO: 501 or 504; (ii) an amino acid sequence that is at least 99%, 95%, 90%, 85%, 80%, 70%, of 60% identical to SEQ ID NO: 501 or 504; and (iii) a contiguous subsequence of at least 20, 30, 40, 50, 60, 70, 80, 90, 100, 150, 200, or 250 amino acids of SEQ ID NO: 501 or 504, and introducing a second TCR sequence selected from: (i) SEQ ID NO: 502 or 505; (ii) an amino acid sequence that is at least 99%, 95%, 90%, 85%, 80%, 70%, of 60% identical to SEQ ID NO: 502 or 505; and (iii) a contiguous subsequence of at least 20, 30, 40, 50, 60, 70, 80, 90, 100, 150, 200, 250, or 300 amino acids of SEQ ID NO: 502 or 505, f. introducing a first TCR sequence selected from: (i) SEQ ID NO:501 or 513; (ii) an amino acid sequence that is at least 99%, 95%, 90%, 85%, 80%, 70%, of 60% identical to SEQ ID NO:510 or 513; and (iii) a contiguous subsequence of at least 20, 30, 40, 50, 60, 70, 80, 90, 100, 150, 200, or 250 amino acids of SEQ ID NO:510 or 513, and introducing a second TCR sequence selected from: (i) SEQ ID NO:511 or 514; (ii) an amino acid sequence that is at least 99%, 95%, 90%, 85%, 80%, 70%, of 60% identical to SEQ ID NO:511 or 514; and (iii) a contiguous subsequence of at least 20, 30, 40, 50, 60, 70, 80, 90, 100, 150, 200, 250, or 300 amino acids of SEQ ID NO:511 or 514, g. introducing a nucleic acid sequence comprising a sequence that encodes a first TCR sequence of (e) or (f);

h. introducing a nucleic acid sequence comprising a sequence that encodes a second TCR sequence of (e)-(f);

i. introducing a nucleic acid sequence comprising the nucleic acid sequence of (g) and (h);

j. introducing a polypeptide selected from SEQ ID NO: 500, 503, 506, 509, 512, 515, 518, or 521 or an amino acid sequence that is at least 99%, 95%, 90% identical thereto, optionally by introducing a nucleic acid sequence encoding the same; or k. introducing a TCR α chain and a TCR β chain polypeptides selected from (i)-(viii) below, or an amino acid sequence that is at least 99%, 95%, 90% identical thereto:

i) SEQ ID NO: 501 and SEQ ID NO:502;

ii) SEQ ID NO: 504 and SEQ ID NO:505;

iii) SEQ ID NO: 507 and SEQ ID NO:508;

iv) SEQ ID NO: 510 and SEQ ID NO:511;

v) SEQ ID NO: 513 and SEQ ID NO:514;

vi) SEQ ID NO: 516 and SEQ ID NO:517;
vii) SEQ ID NO: 519 and SEQ ID NO:520;

l. introducing a nucleic acid sequence encoding a TCR α chain and a TCR β chain polypeptide of (k).

The first nucleic acid sequence may be flanked by sequences homologous to a first target locus. The second nucleic acid sequence may be flanked by sequences homologous to a second target locus. The flanking sequences may be of at least 17, 18, 19, 20, 21, 22, 23, 24, 25, 30, 35, or 40 nucleotides in length.

The first target locus may be the TRAC, TRBC1 or TRBC2 gene, e.g., the TRAC gene. The second target locus may be the TRAC, TRBC1 or TRBC2 gene, e.g., either the TRBC1 or TRBC2 genes.

The introduced nucleic acid sequence, or the first nucleic acid sequence and the second nucleic acid sequence may be constituted without a promoter region, i.e. the nucleic acid may be "promoterless".

The introduced nucleic acid sequence, or the first nucleic acid sequence and the second nucleic acid sequence, may be operably linked to a promoter, optionally wherein the promoter is an EF-1α promoter (SEQ ID NO: 603).

The introduced nucleic acid sequence, or the first nucleic acid sequence and the second nucleic acid sequence, may be introduced via a vector, via transfection, via a lipid nanoparticle, or via microinjection.

The vector may be a viral vector, further optionally wherein the viral vector is an adeno-associated virus vector.

The invention also provides a method of in locus insertion of a TCR (such as a WT1-specific TCR), comprising delivering to a cell a first guide RNA for inserting the TCR that comprises a guide sequence selected from: SEQ ID NOs: 90, 95, 97, 98, 185, 214, and 218, and optionally (i) an RNA-guided DNA binding agent or a nucleic acid encoding an RNA-guided DNA binding agent; and/or (ii) a donor nucleic acid molecule that encodes a TCR (such as a WT1-specific TCR). The method may further comprise delivering a second guide RNA comprising a sequence selected from SEQ ID NOs: 1-89. The method may further comprise delivering a second guide RNA comprising a sequence selected from SEQ ID NOs: 179-184.

The TCR may be a WT1-specific TCR that comprises:

i) a polypeptide selected from SEQ ID NO: 500, 503, 506, 509, 512, 515, 518, or 521 or an amino acid sequence that is at least 99%, 95%, 90% identical thereto; or ii) TCR α chain and a TCR β chain polypeptides selected from (i)-(viii) below, or an amino acid sequence that is at least 99%, 95%, 90% identical thereto:
i) SEQ ID NO: 502 and SEQ ID NO:503;
ii) SEQ ID NO: 504 and SEQ ID NO:505;
iii) SEQ ID NO: 507 and SEQ ID NO:508;
iv) SEQ ID NO: 510 and SEQ ID NO:511;
v) SEQ ID NO: 513 and SEQ ID NO:514;
vi) SEQ ID NO: 516 and SEQ ID NO:517;
vii) SEQ ID NO: 519 and SEQ ID NO:520;
viii) SEQ ID NO: 522 and SEQ ID NO:523.

The invention also provides a composition comprising:

a. a guide RNA comprising
i. a guide sequence selected from SEQ ID NOs: 1-89; or
ii. at least 17, 18, 19, or 20 contiguous nucleotides of a sequence selected from SEQ ID NOs: 1-89; or
iii. a guide sequence that is at least 99%, 98%, 97%, 96%, 95%, 94%, 93%, 92%, 91%, or 90% identical to a sequence selected from SEQ ID NOs: 1-89; or
iv. a guide sequence comprising any one of SEQ ID NOs: 1-24; or
v. a guide sequence comprising any one of SEQ ID NOs: 1-6; and optionally b. an RNA-guided DNA binding agent or nucleic acid encoding an RNA-guided DNA binding agent.

The composition may be for use in altering a DNA sequence within the TRBC1 and/or TRBC2 genes in a cell. The composition may be for use in reducing the expression of the TRBC1 and/or TRBC2 genes in a cell. The guide RNA in the composition may comprise a sequence selected from any of SEQ ID NOs 196-200.

The invention also provides a composition comprising:

a. a guide RNA comprising
i. a guide sequence selected from SEQ ID NOs: 90-178, 185, and 213-218; or
ii. at least 17, 18, 19, or 20 contiguous nucleotides of a sequence selected from SEQ ID NOs: 90-178, 185, and 213-218; or
iii. a guide sequence that is at least 99%, 98%, 97%, 96%, 95%, 94%, 93%, 92%, 91%, or 90% identical to a sequence selected from SEQ ID NOs: 90-178, 185, and 213-218; or
iv. a guide sequence comprising any one of SEQ ID NOs: 90-113 and 213-218; or
v. a guide sequence comprising any one of SEQ ID NOs: 90-95; and optionally b. an RNA-guided DNA binding agent or nucleic acid encoding an RNA-guided DNA binding agent.

The composition may be for use in altering a DNA sequence within the TRAC gene in a cell. The composition may be for use in reducing the expression of the TRAC gene in a cell. The guide RNA may be selected from any of SEQ ID NOs 185-192 and 201-212.

The invention also provides a cell, altered by the methods described herein. The cell may be altered ex vivo.

The cell may be a T cell. The cell may be a $CD3^+$, $CD4^+$ and/or $CD8^+$ T cell. The cell may be a mammalian, primate, or human cell.

The cell may lack an endogenous T-cell receptor. The cell may be suitable for preparation of a T cell expressing a non-endogenous T-cell receptor. The cell may thus be used for preparation of a T cell expressing a CAR.

The cell altered as described herein may be a $CD3^-$ cell. The cell may be a $CD3^+$ cell before being altered.

The cell may additionally comprise one or more nucleic acid sequences encoding a polypeptide of interest, optionally wherein:

(a) the one or more polypeptides of interest comprise a receptor;
(b) the one or more polypeptides of interest comprise an immunological receptor;
(c) the one or more polypeptides of interest comprise a T-cell receptor, further optionally wherein the T-cell receptor is specific for WT1; or
(d) the one or more polypeptides of interest comprise a chimeric antigen receptor, further optionally wherein the chimeric antigen receptor is specific for WT1.

The cell may additionally comprise one or more nucleic acid sequences encoding α and β chains of an exogenous T-cell receptor. The cell may additionally comprise one or more nucleic acid sequences encoding γ and δ chains of an exogenous T-cell receptor.

One or more nucleic acid sequences encoding the α and β chains of the exogenous T-cell receptor of the cells described herein may be in the TRAC locus of the genome. One or more nucleic acid sequences encoding the γ and δ chains of the exogenous T-cell receptor of the cells described herein may be in the TRAC locus of the genome.

The sequence of the TCR α chain may be selected from: (i) SEQ ID NO: 501 or 504; (ii) a sequence that is at least 99%, 95%, 90%, 85%, 80%, 70%, of 60% identical to SEQ ID NO: 501 or 504; and a contiguous subsequence of at least 20, 30, 40, 50, 60, 70, 80, 90, 100, 150, 200, or 250 amino acids of SEQ ID NO: 501 or 504; and the sequence of the TCR β chain may be selected from: (i) SEQ ID NO: 502 or 505; (ii) a sequence that is at least 99%, 95%, 90%, 85%, 80%, 70%, of 60% identical to SEQ ID NO: 502 or 505; and a contiguous subsequence of at least 20, 30, 40, 50, 60, 70, 80, 90, 100, 150, 200, 250, or 300 amino acids of SEQ ID NO: 502 or 505.

The TCR α chain of the cell may be encoded by a nucleic acid sequence according to any of SEQ ID NOs: 500, 501, 503, and 504, and the 13 TCR chain is encoded according to any of SEQ ID NOs: 500, 502, 503, and 505.

The sequence of the TCR α chain may be selected from: (i) SEQ ID NO:513; (ii) a sequence that is at least 99%, 95%, 90%, 85%, 80%, 70%, of 60% identical to SEQ ID NO:513; and a contiguous subsequence of at least 20, 30, 40, 50, 60, 70, 80, 90, 100, 150, 200, 250, 300, 350, 400, 500, 600, 700, or 800 amino acids of SEQ ID NO: 513, and wherein the sequence of the TCR β chain is selected from: (i) SEQ ID NO: 514; (ii) a sequence that is at least 99%, 95%, 90%, 85%, 80%, 70%, of 60% identical to SEQ ID NO: 514; and a contiguous subsequence of at least 20, 30, 40, 50, 60, 70, 80, 90, 100, 150, 200, 250, 300, 350, 400, 500, 600, 700, or 800 amino acids of SEQ ID NO:514.

The α TCR chain may be SEQ ID NO:513 and the β TCR chain may be SEQ ID NO: 514.

The one or more genes of the cells disclosed herein may be expressed from an endogenous promoter.

The one or more genes of the cells disclosed herein may be expressed from a heterologous promoter, optionally wherein the heterologous promoter is an EF-1α promoter.

The altered cell may comprise genes encoding α and β chains of an exogenous T-cell receptor and/or genes encoding γ and δ chains of an exogenous T-cell receptor. Suitable α, β, γ, and δ chains are known in the art. See, e.g., WO2018/197492.

The α and β chains of the exogenous T-cell receptor may be in the TRAC locus of the genome. The α and β chains of the exogenous T-cell receptor provided within a transcript, separated by a P2A or other cleavage sequence.

The invention also provides a population of cells comprising disclosed herein, wherein greater than about 50%, greater than about 55%, greater than about 60%, greater than about 65%, greater than about 70%, greater than about 75%, greater than about 80%, greater than about 85%, greater than about 90%, greater than about 95%, greater than about 98%, or greater than about 99% of the altered population are $CD3^-$ cells.

The invention also provides a population of cells comprising disclosed herein, wherein greater than about 50%, greater than about 55%, greater than about 60%, greater than about 65%, greater than about 70%, greater than about 75%, greater than about 80%, greater than about 85%, greater than about 90%, greater than about 95%, greater than about 98%, or greater than about 99% of the population lacks an endogenous T-cell receptor.

The invention also provides a population of cells comprising disclosed herein, wherein the expression of the TRBC1, TRBC2 and/or TRAC genes in the population has been reduced relative to an unaltered population of the same cell by at least about 50%, at least about 55%, at least about 60%, at least about 65%, at least about 70%, at least about 75%, at least about 80%, at least about 85%, at least about 90%, at least about 95%, at least about 98%, or at least about 99%.

The reduction in expression may be of the TRBC1 gene. The reduction in expression may be of the TRBC2 gene. The reduction in expression may be of the TRAC gene.

Between 10 and 100% of the population of cells, e.g. between 30 and 99% of the population, may have an indel in the TRBC1, TRBC2 and/or TRAC genes.

Furthermore, between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the population may have an indel in the TRBC1, TRBC2 and/or TRAC genes.

The indel or insertion may be in the TRBC1 gene. The indel or insertion may be in the TRBC2 gene. The indel or insertion may be in the TRAC gene.

The method of, or composition for use of, described herein may result in editing of the TRBC1 and/or TRBC2 genes. The method of, or composition for use of, described herein may result in editing of the TRAC gene. The method of, or composition for use of, described herein may result in editing of a TRBC gene and the TRAC gene.

The editing may be calculated as a percentage of the population that is edited (percent editing or percent indels). The percent editing may be between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the population.

The composition described herein may comprise a sgRNA comprising:

(e) any one of SEQ ID NOs: 179-184 and 196-200; or (f) a guide sequence selected from any one of SEQ ID NOs: 1-89; or (g) a guide sequence selected from SEQ ID NOs: 1-24; or (h) a guide sequence selected from SEQ ID NOs: 1-6.

The composition described herein may comprise a sgRNA comprising:

(i) any one of SEQ ID NOs: 186-192 and 201-212; or (j) a guide sequence selected from any one of SEQ ID NOs: 90-178, 185, and 213-218; or (k) a guide sequence selected from SEQ ID NOs: 90-113 and 213-218; or (l) a guide sequence selected from SEQ ID NOs: 90-95.

The target sequence may be in exon 1, 2, 3, or 4 of the TRBC1, TRBC2 and/or TRAC genes. The target sequence may be in in the human TRBC1, TRBC2 and/or TRAC genes.

The target sequence may be in in exon 1 of the TRBC1, TRBC2 and/or TRAC genes. The target sequence may be in in exon 2 of the TRBC1, TRBC2 and/or TRAC genes. The target sequence may be in in exon 3 of the TRBC1, TRBC2 and/or TRAC genes. The target sequence may be in in exon 4 of the TRBC1, TRBC2 and/or TRAC genes.

The guide sequence may be complementary to a target sequence in the positive strand of TRBC1, TRBC2 and/or TRAC genes. The guide sequence may be complementary to a target sequence in the negative strand of TRBC1, TRBC2 and/or TRAC genes.

The first guide sequence may be complementary to a first target sequence in the positive strand of the TRBC1, TRBC2 and/or TRAC genes, and wherein the composition further comprises a second guide sequence that is complementary to a second target sequence in the negative strand of the TRBC1, TRBC2 and/or TRAC genes.

The guide RNA may comprise a guide sequence selected from any one of SEQ ID NOs 1-178 and further comprises a nucleotide sequence of SEQ ID NO: 400, wherein the nucleotides of SEQ ID NO: 400 follow the guide sequence at its 3' end.

The guide RNA may comprise a guide sequence selected from any one of SEQ ID NOs 1-178 and further comprises a nucleotide sequence of SEQ ID NO: 401, wherein the nucleotides of SEQ ID NO: 401 follow the guide sequence at its 3' end.

The guide RNA may be modified according to the pattern of SEQ ID NO: 300, wherein the N's are collectively any one of the guide sequences of SEQ ID NOs 1-89. Each N in SEQ ID NO: 300 may be any natural or non-natural nucleotide, wherein the N's form the guide sequence, and the guide sequence targets Cas9 to the TRBC1, TRBC2 and/or TRAC genes.

The first guide RNA may comprise the sequence of SEQ ID NO: 2 and the second guide RNA may comprise the sequence of SEQ ID NO: 90.

Any of the foregoing methods may further comprise:

(a) introducing a first nucleic acid sequence comprising a nucleic acid sequence selected from: (i) SEQ ID NO: 250; (ii) a nucleic acid sequence that is at least 99%, 95%, 90%, 85%, 80%, 70%, of 60% identical to SEQ ID NO: 250; and (iii) a contiguous subsequence of at least 20, 30, 40, 50, 60, 70, 80, 90, 100, 150, 200, 250, 300, 350, 400, 500, 600, 700, or 800 nucleotides of SEQ ID NO: 250,
    and
    introducing a second nucleic acid sequence comprising a nucleic acid sequence selected from: (i) SEQ ID NO: 252; (ii) a nucleic acid sequence that is at least 99%, 95%, 90%, 85%, 80%, 70%, of 60% identical to SEQ ID NO: 252; and (iii) a contiguous subsequence of at least 20, 30, 40, 50, 60, 70, 80, 90, 100, 150, 200, 250, 300, 350, 400, 500, 600, 700, 800, or 900 nucleotides of SEQ ID NO: 252, (b) introducing a first nucleic acid sequence comprising a nucleic acid sequence selected from: (i) SEQ ID NO:513; (ii) a nucleic acid sequence that is at least 99%, 95%, 90%, 85%, 80%, 70%, of 60% identical to SEQ ID NO: 513; and (iii) a contiguous subsequence of at least 20, 30, 40, 50, 60, 70, 80, 90, 100, 150, 200, 250, 300, 350, 400, 500, 600, 700, or 800 nucleotides of SEQ ID NO: 513,
    and
    introducing a second nucleic acid sequence comprising a nucleic acid sequence selected from: (i) SEQ ID NO:514; (ii) a nucleic acid sequence that is at least 99%, 95%, 90%, 85%, 80%, 70%, of 60% identical to SEQ ID NO:514; and (iii) a contiguous subsequence of at least 20, 30, 40, 50, 60, 70, 80, 90, 100, 150, 200, 250, 300, 350, 400, 500, 600, 700, 800, or 900 nucleotides of SEQ ID NO:514, (c) introducing a nucleic acid sequence comprising a first nucleic acid sequence of (a) and a second nucleic acid sequence of (a); or (d) introducing a nucleic acid sequence comprising a first nucleic acid sequence of (b) and a second nucleic acid sequence of (b).

The sgRNA may comprise a guide sequence that is at least 99%, 98%, 97%, 96%, 95%, 94%, 93%, 92%, 91%, or 90% identical to a sequence selected from SEQ ID NOs: 1-89.

The guide RNA may be chemically synthesized. The guide RNA may be comprised in an RNP. The template nucleic acid may be comprised in a viral vector. The template nucleic acid may be comprised in a nonviral delivery construct. Suitable viral vectors are known in the art, e.g., retroviruses, adenovirus, lentivirus, adeno-associated virus, and hybrids thereof. The viral vector may be a lentiviral (LV) vector or an adeno-associated virus (AAV) vector.

The guide RNA may optionally comprise one or more of the following modifications:

i) a 2'-O-methyl (2'-O-Me) modified nucleotide.
ii) a phosphorothioate (PS) bond between nucleotides.
iii) a 2'-fluoro (2'-F) modified nucleotide.
iv) a modification at one or more of the first five nucleotides at the 5' end of the guide RNA.
v) a modification at one or more of the last five nucleotides at the 3' end of the guide RNA.
vi) a PS bond between the first four nucleotides at the 5' end of the guide RNA.
vii) a PS bond between the last four nucleotides at the 3' end of the guide RNA.
viii) a 2'-O-Me modified nucleotide at the first three nucleotides at the 5' end of the guide RNA.
ix) a 2'-O-Me modified nucleotide at the last three nucleotides at the 3' end of the guide RNA.

The guide RNA may comprise the nucleotides of SEQ ID NO: 300 with modifications as set out above.

The compositions may further comprise a pharmaceutically acceptable excipient.

The LNP may comprises a biodegradable, ionizable lipid, e.g., the ionizable lipid is be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate.

The LNP may comprise a neutral lipid, e.g., the neutral lipid is DSPC.

The LNP may comprise a helper lipid, e.g., the helper lipid is cholesterol.

The LNP may comprise a stealth lipid, e.g., the stealth lipid is PEG2k-DMG.

The composition may further comprise an RNA-guided DNA binding agent. The guide RNA and RNA-guided DNA binding agent composition may be comprised in a ribonucleoprotein (RNP).

The composition may comprise an RNA-guided DNA binding agent, e.g. Cas9, or an mRNA that encodes an RNA-guided DNA binding agent, e.g., the RNA-guided DNA binding agent may be encoded by a Cas9 gene or be a Cas9 protein.

The composition may be a pharmaceutical formulation and further comprise a pharmaceutically acceptable carrier.

The invention also provides for the use of a composition, formulation, population, or cell described herein in the preparation of a medicament.

The invention also provides for the use of a composition, formulation, population, or cell described herein in the treatment of cancer.

The invention also provides for the use of a composition, formulation, population, or cell described herein in immunotherapy of a subject.

The invention also provides for the use of a composition, formulation, population, or cell described herein in the treatment of tumors that overexpress Wilms' tumor antigen (WT1).

The invention also provides a composition, formulation, population, or cell described herein for use in the treatment of a disease or disorder.

The invention also provides a composition, formulation, population, or cell described herein for use in immunotherapy.

The invention also provides a composition, formulation, population, or cell described herein for use in the treatment of cancer.

The invention also provides a composition, formulation, population, or cell described herein for use in the treatment of tumors that overexpress Wilms' tumor antigen (WT1).

The invention also provides a composition, formulation, population, or cell described herein in a method of treatment of a human or animal comprising administration of a composition, formulation, population, or cell as described herein.

The invention also provides a composition, formulation, population, or cell described herein in a method of treatment of cancer in a human or animal comprising administration of a composition, formulation, population, or cell as described herein.

The invention also provides a composition, formulation, population, or cell described herein in a method of immunotherapy of a human or animal comprising administration of a composition, formulation, population, or cell as described herein.

The invention also provides a composition, formulation, population, or cell described herein in a method of treatment of tumors that overexpress Wilms' tumor antigen (WT1) in a human or animal comprising administration of a composition, formulation, population, or cell as described herein.

The guide RNA may have a sequence selected from any of SEQ ID NOs: 1-89.

The guide RNA may have a sequence selected from any of SEQ ID NOs: 90-178, 185, and 213-218.

Also disclosed are embodiments wherein a guide sequence is selected from a group of guide sequences yielding a frequency of indels in the altered products of, respectively, 20% or greater, 30% or greater, 40% or greater, or 50% or greater.

Also disclosed are embodiments wherein a guide sequence is selected from a group of guide sequences yielding a frequency of insertion of donor nucleic acid molecules in the altered products of, respectively, 20% or greater, 30% or greater, 40% or greater, or 50% or greater.

Also disclosed is the use of a composition, formulation, population, or cell of any of the foregoing embodiments for the preparation of a medicament for treating a subject. The subject may be human or animal (e.g. human; cynomolgus monkey). In some embodiments, the subject is human.

Also disclosed are any of the foregoing compositions or formulations for use in treating or for use in modifying (e.g., forming an indel in, or forming a frameshift or nonsense mutation in) any one or more of the TRBC1, TRBC2 and TRAC genes.

In any of the aforementioned cell aspects and embodiments, a gene including a target sequence complementary to the targeting domain of the first gRNA molecule, and, optionally, a gene including a target sequence complementary to the targeting domain of the second gRNA molecule and/or a gene including a target sequence complementary to the targeting domain of the third gRNA molecule, has been altered such that expression of a functional product of the gene including a target sequence complementary to the targeting domain of the first gRNA molecule, and, optionally, the gene including a target sequence complementary to the targeting domain of the second gRNA molecule and/or a functional product of a gene including a target sequence complementary to the targeting domain of the third gRNA molecule, has been reduced or eliminated.

In another aspect, the invention provides a method of providing an immunotherapy in a subject, the method including administering to the subject an effective amount of a cell as described herein, for example, a cell of any of the aforementioned cell aspects and embodiments.

In embodiments of the methods, the method includes administering a lymphodepleting agent or immunosuppressant prior to administering to the subject an effective amount of the cell as described herein, for example, a cell of any of the aforementioned cell aspects and embodiments. In another aspect, the invention provides a method of preparing cells (e.g., a population of cells).

Immunotherapy is the treatment of disease by activating or suppressing the immune system. Immunotherapies designed to elicit or amplify an immune response are classified as activation immunotherapies. Cell-based immunotherapies have been demonstrated to be effective in the treatment of some cancers. Immune effector cells such as lymphocytes, macrophages, dendritic cells, natural killer cells (NK Cell), and/or cytotoxic T lymphocytes (CTL) can be programmed to act in response to abnormal antigens expressed on the surface of tumor cells. Thus, cancer immunotherapy allows components of the immune system to destroy tumors or other cancerous cells.

In another aspect, the invention provides a method of preparing cells (e.g., a population of cells) for immunotherapy, the method including: (a) modifying cells by reducing or eliminating expression of one or more or all components of a T-cell receptor (TCR), for example, by introducing into said cells a gRNA molecule (as described herein), or more than one gRNA molecule, as disclosed herein; and (b) expanding said cells. Cells of the invention are suitable for further engineering, e.g. by introduction of a heterologous sequence coding for a polypeptide that mediates TCR/CD3 zeta chain signaling. In some embodiments, the polypeptide is a wild-type or variant TCR. Cells of the invention may also be suitable for further engineering by introduction of a heterologous sequence coding for an alternative antigen binding moiety, e.g. by introduction of a heterologous sequence coding for an alternative (non-endogenous) T-cell receptor, e.g. a chimeric antigen receptors (CAR) engineered to target a specific protein. CAR are also known as chimeric immunoreceptors, chimeric T-cell receptors or artificial T-cell receptors).

In another aspect, the invention provides a method of treating a subject in need thereof that includes administering cells (e.g., a population of cells) prepared by a method of preparing cells described herein, for example, a method of any of the aforementioned aspects and embodiments of methods of preparing cells.

BRIEF DESCRIPTION OF THE DRAWINGS

FIG. 4A shows editing in TRBC1 and FIG. 4B shows editing in TRBC2.

FIG. 8A shows the efficiency of T-cell receptor knockout. FIG. 8B shows the efficiency of lentiviral transduction of the TCR construct. FIG. 8C shows expression of the TCR insert in edited T cells. FIG. 8D shows the phenotype of TCR edited T cells.

FIGS. 9A to 9C show results obtained with primary AML blasts obtained from 3 different patients harboring the HLA-A*02:01 allele. FIG. 9D shows the results from using the control sample: primary blasts not harboring the specific HLA allele.

FIG. 11A shows the efficiency of T-cell receptor knockout. FIG. 11B shows lentiviral transduction of the HD1-TCR construct in the cells. FIG. 11C shows expression of the TCR insert in edited T cells. FIG. 11D shows the phenotype of TCR edited T cells.

FIG. 12A shows phenotypic percentage of $CD3^-$ T cells following editing of the TRAC and TRBC loci. FIG. 11B shows genotypic percentage of Indel formation in the TRAC and TRBC loci in human $CD3^-$ T cells.

FIG. 16A shows the mock transfection control, with FIG. 16B showing RNP and FIG. 16C showing RNP+AV10-EGFP. X-axis: GFP expression; Y-axis: CD3e expression; as measured by FACS.

FIG. 32A shows percentage of CD107a+ staining cells in CD8+ T-cells. FIG. 31B shows percentage of CD107a+ staining cells in $CD4^+$ T-cells.

DETAILED DESCRIPTION

Figure 1:
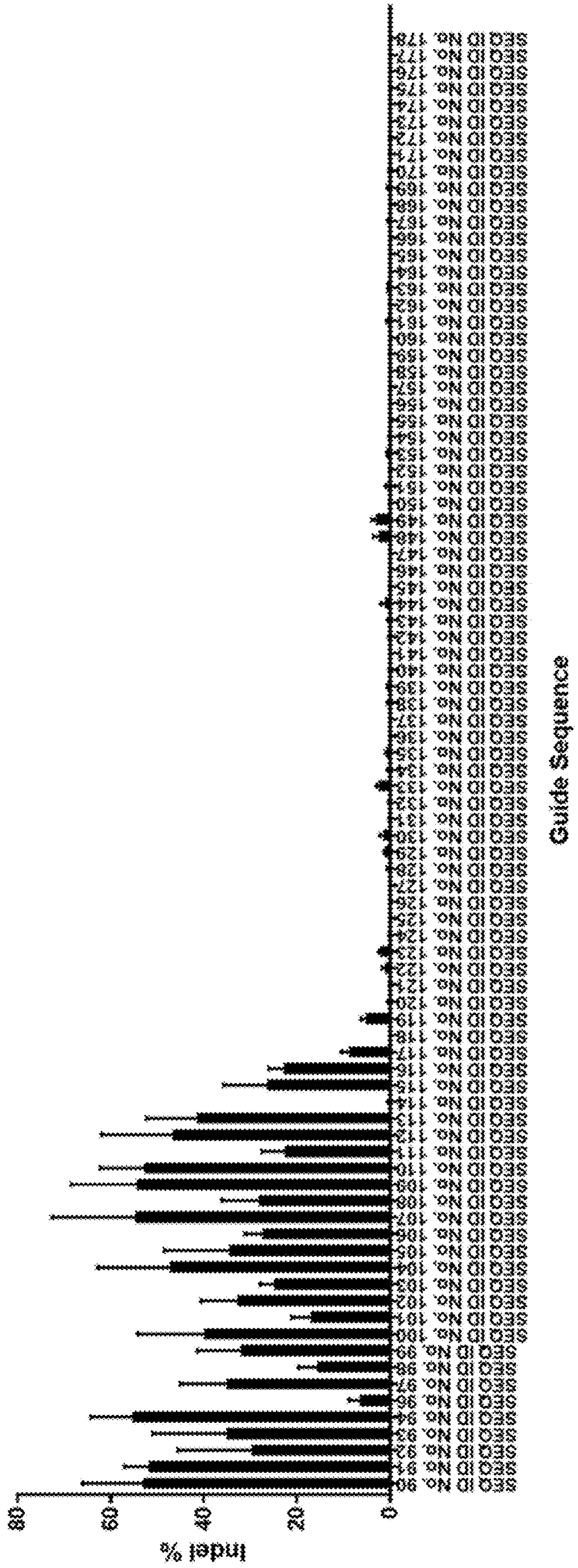
FIG. 1 shows the degree of TRAC editing in HEK-Cas9 cells.

Reference will now be made in detail to certain embodiments of the invention, examples of which are illustrated in the accompanying drawings. While the present teachings are described in conjunction with various embodiments, it is not intended to limit the present teachings to those embodiments. On the contrary, the present teaching encompass various alternatives, modifications, and equivalents, as will be appreciated by those of skill in the art.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measureable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). The term "or" is used in an inclusive sense in the specification, i.e., equivalent to "and/or," unless the context clearly indicates otherwise. The term "about", when used before a list, modifies each member of the list.

The section headings used herein are for organizational purposes only and are not to be construed as limiting the desired subject matter in any way. In the event that any material incorporated by reference contradicts any term defined in this specification or any other express content of this specification, this specification controls.

I. Definitions

Unless stated otherwise, the following terms and phrases as used herein are intended to have the following meanings:

"Polynucleotide" and "nucleic acid" are used herein to refer to a multimeric compound comprising nucleosides or nucleoside analogs which have nitrogenous heterocyclic bases or base analogs linked together along a backbone, including conventional RNA, DNA, mixed RNA-DNA, and polymers that are analogs thereof. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., modified uridines such as 5-methoxyuridine, pseudouridine, or N1-methylpseudouridine, or others); inosine; derivatives of purines or pyrimidines (e.g., $N^4$-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). For general discussion see *The Biochemistry of the Nucleic Acids* 5-36, Adams et al., ed., $11^{th}$ ed., 1992). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional nucleosides with 2' methoxy substituents, or polymers containing both conventional nucleosides and one or more nucleoside analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42):13233-41). RNA and DNA have different sugar moieties and can differ by the presence of uracil or analogs thereof in RNA and thymine or analogs thereof in DNA.

"Guide RNA", "gRNA", and simply "guide" are used herein interchangeably to refer to either a crRNA (also known as CRISPR RNA), or the combination of a crRNA and a trRNA (also known as tracrRNA). The crRNA and trRNA may be associated as a single RNA molecule (single guide RNA, sgRNA) or in two separate RNA molecules (dual guide RNA, dgRNA). "Guide RNA" or "gRNA" refers to each type. The trRNA may be a naturally-occurring sequence, or a trRNA sequence with modifications or variations compared to naturally-occurring sequences.

As used herein, a "guide sequence" refers to a sequence within a guide RNA that is complementary to a target sequence and functions to direct a guide RNA to a target sequence for binding or modification (e.g., cleavage) by an RNA-guided DNA binding agent. A "guide sequence" may also be referred to as a "targeting sequence," or a "spacer sequence." A guide sequence can be 20 base pairs in length, e.g., in the case of *Streptococcus pyogenes* (i.e., Spy Cas9) and related Cas9 homologs/orthologs. Shorter or longer sequences can also be used as guides, e.g., 15-, 16-, 17-, 18-, 19-, 21-, 22-, 23-, 24-, or 25-nucleotides in length. For example, in some embodiments, the guide sequence comprises at least 17, 18, 19, or 20 contiguous nucleotides of a sequence selected from SEQ ID NOs: 1-178. In some embodiments, the target sequence is in a gene or on a chromosome, for example, and is complementary to the guide sequence. In some embodiments, the degree of complementarity or identity between a guide sequence and its corresponding target sequence may be about 75%, 80%, 85%, 90%, 95%, 96%, 97%, 98%, 99%, or 100%. For example, in some embodiments, the guide sequence comprises a sequence with about 75%, 80%, 85%, 90%, 95%, 96%, 97%, 98%, 99%, or 100% identity to at least 17, 18, 19, or 20 contiguous nucleotides of a sequence selected from SEQ ID NOs: 1-178. In some embodiments, the guide sequence and the target region may be 100% complementary or identical. In other embodiments, the guide sequence and the target region may contain at least one mismatch. For example, the guide sequence and the target sequence may contain 1, 2, 3, or 4 mismatches, where the total length of the target sequence is at least 17, 18, 19, 20 or more base pairs. In some embodiments, the guide sequence and the target region may contain 1-4 mismatches where the guide sequence comprises at least 17, 18, 19, 20 or more nucleotides. In some embodiments, the guide sequence and the target region may contain 1, 2, 3, or 4 mismatches where the guide sequence comprises 20 nucleotides.

Target sequences for RNA-guided DNA binding agents include both the positive and negative strands of genomic DNA (i.e., the sequence given and the sequence's reverse compliment), as a nucleic acid substrate for an RNA-guided DNA binding agent is a double stranded nucleic acid. Accordingly, where a guide sequence is said to be "complementary to a target sequence", it is to be understood that the guide sequence may direct a guide RNA to bind to the sense or antisense strand (e.g. reverse complement) of a target sequence. Thus, in some embodiments, where the guide sequence binds the reverse complement of a target sequence, the guide sequence is identical to certain nucleotides of the target sequence (e.g., the target sequence not including the PAM) except for the substitution of U for T in the guide sequence.

As used herein, an "RNA-guided DNA binding agent" means a polypeptide or complex of polypeptides having RNA and DNA binding activity, or a DNA-binding subunit of such a complex, wherein the DNA binding activity is sequence-specific and depends on the sequence of the RNA. Exemplary RNA-guided DNA binding agents include Cas cleavases/nickases and inactivated forms thereof ("dCas DNA binding agents"). "Cas nuclease", as used herein, encompasses Cas cleavases, Cas nickases, and dCas DNA binding agents. In some embodiments the Cas cleavase or Cas nickase encompasses a dCas DNA binding agent modified to permit DNA cleavage, e.g. via fusion with a FokI domain. Cas cleavases/nickases and dCas DNA binding agents include a Csm or Cmr complex of a type III CRISPR system, the Cas10, Csm1, or Cmr2 subunit thereof, a Cascade complex of a type I CRISPR system, the Cas3 subunit thereof, and Class 2 Cas nucleases. As used herein, a "Class 2 Cas nuclease" is a single-chain polypeptide with RNA-guided DNA binding activity. Class 2 Cas nucleases include Class 2 Cas cleavases/nickases (e.g., H840A, D10A, or N863A variants), which further have RNA-guided DNA cleavases or nickase activity, and Class 2 dCas DNA binding agents, in which cleavase/nickase activity is inactivated. Class 2 Cas nucleases include, for example, Cas9, Cpf1, C2c1, C2c2, C2c3, HF Cas9 (e.g., N497A, R661A, Q695A, Q926A variants), HypaCas9 (e.g., N692A, M694A, Q695A, H698A variants), eSPCas9(1.0) (e.g., K810A, K1003A, R1060A variants), and eSPCas9(1.1) (e.g., K848A, K1003A, R1060A variants) proteins and modifications thereof. Cpf1 protein, Zetsche et al., *Cell,* 163: 1-13 (2015), is homologous to Cas9, and contains a RuvC-like nuclease domain. Cpf1 sequences of Zetsche are incorporated by reference in their entirety. See, e.g., Zetsche, Tables S1 and S3. See, e.g., Makarova et al., *Nat Rev Microbiol,* 13(11): 722-36 (2015); Shmakov et al., *Molecular Cell,* 60:385-397 (2015).

As used herein, "ribonucleoprotein" (RNP) or "RNP complex" refers to a guide RNA together with an RNA-guided DNA binding agent, such as a Cas nuclease, e.g., a Cas cleavase, Cas nickase, or dCas DNA binding agent (e.g., Cas9). In some embodiments, the guide RNA guides the RNA-guided DNA binding agent such as Cas9 to a target sequence, and the guide RNA hybridizes with and the agent binds to the target sequence; in cases where the agent is a cleavase or nickase, binding can be followed by cleaving or nicking.

As used herein, a first sequence is considered to "comprise a sequence with at least X % identity to" a second sequence if an alignment of the first sequence to the second sequence shows that X % or more of the positions of the second sequence in its entirety are matched by the first sequence. For example, the sequence AAGA comprises a sequence with 100% identity to the sequence AAG because an alignment would give 100% identity in that there are matches to all three positions of the second sequence. The differences between RNA and DNA (generally the exchange of uridine for thymidine or vice versa) and the presence of nucleoside analogs such as modified uridines do not contribute to differences in identity or complementarity among polynucleotides as long as the relevant nucleotides (such as thymidine, uridine, or modified uridine) have the same complement (e.g., adenosine for all of thymidine, uridine, or modified uridine; another example is cytosine and 5-methylcytosine, both of which have guanosine or modified guanosine as a complement). Thus, for example, the sequence 5'-AXG where X is any modified uridine, such as pseudouridine, N1-methyl pseudouridine, or 5-methoxyuridine, is considered 100% identical to AUG in that both are perfectly complementary to the same sequence (5'-CAU). Exemplary alignment algorithms are the Smith-Waterman and Needleman-Wunsch algorithms, which are well-known in the art. One skilled in the art will understand what choice of algorithm and parameter settings are appropriate for a given pair of sequences to be aligned; for sequences of generally similar length and expected identity >50% for amino acids or >75% for nucleotides, the Needleman-Wunsch algorithm with default settings of the Needleman-Wunsch algorithm interface provided by the EBI at the www.ebi.ac.uk web server is generally appropriate.

"mRNA" is used herein to refer to a polynucleotide that comprises an open reading frame that can be translated into a polypeptide (i.e., can serve as a substrate for translation by a ribosome and amino-acylated tRNAs). mRNA can comprise a phosphate-sugar backbone including ribose residues or analogs thereof, e.g., 2'-methoxy ribose residues. In some embodiments, the sugars of an mRNA phosphate-sugar backbone consist essentially of ribose residues, 2'-methoxy ribose residues, or a combination thereof.

Exemplary guide sequences useful in the guide RNA compositions and methods described herein are shown in Tables 1, 2 and 3 and throughout the application.

As used herein, "indels" refer to insertion/deletion mutations consisting of a number of nucleotides that are either inserted or deleted at the site of double-stranded breaks (DSBs) in a target nucleic acid.

As used herein, "knockdown" refers to a decrease in expression of a particular gene product (e.g., protein, mRNA, or both). Knockdown of a protein can be measured by detecting total cellular amount of the protein from a tissue or cell population of interest. Methods for measuring knockdown of mRNA are known and include sequencing of mRNA isolated from a tissue or cell population of interest. Flow cytometry analysis is a known method for measuring knockdown of protein expression. In some embodiments, "knockdown" may refer to some loss of expression of a particular gene product, for example a decrease in the amount of mRNA transcribed or a decrease in the amount of protein expressed by a population of cells. In some embodiments, "knockdown" may refer to some loss of expression of a particular gene product, for example a TRAC or TRBC gene product at the cell surface.

As used herein, "knockout" refers to a loss of expression of a particular protein in a cell. Knockout can be measured either by detecting total cellular amount of a protein in a cell, a tissue or a population of cells. In some embodiments, the methods of the invention "knockout" TRBC1, TRBC2 and/or TRAC in one or more cells (e.g., in a population of cells. In some embodiments, a knockout is the complete loss of expression of a protein component of the T-cell receptor (e.g. TRBC1, TRBC2 and/or TRAC) in a cell, rather than the formation of a mutant T-cell receptor protein.

As used herein, "TRBC1" and "TRBC2" refer to two homologous genes encoding the T-cell receptor β-chain, which are the gene products of the TRBC1 or TRBC2 genes.

"TRBC" is used herein to refer to TRBC1 and TRBC2.

The human wild-type TRBC1 sequence is available at NCBI Gene ID: 28639; Ensembl: ENSG00000211751. T-cell receptor Beta Constant, V_segment Translation Product, BV05S1J2.2, TCRBC1, and TCRB are gene synonyms for TRBC1.

The human wild-type TRBC2 sequence is available at NCBI Gene ID: 28638; Ensembl: ENSG00000211772. T-cell receptor Beta Constant, V_segment Translation Product, and TCRBC2 are gene synonyms for TRBC2.

The human wild-type TRAC sequence is available at NCBI Gene ID: 28755; Ensembl: ENSG00000277734. T-cell receptor Alpha Constant, TCRA, IMD7, TRCA and TRA are gene synonyms for TRAC.

Wilms' tumor protein (also sometimes referred to as Wilms' tumor antigen) is a protein that is encoded by the WT1 gene. The human wild-type WT1 sequence is available at NCBI Gene ID: 7490; Ensembl: ENSG00000184937. GUD, AWT1, WAGR, WT33, NPHS4, and WIT-2 are gene synonyms for WT1. The Wilms' tumor protein has been reported to be expressed in various cancers including solid tumors (including but not limited to Wilms' tumor) and hematological cancers, and also in tumor vascular endothelial cells and hematopoietic progenitor cells.

As used herein, a "target sequence" refers to a sequence of nucleic acid in a target gene that has complementarity to the guide sequence of the gRNA. The interaction of the target sequence and the guide sequence directs an RNA-guided DNA binding agent to bind, and potentially nick or cleave (depending on the activity of the agent), within the target sequence.

As used herein, "treatment" refers to any administration or application of a therapeutic for disease or disorder in a subject, and includes inhibiting the disease, arresting its development, relieving one or more symptoms of the disease, curing the disease, or preventing reoccurrence of one or more symptoms of the disease.

The term "about" or "approximately" means an acceptable error for a particular value as determined by one of ordinary skill in the art, which depends in part on how the value is measured or determined.

II. Compositions

A. Compositions Comprising Guide RNA (gRNAs)

Provided herein are compositions useful for altering a DNA sequence, e.g. inducing a single-stranded (SSB) or double-stranded break (DSB), within the TRBC and/or TRAC genes, e.g., using a guide RNA with an RNA-guided DNA binding agent (e.g., a CRISPR/Cas system). In some embodiments, the compositions are useful for altering a TRAC and/or TRBC sequence and further inserting a TCR gene.

In some embodiments, altering a TRAC and/or TRBC sequence and further inserting a TCR gene advantageously reduces mispairing of TRAC and/or TRBC as compared to a control, e.g., a control in which TRAC and/or TRBC is not altered. For example, altering a TRBC sequence (e.g., knocking out TRBC) and further inserting a TCR gene may advantageously reduce mispairing between the inserted TCR and native TRBC. Or altering a TRAC sequence (e.g., knocking out TRAC) and further inserting a TCR gene may advantageously reduce mispairing between the inserted TCR and native TRAC. Guide sequences targeting the TRBC gene are shown in Table 1 at SEQ ID NOs: 1-89. Guide sequences targeting the TRAC gene are shown in Table 2 at SEQ ID NOs: 90-178, 185, and 213-218.

In some embodiments, the guide sequences are complementary to the corresponding genomic region shown in the tables below, according to coordinates from human reference genome hg38. Guide sequences of further embodiments may be complementary to sequences in the close vicinity of the genomic coordinate listed in any of Tables, 1, 2 and/or 3. For example, guide sequences of further embodiments may be complementary to sequences that comprise 15 consecutive nucleotides ±10 nucleotides of a genomic coordinate listed in any of Tables, 1, 2 and/or 3.

Each of the guide sequences shown in Table 1 and Table 2 at SEQ ID NOs: 1-89, 90-178, 185, and 213-218 may further comprise additional nucleotides to form a crRNA, e.g., with the following exemplary nucleotide sequence following the guide sequence at its 3' end: GUUUUAGAGCUAUGCUGUUUUG (SEQ ID NO: 400) in 5' to 3' orientation. In the case of a sgRNA, the guide sequences may further comprise additional nucleotides to form a sgRNA, e.g., with the following exemplary nucleotide sequence following the 3' end of the guide sequence:

(SEQ ID NO: 401)
GUUUUAGAGCUAGAAAUAGCAAGUUAAAAUAAGGCUAGUCCGUUAUCAAC

UUGAAAAAGUGGCACCGAGUCGGUGCUUUU in 5' to 3' orientation.

The guide sequences may further comprise additional nucleotides to form a sgRNA, e.g., comprising the following exemplary nucleotide sequence following the 3' end of the guide sequence:

(SEQ ID NO: 402)
GUUUUAGAGCUAGAAAUAGCAAGUUAAAAUAAGGCUAGUCCGUUAUCAAC UUGAAAAAGUGGCACCGAGUCGGUGC in 5' to 3' orientation.

TABLE 1

TRBC targeted and control guide sequences and chromosomal coordinates

| SEQ ID NO: | Guide Sequence | Genomic Coordinates (hg38) |
|---|---|---|
| 1 | GGCUCUCGGAGAAUGACGAG | chr7: 142791996-142792016 |
| 2 | GGCCUCGGCGCUGACGAUCU | chr7: 142792047-142792067 |
| 3 | AUGACGAGUGGACCCAGGAU | chr7: 142792008-142792028 |
| 4 | AGAAGGUGGCCGAGACCCUC | chr7: 142791931-142791951 |
| 5 | UGAGGGUCUCGGCCACCUUC | chr7: 142791930-142791950 |
| 6 | AGAGAUCUCCCACACCCAAA | chr7: 142791748-142791768 |
| 7 | UGGCUCAAACACAGCGACCU | chr7: 142791720-142791740 |
| 8 | GGCGCUGACGAUCUGGGUGA | chr7: 142792041-142792061 |
| 9 | UGGCAGACAGGACCCCUUGC | chr7: 142802114-142802134 |
| 10 | UGACGAGUGGACCCAGGAUA | chr7: 142792009-142792029 |
| 11† | AGACAGGACCCCUUGCUGGU | chr7: 142792697-142792717 |
| 12 | UUGACAGCGGAAGUGGUUGC | chr7: 142791963-142791983 |
| 13 | CGUAGAACUGGACUUGACAG | chr7: 142791976-142791996 |
| 14 | CGCUGUCAAGUCCAGUUCUA | chr7: 142791974-142791994 |
| 15 | ACUGGACUUGACAGCGGAAG | chr7: 142791970-142791990 |
| 16 | GUUGCGGGGGUUCUGCCAGA | chr7: 142791948-142791968 |
| 17 | CUGCCUGAGCAGCCGCCUGA | chr7: 142791913-142791933 |
| 18 | GACAGCGGAAGUGGUUGCGG | chr7: 142791961-142791981 |
| 19 | CCACUCACCUGCUCUACCCC | chr7: 142792068-142792088 |
| 20 | GCUGUCAAGUCCAGUUCUAC | chr7: 142791975-142791995 |
| 21 | ACACUGGUGUGCCUGGCCAC | chr7: 142791773-142791793 |

TABLE 1-continued

TRBC targeted and control guide sequences and chromosomal coordinates

| SEQ ID NO: | Guide Sequence | Genomic Coordinates (hg38) |
|---|---|---|
| 22 | AGACCCUCAGGCGGCUGCUC | chr7: 142791919-142791939 |
| 23 | AUGGGAAGGAGGUGCACAGU | chr7: 142791834-142791854 |
| 24 | AGGGCGGGCUGCUCCUUGAG | chr7: 142791878-142791898 |
| 25 | UCCCUAGCAAGAUCUCAUAG | chr7: 142802141-142802161 |
| 26† | GGUGCACAGUGGGGUCAGCA | chr7: 142791844-142791864 |
| 27 | CCAGCUCAGCUCCACGUGGU | chr7: 142801154-142801174 |
| 28 | CCGCAACCACUUCCGCUGUC | chr7: 142791961-142791981 |
| 29 | GUCCACUCGUCAUUCUCCGA | chr7: 142792001-142792021 |
| 30 | GCCCGUAGAACUGGACUUGA | chr7: 142791979-142791999 |
| 31 | UCACCCAGAUCGUCAGCGCC | chr7: 142792041-142792061 |
| 32 | GGGUCCACUCGUCAUUCUCC | chr7: 142792003-142792023 |
| 33 | UCCAGUUCUACGGGCUCUCG | chr7: 142791984-142792004 |
| 34 | CGGAGAAUGACGAGUGGACC | chr7: 142792002-142792022 |
| 35 | ACCACUUCCGCUGUCAAGUC | chr7: 142791966-142791986 |
| 36 | AAUGACGAGUGGACCCAGGA | chr7: 142792007-142792027 |
| 37 | ACGGGCUCUCGGAGAAUGAC | chr7: 142791993-142792013 |
| 38 | GACUCCAGAUACUGCCUGAG | chr7: 142791902-142791922 |
| 39 | CGCUGUGUUUGAGCCAUCAG | chr7: 142791724-142791744 |
| 40 | AGAACUGGACUUGACAGCGG | chr7: 142791973-142791993 |
| 41 | GAGACCCUCAGGCGGCUGCU | chr7: 142791920-142791940 |
| 42 | CGUCAUUCUCCGAGAGCCCG | chr7: 142791994-142792014 |
| 43 | CAGCCCGCCCUCAAUGACUC | chr7: 142791887-142791907 |
| 44 | GGCUGCUCAGGCAGUAUCUG | chr7: 142791907-142791927 |
| 45 | AGUGGUUGCGGGGGUUCUGC | chr7: 142791952-142791972 |

TABLE 1-continued

TRBC targeted and control guide sequences and chromosomal coordinates

| SEQ ID NO: | Guide Sequence | Genomic Coordinates (hg38) |
|---|---|---|
| 46 | GGUCGCUGUGUUUGAGCCAU | chr7: 142791721-142791741 |
| 47 | GAUCUCAUAGAGGAUGGUGG | chr7: 142792718-142792738 |
| 48 | UGUUUGAGCCAUCAGAAGCA | chr7: 142791729-142791749 |
| 49 | UACUGCCUGAGCAGCCGCCU | chr7: 142791911-142791931 |
| 50 | ACCCGCAGCCCCUCAAGGAG | chr7: 142791867-142791887 |
| 51 | AGGCAGUAUCUGGAGUCAUU | chr7: 142791899-142791919 |
| 52 | UGUGUUUGAGCCAUCAGAAG | chr7: 142791727-142791747 |
| 53 | GGUUGCGGGGGUUCUGCCAG | chr7: 142791949-142791969 |
| 54 | GGGUCUCGGCCACCUUCUGG | chr7: 142791933-142791953 |
| 55 | CAGAAGGUGGCCGAGACCCU | chr7: 142791932-142791952 |
| 56 | CGCCGAGGCCUGGGGUAGAG | chr7: 142792057-142792077 |
| 57 | GGUUCUGCCAGAAGGUGGCC | chr7: 142791940-142791960 |
| 58 | CAGAGAUCUCCCACACCCAA | chr7: 142791747-142791767 |
| 59 | UUGAGGGCGGGCUGCUCCUU | chr7: 142791881-142791901 |
| 60 | AAGCCUGUGGCCAGGCACAC | chr7: 142791779-142791799 |
| 61 | CAGCGCCGAGGCCUGGGGUA | chr7: 142792054-142792074 |
| 62 | CCCACUCACCUGCUCUACCC | chr7: 142792069-142792089 |
| 63 | UGUCUGCCACCAUCCUCUAU | chr7: 142792712-142792732 |
| 64 | UGCUUCUGAUGGCUCAAACA | chr7: 142791729-142791749 |
| 65 | UUCCCAUUCACCCACCAGCU | chr7: 142791821-142791841 |
| 66 | GUCAGCGCCGAGGCCUGGGG | chr7: 142792052-142792072 |
| 67 | CCCUCAGGCGGCUGCUCAGG | chr7: 142791916-142791936 |
| 68 | AAUGACUCCAGAUACUGCCU | chr7: 142791899-142791919 |
| 69 | CACACUGGUGUGCCUGGCCA | chr7: 142791772-142791792 |

TABLE 1-continued

TRBC targeted and control guide sequences and chromosomal coordinates

| SEQ ID NO: | Guide Sequence | Genomic Coordinates (hg38) |
|---|---|---|
| 70 | UCAUAGAGGAUGGUGGCAGA | chr7: 142792714-142792734 |
| 71 | CACCCAGAUCGUCAGCGCCG | chr7: 142792042-142792062 |
| 72 | UGACAGCGGAAGUGGUUGCG | chr7: 142791962-142791982 |
| 73 | UCUCCGAGAGCCCGUAGAAC | chr7: 142791988-142792008 |
| 74 | AGUCCAGUUCUACGGGCUCU | chr7: 142791982-142792002 |
| 75 | AUCGUCAGCGCCGAGGCCUG | chr7: 142792049-142792069 |
| 76 | AAGGAGGUGCACAGUGGGGU | chr7: 142791839-142791859 |
| 77 | UAUCUGGAGUCAUUGAGGGC | chr7: 142791893-142791913 |
| 78 | GCGGGGGUUCUGCCAGAAGG | chr7: 142791945-142791965 |
| 79 | CUUGACAGCGGAAGUGGUUG | chr7: 142791964-142791984 |
| 80 | GUGUGGCCUUUUGGGUGUGG | chr7: 142791757-142791777 |
| 81 | GAUCGUCAGCGCCGAGGCCU | chr7: 142792048-142792068 |
| 82 | UGUGGCCAGGCACACCAGUG | chr7: 142791774-142791794 |
| 83 | AGGCCUCGGCGCUGACGAUC | chr7: 142792048-142792068 |
| 84 | GUGAAUGGGAAGGAGGUGCA | chr7: 142791830-142791850 |
| 85 | GCGGCUGCUCAGGCAGUAUC | chr7: 142791909-142791929 |
| 86 | ACUGCCUGAGCAGCCGCCUG | chr7: 142791912-142791932 |
| 87 | AAAGGCCACACUGGUGUGCC | chr7: 142791766-142791786 |
| 88 | UGAGGGCGGGCUGCUCCUUG | chr7: 142791880-142791900 |
| 89 | GAGCAGCCGCCUGAGGGUCU | chr7: 142791919-142791939 |

Each of these guide sequences generally targets both TRBC1 and TRBC2 genes with the following exceptions, which are marked as follows: † SEQ ID NOs: 11 and 26 target TRBC1 specifically.

TABLE 2

TRAC targeted and control guide sequences and chromosomal coordinates

| SEQ ID NO: | Guide Sequence | Genomic Coordinates (hg38) |
|---|---|---|
| 90 | CUCUCAGCUGGUACACGGCA | chr14: 22547524-22547544 |
| 91 | UUCGGAACCCAAUCACUGAC | chr14: 22550581-22550601 |
| 92 | UAAACCCGGCCACUUUCAGG | chr14: 22550608-22550628 |
| 93 | GAUUAAACCCGGCCACUUUC | chr14: 22550611-22550631 |
| 94 | CGUCAUGAGCAGAUUAAACC | chr14: 22550622-22550642 |
| 95 | AGAGUCUCUCAGCUGGUACA | chr14: 22547529-22547549 |
| 96 | ACACGGCAGGGUCAGGGUUC | chr14: 22547512-22547532 |
| 97 | UCUCUCAGCUGGUACACGGC | chr14: 22547525-22547545 |
| 98 | UGGAUUUAGAGUCUCUCAGC | chr14: 22547536-22547556 |
| 99 | GAGAAUCAAAAUCGGUGAAU | chr14: 22547575-22547595 |
| 100 | ACAAAACUGUGCUAGACAUG | chr14: 22547640-22547660 |
| 101 | UGUGCUAGACAUGAGGUCUA | chr14: 22547647-22547667 |
| 102 | GCACCAAAGCUGCCCUUACC | chr14: 22547777-22547797 |
| 103 | AAGUUCCUGUGAUGUCAAGC | chr14: 22549638-22549658 |
| 104 | CUCGACCAGCUUGACAUCAC | chr14: 22549646-22549666 |
| 105 | AUCCUCCUCCUGAAAGUGGC | chr14: 22550600-22550620 |
| 106 | ACCCGGCCACUUUCAGGAGG | chr14: 22550605-22550625 |
| 107 | UUAAUCUGCUCAUGACGCUG | chr14: 22550625-22550645 |
| 108 | ACACGGAUGAACAAUAAGGC | chr14: 22539116-22539136 |
| 109 | ACUUACACGGAUGAACAAUA | chr14: 22539120-22539140 |
| 110 | GCUGGUACACGGCAGGGUCA | chr14: 22547518-22547538 |
| 111 | GGAAGCUACAUACCUACAUU | chr14: 22539082-22539102 |
| 112 | UCCUCACUGUGUGCAUCAGG | chr14: 22539061-22539081 |
| 113 | CUGGUUCCUCUUCCAAAUGU | chr14: 22539097-22539117 |
| 114 | AAAGUCAGAUUUGUUGCUCC | chr14: 22547697-22547717 |
| 115 | UUCAAAACCUGUCAGUGAUU | chr14: 22550571-22550591 |
| 116 | UGCUCAUGACGCUGCGGCUG | chr14: 22550631-22550651 |
| 117 | UCAAGGCCCCUCACCUCAGC | chr14: 22550658-22550678 |
| 118 | GGCGUUUGCACAUGCAAAGU | chr14: 22547712-22547732 |
| 119 | GACCACAGCCGCAGCGUCAU | chr14: 22550636-22550656 |
| 120 | AUGACGCUGCGGCUGUGGUC | chr14: 22550636-22550656 |
| 121 | AUUCGGAACCCAAUCACUGA | chr14: 22550582-22550602 |
| 122 | AACCCGGCCACUUUCAGGAG | chr14: 22550606-22550626 |
| 123 | UUAAACCCGGCCACUUUCAG | chr14: 22550609-22550629 |
| 124 | AGAUUUGUUGCUCCAGGCCA | chr14: 22547691-22547711 |
| 125 | UGAGAAUCAAAAUCGGUGAA | chr14: 22547576-22547596 |
| 126 | GAUGUCAAGCUGGUCGAGAA | chr14: 22549648-22549668 |

TABLE 2-continued

TRAC targeted and control guide sequences and chromosomal coordinates

| SEQ ID NO: | Guide Sequence | Genomic Coordinates (hg38) |
|---|---|---|
| 127 | GUUUCAAAGCUUUUCUCGAC | chr14: 22549660-22549680 |
| 128 | UGAAGGCGUUUGCACAUGCA | chr14: 22547716-22547736 |
| 129 | ACCCUGACCCUGCCGUGUAC | chr14: 22547514-22547534 |
| 130 | AGCUUCAAGGCCCCUCACCU | chr14: 22550662-22550682 |
| 131 | GUUCCGAAUCCUCCUCCUGA | chr14: 22550593-22550613 |
| 132 | AGAUUAAACCCGGCCACUUU | chr14: 22550612-22550632 |
| 133 | CCCUGCCGUGUACCAGCUGA | chr14: 22547521-22547541 |
| 134 | UCACUGGAUUUAGAGUCUCU | chr14: 22547540-22547560 |
| 135 | UACUUACACGGAUGAACAAU | chr14: 22539121-22539141 |
| 136 | UAUCACAGACAAAACUGUGC | chr14: 22547632-22547652 |
| 137 | CCACAGCACUGUUGCUCUUG | chr14: 22547674-22547694 |
| 138 | CCUGUGAUGUCAAGCUGGUC | chr14: 22549643-22549663 |
| 139 | ACAUGAGGUCUAUGGACUUC | chr14: 22547655-22547675 |
| 140 | ACUGUUGCUCUUGAAGUCCA | chr14: 22547667-22547687 |
| 141 | AGCUACAUACCUACAUUUGG | chr14: 22539085-22539105 |
| 142 | UAGAAAGUUCCUGUGAUGUC | chr14: 22549634-22549654 |
| 143 | UCACUGUGUGCAUCAGGAGG | chr14: 22539064-22539084 |
| 144 | GACAAAACUGUGCUAGACAU | chr14: 22547639-22547659 |
| 145 | CUUCAACAACAGCAUUAUUC | chr14: 22547731-22547751 |
| 146 | CAACAACAGCAUUAUUCCAG | chr14: 22547734-22547754 |
| 147 | UCUCAAACAAAUGUGUCACA | chr14: 22547591-22547611 |
| 148 | AUGAGGUCUAUGGACUUCAA | chr14: 22547657-22547677 |
| 149 | GACCCUGCCGUGUACCAGCU | chr14: 22547519-22547539 |
| 150 | CCCCUGUCUUACCUGUUUCA | chr14: 22549674-22549694 |
| 151 | AGCAACAGUGCUGUGGCCUG | chr14: 22547678-22547698 |
| 152 | CUACAUACCUACAUUUGGAA | chr14: 22539087-22539107 |
| 153 | ACUUUGUGACACAUUUGUUU | chr14: 22547595-22547615 |
| 154 | AUCACAGACAAAACUGUGCU | chr14: 22547633-22547653 |
| 155 | UUCAACAACAGCAUUAUUCC | chr14: 22547732-22547752 |
| 156 | CAUGAGGUCUAUGGACUUCA | chr14: 22547656-22547676 |
| 157 | GCUACAUACCUACAUUUGGA | chr14: 22539086-22539106 |
| 158 | CUCUUGUCCCACAGAUAUCC | chr14: 22547491-22547511 |
| 159 | GAUUCUGAUGUGUAUAUCAC | chr14: 22547618-22547638 |
| 160 | CUGUGAUGUCAAGCUGGUCG | chr14: 22549644-22549664 |
| 161 | CCUGCCGUGUACCAGCUGAG | chr14: 22547522-22547542 |
| 162 | ACAUACCUACAUUUGGAAGA | chr14: 22539089-22539109 |

TABLE 2-continued

TRAC targeted and control guide sequences and chromosomal coordinates

| SEQ ID NO: | Guide Sequence | Genomic Coordinates (hg38) |
|---|---|---|
| 163 | CCUCACUGUGUGCAUCAGGA | chr14: 22539062-22539082 |
| 164 | ACAAAUGUGUCACAAAGUAA | chr14: 22547597-22547617 |
| 165 | GAGCAACAGUGCUGUGGCCU | chr14: 22547677-22547697 |
| 166 | UCGACCAGCUUGACAUCACA | chr14: 22549645-22549665 |
| 167 | AUUAAACCCGGCCACUUUCA | chr14: 22550610-22550630 |
| 168 | CACGGCAGGGUCAGGGUUCU | chr14: 22547511-22547531 |
| 169 | AAACCCGGCCACUUUCAGGA | chr14: 22550607-22550627 |
| 170 | CAAGGCCCCUCACCUCAGCU | chr14: 22550657-22550677 |
| 171 | CCCGGCCACUUUCAGGAGGA | chr14: 22550604-22550624 |
| 172 | CAUUUCUAUAAUACUUACAC | chr14: 22539132-22539152 |
| 173 | ACAGCCGCAGCGUCAUGAGC | chr14: 22550632-22550652 |
| 174 | AUCAAAAUCGGUGAAUAGGC | chr14: 22547571-22547591 |
| 175 | GCGUUUGCACAUGCAAAGUC | chr14: 22547711-22547731 |
| 176 | CUGUUGCUCUUGAAGUCCAU | chr14: 22547666-22547686 |
| 177 | AAAUCGGUGAAUAGGCAGAC | chr14: 22547567-22547587 |
| 178 | UUGUCUGUGAUAUACACAUC | chr14: 22547624-22547644 |
| 185 | UCAGGGUUCUGGAUAUCUGU | chr14: 22547501-22547521 |
| 213 | AGCUGGUACACGGCAGGGUC | chr14: 22547519-22547539 |
| 214 | UAGGCAGACAGACUUGUCAC | chr14: 22547556-22547576 |
| 215 | UCUGUGGGACAAGAGGAUCA | chr14: 22547486-22547506 |
| 216 | AUCUGUGGGACAAGAGGAUC | chr14: 22547487-22547507 |
| 217 | CUGGAUAUCUGUGGGACAAG | chr14: 22547493-22547513 |
| 218 | GUCAGGGUUCUGGAUAUCUG | chr14: 22547502-22547522 |

TABLE 3 sgRNA sequences, nomenclature, and component subsequences

| SEQ ID NO: | sgRNA Sequence | Genomic Coordinates (hg38) |
|---|---|---|
| 179 | GGCUCUCGGAGAAUGACGAGGUUUUAGAGCUAGAAAUAGCAAGUUAAAAUAAGGCUAGUCCGUUAUCAACUUGAAAAAGUGGCACCGAGUCGGUGCUUUU | chr7: 142791996-142792016 |
| 180 | GGCCUCGGCGCUGACGAUCUGUUUUAGAGCUAGAAAUAGCAAGUUAAAAUAAGGCUAGUCCGUUAUCAACUUGAAAAAGUGGCACCGAGUCGGUGCUUUU | chr7: 142792047-142792067 |
| 181 | AUGACGAGUGGACCCAGGAUGUUUUAGAGCUAGAAAUAGCAAGUUAAAAUAAGGCUAGUCCGUUAUCAACUUGAAAAAGUGGCACCGAGUCGGUGCUUUU | chr7: 142792008-142792028 |

TABLE 3-continued sgRNA sequences, nomenclature, and component subsequences

| SEQ ID NO: | sgRNA Sequence | Genomic Coordinates (hg38) |
|---|---|---|
| 182 | AGAAGGUGGCCGAGACCCUCGUUUUAGAGCUAGAAAUAGCAAGUUAAAAUAAGGCUAGUCCGUUAUCAACUUGAAAAAGUGGCACCGAGUCGGUGCUUUU | chr7: 142791931-142791951 |
| 183 | UGAGGGUCUCGGCCACCUUCGUUUUAGAGCUAGAAAUAGCAAGUUAAAAUAAGGCUAGUCCGUUAUCAACUUGAAAAAGUGGCACCGAGUCGGUGCUUUU | chr7: 142791930-142791950 |
| 184 | AGAGAUCUCCCACACCCAAAGUUUUAGAGCUAGAAAUAGCAAGUUAAAAUAAGGCUAGUCCGUUAUCAACUUGAAAAAGUGGCACCGAGUCGGUGCUUUU | chr7: 142791748-142791768 |
| 186 | CUCUCAGCUGGUACACGGCAGUUUUAGAGCUAGAAAUAGCAAGUUAAAAUAAGGCUAGUCCGUUAUCAACUUGAAAAAGUGGCACCGAGUCGGUGCUUUU | chr14: 22547529-22547549 |
| 187 | UUCGGAACCCAAUCACUGACGUUUUAGAGCUAGAAAUAGCAAGUUAAAAUAAGGCUAGUCCGUUAUCAACUUGAAAAAGUGGCACCGAGUCGGUGCUUUU | chr14: 22550611-22550631 |
| 188 | UAAACCCGGCCACUUUCAGGGUUUUAGAGCUAGAAAUAGCAAGUUAAAAUAAGGCUAGUCCGUUAUCAACUUGAAAAAGUGGCACCGAGUCGGUGCUUUU | chr14: 22547501-22547521 |
| 189 | GAUUAAACCCGGCCACUUUCGUUUUAGAGCUAGAAAUAGCAAGUUAAAAUAAGGCUAGUCCGUUAUCAACUUGAAAAAGUGGCACCGAGUCGGUGCUUUU | chr14: 22550608-22550628 |
| 190 | CGUCAUGAGCAGAUUAAACCGUUUUAGAGCUAGAAAUAGCAAGUUAAAAUAAGGCUAGUCCGUUAUCAACUUGAAAAAGUGGCACCGAGUCGGUGCUUUU | chr14: 22547529-22547549 |
| 191 | AGAGUCUCUCAGCUGGUACAGUUUUAGAGCUAGAAAUAGCAAGUUAAAAUAAGGCUAGUCCGUUAUCAACUUGAAAAAGUGGCACCGAGUCGGUGCUUUU | chr14: 22547524-22547544 |
| 192 | UCAGGGUUCUGGAUAUCUGUGUUUUAGAGCUAGAAAUAGCAAGUUAAAAUAAGGCUAGUCCGUUAUCAACUUGAAAAAGUGGCACCGAGUCGGUGCUUUU | chr14: 22550622-22550642 |
| 193 | mG*mA*mG*UCCGAGCAGAAGAAGAAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr2: 72933852-72933872 |
| 194 | mG*mA*mC*CCCCUCCACCCCGCCUCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr6: 43770821-43770841 |
| 195 | AACAGCAUAGCAAGUUAAAAUAAGGCUAGUCCGUUAUCAACUUGAAAAAGUGGCACCGAGUCGGUGCUUUUUUU | chr14: 22550581-22550601 |
| 196 | GGCUCUCGGAGAAUGACGAGGUUUUAGAGCUAGAAAUAGCAAGUUAAAAUAAGGCUAGUCCGUUAUCAACUUGAAAAAGUGGCACCGAGUCGGUGCUUUU | chr7: 142791996-142792016 |

TABLE 3-continued sgRNA sequences, nomenclature, and component subsequences

| SEQ ID NO: | sgRNA Sequence | Genomic Coordinates (hg38) |
|---|---|---|
| 197 | GGCCUCGGCGCUGACGAUCUGUUUUAGAGCUAGAAAUAGCAAGUUAAAAUAAGGCUAGUCCGUUAUCAACUUGAAAAAGUGGCACCGAGUCGGUGCUUUU | chr7: 142792047-142792067 |
| 198 | AUGACGAGUGGACCCAGGAUGUUUUAGAGCUAGAAAUAGCAAGUUAAAAUAAGGCUAGUCCGUUAUCAACUUGAAAAAGUGGCACCGAGUCGGUGCUUUU | chr7: 142792008-142792028 |
| 199 | UGAGGGUCUCGGCCACCUUCGUUUUAGAGCUAGAAAUAGCAAGUUAAAAUAAGGCUAGUCCGUUAUCAACUUGAAAAAGUGGCACCGAGUCGGUGCUUUU | chr7: 142791930-142791950 |
| 200 | AGAGAUCUCCCACACCCAAAGUUUUAGAGCUAGAAAUAGCAAGUUAAAAUAAGGCUAGUCCGUUAUCAACUUGAAAAAGUGGCACCGAGUCGGUGCUUUU | chr7: 142791748-142791768 |
| 201 | mA*mC*mA*CGGCAGGGUCAGGGUUCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547512-22547532 |
| 202 | mA*mG*mC*UGGUACACGGCAGGGUCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547519-22547539 |
| 203 | mC*mU*mC*UCAGCUGGUACACGGCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547524-22547544 |
| 204 | mU*mC*mU*CUCAGCUGGUACACGGCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547525-22547545 |
| 205 | mU*mG*mG*AUUUAGAGUCUCUCAGCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547536-22547556 |
| 206 | mU*mA*mG*GCAGACAGACUUGUCACGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547556-22547576 |
| 207 | mU*mC*mU*GUGGGACAAGAGGAUCAGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547486-22547506 |
| 208 | mA*mU*mC*UGUGGGACAAGAGGAUCGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547487-22547507 |
| 209 | mC*mU*mG*GAUAUCUGUGGGACAAGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547493-22547513 |
| 210 | mG*mU*mC*AGGGUUCUGGAUAUCUGGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547502-22547522 |
| 211 | mU*mC*mA*GGGUUCUGGAUAUCUGUGUUUUAGAmGmCmUmAmGmAmAmAmUmAmGmCAAGUUAAAAUAAGGCUAGUCCGUUAUCAmAmCmUmUmGmAmAmAmAmAmGmUmGmGmCmAmCmCmGmAmGmUmCmGmGmUmGmCmU*mU*mU*mU | chr14: 22547501-22547521 |
| 212 | UAGGCAGACAGACUUGUCACGUUUUAGAGCUAGAAAUAGCAAGUUAAAAUAAGGCUAGUCCGUUAUCAACUUGAAAAAGUGGCACCGAGUCGGUGCUUUU | chr14: 22547556-22547576 |

* = PS linkage; m = 2'-O-Me nucleotide; N = any natural or non-natural nucleotide In some embodiments, the invention provides a composition comprising one or more guide RNA (gRNA) comprising guide sequences that direct an RNA-guided DNA binding agent, which can be a nuclease (e.g., a Cas nuclease such as Cas9), to a target DNA sequence in TRBC1, TRBC2 and/or TRAC. The gRNA may comprise a guide sequence shown in Tables 1 or 2. In some embodiments, the gRNA comprises the following sequence: $(N)_x$GUUUUAGAGCUAGAAAUAGCAAGUUAAAAUAAGGCUAGUCCGUUAUCAAC UUGAAAAAGUGGCAC CGAGUCGGUGC (SEQ ID NO: 403), where "N" may be any natural or non-natural nucleotide, and wherein the totality of N's comprise a TRBC or TRAC guide sequence as described herein. The gRNA may comprise a crRNA comprising a guide sequence shown in Tables 1-3. The gRNA may comprise a crRNA comprising 17, 18, 19, or 20 contiguous nucleotides of a guide sequence shown in Tables 1 and 2. In some embodiments, the gRNA comprises a crRNA comprising a sequence with about 75%, 80%, 85%, 90%, 95%, 96%, 97%, 98%, 99%, or 100% identity to at least 17, 18, 19, or 20 contiguous nucleotides of a guide sequence shown in Tables 1 and 2. In some embodiments, the gRNA comprises a crRNA comprising a sequence with about 75%, 80%, 85%, 90%, 95%, 96%, 97%, 98%, 99%, or 100% identity to a guide sequence shown in Tables 1 and 2. The gRNA may further comprise a trRNA. In each embodiment described herein, the crRNA and trRNA may be associated as a single RNA (sgRNA) or may be on separate RNAs (dgRNA). In the context of sgRNAs, the crRNA and trRNA components may be covalently linked, e.g., via a phosphodiester bond or other covalent bond.

In each embodiment described herein, the guide RNA may comprise two RNA molecules as a "dual guide RNA" or "dgRNA". The dgRNA comprises a first RNA molecule comprising a crRNA comprising, e.g., a guide sequence shown in Tables 1 and 2, and a second RNA molecule comprising a trRNA. The first and second RNA molecules may not be covalently linked, but may form a RNA duplex via the base pairing between portions of the crRNA and the trRNA.

In each embodiment described herein, the guide RNA may comprise a single RNA molecule as a "single guide RNA" or "sgRNA". The sgRNA may comprise a crRNA (or a portion thereof) comprising a guide sequence shown in Tables 1 and 2 covalently linked to a trRNA. The sgRNA may comprise 17, 18, 19, or 20 contiguous nucleotides of a guide sequence shown in Tables 1 and 2. In some embodiments, the crRNA and the trRNA are covalently linked via a linker. In some embodiments, the sgRNA forms a stem-loop structure via the base pairing between portions of the crRNA and the trRNA. In some embodiments, the crRNA and the trRNA are covalently linked via one or more bonds that are not a phosphodiester bond.

In some embodiments, the trRNA may comprise all or a portion of a trRNA sequence derived from a naturally-occurring CRISPR/Cas system. In some embodiments, the trRNA comprises a truncated or modified wild type trRNA. The length of the trRNA depends on the CRISPR/Cas system used. In some embodiments, the trRNA comprises or consists of 5, 6, 7, 8, 9, 10, 11, 12, 13, 14, 15, 16, 17, 18, 19, 20, 25, 30, 40, 50, 60, 70, 80, 90, 100, or more than 100 nucleotides. In some embodiments, the trRNA may comprise certain secondary structures, such as, for example, one or more hairpin or stem-loop structures, or one or more bulge structures.

In some embodiments, the invention provides a composition comprising one or more guide RNAs comprising a guide sequence of any one of SEQ ID NOs: 1-89 and 90-178.

In some embodiments, the invention provides a composition comprising one or more sgRNAs comprising any one of SEQ ID NOs: 179-184.

In one aspect, the invention provides a composition comprising a gRNA that comprises a guide sequence that is at least 99%, 98%, 97%, 96%, 95%, 94%, 93%, 92%, 91%, or 90% identical to any of the nucleic acids of SEQ ID NOs: 1-89, 90-178, 185, and 213-218.

In other embodiments, the composition comprises at least one, e.g., at least two gRNA's comprising guide sequences selected from any two or more of the guide sequences of SEQ ID NOs: 1-89, 90-178, 185, and 213-218. In some embodiments, the composition comprises at least two gRNA's that each comprise a guide sequence at least 99%, 98%, 97%, 96%, 95%, 94%, 93%, 92%, 91%, or 90% identical to any of the nucleic acids of SEQ ID NOs: 1-89, 90-178, 185, and 213-218.

The guide RNA compositions of the present invention are designed to recognize (e.g., hybridize to) a target sequence in the TRBC1, TRBC2 and/or TRAC genes. For example, the TRBC1, TRBC2 and/or TRAC target sequence may be recognized and cleaved by a provided Cas cleavase comprising a guide RNA. In some embodiments, an RNA-guided DNA binding agent, such as a Cas cleavase, may be directed by a guide RNA to a target sequence of the TRBC1, TRBC2 and/or TRAC genes, where the guide sequence of the guide RNA hybridizes with the target sequence and the RNA-guided DNA binding agent, such as a Cas cleavase, cleaves the target sequence.

In some embodiments, the selection of the one or more guide RNAs is determined based on target sequences within the TRBC1, TRBC2 and/or TRAC genes.

Without being bound by any particular theory, mutations (e.g., frameshift mutations resulting from indels occurring as a result of a nuclease-mediated DSB) in certain regions of the gene may be less tolerable than mutations in other regions of the gene, thus the location of a DSB is an important factor in the amount or type of protein knockdown that may result. In some embodiments, a gRNA complementary or having complementarity to a target sequence within TRBC1, TRBC2 and/or TRAC is used to direct the RNA-guided DNA binding agent to a particular location in the appropriate TRBC1, TRBC2 and/or TRAC gene. In some embodiments, gRNAs are designed to have guide sequences that are complementary or have complementarity to target sequences in exon 1, exon 2, exon 3, or exon 4 of TRBC1 and/or TRBC2, and/or target sequences in exon 1, exon 2, exon 3, or exon 4 of TRAC.

In some embodiments, the guide sequence is at least 99%, 98%, 97%, 96%, 95%, 94%, 93%, 92%, 91%, or 90% identical to a target sequence present in the human TRBC1, TRBC2 and/or TRAC genes. In some embodiments, the target sequence may be complementary to the guide sequence of the guide RNA. In some embodiments, the degree of complementarity or identity between a guide sequence of a guide RNA and its corresponding target sequence may be at least 80%, 85%, 90%, 95%, 96%, 97%, 98%, 99%, or 100%. In some embodiments, the target sequence and the guide sequence of the gRNA may be 100% complementary or identical. In other embodiments, the target sequence and the guide sequence of the gRNA may contain at least one mismatch. For example, the target sequence and the guide sequence of the gRNA may contain 1, 2, 3, or 4 mismatches, where the total length of the guide sequence is 20. In some embodiments, the target sequence and the guide sequence of the gRNA may contain 1-4 mismatches where the guide sequence is 20 nucleotides.

In some embodiments, a composition or formulation disclosed herein comprises an mRNA comprising an open reading frame (ORF) encoding an RNA-guided DNA binding agent, such as a Cas nuclease as described herein. In some embodiments, an mRNA comprising an ORF encoding an RNA-guided DNA binding agent, such as a Cas nuclease, is provided, used, or administered.

B. Modified gRNAs and mRNAs

In some embodiments, the gRNA is chemically modified. In some embodiments, a gRNA comprises one or more modified nucleosides or nucleotides and can be called a "modified" gRNA or "chemically modified" gRNA, to describe the presence of one or more non-naturally and/or naturally occurring components or configurations that are used instead of or in addition to the canonical A, G, C, and U residues. In some embodiments, a modified gRNA is synthesized with a non-canonical nucleoside or nucleotide, is here called "modified." Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii) modification or replacement of the sugar (an exemplary sugar modification).

Chemical modifications such as those listed above can be combined to provide modified gRNAs and/or mRNAs comprising nucleosides and nucleotides (collectively "residues") that can have two, three, four, or more modifications. For example, a modified residue can have a modified sugar and a modified nucleobase. In some embodiments, every base of a gRNA is modified, e.g., all bases have a modified phosphate group, such as a phosphorothioate group. In certain embodiments, all, or substantially all, of the phosphate groups of a gRNA molecule are replaced with phosphorothioate groups. In some embodiments, modified gRNAs comprise at least one modified residue at or near the 5' end of the RNA. In some embodiments, modified gRNAs comprise at least one modified residue at or near the 3' end of the RNA.

In some embodiments, the gRNA comprises one, two, three or more modified residues. In some embodiments, at least 5% (e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%) of the positions in a modified gRNA are modified nucleosides or nucleotides.

Unmodified nucleic acids can be prone to degradation by, e.g., intracellular nucleases or those found in serum. For example, nucleases can hydrolyze nucleic acid phosphodiester bonds. Accordingly, in one aspect the gRNAs described herein can contain one or more modified nucleosides or nucleotides, e.g., to introduce stability toward intracellular or serum-based nucleases. In some embodiments, the modified gRNA molecules described herein can exhibit a reduced innate immune response when introduced into a population of cells, both in vivo and ex vivo. The term "innate immune response" includes a cellular response to exogenous nucleic acids, including single stranded nucleic acids, which involves the induction of cytokine expression and release, particularly the interferons, and cell death.

In some embodiments of a backbone modification, the phosphate group of a modified residue can be modified by replacing one or more of the oxygens with a different substituent. Further, the modified residue, e.g., modified residue present in a modified nucleic acid, can include the wholesale replacement of an unmodified phosphate moiety with a modified phosphate group as described herein. In some embodiments, the backbone modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. The phosphorous atom is in an unmodified phosphate group is achiral. However, replacement of one of the non-bridging oxygens with one of the above atoms or groups of atoms can render the phosphorous atom chiral. The stereogenic phosphorous atom can possess either the "R" configuration (herein Rp) or the "S" configuration (herein Sp). The backbone can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

The phosphate group can be replaced by non-phosphorus containing connectors in certain backbone modifications. In some embodiments, the charged phosphate group can be replaced by a neutral moiety. Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Scaffolds that can mimic nucleic acids can also be constructed wherein the phosphate linker and ribose sugar are replaced by nuclease resistant nucleoside or nucleotide surrogates. Such modifications may comprise backbone and sugar modifications. In some embodiments, the nucleobases can be tethered by a surrogate backbone. Examples can include, without limitation, the morpholino, cyclobutyl, pyrrolidine and peptide nucleic acid (PNA) nucleoside surrogates.

The modified nucleosides and modified nucleotides can include one or more modifications to the sugar group, i.e. at sugar modification. For example, the 2' hydroxyl group (OH) can be modified, e.g. replaced with a number of different "oxy" or "deoxy" substituents. In some embodiments, modifications to the 2' hydroxyl group can enhance the stability of the nucleic acid since the hydroxyl can no longer be deprotonated to form a 2'-alkoxide ion.

Examples of 2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to is 10, from 4 to 16, and from 4 to 20). In some embodiments, the 2' hydroxyl group modification can be 2'-O-Me. In some embodiments, the 2' hydroxyl group modification can be a 2'-fluoro modification, which replaces the 2' hydroxyl group with a fluoride. In some embodiments, the 2' hydroxyl group modification can include "locked" nucleic acids (LNA) in which the 2' hydroxyl can be connected, e.g., by a C1-6 alkylene or C1-6 heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In some embodiments, the 2' hydroxyl group modification can include "unlocked" nucleic acids (UNA) in which the ribose ring lacks the C2'-C3' bond. In some embodiments, the 2' hydroxyl group modification can include the methoxyethyl group (MOE), ($OCH_2CH_2OCH_3$, e.g., a PEG derivative).

"Deoxy" 2' modifications can include hydrogen (i.e. deoxyribose sugars, e.g., at the overhang portions of partially dsRNA); halo (e.g., bromo, chloro, fluoro, or iodo);

amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH2CH_2$— amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar modification can comprise a sugar group which may also contain one or more carbons that possess the opposite stereochemical configuration than that of the corresponding carbon in ribose. Thus, a modified nucleic acid can include nucleotides containing e.g., arabinose, as the sugar. The modified nucleic acids can also include abasic sugars. These abasic sugars can also be further modified at one or more of the constituent sugar atoms. The modified nucleic acids can also include one or more sugars that are in the L form, e.g. L-nucleosides.

The modified nucleosides and modified nucleotides described herein, which can be incorporated into a modified nucleic acid, can include a modified base, also called a nucleobase. Examples of nucleobases include, but are not limited to, adenine (A), guanine (G), cytosine (C), and uracil (U). These nucleobases can be modified or wholly replaced to provide modified residues that can be incorporated into modified nucleic acids. The nucleobase of the nucleotide can be independently selected from a purine, a pyrimidine, a purine analog, or pyrimidine analog. In some embodiments, the nucleobase can include, for example, naturally-occurring and synthetic derivatives of a base.

In embodiments employing a dual guide RNA, each of the crRNA and the tracr RNA can contain modifications. Such modifications may be at one or both ends of the crRNA and/or tracr RNA. In embodiments comprising an sgRNA, one or more residues at one or both ends of the sgRNA may be chemically modified, and/or internal nucleosides may be modified, and/or the entire sgRNA may be chemically modified. Certain embodiments comprise a 5' end modification. Certain embodiments comprise a 3' end modification. Certain embodiments comprise a 5' end modification and a 3' end modification.

In some embodiments, the guide RNAs disclosed herein comprise one of the modification patterns disclosed in WO2018/107028 A1, filed Dec. 8, 2017, titled "Chemically Modified Guide RNAs," the contents of which are hereby incorporated by reference in their entirety. In some embodiments, the guide RNAs disclosed herein comprise one of the structures/modification patterns disclosed in US20170114334, the contents of which are hereby incorporated by reference in their entirety. In some embodiments, the guide RNAs disclosed herein comprise one of the structures/modification patterns disclosed in WO2017/136794, the contents of which are hereby incorporated by reference in their entirety.

In some embodiments, the sgRNA comprises any of the modification patterns shown herein, where N is any natural or non-natural nucleotide, and wherein the totality of the N's comprise a TRBC1, TRBC2 and/or TRAC guide sequence as described herein in Tables 1-3. In some embodiments, the modified sgRNA comprises the following sequence: mN*mN*mN*NNNNNNNNNNNNNNNNNGUUUUAGA mGmCmUmAmGmAmAmAmU mAmGmCAAGUUAAAAUAAGGCUAGUCCGUUAUCAmAmCmUmUmGmAmAmAm AmAmGmUmGmGmCmAmCmCmGmAmGmUmCmGm GmUmGmCmU*mU*mU*mU (SEQ ID NO: 300), where "N" may be any natural or non-natural nucleotide, and wherein the totality of N's comprise an TRBC1, TRBC2 and/or TRAC guide sequence as described in Tables 1 and 2 or as described herein. For example, encompassed herein is SEQ ID NO: 300, where the N's are replaced with any of the guide sequences disclosed herein in Tables 1 and 2 (SEQ ID NOs: 1-89, 90-178, 185, and 213-218).

Any of the modifications described below may be present in the gRNAs and mRNAs described herein.

The terms "mA," "mC," "mU," or "mG" may be used to denote a nucleotide that has been modified with 2'-O-Me.

Modification of 2'-O-methyl can be depicted as follows:

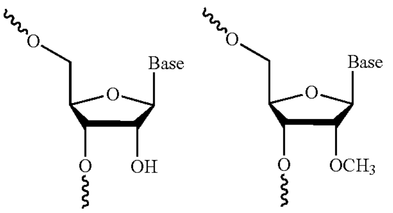

RNA 2'-O-Me

Another chemical modification that has been shown to influence nucleotide sugar rings is halogen substitution. For example, 2'-fluoro (2'-F) substitution on nucleotide sugar rings can increase oligonucleotide binding affinity and nuclease stability.

In this application, the terms "fA," "fC," "fU," or "fG" may be used to denote a nucleotide that has been substituted with 2'-F.

Substitution of 2'-F can be depicted as follows:

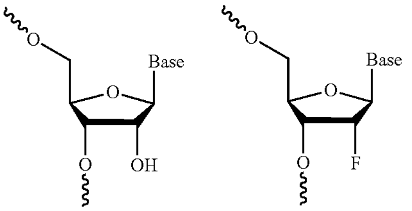

RNA
Natural composition of RNA

2'F-RNA
2'F substitution

Phosphorothioate (PS) linkage or bond refers to a bond where a sulfur is substituted for one non-bridging phosphate oxygen in a phosphodiester linkage, for example in the bonds between nucleotides bases. When phosphorothioates are used to generate oligonucleotides, the modified oligonucleotides may also be referred to as S-oligos.

A "*" may be used to depict a PS modification. In this application, the terms A*, C*, U*, or G* may be used to denote a nucleotide that is linked to the next (e.g., 3') nucleotide with a PS bond.

In this application, the terms "mA*," "mC*," "mU*," or "mG*" may be used to denote a nucleotide that has been substituted with 2'-O-Me and that is linked to the next (e.g., 3') nucleotide with a PS bond.

The diagram below shows the substitution of S— into a non-bridging phosphate oxygen, generating a PS bond in lieu of a phosphodiester bond:

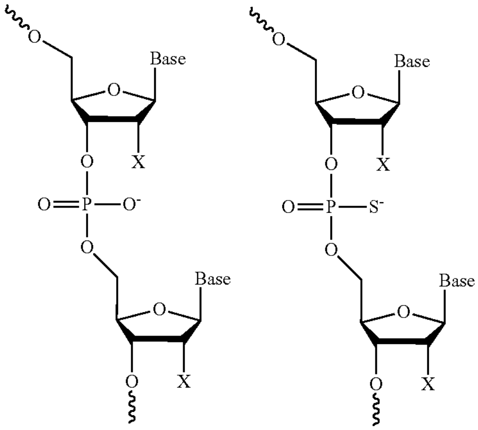

Phosphoediester Natural phosphodiester linkage of RNA

Phosphorothioate (PS) Modified phosphorothioate (PS) bond

Abasic nucleotides refer to those which lack nitrogenous bases. The figure below depicts an oligonucleotide with an abasic (also known as apurinic) site that lacks a base:

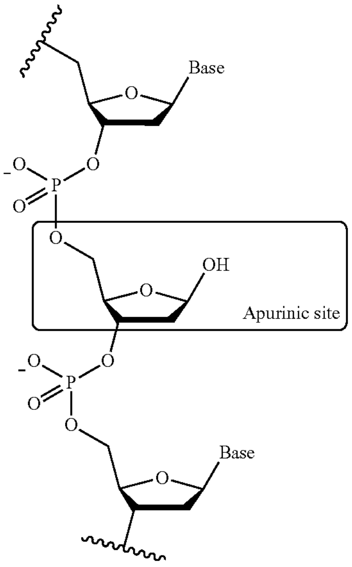

Inverted bases refer to those with linkages that are inverted from the normal 5' to 3' linkage (i.e., either a 5' to 5' linkage or a 3' to 3' linkage). For example:

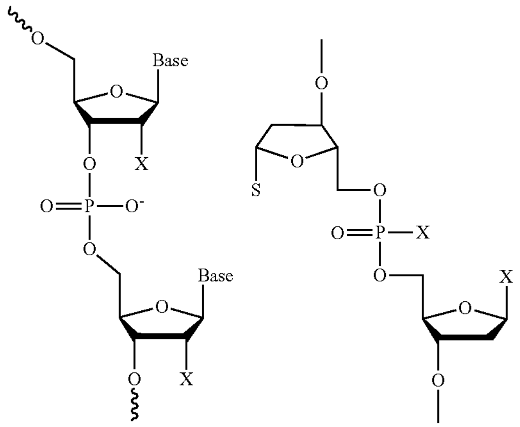

Normal oligonucleotide linkage

Inverted oligonucleotide linkage

An abasic nucleotide can be attached with an inverted linkage. For example, an abasic nucleotide may be attached to the terminal 5' nucleotide via a 5' to 5' linkage, or an abasic nucleotide may be attached to the terminal 3' nucleotide via a 3' to 3' linkage. An inverted abasic nucleotide at either the terminal 5' or 3' nucleotide may also be called an inverted abasic end cap.

In some embodiments, one or more of the first three, four, or five nucleotides at the 5' terminus, and one or more of the last three, four, or five nucleotides at the 3' terminus are modified. In some embodiments, the modification is a 2'-O-Me, 2'-F, inverted abasic nucleotide, PS bond, or other nucleotide modification well-known in the art to increase stability and/or performance.

In some embodiments, the first four nucleotides at the 5' terminus, and the last four nucleotides at the 3' terminus are linked with phosphorothioate (PS) bonds.

In some embodiments, the first three nucleotides at the 5' terminus, and the last three nucleotides at the 3' terminus comprise a 2'-O-methyl (2'-O-Me) modified nucleotide. In some embodiments, the first three nucleotides at the 5' terminus, and the last three nucleotides at the 3' terminus comprise a 2'-fluoro (2'-F) modified nucleotide. In some embodiments, the first three nucleotides at the 5' terminus, and the last three nucleotides at the 3' terminus comprise an inverted abasic nucleotide.

In some embodiments, the guide RNA comprises a modified sgRNA. In some embodiments, the sgRNA comprises the modification pattern shown in SEQ ID NO: 401, where N is any natural or non-natural nucleotide, and where the totality of the N's comprise a guide sequence that directs a nuclease to a target sequence in TRBC1, TRBC2 and/or TRAC, e.g., as shown in Tables 1 and 2.

In some embodiments, the guide RNA comprises a sgRNA shown in any one of SEQ ID NOs: 179-184. In some embodiments, the guide RNA comprises a sgRNA comprising any one of the guide sequences of SEQ ID NOs: 1-178 and the nucleotides of SEQ ID NO: 401, wherein the nucleotides of SEQ ID NO: 401 are on the 3' end of the guide sequence, and wherein the sgRNA may be modified as shown herein or SEQ ID NO: 300.

As noted above, in some embodiments, a composition or formulation disclosed herein comprises an mRNA comprising an open reading frame (ORF) encoding an RNA-guided DNA binding agent, such as a Cas nuclease as described herein. In some embodiments, an mRNA comprising an ORF encoding an RNA-guided DNA binding agent, such as a Cas nuclease, is provided, used, or administered. In some embodiments, the ORF encoding an RNA-guided DNA nuclease is a "modified RNA-guided DNA binding agent ORF" or simply a "modified ORF," which is used as shorthand to indicate that the ORF is modified.

In some embodiments, the modified ORF may comprise a modified uridine at least at one, a plurality of, or all uridine positions. In some embodiments, the modified uridine is a uridine modified at the 5 position, e.g., with a halogen, methyl, or ethyl. In some embodiments, the modified uridine is a pseudouridine modified at the 1 position, e.g., with a halogen, methyl, or ethyl. The modified uridine can be, for example, pseudouridine, N1-methyl-pseudouridine, 5-methoxyuridine, 5-iodouridine, or a combination thereof. In some embodiments, the modified uridine is 5-methoxyuridine. In some embodiments, the modified uridine is 5-iodouridine. In some embodiments, the modified uridine is pseudouridine. In some embodiments, the modified uridine is N1-methyl-pseudouridine. In some embodiments, the modified uridine is a combination of pseudouridine and N1-methyl-pseudouridine. In some embodiments, the modified uridine is a combination of pseudouridine and 5-methoxyuridine. In some embodiments, the modified uridine is a combination of N1-methyl pseudouridine and 5-methoxyuridine. In some embodiments, the modified uridine is a combination of 5-iodouridine and N1-methyl-pseudouridine. In some embodiments, the modified uridine is a combination of pseudouridine and 5-iodouridine. In some embodiments, the modified uridine is a combination of 5-iodouridine and 5-methoxyuridine.

In some embodiments, an mRNA disclosed herein comprises a 5' cap, such as a Cap0, Cap1, or Cap2. A 5' cap is generally a 7-methylguanine ribonucleotide (which may be further modified, as discussed below e.g. with respect to ARCA) linked through a 5'-triphosphate to the 5' position of the first nucleotide of the 5'-to-3' chain of the mRNA, i.e., the first cap-proximal nucleotide. In Cap0, the riboses of the first and second cap-proximal nucleotides of the mRNA both comprise a 2'-hydroxyl. In Cap1, the riboses of the first and second transcribed nucleotides of the mRNA comprise a 2'-methoxy and a 2'-hydroxyl, respectively. In Cap2, the riboses of the first and second cap-proximal nucleotides of the mRNA both comprise a 2'-methoxy. See, e.g., Katibah et al. (2014) *Proc Natl Acad Sci USA* 111(33):12025-30; Abbas et al. (2017) *Proc Natl Acad Sci USA* 114(11):E2106-E2115. Most endogenous higher eukaryotic mRNAs, including mammalian mRNAs such as human mRNAs, comprise Cap1 or Cap2. Cap0 and other cap structures differing from Cap1 and Cap2 may be immunogenic in mammals, such as humans, due to recognition as "non-self" by components of the innate immune system such as IFIT-1 and IFIT-5, which can result in elevated cytokine levels including type I interferon. Components of the innate immune system such as IFIT-1 and IFIT-5 may also compete with eIF4E for binding of an mRNA with a cap other than Cap1 or Cap2, potentially inhibiting translation of the mRNA.

A cap can be included co-transcriptionally. For example, ARCA (anti-reverse cap analog; Thermo Fisher Scientific Cat. No. AM8045) is a cap analog comprising a 7-methylguanine 3'-methoxy-5'-triphosphate linked to the 5' position of a guanine ribonucleotide which can be incorporated in vitro into a transcript at initiation. ARCA results in a Cap0 cap in which the 2' position of the first cap-proximal nucleotide is hydroxyl. See, e.g., Stepinski et al., (2001) "Synthesis and properties of mRNAs containing the novel 'anti-reverse' cap analogs 7-methyl(3'-O-methyl)GpppG and 7-methyl(3'deoxy)GpppG," *RNA* 7: 1486-1495. The ARCA structure is shown below.

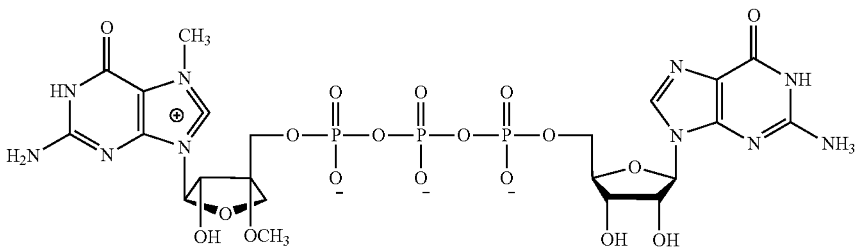

CleanCap™ AG (m7G(5')ppp(5')(2'OMeA)pG; TriLink Biotechnologies Cat. No. N-7113) or CleanCap™ GG (m7G (5')ppp(5')(2'OMeG)pG; TriLink Biotechnologies Cat. No. N-7133) can be used to provide a Cap1 structure co-transcriptionally. 3'-O-methylated versions of CleanCap™ AG and CleanCap™ GG are also available from TriLink Biotechnologies as Cat. Nos. N-7413 and N-7433, respectively. The CleanCap™ AG structure is shown below.

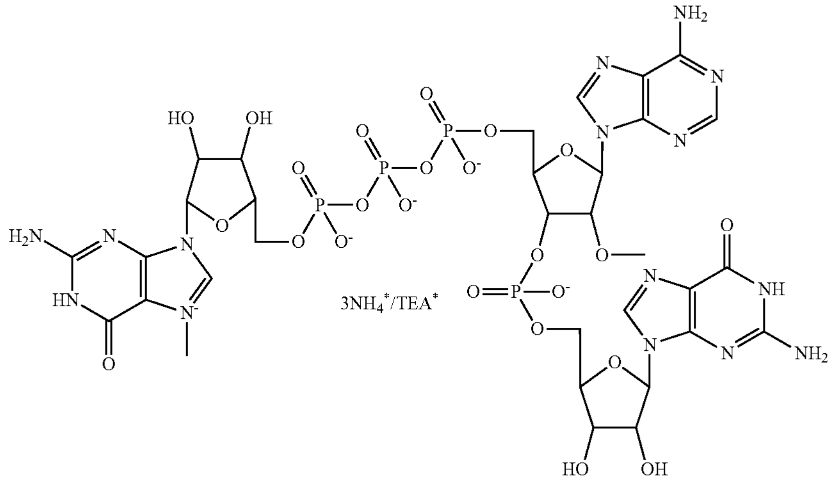

Alternatively, a cap can be added to an RNA post-transcriptionally. For example, Vaccinia capping enzyme is commercially available (New England Biolabs Cat. No. M2080S) and has RNA triphosphatase and guanylyltransferase activities, provided by its D1 subunit, and guanine methyltransferase, provided by its D12 subunit. As such, it can add a 7-methylguanine to an RNA, so as to give Cap0, in the presence of S-adenosyl methionine and GTP. See, e.g., Guo, P. and Moss, B. (1990) *Proc. Natl. Acad. Sci. USA* 87, 4023-4027; Mao, X. and Shuman, S. (1994) *J. Biol. Chem.* 269, 24472-24479.

In some embodiments, the mRNA further comprises a poly-adenylated (poly-A) tail. In some embodiments, the poly-A tail comprises at least 20, 30, 40, 50, 60, 70, 80, 90, or 100 adenines, optionally up to 300 adenines. In some embodiments, the poly-A tail comprises 95, 96, 97, 98, 99, or 100 adenine nucleotides.

C. Ribonucleoprotein Complex

In some embodiments, a composition is encompassed comprising one or more gRNAs comprising one or more guide sequences from Tables 1 and 2 or one or more sgRNAs from Table 3 and an RNA-guided DNA binding agent, e.g., a nuclease, such as a Cas nuclease, such as Cas9. In some embodiments, the RNA-guided DNA-binding agent. e.g. Cas9, has cleavase activity, which can also be referred to as double-strand endonuclease activity. In some embodiments, the RNA-guided DNA-binding agent comprises a Cas9 nuclease. Examples of Cas9 nucleases include those of the type II CRISPR systems of *S. pyogenes*, *S. aureus*, and other prokaryotes (see, e.g., the list in the next paragraph), and modified (e.g., engineered or mutant) versions thereof. See, e.g., US2016/0312198 A1; US 2016/0312199 A1. Other examples of Cas nucleases include a Csm or Cmr complex of a type III CRISPR system or the Cas10, Csm1, or Cmr2 subunit thereof; and a Cascade complex of a type I CRISPR system, or the Cas3 subunit thereof. In some embodiments, the Cas nuclease may be from a Type-IIA, Type-IIB, or Type-IIC system. For discussion of various CRISPR systems and Cas nucleases see, e.g., Makarova et al., Nat. Rev. Microbiol. 9:467-477 (2011); Makarova et al., Nat. Rev. Microbiol, 13: 722-36 (2015); Shmakov et al., Molecular Cell, 60:385-397 (2015).

Non-limiting exemplary species that the Cas nuclease can be derived from include *Streptococcus pyogenes, Streptococcus thermophilus, Streptococcus* sp., *Staphylococcus aureus, Listeria innocua, Lactobacillus gasseri, Francisella novicida, Wolinella succinogenes, Sutterella wadsworthensis, Gammaproteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria, Acidaminococcus* sp., *Lachnospiraceae bacterium* ND2006, and *Acaryochloris marina.*

In some embodiments, the Cas nuclease is the Cas9 nuclease from *Streptococcus pyogenes*. In some embodiments, the Cas nuclease is the Cas9 nuclease from *Streptococcus thermophilus*. In some embodiments, the Cas nuclease is the Cas9 nuclease from *Neisseria meningitidis*. In some embodiments, the Cas nuclease is the Cas9 nuclease is from *Staphylococcus aureus*. In some embodiments, the Cas nuclease is the Cpf1 nuclease from *Francisella novicida*. In some embodiments, the Cas nuclease is the Cpf1 nuclease from Acidaminococcus sp. In some embodiments, the Cas nuclease is the Cpf1 nuclease from *Lachnospiraceae bac-*

*terium* ND2006. In further embodiments, the Cas nuclease is the Cpf1 nuclease from *Francisella tularensis, Lachnospiraceae bacterium, Butyrivibrio proteoclasticus, Peregrinibacteria bacterium, Parcubacteria bacterium, Smithella, Acidaminococcus, Candidatus Methanoplasma termitum, Eubacterium eligens, Moraxella bovoculi, Leptospira inadai, Porphyromonas crevioricanis, Prevotella disiens*, or *Porphyromonas macacae*. In certain embodiments, the Cas nuclease is a Cpf1 nuclease from an Acidaminococcus or Lachnospiraceae.

In some embodiments, the gRNA together with an RNA-guided DNA binding agent is called a ribonucleoprotein complex (RNP). In some embodiments, the RNA-guided DNA binding agent is a Cas nuclease. In some embodiments, the gRNA together with a Cas nuclease is called a Cas RNP. In some embodiments, the RNP comprises Type-I, Type-II, or Type-III components. In some embodiments, the Cas nuclease is the Cas9 protein from the Type-II CRISPR/Cas system. In some embodiment, the gRNA together with Cas9 is called a Cas9 RNP.

Wild type Cas9 has two nuclease domains: RuvC and HNH. The RuvC domain cleaves the non-target DNA strand, and the HNH domain cleaves the target strand of DNA. In some embodiments, the Cas9 protein comprises more than one RuvC domain and/or more than one HNH domain. In some embodiments, the Cas9 protein is a wild type Cas9. In each of the composition, use, and method embodiments, the Cas induces a double strand break in target DNA.

In some embodiments, chimeric Cas nucleases are used, where one domain or region of the protein is replaced by a portion of a different protein. In some embodiments, a Cas nuclease domain may be replaced with a domain from a different nuclease such as Fokl. In some embodiments, a Cas nuclease may be a modified nuclease.

In other embodiments, the Cas nuclease may be from a Type-I CRISPR/Cas system. In some embodiments, the Cas nuclease may be a component of the Cascade complex of a Type-I CRISPR/Cas system. In some embodiments, the Cas nuclease may be a Cas3 protein. In some embodiments, the Cas nuclease may be from a Type-III CRISPR/Cas system. In some embodiments, the Cas nuclease may have an RNA cleavage activity.

In some embodiments, the RNA-guided DNA-binding agent has single-strand nickase activity, i.e., can cut one DNA strand to produce a single-strand break, also known as a "nick." In some embodiments, the RNA-guided DNA-binding agent comprises a Cas nickase. A nickase is an enzyme that creates a nick in dsDNA, i.e., cuts one strand but not the other of the DNA double helix. In some embodiments, a Cas nickase is a version of a Cas nuclease (e.g., a Cas nuclease discussed above) in which an endonucleolytic active site is inactivated, e.g., by one or more alterations (e.g., point mutations) in a catalytic domain. See, e.g., U.S. Pat. No. 8,889,356 for discussion of Cas nickases and exemplary catalytic domain alterations. In some embodiments, a Cas nickase such as a Cas9 nickase has an inactivated RuvC or HNH domain.

In some embodiments, the RNA-guided DNA-binding agent is modified to contain only one functional nuclease domain. For example, the agent protein may be modified such that one of the nuclease domains is mutated or fully or partially deleted to reduce its nucleic acid cleavage activity. In some embodiments, a nickase is used having a RuvC domain with reduced activity. In some embodiments, a nickase is used having an inactive RuvC domain. In some embodiments, a nickase is used having an HNH domain with reduced activity. In some embodiments, a nickase is used having an inactive HNH domain.

In some embodiments, a conserved amino acid within a Cas protein nuclease domain is substituted to reduce or alter nuclease activity. In some embodiments, a Cas nuclease may comprise an amino acid substitution in the RuvC or RuvC-like nuclease domain. Exemplary amino acid substitutions in the RuvC or RuvC-like nuclease domain include D10A (based on the *S. pyogenes* Cas9 protein). See, e.g., Zetsche et al. (2015) *Cell October* 22:163(3): 759-771. In some embodiments, the Cas nuclease may comprise an amino acid substitution in the HNH or HNH-like nuclease domain. Exemplary amino acid substitutions in the HNH or HNH-like nuclease domain include E762A, H840A, N863A, H983A, and D986A (based on the *S. pyogenes* Cas9 protein). See, e.g., Zetsche et al. (2015). Further exemplary amino acid substitutions include D917A, E1006A, and D1255A (based on the *Francisella novicida* U112 Cpf1 (FnCpf1) sequence (UniProtKB—A0Q7Q2 (CPF1_FRATN)).

In some embodiments, an mRNA encoding a nickase is provided in combination with a pair of guide RNAs that are complementary to the sense and antisense strands of the target sequence, respectively. In this embodiment, the guide RNAs direct the nickase to a target sequence and introduce a DSB by generating a nick on opposite strands of the target sequence (i.e., double nicking). In some embodiments, use of double nicking may improve specificity and reduce off-target effects. In some embodiments, a nickase is used together with two separate guide RNAs targeting opposite strands of DNA to produce a double nick in the target DNA. In some embodiments, a nickase is used together with two separate guide RNAs that are selected to be in close proximity to produce a double nick in the target DNA.

In some embodiments, the RNA-guided DNA-binding agent lacks cleavase and nickase activity. In some embodiments, the RNA-guided DNA-binding agent comprises a dCas DNA-binding polypeptide. A dCas polypeptide has DNA-binding activity while essentially lacking catalytic (cleavase/nickase) activity. In some embodiments, the dCas polypeptide is a dCas9 polypeptide. In some embodiments, the RNA-guided DNA-binding agent lacking cleavase and nickase activity or the dCas DNA-binding polypeptide is a version of a Cas nuclease (e.g., a Cas nuclease discussed above) in which its endonucleolytic active sites are inactivated, e.g., by one or more alterations (e.g., point mutations) in its catalytic domains. See, e.g., US 2014/0186958 A1; US 2015/0166980 A1.

In some embodiments, the RNA-guided DNA-binding agent comprises one or more heterologous functional domains (e.g., is or comprises a fusion polypeptide).

In some embodiments, the heterologous functional domain may facilitate transport of the RNA-guided DNA-binding agent into the nucleus of a cell. For example, the heterologous functional domain may be a nuclear localization signal (NLS). In some embodiments, the RNA-guided DNA-binding agent may be fused with 1-10 NLS(s). In some embodiments, the RNA-guided DNA-binding agent may be fused with 1-5 NLS(s). In some embodiments, the RNA-guided DNA-binding agent may be fused with one NLS. Where one NLS is used, the NLS may be linked at the N-terminus or the C-terminus of the RNA-guided DNA-binding agent sequence. It may also be inserted within the RNA-guided DNA binding agent sequence. In other embodiments, the RNA-guided DNA-binding agent may be fused with more than one NLS. In some embodiments, the RNA-guided DNA-binding agent may be fused with 2, 3, 4, or 5 NLSs. In some embodiments, the RNA-guided DNA-binding agent may be fused with two NLSs. In certain circumstances, the two NLSs may be the same (e.g., two SV40 NLSs) or different. In some embodiments, the RNA-guided DNA-binding agent is fused to two SV40 NLS sequences linked at the carboxy terminus. In some embodiments, the RNA-guided DNA-binding agent may be fused with two NLSs, one linked at the N-terminus and one at the C-terminus. In some embodiments, the RNA-guided DNA-binding agent may be fused with 3 NLSs. In some embodiments, the RNA-guided DNA-binding agent may be fused with no NLS. In some embodiments, the NLS may be a monopartite sequence, such as, e.g., the SV40 NLS, PKKKRKV (SEQ ID NO: 600) or PKKKRRV (SEQ ID NO: 601). In some embodiments, the NLS may be a bipartite sequence, such as the NLS of nucleoplasmin, KRPAATKKAGQAKKKK (SEQ ID NO: 602). In a specific embodiment, a single PKKKRKV (SEQ ID NO: 600) NLS may be linked at the C-terminus of the RNA-guided DNA-binding agent. One or more linkers are optionally included at the fusion site.

In some embodiments, the heterologous functional domain may be capable of modifying the intracellular half-life of the RNA-guided DNA binding agent. In some embodiments, the half-life of the RNA-guided DNA binding agent may be increased. In some embodiments, the half-life of the RNA-guided DNA-binding agent may be reduced. In some embodiments, the heterologous functional domain may be capable of increasing the stability of the RNA-guided DNA-binding agent. In some embodiments, the heterologous functional domain may be capable of reducing the stability of the RNA-guided DNA-binding agent. In some embodiments, the heterologous functional domain may act as a signal peptide for protein degradation. In some embodiments, the protein degradation may be mediated by proteolytic enzymes, such as, for example, proteasomes, lysosomal proteases, or calpain proteases. In some embodiments, the heterologous functional domain may comprise a PEST sequence. In some embodiments, the RNA-guided DNA-binding agent may be modified by addition of ubiquitin or a polyubiquitin chain. In some embodiments, the ubiquitin may be a ubiquitin-like protein (UBL). Non-limiting examples of ubiquitin-like proteins include small ubiquitin-like modifier (SUMO), ubiquitin cross-reactive protein (UCRP, also known as interferon-stimulated gene-15 (ISG15)), ubiquitin-related modifier-1 (URM1), neuronal-precursor-cell-expressed developmentally downregulated protein-8 (NEDD8, also called Rubl in *S. cerevisiae*), human leukocyte antigen F-associated (FAT10), autophagy-8 (ATG8) and -12 (ATG12), Fau ubiquitin-like protein (FUB1), membrane-anchored UBL (MUB), ubiquitin fold-modifier-1 (UFM1), and ubiquitin-like protein-5 (UBL5).

In some embodiments, the heterologous functional domain may be a marker domain. Non-limiting examples of marker domains include fluorescent proteins, purification tags, epitope tags, and reporter gene sequences. In some embodiments, the marker domain may be a fluorescent protein. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., EBFP, EBFP2, Azurite, mKalamal, GFPuv, Sapphire, T-sapphire,), cyan fluorescent proteins (e.g., ECFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In other embodiments, the marker domain may be a purification tag and/or an epitope tag. Non-limiting exemplary tags include glutathione-S-transferase (GST), chitin binding protein (CBP), maltose binding protein (MBP), thioredoxin (TRX), poly(NANP), tandem affinity purification (TAP) tag, myc, AcV5, AU1, AUS, E, ECS, E2, FLAG, HA, nus, Softag 1, Softag 3, Strep, SBP, Glu-Glu, HSV, KT3, S, S1, T7, V5, VSV-G, 6×His, 8×His, biotin carboxyl carrier protein (BCCP), poly-His, and calmodulin. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the heterologous functional domain may target the RNA-guided DNA-binding agent to a specific organelle, cell type, tissue, or organ. In some embodiments, the heterologous functional domain may target the RNA-guided DNA-binding agent to mitochondria.

In further embodiments, the heterologous functional domain may be an effector domain. When the RNA-guided DNA-binding agent is directed to its target sequence, e.g., when a Cas nuclease is directed to a target sequence by a gRNA, the effector domain may modify or affect the target sequence. In some embodiments, the effector domain may be chosen from a nucleic acid binding domain, a nuclease domain (e.g., a non-Cas nuclease domain), an epigenetic modification domain, a transcriptional activation domain, or a transcriptional repressor domain. In some embodiments, the heterologous functional domain is a nuclease, such as a Fokl nuclease. See, e.g., U.S. Pat. No. 9,023,649. In some embodiments, the heterologous functional domain is a transcriptional activator or repressor. See, e.g., Qi et al., "Repurposing CRISPR as an RNA-guided platform for sequence-specific control of gene expression," *Cell* 152:1173-83 (2013); Perez-Pinera et al., "RNA-guided gene activation by CRISPR-Cas9-based transcription factors," *Nat. Methods* 10:973-6 (2013); Mali et al., "CAS9 transcriptional activators for target specificity screening and paired nickases for cooperative genome engineering," *Nat. Biotechnol.* 31:833-8 (2013); Gilbert et al., "CRISPR-mediated modular RNA-guided regulation of transcription in eukaryotes," *Cell* 154:442-51 (2013). As such, the RNA-guided DNA-binding agent essentially becomes a transcription factor that can be directed to bind a desired target sequence using a guide RNA.

D. Determination of Efficacy of gRNAs

In some embodiments, the efficacy of a gRNA is determined when delivered or expressed together with other components forming an RNP. In some embodiments, the gRNA is expressed together with an RNA-guided DNA binding agent, such as a Cas protein, e.g. Cas9. In some embodiments, the gRNA is delivered to or expressed in a cell line that already stably expresses an RNA-guided DNA nuclease, such as a Cas nuclease or nickase, e.g. Cas9 nuclease or nickase. In some embodiments the gRNA is delivered to a cell as part of a RNP. In some embodiments, the gRNA is delivered to a cell along with a mRNA encoding an RNA-guided DNA nuclease, such as a Cas nuclease or nickase, e.g. Cas9 nuclease or nickase.

As described herein, use of an RNA-guided DNA nuclease and a guide RNA disclosed herein can lead to double-stranded breaks in the DNA which can produce errors in the form of insertion/deletion (indel) mutations upon repair by cellular machinery. Many mutations due to indels alter the reading frame or introduce premature stop codons and, therefore, produce a non-functional protein.

In some embodiments, the efficacy of particular gRNAs is determined based on in vitro models. In some embodiments, the in vitro model is HEK293 cells stably expressing Cas9 (HEK293_Cas9). In some embodiments the in vitro model is a peripheral blood mononuclear cell (PBMC). In some embodiments, the in vitro model is a T cell, such as primary human T cells. With respect to using primary cells, commercially available primary cells can be used to provide greater consistency between experiments. In some embodiments, the number of off-target sites at which a deletion or insertion occurs in an in vitro model (e.g., in T cell) is determined, e.g., by analyzing genomic DNA from transfected cells in vitro with Cas9 mRNA and the guide RNA. In some embodiments, such a determination comprises analyzing genomic DNA from the cells transfected in vitro with Cas9 mRNA, the guide RNA, and a donor oligonucleotide. Exemplary procedures for such determinations are provided in the working examples in which HEK293 cells, PBMCs, and human $CD3^+$ T cells are used.

In some embodiments, the efficacy of particular gRNAs is determined across multiple in vitro cell models for a gRNA selection process. In some embodiments, a cell line comparison of data with selected gRNAs is performed. In some embodiments, cross screening in multiple cell models is performed.

In some embodiments, the efficacy of a guide RNA is measured by percent indels of TRBC1, TRBC2 and/or TRAC. In some embodiments, the efficacy of a guide RNA is measured by percent indels of TRBC and/or TRAC. In some embodiments, the efficacy of a guide RNA is measured by percent indels of TRBC or TRAC. In some embodiments, the percent editing of TRBC1, TRBC2 and/or TRAC is compared to the percent indels necessary to achieve knockdown of the TRBC1, TRBC2 and/or TRAC protein products In some embodiments, the efficacy of a guide RNA is measured by reduced or eliminated expression of a component of the T-cell receptor (TCR). In embodiments, the reduced or eliminated expression of a component of the T-cell receptor (TCR) includes reduced or eliminated expression of TRAC, TRBC1, TRBC2, CD3E, CD3G, and/or CD3D. In embodiments, said reduced or eliminated expression of said component of the TCR is the result of introduction of one or more, e.g., one or two, e.g., one gRNA molecule described herein to said component of the TCR into said cell. In embodiments, said reduced or eliminated expression of a component of the TCR is as measured by flow cytometry, e.g., as described herein.

In some embodiments, the efficacy of a guide RNA is measured by the number and/or frequency of indels at off-target sequences within the genome of the target cell type, such as a T cell. In some embodiments, efficacious guide RNAs are provided which produce indels at off target sites at very low frequencies (e.g., <5%) in a cell population and/or relative to the frequency of indel creation at the target site. Thus, the disclosure provides for guide RNAs which do not exhibit off-target indel formation in the target cell type (e.g., a T cell), or which produce a frequency of off-target indel formation of <5% in a cell population and/or relative to the frequency of indel creation at the target site. In some embodiments, the disclosure provides guide RNAs which do not exhibit any off target indel formation in the target cell type (e.g., T cell). In some embodiments, guide RNAs are provided which produce indels at less than 5 off-target sites, e.g., as evaluated by one or more methods described herein. In some embodiments, guide RNAs are provided which produce indels at less than or equal to 4, 3, 2, or 1 off-target site(s) e.g., as evaluated by one or more methods described herein. In some embodiments, the off-target site(s) does not occur in a protein coding region in the target cell (e.g., hepatocyte) genome.

In some embodiments, detecting gene editing events, such as the formation of insertion/deletion ("indel") mutations and homology directed repair (HDR) events in target DNA utilize linear amplification with a tagged primer and isolating the tagged amplification products (herein after referred to as "LAM-PCR," or "Linear Amplification (LA)" method).

In some embodiments, the efficacy of a guide RNA is measured by the levels of functional protein complexes comprising the expressed protein product of the gene. In some embodiments, the efficacy of a guide RNA is measured by flow cytometric analysis of TCR expression by which the live population of edited cells is analyzed for loss of the TCR.

III. Methods Including Therapeutic Methods and Methods of Preparing Engineered Cells or Immunotherapy Reagents The gRNAs and associated methods and compositions disclosed herein are useful in immunotherapies and for making immunotherapy reagents, such as engineered cells.

In some embodiments, the gRNAs comprising the guide sequences of Tables 1 and 2 together with an RNA-guided DNA nuclease such as a Cas nuclease induce DSBs, and non-homologous ending joining (NHEJ) during repair leads to a mutation in the TRBC1, TRBC2 and/or TRAC genes. In some embodiments, NHEJ leads to a deletion or insertion of a nucleotide(s), which induces a frame shift or nonsense mutation in the TRBC1, TRBC2 and/or TRAC genes.

In some embodiments, the subject is mammalian. In some embodiments, the subject is human. In some embodiments, the subject is cow, pig, monkey, sheep, dog, cat, fish, or poultry.

In some embodiments, the use of a guide RNAs comprising any one or more of the guide sequences in Tables 1 and 2 or one or more sgRNAs from Table 3 (e.g., in a composition provided herein) is provided for the preparation of a medicament for treating a human subject having need for immunotherapy.

In some embodiments, the guide RNAs, compositions, and formulations are used to produce ex vivo a T cell with mutated TRBC1, TRBC2 and/or TRAC genes. The modified T cell may be a natural killer (NK) T cell. The modified T cell may express a T-cell receptor, such as a universal TCR or a modified TCR. The T cell may express a CAR or a CAR construct with a zeta chain signaling motif.

In some embodiments, a single administration of a composition comprising a guide RNA provided herein is sufficient to knock down expression of TRBC1, TRBC2 or TRAC. In other embodiments, more than one administration of a composition comprising a guide RNA provided herein may be beneficial to increase therapeutic effects.

Delivery of gRNA Compositions

Lipid nanoparticles (LNPs) are a useful means for delivery of nucleotide and protein cargo, and may be used for delivery of the guide RNAs, compositions, or pharmaceutical formulations disclosed herein. In some embodiments, the LNPs deliver nucleic acid, protein, or nucleic acid together with protein.

The guide RNA or other nucleic acid (e.g. encoding a polypeptide) may be associated with a lipid nanoparticle (LNP). Suitable LNPs are known in the art. See, e.g., lipids of PCT/US2018/053559, WO/2017/173054, WO2015/095340, and WO2014/136086, as well as references provided therein.

In some embodiments, the invention comprises a method for delivering any one of the gRNAs disclosed herein to a subject, wherein the gRNA is delivered via an LNP. In some embodiments, the gRNA/LNP is also associated with a Cas9 or an mRNA encoding Cas9.

In some embodiments, the invention comprises a composition comprising any one of the gRNAs disclosed and an LNP. In some embodiments, the composition further comprises a Cas9 or an mRNA encoding Cas9.

In some embodiments, the LNPs comprise an ionizable lipid. In some embodiments, the LNPs comprise (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate) or another ionizable lipid. See, e.g., lipids of PCT/US2018/053559 (filed Sep. 28, 2018), WO/2017/173054, WO2015/095340, and WO2014/136086, as well as references provided therein. In some embodiments, the term cationic and ionizable in the context of LNP lipids is interchangeable, e.g., wherein ionizable lipids are cationic depending on the pH.

In some embodiments, LNPs associated with the gRNAs disclosed herein are for use in preparing a medicament for treating a disease or disorder.

Electroporation is another useful means for delivery of cargo, and any electroporation methodology may be used for delivery of any one of the gRNAs disclosed herein. In some embodiments, electroporation may be used to deliver any one of the gRNAs disclosed herein and Cas9 or an mRNA encoding Cas9.

In some embodiments, the invention comprises a method for delivering any one of the gRNAs disclosed herein to an ex vivo cell, wherein the gRNA is associated with an LNP or not associated with an LNP. In some embodiments, the gRNA/LNP or gRNA is also associated with a Cas9 or an mRNA encoding Cas9.

In some embodiments, the guide RNA compositions described herein, alone or encoded on one or more vectors, are formulated in or administered via a lipid nanoparticle; see e.g., WO/2017/173054, the contents of which are hereby incorporated by reference in their entirety.

In certain embodiments, the invention comprises DNA or RNA vectors encoding any of the guide RNAs comprising any one or more of the guide sequences described herein. In some embodiments, in addition to guide RNA sequences, the vectors further comprise nucleic acids that do not encode guide RNAs. Nucleic acids that do not encode guide RNA include, but are not limited to, promoters, enhancers, regulatory sequences, and nucleic acids encoding an RNA-guided DNA nuclease, which can be a nuclease such as Cas9. In some embodiments, the vector comprises one or more nucleotide sequence(s) encoding a crRNA, a trRNA, or a crRNA and trRNA. In some embodiments, the vector comprises one or more nucleotide sequence(s) encoding a sgRNA and an mRNA encoding an RNA-guided DNA nuclease, which can be a Cas nuclease, such as Cas9 or Cpf1. In some embodiments, the vector comprises one or more nucleotide sequence(s) encoding a crRNA, a trRNA, and an mRNA encoding an RNA-guided DNA nuclease, which can be a Cas protein, such as, Cas9. In one embodiment, the Cas9 is from *Streptococcus pyogenes* (i.e., Spy Cas9). In some embodiments, the nucleotide sequence encoding the crRNA, trRNA, or crRNA and trRNA (which may be a sgRNA) comprises or consists of a guide sequence flanked by all or a portion of a repeat sequence from a naturally-occurring CRISPR/Cas system. The nucleic acid comprising or consisting of the crRNA, trRNA, or crRNA and trRNA may further comprise a vector sequence wherein the vector sequence comprises or consists of nucleic acids that are not naturally found together with the crRNA, trRNA, or crRNA and trRNA.

In some embodiments, the components can be introduced as naked nucleic acid, as nucleic acid complexed with an agent such as a liposome or poloxamer, or they can be introduced as nucleic acid (e.g. gRNA) and protein as a ribonucleoprotein complex (RNP). In some embodiments, the components may be delivered by vectors, such as viral vectors (e.g., adenovirus, AAV, herpesvirus, retrovirus, lentivirus). Methods and compositions for non-viral delivery of nucleic acids include electroporation, lipofection, microinjection, biolistics, virosomes, liposomes, immunoliposomes, LNPs, polycation or lipid:nucleic acid conjugates, naked nucleic acid (e.g., naked DNA/RNA), artificial virions, and agent-enhanced uptake of DNA. Sonoporation using, e.g., the Sonitron 2000 system (Rich-Mar) can also be used for delivery of nucleic acids.

A polypeptide can be introduced to a cell by delivering a nucleic acid, such as a nucleic acid template that encodes the polypeptide of interest to the cell. A nucleic acid template may encode a polypeptide of interest, optionally as part of an expression cassette, wherein the template further comprises flanking sequences. Such flanking sequences are optionally homology arms, designed to facilitate homology-directed repair and integration of the template nucleic acid in the cell. A nucleic acid template may include an open reading frame (ORF) for a polypeptide of interest flanked by sequences homologous to a first target locus to facilitate homologous recombination at the target locus. A template may include is homology arms flanking a gRNA cleavage site, e.g. wherein the homology arms comprise flanking sequences. In certain embodiments, the flanking sequences are designed to omit a region of the target locus at or around the cleavage site to yield a deletion of this region that thus prevents cutting of the site after repair and also prevents the gRNA/Cas9 from cutting the template nucleic acid. The omitted region or "gap" that includes the gRNA cleavage site may be 5, 10, 20, 30, 40, 50, 60, 70, 80, 90, 100, 150, or more nucleotides in length. The flanking sequences may be designed to delete a 10-100 nucleotide gap, a 10-50 nucleotide gap, a 25-100, nucleotide gap, or a 50-100 nucleotide gap, for example.

A nucleic acid encoding a polypeptide of interest may be comprised in a viral template or a nonviral template. A viral vector may be any suitable virus, such as a retrovirus, adenovirus, lentivirus, adeno-associated virus, or hybrid thereof. In some embodiments, the viral vector may be an adeno-associated virus (AAV) vector. The nucleic acid template may comprise an exogenous promoter sequence upstream of an ORF. The nucleic acid template may be promoterless, in that the endogenous TRAC promoter may drive expression of the polypeptide of interest after it is inserted.

In addition to a sequence encoding a polypeptide of interest, a nucleic acid template may comprise one or more of a promoter sequence, a Kozak sequence, an IRES sequence, a splice acceptor squence, a polyA sequence, and a sequence that encodes a cleavable peptide such as P2A, T2A, E2A, and the like.

In some embodiments, methods described herein further comprise delivering one or more sequences comprising one or more genes encoding one or more polypeptides of interest to a cell. In some embodiments, the polypeptide of interest is involved in regulation of immune tolerance. In some embodiments, the polypeptide of interest is involved in regulation of a cancer phenotype.

In some embodiments, the one or more polypeptides comprise a receptor, e.g., an immunological receptor. An immunological receptor means a receptor that can recognize an antigen. Exemplary types of immunological receptors are T-cell receptors (TCR) and chimeric antigen receptors (CAR). In some embodiments, the immunological receptor recognizes a cancer antigen, such as WT1. In certain embodiments, the polypeptide of interest is a WT1 TCR. The WT1 TCR may recognize the VLDFAPPGA (VLD) or RMFPNAPYL (RMF) WT1 peptide. In certain embodiments the WT1 TCR recognizes the VLD peptide. The polypeptide of interest may comprise a WT1 TCR α chain. The polypeptide of interest may comprise a WT1 TCR β chain. In certain embodiments, the polypeptide of interest may comprise a WT1 TCR α chain and a WT1 TCR β chain. Exemplary WT1-specific TCR sequences are known in the art and include:

TABLE 4

| TCR ID | Amino Acid Sequence | SEQ ID NO: |
|---|---|---|
| TCR-A (β-linker-α configuration) | MGSWTLCCVSLCILVAKHTDAGVIQSPRHEVTEMGQEVT<br>LRCKPI**SGHDY**LFWYRQTMMRGLELLIY**FNNNVP**IDDSG<br>MPEDRFSAKMPNASFSTLKIQPSEPRDSAVYF**CASRKTGG**<br>**YSNQPQHF**GDGTRLSILEDLKNVFPPEVAVFEPSEAEISHT<br>QKATLVCLATGFYPDHVELSWWVNGKEVHSGVSTDPQPL<br>KEQPALNDSRYCLSSRLRVSATFWQNPRNHFRCQVQFYG<br>LSENDEWTQDRAKPVTQIVSAEAWGRADCGFTSESYQQG<br>VLSATILYEILLGKATLYAVLVSALVLMAMVKRKDSRGGS<br>GATNFSLLKQAGDVEENPGPMETLLKVLSGTLLWQLTWV<br>RSQQPVQSPQAVILREGEDAVINCSSS**KALYS**VHWYRQKH<br>GEAPVFLMI**LLKGGEQ**KGHEKISASFNEKKQQSSLYLTAS<br>QLSYSGTYF**CGTAWINDYKLSF**GAGTTVTVRANIQNPDP<br>AVYQLRDSKSSDKSVCLFTDFDSQTNVSQSKDSDVYITDK<br>TVLDMRSMDFKSNSAVAWSNKSDFACANAFNNSIIPEDTF<br>FPSPESSCDVKLVEKSFETDTNLNFQNLSVIGFRILLLKVAG<br>FNLLMTLRLWSS | 500 |
| TCR-A, α chain | METLLKVLSGTLLWQLTWVRSQQPVQSPQAVILREGEDA<br>VINCSSS**KALYS**VHWYRQKHGEAPVFLMI**LLKGGEQ**KG<br>HEKISASFNEKKQQSSLYLTASQLSYSGTYF**CGTAWINDY**<br>**KLSF**GAGTTVTVRANIQNPDPAVYQLRDSKSSDKSVCLFT<br>DFDSQTNVSQSKDSDVYITDKTVLDMRSMDFKSNSAVAW<br>SNKSDFACANAFNNSIIPEDTFFPSPESSCDVKLVEKSFETD<br>TNLNFQNLSVIGFRILLLKVAGFNLLMTLRLWSS | 501 |
| TCR-A, β chain | MGSWTLCCVSLCILVAKHTDAGVIQSPRHEVTEMGQEVT<br>LRCKPI**SGHDY**LFWYRQTMMRGLELLIY**FNNNVP**IDDSG<br>MPEDRFSAKMPNASFSTLKIQPSEPRDSAVYF**CASRKTGG**<br>**YSNQPQHF**GDGTRLSILEDLKNVFPPEVAVFEPSEAEISHT<br>QKATLVCLATGFYPDHVELSWWVNGKEVHSGVSTDPQPL<br>KEQPALNDSRYCLSSRLRVSATFWQNPRNHFRCQVQFYG<br>LSENDEWTQDRAKPVTQIVSAEAWGRADCGFTSESYQQG<br>VLSATILYEILLGKATLYAVLVSALVLMAMVKRKDSRG | 502 |
| TCR-B (β-linker-α configuration) | MGSWTLCCVSLCILVAKHTDAGVIQSPRHEVTEMGQEVT<br>LRCKPI**SGHDY**LFWYRQTMMRGLELLIY**FNNNVP**IDDSG<br>MPEDRFSAKMPNASFSTLKIQPSEPRDSAVYF**CASRKTGG**<br>**YSNQPQHF**GDGTRLSILEDLKNVFPPEVAVFEPSEAEISHT<br>QKATLVCLATGFYPDHVELSWWVNGKEVHSGVSTDPQPL<br>KEQPALNDSRYCLSSRLRVSATFWQNPRNHFRCQVQFYG<br>LSENDEWTQDRAKPVTQIVSAEAWGRADCGFTSESYQQG<br>VLSATILYEILLGKATLYAVLVSALVLMAMVKRKDSRGGS<br>GATNFSLLKQAGDVEENPGPMETLLKVLSGTLLWQLTWV<br>RSQQPVQSPQAVILREGEDAVINCSSS**KALYS**VHWYRQKH<br>GEAPVFLMI**LLKGGEQ**KGHEKISASFNEKKQQSSLYLTAS<br>QLSYSGTYF**CGTAWINDYKLSF**GAGTTVTVRANIQNPDP<br>AVYQLRDSKSSDKSVCLFTDFDSQTNVSQSKDSDVYITDK<br>TVLDMRSMDFKSNSAVAWSNKSDFACANAFNNSIIPEDTF<br>FPSPESSCDVKLVEKSFETDTNLNFQNLSVIGFRILLLKVAG<br>FNLLMTLRLWSS | 503 |
| TCR-B, α chain | METLLKVLSGTLLWQLTWVRSQQPVQSPQAVILREGEDA<br>VINCSSS**KALYS**VHWYRQKHGEAPVFLMI**LLKGGEQ**KG<br>HEKISASFNEKKQQSSLYLTASQLSYSGTYF**CGTAWINDY**<br>**KLSF**GAGTTVTVRANIQNPDPAVYQLRDSKSSDKSVCLFT<br>DFDSQTNVSQSKDSDVYITDKCVLDMRSMDFKSNSAVAW<br>SNKSDFACANAFNNSIIPEDTFFPSPESSCDVKLVEKSFETD<br>TNLNFQNLSVIGFRILLLKVAGFNLLMTLRLWSS | 504 |

TABLE 4-continued

| TCR ID | Amino Acid Sequence | SEQ ID NO: |
|---|---|---|
| TCR-B, β chain | MGSWTLCCVSLCILVAKHTDAGVIQSPRHEVTEMGQEVT<br>LRCKPI**SGHDY**LFWYRQTMMRGLELLIY**FNNNVP**IDDSG<br>MPEDRFSAKMPNASFSTLKIQPSEPRDSAVYF**CASRKTGG**<br>**YSNQPQHF**GDGTRLSILEDLKNVFPPEVAVFEPSEAEISHT<br>QKATLVCLATGFYPDHVELSWWVNGKEVHSGVSTDPQPL<br>KEQPALNDSRYCLSSRLRVSATFWQNPRNHFRCQVQFYG<br>LSENDEWTQDRAKPVTQIVSAEAWGRADCGFTSESYQQG<br>VLSATILYEILLGKATLYAVLVSALVLMAMVKRKDSRG | 505 |
| TCR-C (β-linker-α configuration) | MSNQVLCCVVLCFLGANTVDGGITQSPKYLFRKEGQNVT<br>LSCEQNLNHDAMYWYRQDPGQGLRLIYYSQIVNDFQKGD<br>IAEGYSVSREKKESFPLTVTSAQKNPTAFYLCASSPGALYE<br>QYFGPGTRLTVTEDLKNVFPPEVAVFEPSEAEISHTQKATL<br>VCLATGFYPDHVELSWWVNGKEVHSGVCTDPQPLKEQPA<br>LNDSRYCLSSRLRVSATFWQNPRNHFRCQVQFYGLSENDE<br>WTQDRAKPVTQIVSAEAWGRADCGFTSESYQQGVLSATI<br>LYEILLGKATLYAVLVSALVLMAMVKRKDSRGGSGATNF<br>SLLKQAGDVEENPGPMTSIRAVFIFLWLQLDLVNGENVEQ<br>HPSTLSVQEGDSAVIKCTYSDSASNYFPWYKQELGKRPQL<br>IIDIRSNVGEKKDQRIAVTLNKTAKHFSLHITETQPEDSAVY<br>FCAATEDLTLIWGAGTKLIIKPDIQNPDPAVYQLRDSKSSD<br>KSVCLFTDFDSQTNVSQSKDSDVYITDKCVLDMRSMDFKS<br>NSAVAWSNKSDFACANAFNNSIIPEDTFFPSPESSCDVKLV<br>EKSFETDTNLNFQNLSVIGFRILLLKVAGFNLLMTLRLWSS | 506 |
| TCR-C, α chain | MTSIRAVFIFLWLQLDLVNGENVEQHPSTLSVQEGDSAVI<br>KCTYSDSASNYFPWYKQELGKRPQLIIDIRSNVGEKKDQRI<br>AVTLNKTAKHFSLHITETQPEDSAVYFCAATEDLTLIWGA<br>GTKLIIKPDIQNPDPAVYQLRDSKSSDKSVCLFTDFDSQTN<br>VSQSKDSDVYITDKCVLDMRSMDFKSNSAVAWSNKSDFA<br>CANAFNNSIIPEDTFFPSPESSCDVKLVEKSFETDTNLNFQN<br>LSVIGFRILLLKVAGFNLLMTLRLWSS | 507 |
| TCR-C, β chain | MSNQVLCCVVLCFLGANTVDGGITQSPKYLFRKEGQNVT<br>LSCEQNLNHDAMYWYRQDPGQGLRLIYYSQIVNDFQKGD<br>IAEGYSVSREKKESFPLTVTSAQKNPTAFYLCASSPGALYE<br>QYFGPGTRLTVTEDLKNVFPPEVAVFEPSEAEISHTQKATL<br>VCLATGFYPDHVELSWWVNGKEVHSGVCTDPQPLKEQPA<br>LNDSRYCLSSRLRVSATFWQNPRNHFRCQVQFYGLSENDE<br>WTQDRAKPVTQIVSAEAWGRADCGFTSESYQQGVLSATI<br>LYEILLGKATLYAVLVSALVLMAMVKRKDSRG | 508 |
| TCR-D (β-linker-α configuration) | MGCRLLCCAVLCLLGAGELVPMETGVTQTPRHLVMGMT<br>NKKSLKCEQHLGHNAMYWYKQSAKKPLELMFVYSLEER<br>VENNSVPSRFSPECPNSSHLFLHLHTLQPEDSALYLCASSQ<br>DYLVSNEKLFFGSGTQLSVLEDLKNVFPPEVAVFEPSEAEI<br>SHTQKATLVCLATGFYPDHVELSWWVNGKEVHSGVSTDP<br>QPLKEQPALNDSRYCLSSRLRVSATFWQNPRNHFRCQVQF<br>YGLSENDEWTQDRAKPVTQIVSAEAWGRADCGFTSESYQ<br>QGVLSATILYEILLGKATLYAVLVSALVLMAMVKRKDSR<br>GGSGATNFSLLKQAGDVEENPGPMISLRVLLVILWLQLSW<br>VWSQRKEVEQDPGPFNVPEGATVAFNCTYSNSASQSFFW<br>YRQDCRKEPKLLMSVYSSGNEDGRFTAQLNRASQYISLLI<br>RDSKLSDSATYLCVVNLLSNQGGKLIFGQGTELSVKPNIQ<br>NPDPAVYQLRDSKSSDKSVCLFTDFDSQTNVSQSKDSDVY<br>ITDKTVLDMRSMDFKSNSAVAWSNKSDFACANAFNNSIIP<br>EDTFFPSPESSCDVKLVEKSFETDTNLNFQNLSVIGFRILLL<br>KVAGFNLLMTLRLWSS | 509 |
| TCR-D, α chain | MISLRVLLVILWLQLSWVWSQRKEVEQDPGPFNVPEGAT<br>VAFNCTYSNSASQSFFWYRQDCRKEPKLLMSVYSSGNED<br>GRFTAQLNRASQYISLLIRDSKLSDSATYLCVVNLLSNQGG<br>KLIFGQGTELSVKPNIQNPDPAVYQLRDSKSSDKSVCLFTD<br>FDSQTNVSQSKDSDVYITDKTVLDMRSMDFKSNSAVAWS<br>NKSDFACANAFNNSIIPEDTFFPSPESSCDVKLVEKSFETDT<br>NLNFQNLSVIGFRILLLKVAGFNLLMTLRLWSS | 510 |
| TCR-D, β chain | MGCRLLCCAVLCLLGAGELVPMETGVTQTPRHLVMGMT<br>NKKSLKCEQHLGHNAMYWYKQSAKKPLELMFVYSLEER<br>VENNSVPSRFSPECPNSSHLFLHLHTLQPEDSALYLCASSQ<br>DYLVSNEKLFFGSGTQLSVLEDLKNVFPPEVAVFEPSEAEI<br>SHTQKATLVCLATGFYPDHVELSWWVNGKEVHSGVSTDP | 511 |

TABLE 4-continued

| TCR ID | Amino Acid Sequence | SEQ ID NO: |
|---|---|---|
| | QPLKEQPALNDSRYCLSSRLRVSATFWQNPRNHFRCQVQF YGLSENDEWTQDRAKPVTQIVSAEAWGRADCGFTSESYQ QGVLSATILYEILLGKATLYAVLVSALVLMAMVKRKDSR G | |
| TCR-E (β-linker-α configuration) | MGCRLLCCAVLCLLGAGELVPMETGVTQTPRHLVMGMT NKKSLKCEQHLGHNAMYWYKQSAKKPLELMFVYSLEER VENNSVPSRFSPECPNSSHLFLHLHTLQPEDSALYLCASSQ DYLVSNEKLFFGSGTQLSVLEDLKNVFPPEVAVFEPSEAEI SHTQKATLVCLATGFYPDHVELSWWVNGKEVHSGVSTDP QPLKEQPALNDSRYCLSSRLRVSATFWQNPRNHFRCQVQF YGLSENDEWTQDRAKPVTQIVSAEAWGRADCGFTSESYQ QGVLSATILYEILLGKATLYAVLVSALVLMAMVKRKDSR GGSGATNFSLLKQAGDVEENPGPMISLRVLLVILWLQLSW VWSQRKEVEQDPGPFNVPEGATVAFNCTYSNSASQSFFW YRQDCRKEPKLLMSVYSSGNEDGRFTAQLNRASQYISLLI RDSKLSDSATYLCVVNLLSNQGGKLIFGQGTELSVKPNIQ NPDPAVYQLRDSKSSDKSVCLFTDFDSQTNVSQSKDSDVY ITDKTVLDMRSMDFKSNSAVAWSNKSDFACANAFNNSIIP EDTFFPSPESSCDVKLVEKSFETDTNLNFQNLSVIGFRILLL KVAGFNLLMTLRLWSS | 512 |
| TCR-E, α chain | MISLRVLLVILWLQLSWVWSQRKEVEQDPGPFNVPEGAT VAFNCTYSNSASQSFFWYRQDCRKEPKLLMSVYSSGNED GRFTAQLNRASQYISLLIRDSKLSDSATYLCVVNLLSNQGG KLIFGQGTELSVKPNIQNPDPAVYQLRDSKSSDKSVCLFTD FDSQTNVSQSKDSDVYITDKTVLDMRSMDFKSNSAVAWS NKSDFACANAFNNSIIPEDTFFPSPESSCDVKLVEKSFETDT NLNFQNLSVIGFRILLLKVAGFNLLMTLRLWSS | 513 |
| TCR-E, β chain | MGCRLLCCAVLCLLGAGELVPMETGVTQTPRHLVMGMT NKKSLKCEQHLGHNAMYWYKQSAKKPLELMFVYSLEER VENNSVPSRFSPECPNSSHLFLHLHTLQPEDSALYLCASSQ DYLVSNEKLFFGSGTQLSVLEDLKNVFPPEVAVFEPSEAEI SHTQKATLVCLATGFYPDHVELSWWVNGKEVHSGVSTDP QPLKEQPALNDSRYCLSSRLRVSATFWQNPRNHFRCQVQF YGLSENDEWTQDRAKPVTQIVSAEAWGRADCGFTSESYQ QGVLSATILYEILLGKATLYAVLVSALVLMAMVKRKDSR G | 514 |
| TCR-F (β-linker-α configuration) | MLSPDLPDSAWNTRLLCHVMLCLLGAVSVAAGVIQSPRH LIKEKRETATLKCYPIPRHDTVYWYQQGPGQDPQFLISFYE KMQSDKGSIPDRFSAQQFSDYHSELNMSSLELGDSALYFC ASSLRGGLEKLFFGSGTQLSVLEDLNKVFPPEVAVFEPSEA EISHTQKATLVCLATGFFPDHVELSWWVNGKEVHSGVCT DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKD FGSGATNFSLLKQAGDVEENPGPMSLSSLLKVVTASLWLG PGIAQKITQTQPGMFVQEKEAVTLDCTYDTSDPSYGLFWY KQPSSGEMIFLIYQGSYDQQNATEGRYSLNFQKARKSANL VISASQLGDSAMYFCAISGNTPLVFGKGTRLSVIANIQNPD PAVYQLRDSKSSDKSVCLFTDFDSQTNVSQSKDSDVYITD KCVLDMRSMDFKSNSAVAWSNKSDFACANAFNNSIIPED TFFPSPESSCDVKLVEKSFETDTNLNFQNLSVIGFRILLLKV AGFNLLMTLRLWSS | 515 |
| TCR-F, α chain | MSLSSLLKVVTASLWLGPGIAQKITQTQPGMFVQEKEAVT LDCTYDTSDPSYGLFWYKQPSSGEMIFLIYQGSYDQQNAT EGRYSLNFQKARKSANLVISASQLGDSAMYFCAISGNTPL VFGKGTRLSVIANIQNPDPAVYQLRDSKSSDKSVCLFTDFD SQTNVSQSKDSDVYITDKCVLDMRSMDFKSNSAVAWSNK SDFACANAFNNSIIPEDTFFPSPESSCDVKLVEKSFETDTNL NFQNLSVIGFRILLLKVAGFNLLMTLRLWSS | 516 |
| TCR-F, β chain | MLSPDLPDSAWNTRLLCHVMLCLLGAVSVAAGVIQSPRH LIKEKRETATLKCYPIPRHDTVYWYQQGPGQDPQFLISFYE KMQSDKGSIPDRFSAQQFSDYHSELNMSSLELGDSALYFC ASSLRGGLEKLFFGSGTQLSVLEDLNKVFPPEVAVFEPSEA EISHTQKATLVCLATGFFPDHVELSWWVNGKEVHSGVCT DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKD F | 517 |

TABLE 4-continued

| TCR ID | Amino Acid Sequence | SEQ ID NO: |
|---|---|---|
| TCR-G (β-linker-α configuration) | MGTRLLCWAALCLLGAELTEAGVAQSPRYKIIEKRQSVAF WCNPISGHATLYWYQQILGQGPKLLIQFQNNGVVDDSQLP KDRFSAERLKGVDSTLKIQPAKLEDSAVYLCASSLYRGEQ YFGPGTRLTVTEDLKNVFPPEVAVFEPSEAEISHTQKATLV CLATGFYPDHVELSWWVNGKEVHSGVCTDPQPLKEQPAL NDSRYCLSSRLRVSATFWQNPRNHFRCQVQFYGLSENDE WTQDRAKPVTQIVSAEAWGRADCGFTSESYQQGVLSATI LYEILLGKATLYAVLVSALVLMAMVKRKDSRGGSGATNF SLLKQAGDVEENPGPMAMLLGASVLILWLQPDWVNSQQ KNDDQQVKQNSPSLSVQEGRISILNCDYTNSMFDYFLWY KKYPAEGPTFLISISSIKDKNEDGRFTVFLNKSAKHLSLHIV PSQPGDSAVYFCAARGQGNLIFGKGTKLSVKPNIQNPDPA VYQLRDSKSSDKSVCLFTDFDSQTNVSQSKDSDVYITDKC VLDMRSMDFKSNSAVAWSNKSDFACANAFNNSIIPEDTFF PSPESSCDVKLVEKSFETDTNLNFQNLSVIGFRILLLKVAGF NLLMTLRLWSS | 518 |
| TCR-G, α chain (amino acid sequence) | MAMLLGASVLILWLQPDWVNSQQKNDDQQVKQNSPSLS VQEGRISILNCDYTNSMFDYFLWYKKYPAEGPTFLISISSIK DKNEDGRFTVFLNKSAKHLSLHIVPSQPGDSAVYFCAARG QGNLIFGKGTKLSVKPNIQNPDPAVYQLRDSKSSDKSVCL FTDFDSQTNVSQSKDSDVYITDKCVLDMRSMDFKSNSAV AWSNKSDFACANAFNNSIIPEDTFFPSPESSCDVKLVEKSF ETDTNLNFQNLSVIGFRILLLKVAGFNLLMTLRLWSS | 519 |
| TCR-G, β chain (amino acid sequence) | MGTRLLCWAALCLLGAELTEAGVAQSPRYKIIEKRQSVAF WCNPISGHATLYWYQQILGQGPKLLIQFQNNGVVDDSQLP KDRFSAERLKGVDSTLKIQPAKLEDSAVYLCASSLYRGEQ YFGPGTRLTVTEDLKNVFPPEVAVFEPSEAEISHTQKATLV CLATGFYPDHVELSWWVNGKEVHSGVCTDPQPLKEQPAL NDSRYCLSSRLRVSATFWQNPRNHFRCQVQFYGLSENDE WTQDRAKPVTQIVSAEAWGRADCGFTSESYQQGVLSATI LYEILLGKATLYAVLVSALVLMAMVKRKDSRG | 520 |
| TCR-H (β-linker-α configuration) | MSLGLLCCGAFSLLWAGPVNAGVTQTPKFRVLKTGQSMT LLCAQDMNHEYMYWYRQDPGMGLRLIHYSVGEGTTAKG EVPDGYNVSRLKKQNFLLGLESAAPSQTSVYFCASRGYHR LNNEQFFGPGTRLTVLEDLKNVFPPEVAVFEPSEAEISHTQ KATLVCLATGFYPDHVELSWWVNGKEVHSGVCTDPQPL KEQPALNDSRYCLSSRLRVSATFWQNPRNHFRCQVQFYG LSENDEWTQDRAKPVTQIVSAEAWGRADCGFTSESYQQG VLSATILYEILLGKATLYAVLVSALVLMAMVKRKDSRGGS GATNFSLLKQAGDVEENPGPMISLRVLLVILWLQLSWVW SGGGSWSHPQFEKGGGSGGGSGGSAWSHPQFEKQRKEVE QDPGPFNVPEGATVAFNCTYSNSASQSFFWYRQDCRKEPK LLMSVYSSGNEDGRFTAQLNRASQYISLLIRDSKLSDSATY LCVVKPDPGAGSYQLTFGKGTKLSVIPNIQNPDPAVYQLR DSKSSDKSVCLFTDFDSQTNVSQSKDSDVYITDKCVLDMR SMDFKSNSAVAWSNKSDFACANAFNNSIIPEDTFFPSPESS CDVKLVEKSFETDTNLNFQNLSVIGFRILLLKVAGFNLLMT LRLWSS | 521 |
| TCR-H, α chain (amino acid sequence) | MISLRVLLVILWLQLSWVWSGGGSWSHPQFEKGGGSGGG SGGSAWSHPQFEKQRKEVEQDPGPFNVPEGATVAFNCTY SNSASQSFFWYRQDCRKEPKLLMSVYSSGNEDGRFTAQL NRASQYISLLIRDSKLSDSATYLCVVKPDPGAGSYQLTFGK GTKLSVIPNIQNPDPAVYQLRDSKSSDKSVCLFTDFDSQTN VSQSKDSDVYITDKCVLDMRSMDFKSNSAVAWSNKSDFA CANAFNNSIIPEDTFFPSPESSCDVKLVEKSFETDTNLNFQN LSVIGFRILLLKVAGFNLLMTLRLWSS | 522 |
| TCR-H, β chain (amino acid sequence) | MSLGLLCCGAFSLLWAGPVNAGVTQTPKFRVLKTGQSMT LLCAQDMNHEYMYWYRQDPGMGLRLIHYSVGEGTTAKG EVPDGYNVSRLKKQNFLLGLESAAPSQTSVYFCASRGYHR LNNEQFFGPGTRLTVLEDLKNVFPPEVAVFEPSEAEISHTQ KATLVCLATGFYPDHVELSWWVNGKEVHSGVCTDPQPL KEQPALNDSRYCLSSRLRVSATFWQNPRNHFRCQVQFYG LSENDEWTQDRAKPVTQIVSAEAWGRADCGFTSESYQQG VLSATILYEILLGKATLYAVLVSALVLMAMVKRKDSRG | 523 |

Complementarity determining regions (CDRs) exist within variable domains, e.g., of TCRs and antibodies. There are three CDRs in each of the variable domains of TCR alpha and TCR beta, which are designated CDR1, CDR2 and CDR3 for each of the variable domains. The exact boundaries of these CDRs may be defined according to known methods, see, e.g., Kabat et al., "Sequences of Proteins of Immunological Interest" and Dunbar et al., "ANARCI: antigen receptor numbering and receptor classification," which provide a residue numbering system applicable to a variable domain as well as residue boundaries defining the three CDRs. Other CDR definitions methods may produce CDRs that overlap with the Kabat-based CDRs and are shortened or lengthened in light of prediction or experimental findings that particular residues or groups of residues or even entire CDRs do not significantly impact antigen binding. The CDRs herein may be defined according to any of these methods.

The one or more sequences may insert, e.g., undergo integration, into a locus such as TRAC, TRBC1, and/or TRBC2. In some embodiments, the one or more genes insert, e.g., undergo integration, into the TRAC locus. The one or more genes may be provided in a form operably linked to a heterologous promoter, such as an EF-1α promoter. Alternatively, the one or more genes may be provided such that they are configured to be expressed from an endogenous promoter upon integration, e.g., the TRAC, TRBC1, or TRBC2 promoter. The one or more genes may comprise a translational fusion of two or more polypeptides linked by a self-cleaving sequence. This approach can be helpful where coding sequences for a multi-chain receptor (e.g., T-cell receptor) are provided and it is desired to use a single promoter (whether endogenous or heterologous) to drive expression of the receptor. As such, the activity of the promoter results in an mRNA comprising a continuous coding sequence including the amino acids of a plurality of receptor chains that is translated into a polypeptide that undergoes cleavage to provide the individual receptor chains.

The one or more sequences may be delivered by any appropriate means, e.g., transfection, lipid nanoparticle, electroporation, microinjection, or viral vector. In some embodiments, a viral vector such as an adeno-associated virus vector is used.

IV. Additional Exemplary Embodiments

The following additional exemplary embodiments are provided.

Embodiment 001. A method of altering a DNA sequence within the TRBC1 and/or TRBC2 gene, comprising delivering a composition to a cell, wherein the composition comprises:
- a. a guide RNA comprising a sequence chosen from:
  - i. a guide sequence selected from SEQ ID NOs: 1-89;
  - ii. at least 17, 18, 19, or 20 contiguous nucleotides of a sequence selected from SEQ ID NOs: 1-89;
  - iii. a guide sequence that is at least 99%, 98%, 97%, 96%, 95%, 94%, 93%, 92%, 91%, or 90% identical to a sequence selected from SEQ ID NOs: 1-89;
  - iv. a guide sequence comprising any one of SEQ ID Nos: 1-24; and
  - v. a guide sequence comprising any one of SEQ ID Nos: 1-6; or
- b. a nucleic acid encoding a guide RNA of (a.); and optionally
- c. an RNA-guided DNA binding agent or a nucleic acid encoding an RNA-guided DNA binding agent.

Embodiment 002. A method of reducing the expression of the TRBC1 and/or TRBC2 gene comprising delivering a composition to a cell, wherein the composition comprises:
- a. a guide RNA comprising a sequence chosen from:
  - i. a guide sequence selected from SEQ ID NOs: 1-89;
  - ii. at least 17, 18, 19, or 20 contiguous nucleotides of a sequence selected from SEQ ID NOs: 1-89;
  - iii. a guide sequence that is at least 99%, 98%, 97%, 96%, 95%, 94%, 93%, 92%, 91%, or 90% identical to a sequence selected from SEQ ID NOs: 1-89;
  - iv. a guide sequence comprising any one of SEQ ID Nos: 1-24; and
  - v. a guide sequence comprising any one of SEQ ID Nos: 1-6; or
- b. a nucleic acid encoding a guide RNA of (a.); and optionally
- c. an RNA-guided DNA binding agent or a nucleic acid encoding an RNA-guided DNA binding agent.

Embodiment 003. A method of immunotherapy comprising administering a composition to a subject, an autologous cell thereof, and/or an allogeneic cell, wherein the composition comprises:
- a. a guide RNA comprising a sequence chosen from:
  - i. a guide sequence selected from SEQ ID NOs: 1-89;
  - ii. at least 17, 18, 19, or 20 contiguous nucleotides of a sequence selected from SEQ ID NOs: 1-89;
  - iii. a guide sequence that is at least 99%, 98%, 97%, 96%, 95%, 94%, 93%, 92%, 91%, or 90% identical to a sequence selected from SEQ ID NOs: 1-89;
  - iv. a guide sequence comprising any one of SEQ ID Nos: 1-24; and
  - v. a guide sequence comprising any one of SEQ ID Nos: 1-6; or
- b. a nucleic acid encoding a guide RNA of (a.); and optionally
- c. an RNA-guided DNA binding agent or nucleic acid encoding an RNA-guided DNA binding agent.

Embodiment 004. A method of altering a DNA sequence within the TRAC gene, comprising delivering a composition to a cell, wherein the composition comprises:
- a. a guide RNA comprising a sequence chosen from:
  - i. a guide sequence selected from SEQ ID NOs: 90-178;
  - ii. at least 17, 18, 19, or 20 contiguous nucleotides of a sequence selected from SEQ ID NOs: 90-178;
  - iii. a guide sequence that is at least 99%, 98%, 97%, 96%, 95%, 94%, 93%, 92%, 91%, or 90% identical to a sequence selected from SEQ ID NOs: 90-178;
  - iv. a guide sequence comprising any one of SEQ ID Nos: 90-113; and
  - v. a guide sequence comprising any one of SEQ ID Nos: 90-95; or
- b. a nucleic acid encoding a guide RNA of (a.); and optionally
- c. an RNA-guided DNA binding agent or a nucleic acid encoding an RNA-guided DNA binding agent.

Embodiment 005. A method of reducing the expression of the TRAC gene comprising delivering a composition to a cell, wherein the composition comprises:

a. a guide RNA comprising a sequence chosen from:
   i. a guide sequence selected from SEQ ID NOs: 90-178;
   ii. at least 17, 18, 19, or 20 contiguous nucleotides of a sequence selected from SEQ ID NOs: 90-178;
   iii. a guide sequence that is at least 99%, 98%, 97%, 96%, 95%, 94%, 93%, 92%, 91%, or 90% identical to a sequence selected from SEQ ID NOs: 90-178;
   iv. a guide sequence comprising any one of SEQ ID Nos: 90-113; and
   v. a guide sequence comprising any one of SEQ ID Nos: 90-95; or
b. a nucleic acid encoding a guide RNA of (a.); and optionally
c. an RNA-guided DNA binding agent or a nucleic acid encoding an RNA-guided DNA binding agent.

Embodiment 006. A method of immunotherapy comprising administering a composition to a subject, an autologous cell thereof, and/or an allogeneic cell, wherein the composition comprises:
a. a guide RNA comprising a sequence chosen from:
   i. a guide sequence selected from SEQ ID NOs: 90-178;
   ii. at least 17, 18, 19, or 20 contiguous nucleotides of a sequence selected from SEQ ID NOs: 90-178;
   iii. a guide sequence that is at least 99%, 98%, 97%, 96%, 95%, 94%, 93%, 92%, 91%, or 90% identical to a sequence selected from SEQ ID NOs: 90-178;
   iv. a guide sequence comprising any one of SEQ ID Nos: 90-113; and
   v. a guide sequence comprising any one of SEQ ID Nos: 90-95; or
b. a nucleic acid encoding a guide RNA of (a.); and optionally
c. an RNA-guided DNA binding agent or nucleic acid encoding an RNA-guided DNA binding agent.

Embodiment 007. A method of altering a DNA sequence within the TRBC1, TRBC2 and/or TRAC genes, comprising delivering to a cell a first guide RNA, a second guide RNA and optionally an RNA-guided DNA binding agent or a nucleic acid encoding an RNA-guided DNA binding agent, wherein the first guide RNA comprises a sequence chosen from:
i. a guide sequence selected from SEQ ID NOs: 1-89;
ii. at least 17, 18, 19, or 20 contiguous nucleotides of a sequence selected from SEQ ID NOs: 1-89;
iii. a guide sequence that is at least 99%, 98%, 97%, 96%, 95%, 94%, 93%, 92%, 91%, or 90% identical to a sequence selected from SEQ ID NOs: 1-89;
iv. a guide sequence comprising any one of SEQ ID Nos: 1-24; and
v. a guide sequence comprising any one of SEQ ID Nos: 1-6, and
wherein the second guide RNA comprises a sequence chosen from:
i. a guide sequence selected from SEQ ID NOs: 90-178;
ii. at least 17, 18, 19, or 20 contiguous nucleotides of a sequence selected from SEQ ID NOs: 90-178;
iii. a guide sequence that is at least 99%, 98%, 97%, 96%, 95%, 94%, 93%, 92%, 91%, or 90% identical to a sequence selected from SEQ ID NOs: 90-178;
iv. a guide sequence comprising any one of SEQ ID Nos: 90-113; and
v. a guide sequence comprising any one of SEQ ID Nos: 90-95.

Embodiment 008. A method of reducing the expression of the TRBC1, TRBC2 and/or TRAC genes, comprising delivering to a cell a first guide RNA, a second guide RNA and optionally an RNA-guided DNA binding agent or a nucleic acid encoding an RNA-guided DNA binding agent, wherein the first guide RNA comprises a sequence chosen from:
i. a guide sequence selected from SEQ ID NOs: 1-89;
ii. at least 17, 18, 19, or 20 contiguous nucleotides of a sequence selected from SEQ ID NOs: 1-89;
iii. a guide sequence that is at least 99%, 98%, 97%, 96%, 95%, 94%, 93%, 92%, 91%, or 90% identical to a sequence selected from SEQ ID NOs: 1-89;
iv. a guide sequence comprising any one of SEQ ID Nos: 1-24; and
v. a guide sequence comprising any one of SEQ ID Nos: 1-6, and
wherein the second guide RNA comprises a sequence chosen from:
i. a guide sequence selected from SEQ ID NOs: 90-178;
ii. at least 17, 18, 19, or 20 contiguous nucleotides of a sequence selected from SEQ ID NOs: 90-178;
iii. a guide sequence that is at least 99%, 98%, 97%, 96%, 95%, 94%, 93%, 92%, 91%, or 90% identical to a sequence selected from SEQ ID NOs: 90-178;
iv. a guide sequence comprising any one of SEQ ID Nos: 90-113; and
v. a guide sequence comprising any one of SEQ ID Nos: 90-95.

Embodiment 009. A method of immunotherapy comprising administering a composition to a subject, an autologous cell thereof, or an allogeneic cell, wherein the composition comprises: a first guide RNA, a second guide RNA, and optionally an RNA-guided DNA binding agent or a nucleic acid encoding an RNA-guided DNA binding agent, wherein the first guide RNA comprises a sequence chosen from:
i. a guide sequence selected from SEQ ID NOs: 1-89;
ii. at least 17, 18, 19, or 20 contiguous nucleotides of a sequence selected from SEQ ID NOs: 1-89;
iii. a guide sequence that is at least 99%, 98%, 97%, 96%, 95%, 94%, 93%, 92%, 91%, or 90% identical to a sequence selected from SEQ ID NOs: 1-89;
iv. a guide sequence comprising any one of SEQ ID Nos: 1-24; and
v. a guide sequence comprising any one of SEQ ID Nos: 1-6, and
wherein the second guide RNA comprises a sequence chosen from:
i. a guide sequence selected from SEQ ID NOs: 90-178;
ii. at least 17, 18, 19, or 20 contiguous nucleotides of a sequence selected from SEQ ID NOs: 90-178;
iii. a guide sequence that is at least 99%, 98%, 97%, 96%, 95%, 94%, 93%, 92%, 91%, or 90% identical to a sequence selected from SEQ ID NOs: 90-178;
iv. a guide sequence comprising any one of SEQ ID Nos: 90-113; and
v. a guide sequence comprising any one of SEQ ID Nos: 90-95.

Embodiment 010. The method of any one of the preceding Embodiments, wherein an RNA-guided DNA binding agent or nucleic acid encoding an RNA-guided DNA binding agent is administered.

Embodiment 011. A composition comprising:
a. a guide RNA comprising
   i. a guide sequence selected from SEQ ID NOs: 1-89; or ii. at least 17, 18, 19, or 20 contiguous nucleotides of a sequence selected from SEQ ID NOs: 1-89; or iii. a guide sequence that is at least 99%, 98%, 97%, 96%, 95%, 94%, 93%, 92%, 91%, or 90% identical to a sequence selected from SEQ ID NOs: 1-89; or iv. a guide sequence comprising any one of SEQ ID Nos: 1-24; or v. a guide sequence comprising any one of SEQ ID Nos: 1-6; and optionally b. an RNA-guided DNA binding agent or nucleic acid encoding an RNA-guided DNA binding agent.

Embodiment 012. The composition of Embodiment 11, for use in altering a DNA sequence within the TRBC1 and/or TRBC2 genes in a cell.

Embodiment 013. The composition of Embodiment 11, for use in reducing the expression of the TRBC1 and/or TRBC2 genes in a cell.

Embodiment 014. A composition comprising:

a. a guide RNA comprising:

i. a guide sequence selected from SEQ ID NOs: 90-178; or ii. at least 17, 18, 19, or 20 contiguous nucleotides of a sequence selected from SEQ ID NOs: 90-178; or iii. a guide sequence that is at least 99%, 98%, 97%, 96%, 95%, 94%, 93%, 92%, 91%, or 90% identical to a sequence selected from SEQ ID NOs: 90-178; or iv. a guide sequence comprising any one of SEQ ID Nos: 90-113; or v. a guide sequence comprising any one of SEQ ID Nos: 90-95; and optionally b. an RNA-guided DNA binding agent or nucleic acid encoding an RNA-guided DNA binding agent.

Embodiment 015. The composition of Embodiment 14, for use in altering a DNA sequence within the TRAC gene in a cell.

Embodiment 016. The composition of Embodiment 14, for use in reducing the expression of the TRAC gene in a cell.

Embodiment 017. The composition of any of Embodiments 11-17, for use in immunotherapy of a subject.

Embodiment 018. A cell, altered by the method of any of Embodiments 1-10.

Embodiment 019. The cell according to Embodiment 18, wherein the cell is altered ex vivo.

Embodiment 020. The cell according to Embodiment 18 or Embodiment 19, wherein the cell is a T cell.

Embodiment 021. The cell according to any of Embodiments 18-20, wherein the cell is a $CD3^+$, $CD4^+$, and/or $CD8^+$ T cell.

Embodiment 022. The cell according to any of Embodiments 18-21, wherein the cell is a mammalian, primate, or human cell.

Embodiment 023. The cell according to any of Embodiments 18-21, for use in immunotherapy of a subject.

Embodiment 024. The method of any of Embodiments 1-10, further comprising:

a. inducing a double-stranded break (DSB) within the TRBC1, TRBC2 and/or TRAC genes in a cell and/or subject; or b. inducing a single-stranded break (SSB) within the TRBC1, TRBC2 and/or TRAC genes in a cell and/or a subject; or c. reducing the expression of the TRBC1, TRBC2 and/or TRAC genes in a cell and/or subject.

Embodiment 025. The method or composition for use in any one of Embodiments 1-3, 7-13, wherein the composition results in editing of the TRBC1 and/or TRBC2 genes.

Embodiment 026. The method or composition for use in any one of Embodiments 4-10 and 14-17, wherein the composition results in editing of the TRAC gene.

Embodiment 027. The method or composition for use in any one of Embodiments 7-10, wherein the composition results in editing of a TRBC gene and the TRAC gene.

Embodiment 028. The method or composition for use in any of Embodiments 25-27, wherein the editing is calculated as a percentage of the population that is edited (percent editing or percent indels).

Embodiment 029. The method or composition for use in any of Embodiments 25-28, wherein the percent editing is between 10 and 100% of the population, e.g. between 30 and 99% of the population.

Embodiment 030. The method or composition for use in any of Embodiments 25-29, wherein the percent editing is between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the population.

Embodiment 031. The method or composition of any one of Embodiments 1-3, 7-13, 17, and 24-30, wherein the composition comprises a sgRNA comprising a. any one of SEQ ID NOs: 179-184; or b. a guide sequence selected from any one of SEQ ID NOs: 1-89; or c. a guide sequence selected from SEQ ID Nos: 1-24; or d. a guide sequence selected from SEQ ID Nos: 1-6.

Embodiment 032. The method or composition of any one of Embodiments 4-10, 14-17, and 24-30, wherein the composition comprises a sgRNA comprising a. a guide sequence selected from any one of SEQ ID NOs: 90-178; or b. a guide sequence selected from SEQ ID Nos: 90-113; or c. a guide sequence selected from SEQ ID Nos: 90-95.

Embodiment 033. The method or composition of any one of Embodiments 1-17 and 24-32, wherein the target sequence is in exon 1, 2, 3, or 4 of the TRBC1, TRBC2 and/or TRAC genes.

Embodiment 034. The method or composition of Embodiment 33, wherein the target sequence is in exon 1 of the TRBC1, TRBC2 and/or TRAC genes.

Embodiment 035. The method or composition of Embodiment 33, wherein the target sequence is in exon 2 of the TRBC1, TRBC2 and/or TRAC genes.

Embodiment 036. The method or composition of Embodiment 33, wherein the target sequence is in exon 3 of the TRBC1, TRBC2 and/or TRAC genes.

Embodiment 037. The method or composition of Embodiment 33, wherein the target sequence is in exon 4 of the TRBC1, TRBC2 and/or TRAC genes.

Embodiment 038. The method or composition of any of Embodiments 33-37, wherein the target sequence is in the human TRBC1, TRBC2 and/or TRAC genes.

Embodiment 039. The method or composition of any one of Embodiments 1-17 or 24-38, wherein the guide sequence is complementary to a target sequence in the positive strand of TRBC1, TRBC2 and/or TRAC.

Embodiment 040. The method or composition of any one of Embodiments 1-17 or 24-38, wherein the guide sequence is complementary to a target sequence in the negative strand of the TRBC1, TRBC2 and/or TRAC genes.

Embodiment 041. The method or composition of any one of Embodiments 1-17 or 24-40, wherein the first guide sequence is complementary to a first target sequence in the positive strand of the TRBC1, TRBC2 and/or TRAC genes, and wherein the composition further comprises a second guide sequence that is complementary to a second target sequence in the negative strand of the TRBC1, TRBC2 and/or TRAC genes.

Embodiment 042. The method or composition of any one of any one of Embodiments 1-17 or 24-41, wherein the guide RNA comprises a guide sequence selected from any one of SEQ ID Nos 1-178 and further comprises a nucleotide sequence of SEQ ID NO: 200, wherein the nucleotides of SEQ ID NO: 200 follow the guide sequence at its 3' end.

Embodiment 043. The method or composition of any one of any one of Embodiments 1-17 or 24-41, wherein the guide RNA comprises a guide sequence selected from any one of SEQ ID Nos 1-178 and further comprises a nucleotide sequence of SEQ ID NO: 201, wherein the nucleotides of SEQ ID NO: 201 follow the guide sequence at its 3' end.

Embodiment 044. The method or composition of any one of any one of Embodiments 1-17 or 24-43, wherein the guide RNA is modified according to the pattern of SEQ ID NO: 300, wherein the N's are collectively any one of the guide sequences of Table 1 (SEQ ID Nos 1-89).

Embodiment 045. The method or composition of Embodiment 44, wherein each N in SEQ ID NO: 300 is any natural or non-natural nucleotide, wherein the N's form the guide sequence, and the guide sequence targets Cas9 to the TRBC1, TRBC2 and/or TRAC genes.

Embodiment 046. The method or composition of any one of Embodiments 42-44, wherein the sgRNA comprises a guide sequence that is at least 99%, 98%, 97%, 96%, 95%, 94%, 93%, 92%, 91%, or 90% identical to a sequence selected from SEQ ID Nos: 1-89.

Embodiment 047. The method or composition any one of any one of Embodiments 1-17 or 24-46, wherein the guide RNA comprises at least one modification.

Embodiment 048. The method or composition of Embodiment 47, wherein the at least one modification includes a 2'-O-methyl (2'-O-Me) modified nucleotide.

Embodiment 049. The method or composition of Embodiment 47 or 48, comprising a phosphorothioate (PS) bond between nucleotides.

Embodiment 050. The method or composition of any one of Embodiments 47-49, comprising a 2'-fluoro (2'-F) modified nucleotide.

Embodiment 051. The method or composition of any one of Embodiments 47-50, comprising a modification at one or more of the first five nucleotides at the 5' end of the guide RNA.

Embodiment 052. The method or composition of any one of Embodiments 47-51, comprising a modification at one or more of the last five nucleotides at the 3' end of the guide RNA.

Embodiment 053. The method or composition of any one of Embodiments 47-52, comprising a PS bond between the first four nucleotides of the guide RNA.

Embodiment 054. The method or composition of any one of Embodiments 47-53, comprising a PS bond between the last four nucleotides of the guide RNA.

Embodiment 055. The method or composition of any one of Embodiments 47-54, comprising a 2'-O-Me modified nucleotide at the first three nucleotides at the 5' end of the guide RNA.

Embodiment 056. The method or composition of any one of Embodiments 47-55, comprising a 2'-O-Me modified nucleotide at the last three nucleotides at the 3' end of the guide RNA.

Embodiment 057. The method or composition of any one of Embodiments 47-56, wherein the guide RNA comprises the modified nucleotides of SEQ ID NO: 300.

Embodiment 058. The method or composition any one of any one of Embodiments 1-17 or 24-57, wherein the composition further comprises a pharmaceutically acceptable excipient.

Embodiment 059. The method or composition of any one of Embodiments 1-58, wherein the guide RNA is associated with a lipid nanoparticle (LNP).

Embodiment 060. The method or composition of Embodiment 59, wherein the LNP comprises a biodegradable, ionizable lipid.

Embodiment 061. The method or composition of Embodiment 60, wherein the ionizable lipid is (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate.

Embodiment 062. The method or composition of any one of Embodiments 59-61, wherein the LNP comprises a neutral lipid.

Embodiment 063. The method or composition of Embodiment 62, wherein the neutral lipid is DSPC.

Embodiment 064. The method or composition of any one of Embodiments 59-63, wherein the LNP comprises a helper lipid.

Embodiment 065. The method or composition of Embodiment 64, wherein the helper lipid is cholesterol.

Embodiment 066. The method or composition of any one of Embodiments 59-65, wherein the LNP comprises a stealth lipid.

Embodiment 067. The method or composition of Embodiment 66, wherein the stealth lipid is PEG2k-DMG.

Embodiment 068. The method or composition any one of any one of Embodiments 1-17 or 24-66, wherein the composition further comprises an RNA-guided DNA binding agent.

Embodiment 069. The method or composition any one of any one of Embodiments 1-17 or 24-68, wherein the composition further comprises an mRNA that encodes an RNA-guided DNA binding agent.

Embodiment 070. The method or composition of Embodiment 68 or 69, wherein the RNA-guided DNA binding agent is Cas9.

Embodiment 071. The method or composition any one of any one of Embodiments 1-17 or 24-70, wherein the composition is a pharmaceutical formulation and further comprises a pharmaceutically acceptable carrier.

Embodiment 072. The method, composition or cell of any one of Embodiments 1-3, 7-13, 17, 24, 25, 27-31, or 33-71, wherein the sequence selected from SEQ ID NOs: 1-89 is SEQ ID NO: 1.

Embodiment 073. The method or composition of any one of Embodiments 1-3, 7-13, 17, 24, 25, 27-31, or 33-71, wherein the sequence selected from SEQ ID NOs: 1-89 is SEQ ID NO: 2.

Embodiment 074. The method or composition of any one of Embodiments 1-3, 7-13, 17, 24, 25, 27-31, or 33-71, wherein the sequence selected from SEQ ID NOs: 1-89 is SEQ ID NO: 3.

Embodiment 075. The method or composition of any one of Embodiments 1-3, 7-13, 17, 24, 25, 27-31, or 33-71, wherein the sequence selected from SEQ ID NOs: 1-89 is SEQ ID NO: 4.

Embodiment 076. The method or composition of any one of Embodiments 1-3, 7-13, 17, 24, 25, 27-31, or 33-71, wherein the sequence selected from SEQ ID NOs: 1-89 is SEQ ID NO: 5.

Embodiment 077. The method or composition of any one of Embodiments 1-3, 7-13, 17, 24, 25, 27-31, or 33-71, wherein the sequence selected from SEQ ID NOs: 1-89 is SEQ ID NO: 6.

Embodiment 078. The method or composition of any one of Embodiments 1-3, 7-13, 17, 24, 25, 27-31, or 33-71, wherein the sequence selected from SEQ ID NOs: 1-89 is SEQ ID NO: 7.

Embodiment 079. The method or composition of any one of Embodiments 1-3, 7-13, 17, 24, 25, 27-31, or 33-71, wherein the sequence selected from SEQ ID NOs: 1-89 is SEQ ID NO: 8.

Embodiment 080. The method or composition of any one of Embodiments 1-3, 7-13, 17, 24, 25, 27-31, or 33-71, wherein the sequence selected from SEQ ID NOs: 1-89 is SEQ ID NO: 9.

Embodiment 081. The method or composition of any one of Embodiments 1-3, 7-13, 17, 24, 25, 27-31, or 33-71, wherein the sequence selected from SEQ ID NOs: 1-89 is SEQ ID NO: 10.

Embodiment 082. The method or composition of any one of Embodiments 1-3, 7-13, 17, 24, 25, 27-31, or 33-71, wherein the sequence selected from SEQ ID NOs: 1-89 is SEQ ID NO: 11.

Embodiment 083. The method or composition of any one of Embodiments 1-3, 7-13, 17, 24, 25, 27-31, or 33-71, wherein the sequence selected from SEQ ID NOs: 1-89 is SEQ ID NO: 12.

Embodiment 084. The method or composition of any one of Embodiments 1-3, 7-13, 17, 24, 25, 27-31, or 33-71, wherein the sequence selected from SEQ ID NOs: 1-89 is SEQ ID NO: 13.

Embodiment 085. The method or composition of any one of Embodiments 1-3, 7-13, 17, 24, 25, 27-31, or 33-71, wherein the sequence selected from SEQ ID NOs: 1-89 is SEQ ID NO: 14.

Embodiment 086. The method or composition of any one of Embodiments 1-3, 7-13, 17, 24, 25, 27-31, or 33-71, wherein the sequence selected from SEQ ID NOs: 1-89 is SEQ ID NO: 15.

Embodiment 087. The method or composition of any one of Embodiments 1-3, 7-13, 17, 24, 25, 27-31, or 33-71, wherein the sequence selected from SEQ ID NOs: 1-89 is SEQ ID NO: 16.

Embodiment 088. The method or composition of any one of Embodiments 1-3, 7-13, 17, 24, 25, 27-31, or 33-71, wherein the sequence selected from SEQ ID NOs: 1-89 is SEQ ID NO: 17.

Embodiment 089. The method or composition of any one of Embodiments 1-3, 7-13, 17, 24, 25, 27-31, or 33-71, wherein the sequence selected from SEQ ID NOs: 1-89 is SEQ ID NO: 18.

Embodiment 090. The method or composition of any one of Embodiments 1-3, 7-13, 17, 24, 25, 27-31, or 33-71, wherein the sequence selected from SEQ ID NOs: 1-89 is SEQ ID NO: 19.

Embodiment 091. The method or composition of any one of Embodiments 1-3, 7-13, 17, 24, 25, 27-31, or 33-71, wherein the sequence selected from SEQ ID NOs: 1-89 is SEQ ID NO: 20.

Embodiment 092. The method or composition of any one of Embodiments 1-3, 7-13, 17, 24, 25, 27-31, or 33-71, wherein the sequence selected from SEQ ID NOs: 1-89 is SEQ ID NO: 21.

Embodiment 093. The method or composition of any one of Embodiments 1-3, 7-13, 17, 24, 25, 27-31, or 33-71, wherein the sequence selected from SEQ ID NOs: 1-89 is SEQ ID NO: 22.

Embodiment 094. The method or composition of any one of Embodiments 1-3, 7-13, 17, 24, 25, 27-31, or 33-71, wherein the sequence selected from SEQ ID NOs: 1-89 is SEQ ID NO: 23.

Embodiment 095. The method or composition of any one of Embodiments 1-3, 7-13, 17, 24, 25, 27-31, or 33-71, wherein the sequence selected from SEQ ID NOs: 1-89 is SEQ ID NO: 24.

Embodiment 096. The method or composition of any one of Embodiments 1-3, 7-13, 17, 24, 25, 27-31, or 33-71, wherein the sequence selected from SEQ ID NOs: 1-89 is SEQ ID NO: 25.

Embodiment 097. The method or composition of any one of Embodiments 1-3, 7-13, 17, 24, 25, 27-31, or 33-71, wherein the sequence selected from SEQ ID NOs: 1-89 is SEQ ID NO: 26.

Embodiment 098. The method or composition of any one of Embodiments 1-3, 7-13, 17, 24, 25, 27-31, or 33-71, wherein the sequence selected from SEQ ID NOs: 1-89 is SEQ ID NO: 27.

Embodiment 099. The method or composition of any one of Embodiments 1-3, 7-13, 17, 24, 25, 27-31, or 33-71, wherein the sequence selected from SEQ ID NOs: 1-89 is SEQ ID NO: 28.

Embodiment 100. The method or composition of any one of Embodiments 1-3, 7-13, 17, 24, 25, 27-31, or 33-71, wherein the sequence selected from SEQ ID NOs: 1-89 is SEQ ID NO: 29.

Embodiment 101. The method or composition of any one of Embodiments 1-3, 7-13, 17, 24, 25, 27-31, or 33-71, wherein the sequence selected from SEQ ID NOs: 1-89 is SEQ ID NO: 30.

Embodiment 102. The method or composition of any one of Embodiments 1-3, 7-13, 17, 24, 25, 27-31, or 33-71, wherein the sequence selected from SEQ ID NOs: 1-89 is SEQ ID NO: 31.

Embodiment 103. The method or composition of any one of Embodiments 1-3, 7-13, 17, 24, 25, 27-31, or 33-71, wherein the sequence selected from SEQ ID NOs: 1-89 is SEQ ID NO: 32.

Embodiment 104. The method or composition of any one of Embodiments 1-3, 7-13, 17, 24, 25, 27-31, or 33-71, wherein the sequence selected from SEQ ID NOs: 1-89 is SEQ ID NO: 33.

Embodiment 105. The method or composition of any one of Embodiments 1-3, 7-13, 17, 24, 25, 27-31, or 33-71, wherein the sequence selected from SEQ ID NOs: 1-89 is SEQ ID NO: 34.

Embodiment 106. The method or composition of any one of Embodiments 1-3, 7-13, 17, 24, 25, 27-31, or 33-71, wherein the sequence selected from SEQ ID NOs: 1-89 is SEQ ID NO: 35.

Embodiment 107. The method or composition of any one of Embodiments 1-3, 7-13, 17, 24, 25, 27-31, or 33-71, wherein the sequence selected from SEQ ID NOs: 1-89 is SEQ ID NO: 36.

Embodiment 108. The method or composition of any one of Embodiments 1-3, 7-13, 17, 24, 25, 27-31, or 33-71, wherein the sequence selected from SEQ ID NOs: 1-89 is SEQ ID NO: 37.

Embodiment 109. The method or composition of any one of Embodiments 1-3, 7-13, 17, 24, 25, 27-31, or 33-71, wherein the sequence selected from SEQ ID NOs: 1-89 is SEQ ID NO: 38.

Embodiment 110. The method or composition of any one of Embodiments 1-3, 7-13, 17, 24, 25, 27-31, or 33-71, wherein the sequence selected from SEQ ID NOs: 1-89 is SEQ ID NO: 39.

Embodiment 111. The method or composition of any one of Embodiments 1-3, 7-13, 17, 24, 25, 27-31, or 33-71, wherein the sequence selected from SEQ ID NOs: 1-89 is SEQ ID NO: 40.

Embodiment 112. The method or composition of any one of Embodiments 1-3, 7-13, 17, 24, 25, 27-31, or 33-71, wherein the sequence selected from SEQ ID NOs: 1-89 is SEQ ID NO: 41.

Embodiment 113. The method or composition of any one of Embodiments 1-3, 7-13, 17, 24, 25, 27-31, or 33-71, wherein the sequence selected from SEQ ID NOs: 1-89 is SEQ ID NO: 42.

Embodiment 114. The method or composition of any one of Embodiments 1-3, 7-13, 17, 24, 25, 27-31, or 33-71, wherein the sequence selected from SEQ ID NOs: 1-89 is SEQ ID NO: 43.

Embodiment 115. The method or composition of any one of Embodiments 1-3, 7-13, 17, 24, 25, 27-31, or 33-71, wherein the sequence selected from SEQ ID NOs: 1-89 is SEQ ID NO: 44.

Embodiment 116. The method or composition of any one of Embodiments 1-3, 7-13, 17, 24, 25, 27-31, or 33-71, wherein the sequence selected from SEQ ID NOs: 1-89 is SEQ ID NO: 45.

Embodiment 117. The method or composition of any one of Embodiments 1-3, 7-13, 17, 24, 25, 27-31, or 33-71, wherein the sequence selected from SEQ ID NOs: 1-89 is SEQ ID NO: 46.

Embodiment 118. The method or composition of any one of Embodiments 1-3, 7-13, 17, 24, 25, 27-31, or 33-71, wherein the sequence selected from SEQ ID NOs: 1-89 is SEQ ID NO: 47.

Embodiment 119. The method or composition of any one of Embodiments 1-3, 7-13, 17, 24, 25, 27-31, or 33-71, wherein the sequence selected from SEQ ID NOs: 1-89 is SEQ ID NO: 48.

Embodiment 120. The method or composition of any one of Embodiments 1-3, 7-13, 17, 24, 25, 27-31, or 33-71, wherein the sequence selected from SEQ ID NOs: 1-89 is SEQ ID NO: 49.

Embodiment 121. The method or composition of any one of Embodiments 1-3, 7-13, 17, 24, 25, 27-31, or 33-71, wherein the sequence selected from SEQ ID NOs: 1-89 is SEQ ID NO: 50.

Embodiment 122. The method or composition of any one of Embodiments 1-3, 7-13, 17, 24, 25, 27-31, or 33-71, wherein the sequence selected from SEQ ID NOs: 1-89 is SEQ ID NO: 51.

Embodiment 123. The method or composition of any one of Embodiments 1-3, 7-13, 17, 24, 25, 27-31, or 33-71, wherein the sequence selected from SEQ ID NOs: 1-89 is SEQ ID NO: 52.

Embodiment 124. The method or composition of any one of Embodiments 1-3, 7-13, 17, 24, 25, 27-31, or 33-71, wherein the sequence selected from SEQ ID NOs: 1-89 is SEQ ID NO: 53.

Embodiment 125. The method or composition of any one of Embodiments 1-3, 7-13, 17, 24, 25, 27-31, or 33-71, wherein the sequence selected from SEQ ID NOs: 1-89 is SEQ ID NO: 54.

Embodiment 126. The method or composition of any one of Embodiments 1-3, 7-13, 17, 24, 25, 27-31, or 33-71, wherein the sequence selected from SEQ ID NOs: 1-89 is SEQ ID NO: 55.

Embodiment 127. The method or composition of any one of Embodiments 1-3, 7-13, 17, 24, 25, 27-31, or 33-71, wherein the sequence selected from SEQ ID NOs: 1-89 is SEQ ID NO: 56.

Embodiment 128. The method or composition of any one of Embodiments 1-3, 7-13, 17, 24, 25, 27-31, or 33-71, wherein the sequence selected from SEQ ID NOs: 1-89 is SEQ ID NO: 57.

Embodiment 129. The method or composition of any one of Embodiments 1-3, 7-13, 17, 24, 25, 27-31, or 33-71, wherein the sequence selected from SEQ ID NOs: 1-89 is SEQ ID NO: 58.

Embodiment 130. The method or composition of any one of Embodiments 1-3, 7-13, 17, 24, 25, 27-31, or 33-71, wherein the sequence selected from SEQ ID NOs: 1-89 is SEQ ID NO: 59.

Embodiment 131. The method or composition of any one of Embodiments 1-3, 7-13, 17, 24, 25, 27-31, or 33-71, wherein the sequence selected from SEQ ID NOs: 1-89 is SEQ ID NO: 60.

Embodiment 132. The method or composition of any one of Embodiments 1-3, 7-13, 17, 24, 25, 27-31, or 33-71, wherein the sequence selected from SEQ ID NOs: 1-89 is SEQ ID NO: 61.

Embodiment 133. The method or composition of any one of Embodiments 1-3, 7-13, 17, 24, 25, 27-31, or 33-71, wherein the sequence selected from SEQ ID NOs: 1-89 is SEQ ID NO: 62.

Embodiment 134. The method or composition of any one of Embodiments 1-3, 7-13, 17, 24, 25, 27-31, or 33-71, wherein the sequence selected from SEQ ID NOs: 1-89 is SEQ ID NO: 63.

Embodiment 135. The method or composition of any one of Embodiments 1-3, 7-13, 17, 24, 25, 27-31, or 33-71, wherein the sequence selected from SEQ ID NOs: 1-89 is SEQ ID NO: 64.

Embodiment 136. The method or composition of any one of Embodiments 1-3, 7-13, 17, 24, 25, 27-31, or 33-71, wherein the sequence selected from SEQ ID NOs: 1-89 is SEQ ID NO: 65.

Embodiment 137. The method or composition of any one of Embodiments 1-3, 7-13, 17, 24, 25, 27-31, or 33-71, wherein the sequence selected from SEQ ID NOs: 1-89 is SEQ ID NO: 66.

Embodiment 138. The method or composition of any one of Embodiments 1-3, 7-13, 17, 24, 25, 27-31, or 33-71, wherein the sequence selected from SEQ ID NOs: 1-89 is SEQ ID NO: 67.

Embodiment 139. The method or composition of any one of Embodiments 1-3, 7-13, 17, 24, 25, 27-31, or 33-71, wherein the sequence selected from SEQ ID NOs: 1-89 is SEQ ID NO: 68.

Embodiment 140. The method or composition of any one of Embodiments 1-3, 7-13, 17, 24, 25, 27-31, or 33-71, wherein the sequence selected from SEQ ID NOs: 1-89 is SEQ ID NO: 69.

Embodiment 141. The method or composition of any one of Embodiments 1-3, 7-13, 17, 24, 25, 27-31, or 33-71, wherein the sequence selected from SEQ ID NOs: 1-89 is SEQ ID NO: 70.

Embodiment 142. The method or composition of any one of Embodiments 1-3, 7-13, 17, 24, 25, 27-31, or 33-71, wherein the sequence selected from SEQ ID NOs: 1-89 is SEQ ID NO: 71.

Embodiment 143. The method or composition of any one of Embodiments 1-3, 7-13, 17, 24, 25, 27-31, or 33-71, wherein the sequence selected from SEQ ID NOs: 1-89 is SEQ ID NO: 72.

Embodiment 144. The method or composition of any one of Embodiments 1-3, 7-13, 17, 24, 25, 27-31, or 33-71, wherein the sequence selected from SEQ ID NOs: 1-89 is SEQ ID NO: 73.

Embodiment 145. The method or composition of any one of Embodiments 1-3, 7-13, 17, 24, 25, 27-31, or 33-71, wherein the sequence selected from SEQ ID NOs: 1-89 is SEQ ID NO: 74.

Embodiment 146. The method or composition of any one of Embodiments 1-3, 7-13, 17, 24, 25, 27-31, or 33-71, wherein the sequence selected from SEQ ID NOs: 1-89 is SEQ ID NO: 75.

Embodiment 147. The method or composition of any one of Embodiments 1-3, 7-13, 17, 24, 25, 27-31, or 33-71, wherein the sequence selected from SEQ ID NOs: 1-89 is SEQ ID NO: 76.

Embodiment 148. The method or composition of any one of Embodiments 1-3, 7-13, 17, 24, 25, 27-31, or 33-71, wherein the sequence selected from SEQ ID NOs: 1-89 is SEQ ID NO: 77.

Embodiment 149. The method or composition of any one of Embodiments 1-3, 7-13, 17, 24, 25, 27-31, or 33-71, wherein the sequence selected from SEQ ID NOs: 1-89 is SEQ ID NO: 78.

Embodiment 150. The method or composition of any one of Embodiments 1-3, 7-13, 17, 24, 25, 27-31, or 33-71, wherein the sequence selected from SEQ ID NOs: 1-89 is SEQ ID NO: 79.

Embodiment 151. The method or composition of any one of Embodiments 1-3, 7-13, 17, 24, 25, 27-31, or 33-71, wherein the sequence selected from SEQ ID NOs: 1-89 is SEQ ID NO: 80.

Embodiment 152. The method or composition of any one of Embodiments 1-3, 7-13, 17, 24, 25, 27-31, or 33-71, wherein the sequence selected from SEQ ID NOs: 1-89 is SEQ ID NO: 81.

Embodiment 153. The method or composition of any one of Embodiments 1-3, 7-13, 17, 24, 25, 27-31, or 33-71, wherein the sequence selected from SEQ ID NOs: 1-89 is SEQ ID NO: 82.

Embodiment 154. The method or composition of any one of Embodiments 1-3, 7-13, 17, 24, 25, 27-31, or 33-71, wherein the sequence selected from SEQ ID NOs: 1-89 is SEQ ID NO: 83.

Embodiment 155. The method or composition of any one of Embodiments 1-3, 7-13, 17, 24, 25, 27-31, or 33-71, wherein the sequence selected from SEQ ID NOs: 1-89 is SEQ ID NO: 84.

Embodiment 156. The method or composition of any one of Embodiments 1-3, 7-13, 17, 24, 25, 27-31, or 33-71, wherein the sequence selected from SEQ ID NOs: 1-89 is SEQ ID NO: 85.

Embodiment 157. The method or composition of any one of Embodiments 1-3, 7-13, 17, 24, 25, 27-31, or 33-71, wherein the sequence selected from SEQ ID NOs: 1-89 is SEQ ID NO: 86.

Embodiment 158. The method or composition of any one of Embodiments 1-3, 7-13, 17, 24, 25, 27-31, or 33-71, wherein the sequence selected from SEQ ID NOs: 1-89 is SEQ ID NO: 87.

Embodiment 159. The method or composition of any one of Embodiments 1-3, 7-13, 17, 24, 25, 27-31, or 33-71, wherein the sequence selected from SEQ ID NOs: 1-89 is SEQ ID NO: 88.

Embodiment 160. The method or composition of any one of Embodiments 1-3, 7-13, 17, 24, 25, 27-31, or 33-71, wherein the sequence selected from SEQ ID NOs: 1-89 is SEQ ID NO: 89.

Embodiment 161. The method or composition of any one of Embodiments 4-10, 14-17, 24, 26-30, or 32-71, wherein the sequence selected from SEQ ID NOs: 90-178 is SEQ ID NO: 90.

Embodiment 162. The method or composition of any one of Embodiments 4-10, 14-17, 24, 26-30, or 32-71, wherein the sequence selected from SEQ ID NOs: 90-178 is SEQ ID NO: 91.

Embodiment 163. The method or composition of any one of Embodiments 4-10, 14-17, 24, 26-30, or 32-71, wherein the sequence selected from SEQ ID NOs: 90-178 is SEQ ID NO: 92.

Embodiment 164. The method or composition of any one of Embodiments 4-10, 14-17, 24, 26-30, or 32-71, wherein the sequence selected from SEQ ID NOs: 90-178 is SEQ ID NO: 93.

Embodiment 165. The method or composition of any one of Embodiments 4-10, 14-17, 24, 26-30, or 32-71, wherein the sequence selected from SEQ ID NOs: 90-178 is SEQ ID NO: 94.

Embodiment 166. The method or composition of any one of Embodiments 4-10, 14-17, 24, 26-30, or 32-71, wherein the sequence selected from SEQ ID NOs: 90-178 is SEQ ID NO: 95.

Embodiment 167. The method or composition of any one of Embodiments 4-10, 14-17, 24, 26-30, or 32-71, wherein the sequence selected from SEQ ID NOs: 90-178 is SEQ ID NO: 96.

Embodiment 168. The method or composition of any one of Embodiments 4-10, 14-17, 24, 26-30, or 32-71, wherein the sequence selected from SEQ ID NOs: 90-178 is SEQ ID NO: 97.

Embodiment 169. The method or composition of any one of Embodiments 4-10, 14-17, 24, 26-30, or 32-71, wherein the sequence selected from SEQ ID NOs: 90-178 is SEQ ID NO: 98.

Embodiment 170. The method or composition of any one of Embodiments 4-10, 14-17, 24, 26-30, or 32-71, wherein the sequence selected from SEQ ID NOs: 90-178 is SEQ ID NO: 99.

Embodiment 171. The method or composition of any one of Embodiments 4-10, 14-17, 24, 26-30, or 32-71, wherein the sequence selected from SEQ ID NOs: 90-178 is SEQ ID NO: 100.

Embodiment 172. The method or composition of any one of Embodiments 4-10, 14-17, 24, 26-30, or 32-71, wherein the sequence selected from SEQ ID NOs: 90-178 is SEQ ID NO: 101.

Embodiment 173. The method or composition of any one of Embodiments 4-10, 14-17, 24, 26-30, or 32-71, wherein the sequence selected from SEQ ID NOs: 90-178 is SEQ ID NO: 102.

Embodiment 174. The method or composition of any one of Embodiments 4-10, 14-17, 24, 26-30, or 32-71, wherein the sequence selected from SEQ ID NOs: 90-178 is SEQ ID NO: 103.

Embodiment 175. The method or composition of any one of Embodiments 4-10, 14-17, 24, 26-30, or 32-71, wherein the sequence selected from SEQ ID NOs: 90-178 is SEQ ID NO: 104.

Embodiment 176. The method or composition of any one of Embodiments 4-10, 14-17, 24, 26-30, or 32-71, wherein the sequence selected from SEQ ID NOs: 90-178 is SEQ ID NO: 105.

Embodiment 177. The method or composition of any one of Embodiments 4-10, 14-17, 24, 26-30, or 32-71, wherein the sequence selected from SEQ ID NOs: 90-178 is SEQ ID NO: 106.

Embodiment 178. The method or composition of any one of Embodiments 4-10, 14-17, 24, 26-30, or 32-71, wherein the sequence selected from SEQ ID NOs: 90-178 is SEQ ID NO: 107.

Embodiment 179. The method or composition of any one of Embodiments 4-10, 14-17, 24, 26-30, or 32-71, wherein the sequence selected from SEQ ID NOs: 90-178 is SEQ ID NO: 108.

Embodiment 180. The method or composition of any one of Embodiments 4-10, 14-17, 24, 26-30, or 32-71, wherein the sequence selected from SEQ ID NOs: 90-178 is SEQ ID NO: 109.

Embodiment 181. The method or composition of any one of Embodiments 4-10, 14-17, 24, 26-30, or 32-71, wherein the sequence selected from SEQ ID NOs: 90-178 is SEQ ID NO: 110.

Embodiment 182. The method or composition of any one of Embodiments 4-10, 14-17, 24, 26-30, or 32-71, wherein the sequence selected from SEQ ID NOs: 90-178 is SEQ ID NO: 111.

Embodiment 183. The method or composition of any one of Embodiments 4-10, 14-17, 24, 26-30, or 32-71, wherein the sequence selected from SEQ ID NOs: 90-178 is SEQ ID NO: 112.

Embodiment 184. The method or composition of any one of Embodiments 4-10, 14-17, 24, 26-30, or 32-71, wherein the sequence selected from SEQ ID NOs: 90-178 is SEQ ID NO: 113.

Embodiment 185. The method or composition of any one of Embodiments 4-10, 14-17, 24, 26-30, or 32-71, wherein the sequence selected from SEQ ID NOs: 90-178 is SEQ ID NO: 114.

Embodiment 186. The method or composition of any one of Embodiments 4-10, 14-17, 24, 26-30, or 32-71, wherein the sequence selected from SEQ ID NOs: 90-178 is SEQ ID NO: 115.

Embodiment 187. The method or composition of any one of Embodiments 4-10, 14-17, 24, 26-30, or 32-71, wherein the sequence selected from SEQ ID NOs: 90-178 is SEQ ID NO: 116.

Embodiment 188. The method or composition of any one of Embodiments 4-10, 14-17, 24, 26-30, or 32-71, wherein the sequence selected from SEQ ID NOs: 90-178 is SEQ ID NO: 117.

Embodiment 189. The method or composition of any one of Embodiments 4-10, 14-17, 24, 26-30, or 32-71, wherein the sequence selected from SEQ ID NOs: 90-178 is SEQ ID NO: 118.

Embodiment 190. The method or composition of any one of Embodiments 4-10, 14-17, 24, 26-30, or 32-71, wherein the sequence selected from SEQ ID NOs: 90-178 is SEQ ID NO: 119.

Embodiment 191. The method or composition of any one of Embodiments 4-10, 14-17, 24, 26-30, or 32-71, wherein the sequence selected from SEQ ID NOs: 90-178 is SEQ ID NO: 120.

Embodiment 192. The method or composition of any one of Embodiments 4-10, 14-17, 24, 26-30, or 32-71, wherein the sequence selected from SEQ ID NOs: 90-178 is SEQ ID NO: 121.

Embodiment 193. The method or composition of any one of Embodiments 4-10, 14-17, 24, 26-30, or 32-71, wherein the sequence selected from SEQ ID NOs: 90-178 is SEQ ID NO: 122.

Embodiment 194. The method or composition of any one of Embodiments 4-10, 14-17, 24, 26-30, or 32-71, wherein the sequence selected from SEQ ID NOs: 90-178 is SEQ ID NO: 123.

Embodiment 195. The method or composition of any one of Embodiments 4-10, 14-17, 24, 26-30, or 32-71, wherein the sequence selected from SEQ ID NOs: 90-178 is SEQ ID NO: 124.

Embodiment 196. The method or composition of any one of Embodiments 4-10, 14-17, 24, 26-30, or 32-71, wherein the sequence selected from SEQ ID NOs: 90-178 is SEQ ID NO: 125.

Embodiment 197. The method or composition of any one of Embodiments 4-10, 14-17, 24, 26-30, or 32-71, wherein the sequence selected from SEQ ID NOs: 90-178 is SEQ ID NO: 126.

Embodiment 198. The method or composition of any one of Embodiments 4-10, 14-17, 24, 26-30, or 32-71, wherein the sequence selected from SEQ ID NOs: 90-178 is SEQ ID NO: 127.

Embodiment 199. The method or composition of any one of Embodiments 4-10, 14-17, 24, 26-30, or 32-71, wherein the sequence selected from SEQ ID NOs: 90-178 is SEQ ID NO: 128.

Embodiment 200. The method or composition of any one of Embodiments 4-10, 14-17, 24, 26-30, or 32-71, wherein the sequence selected from SEQ ID NOs: 90-178 is SEQ ID NO: 129.

Embodiment 201. The method or composition of any one of Embodiments 4-10, 14-17, 24, 26-30, or 32-71, wherein the sequence selected from SEQ ID NOs: 90-178 is SEQ ID NO: 130.

Embodiment 202. The method or composition of any one of Embodiments 4-10, 14-17, 24, 26-30, or 32-71, wherein the sequence selected from SEQ ID NOs: 90-178 is SEQ ID NO: 131.

Embodiment 203. The method or composition of any one of Embodiments 4-10, 14-17, 24, 26-30, or 32-71, wherein the sequence selected from SEQ ID NOs: 90-178 is SEQ ID NO: 132.

Embodiment 204. The method or composition of any one of Embodiments 4-10, 14-17, 24, 26-30, or 32-71, wherein the sequence selected from SEQ ID NOs: 90-178 is SEQ ID NO: 133.

Embodiment 205. The method or composition of any one of Embodiments 4-10, 14-17, 24, 26-30, or 32-71, wherein the sequence selected from SEQ ID NOs: 90-178 is SEQ ID NO: 134.

Embodiment 206. The method or composition of any one of Embodiments 4-10, 14-17, 24, 26-30, or 32-71, wherein the sequence selected from SEQ ID NOs: 90-178 is SEQ ID NO: 135.

Embodiment 207. The method or composition of any one of Embodiments 4-10, 14-17, 24, 26-30, or 32-71, wherein the sequence selected from SEQ ID NOs: 90-178 is SEQ ID NO: 136.

Embodiment 208. The method or composition of any one of Embodiments 4-10, 14-17, 24, 26-30, or 32-71, wherein the sequence selected from SEQ ID NOs: 90-178 is SEQ ID NO: 137.

Embodiment 209. The method or composition of any one of Embodiments 4-10, 14-17, 24, 26-30, or 32-71, wherein the sequence selected from SEQ ID NOs: 90-178 is SEQ ID NO: 138.

Embodiment 210. The method or composition of any one of Embodiments 4-10, 14-17, 24, 26-30, or 32-71, wherein the sequence selected from SEQ ID NOs: 90-178 is SEQ ID NO: 139.

Embodiment 211. The method or composition of any one of Embodiments 4-10, 14-17, 24, 26-30, or 32-71, wherein the sequence selected from SEQ ID NOs: 90-178 is SEQ ID NO: 140.

Embodiment 212. The method or composition of any one of Embodiments 4-10, 14-17, 24, 26-30, or 32-71, wherein the sequence selected from SEQ ID NOs: 90-178 is SEQ ID NO: 141.

Embodiment 213. The method or composition of any one of Embodiments 4-10, 14-17, 24, 26-30, or 32-71, wherein the sequence selected from SEQ ID NOs: 90-178 is SEQ ID NO: 142.

Embodiment 214. The method or composition of any one of Embodiments 4-10, 14-17, 24, 26-30, or 32-71, wherein the sequence selected from SEQ ID NOs: 90-178 is SEQ ID NO: 143.

Embodiment 215. The method or composition of any one of Embodiments 4-10, 14-17, 24, 26-30, or 32-71, wherein the sequence selected from SEQ ID NOs: 90-178 is SEQ ID NO: 144.

Embodiment 216. The method or composition of any one of Embodiments 4-10, 14-17, 24, 26-30, or 32-71, wherein the sequence selected from SEQ ID NOs: 90-178 is SEQ ID NO: 145.

Embodiment 217. The method or composition of any one of Embodiments 4-10, 14-17, 24, 26-30, or 32-71, wherein the sequence selected from SEQ ID NOs: 90-178 is SEQ ID NO: 146.

Embodiment 218. The method or composition of any one of Embodiments 4-10, 14-17, 24, 26-30, or 32-71, wherein the sequence selected from SEQ ID NOs: 90-178 is SEQ ID NO: 147.

Embodiment 219. The method or composition of any one of Embodiments 4-10, 14-17, 24, 26-30, or 32-71, wherein the sequence selected from SEQ ID NOs: 90-178 is SEQ ID NO: 148.

Embodiment 220. The method or composition of any one of Embodiments 4-10, 14-17, 24, 26-30, or 32-71, wherein the sequence selected from SEQ ID NOs: 90-178 is SEQ ID NO: 149.

Embodiment 221. The method or composition of any one of Embodiments 4-10, 14-17, 24, 26-30, or 32-71, wherein the sequence selected from SEQ ID NOs: 90-178 is SEQ ID NO: 150.

Embodiment 222. The method or composition of any one of Embodiments 4-10, 14-17, 24, 26-30, or 32-71, wherein the sequence selected from SEQ ID NOs: 90-178 is SEQ ID NO: 151.

Embodiment 223. The method or composition of any one of Embodiments 4-10, 14-17, 24, 26-30, or 32-71, wherein the sequence selected from SEQ ID NOs: 90-178 is SEQ ID NO: 152.

Embodiment 224. The method or composition of any one of Embodiments 4-10, 14-17, 24, 26-30, or 32-71, wherein the sequence selected from SEQ ID NOs: 90-178 is SEQ ID NO: 153.

Embodiment 225. The method or composition of any one of Embodiments 4-10, 14-17, 24, 26-30, or 32-71, wherein the sequence selected from SEQ ID NOs: 90-178 is SEQ ID NO: 154.

Embodiment 226. The method or composition of any one of Embodiments 4-10, 14-17, 24, 26-30, or 32-71, wherein the sequence selected from SEQ ID NOs: 90-178 is SEQ ID NO: 155.

Embodiment 227. The method or composition of any one of Embodiments 4-10, 14-17, 24, 26-30, or 32-71, wherein the sequence selected from SEQ ID NOs: 90-178 is SEQ ID NO: 156.

Embodiment 228. The method or composition of any one of Embodiments 4-10, 14-17, 24, 26-30, or 32-71, wherein the sequence selected from SEQ ID NOs: 90-178 is SEQ ID NO: 157.

Embodiment 229. The method or composition of any one of Embodiments 4-10, 14-17, 24, 26-30, or 32-71, wherein the sequence selected from SEQ ID NOs: 90-178 is SEQ ID NO: 158.

Embodiment 230. The method or composition of any one of Embodiments 4-10, 14-17, 24, 26-30, or 32-71, wherein the sequence selected from SEQ ID NOs: 90-178 is SEQ ID NO: 159.

Embodiment 231. The method or composition of any one of Embodiments 4-10, 14-17, 24, 26-30, or 32-71, wherein the sequence selected from SEQ ID NOs: 90-178 is SEQ ID NO: 160.

Embodiment 232. The method or composition of any one of Embodiments 4-10, 14-17, 24, 26-30, or 32-71, wherein the sequence selected from SEQ ID NOs: 90-178 is SEQ ID NO: 161.

Embodiment 233. The method or composition of any one of Embodiments 4-10, 14-17, 24, 26-30, or 32-71, wherein the sequence selected from SEQ ID NOs: 90-178 is SEQ ID NO: 162.

Embodiment 234. The method or composition of any one of Embodiments 4-10, 14-17, 24, 26-30, or 32-71, wherein the sequence selected from SEQ ID NOs: 90-178 is SEQ ID NO: 163.

Embodiment 235. The method or composition of any one of Embodiments 4-10, 14-17, 24, 26-30, or 32-71, wherein the sequence selected from SEQ ID NOs: 90-178 is SEQ ID NO: 164.

Embodiment 236. The method or composition of any one of Embodiments 4-10, 14-17, 24, 26-30, or 32-71, wherein the sequence selected from SEQ ID NOs: 90-178 is SEQ ID NO: 165.

Embodiment 237. The method or composition of any one of Embodiments 4-10, 14-17, 24, 26-30, or 32-71, wherein the sequence selected from SEQ ID NOs: 90-178 is SEQ ID NO: 166.

Embodiment 238. The method or composition of any one of Embodiments 4-10, 14-17, 24, 26-30, or 32-71, wherein the sequence selected from SEQ ID NOs: 90-178 is SEQ ID NO: 167.

Embodiment 239. The method or composition of any one of Embodiments 4-10, 14-17, 24, 26-30, or 32-71, wherein the sequence selected from SEQ ID NOs: 90-178 is SEQ ID NO: 168.

Embodiment 240. The method or composition of any one of Embodiments 4-10, 14-17, 24, 26-30, or 32-71, wherein the sequence selected from SEQ ID NOs: 90-178 is SEQ ID NO: 169.

Embodiment 241. The method or composition of any one of Embodiments 4-10, 14-17, 24, 26-30, or 32-71, wherein the sequence selected from SEQ ID NOs: 90-178 is SEQ ID NO: 170.

Embodiment 242. The method or composition of any one of Embodiments 4-10, 14-17, 24, 26-30, or 32-71, wherein the sequence selected from SEQ ID NOs: 90-178 is SEQ ID NO: 171.

Embodiment 243. The method or composition of any one of Embodiments 4-10, 14-17, 24, 26-30, or 32-71, wherein the sequence selected from SEQ ID NOs: 90-178 is SEQ ID NO: 172.

Embodiment 244. The method or composition of any one of Embodiments 4-10, 14-17, 24, 26-30, or 32-71, wherein the sequence selected from SEQ ID NOs: 90-178 is SEQ ID NO: 173.

Embodiment 245. The method or composition of any one of Embodiments 4-10, 14-17, 24, 26-30, or 32-71, wherein the sequence selected from SEQ ID NOs: 90-178 is SEQ ID NO: 174.

Embodiment 246. The method or composition of any one of Embodiments 4-10, 14-17, 24, 26-30, or 32-71, wherein the sequence selected from SEQ ID NOs: 90-178 is SEQ ID NO: 175.

Embodiment 247. The method or composition of any one of Embodiments 4-10, 14-17, 24, 26-30, or 32-71, wherein the sequence selected from SEQ ID NOs: 90-178 is SEQ ID NO: 176.

Embodiment 248. The method or composition of any one of Embodiments 4-10, 14-17, 24, 26-30, or 32-71, wherein the sequence selected from SEQ ID NOs: 90-178 is SEQ ID NO: 177.

Embodiment 249. The method or composition of any one of Embodiments 4-10, 14-17, 24, 26-30, or 32-71, wherein the sequence selected from SEQ ID NOs: 90-178 is SEQ ID NO: 178.

Embodiment 250. Use of a composition, formulation or cell of any preceding Embodiment for the preparation of a medicament.

Embodiment 251. A composition, formulation or cell of any preceding Embodiment for use as a medicament.

Embodiment 252. The cell of any of Embodiments 18-23, lacking an endogenous T cell receptor, for preparation of a T cell expressing a non-endogenous T cell receptor.

Embodiment 253. The cell of any of Embodiments 18-23, lacking an endogenous T cell receptor, for preparation of a T cell expressing a CAR.

Embodiment 254. The cell of any of Embodiments 18-23, wherein the altered cell is a $CD3^-$ cell.

Embodiment 255. The cell of any of Embodiments 18-23, wherein the cell is a $CD3^+$ cell before being altered and the altered cell is a $CD3^-$ cell.

Embodiment 256. A population of cells comprising cells of any one of embodiments 18-23, wherein greater than about 50%, greater than about 55%, greater than about 60%, greater than about 65%, greater than about 70%, greater than about 75%, greater than about 80%, greater than about 85%, greater than about 90%, greater than about 95%, greater than about 98%, or greater than about 99% of the altered population are $CD3^-$ cells.

Embodiment 257. The population of embodiment 256, wherein greater than about 90% of the population is $CD3^-$.

Embodiment 258. The population of embodiment 256, wherein greater than about 95% of the population is $CD3^-$.

Embodiment 259. The population of embodiment 256, wherein greater than about 99% of the population is $CD3^-$.

Embodiment 260. A population of cells comprising cells of any one of embodiments 18-23, wherein greater than about 50%, greater than about 55%, greater than about 60%, greater than about 65%, greater than about 70%, greater than about 75%, greater than about 80%, greater than about 85%, greater than about 90%, greater than about 95%, greater than about 98%, or greater than about 99% of the population lacks an endogenous T cell receptor.

Embodiment 261. The population of embodiment 260, wherein greater than about 90% of the population lacks an endogenous T cell receptor.

Embodiment 262. The population of embodiment 260, wherein greater than about 95% of the population lacks an endogenous T cell receptor.

Embodiment 263. The population of embodiment 260, wherein greater than about 99% of the population lacks an endogenous T cell receptor.

Embodiment 264. A population of cells comprising cells of any one of embodiments 18-23, wherein the expression of the TRBC1, TRBC2 and/or TRAC genes in the population has been reduced relative to an unaltered population of the same cell by at least about 50%, at least about 55%, at least about 60%, at least about 65%, at least about 70%, at least about 75%, at least about 80%, at least about 85%, at least about 90%, at least about 95%, at least about 98%, or at least about 99%.

Embodiment 265. The population of embodiment 264, wherein the reduction in the expression of the TRBC1, TRBC2 and/or TRAC genes is at least about 90%.

Embodiment 266. The population of embodiment 264, wherein the reduction in the expression of the TRBC1, TRBC2 and/or TRAC genes is at least about 95%.

Embodiment 267. The population of embodiment 264, wherein the reduction in the expression of the TRBC1, TRBC2 and/or TRAC genes is at least about 99%.

Embodiment 268. The population of any of embodiments 264-267, wherein the reduction is in the expression of the TRBC1 gene.

Embodiment 269. The population of any of embodiments 264-267, wherein the reduction is in the expression of the TRBC2 gene.

Embodiment 270. The population of any of embodiments 264-267, wherein the reduction is in the expression of the TRAC gene.

Embodiment 271. A population of cells comprising cells of any one of embodiments 18-23, wherein between 10 and 100% of the population, e.g. between 30 and 99% of the population, has an indel in the TRBC1, TRBC2 and/or TRAC genes.

Embodiment 272. The population of embodiment 271, wherein between 30 and 35%, 35 and 40%, 40 and 45%, 45 and 50%, 50 and 55%, 55 and 60%, 60 and 65%, 65 and 70%, 70 and 75%, 75 and 80%, 80 and 85%, 85 and 90%, 90 and 95%, or 95 and 99% of the population has an indel in the TRBC1, TRBC2 and/or TRAC genes.

Embodiment 273. The population of embodiments 271 or 272, wherein the indel is in the TRBC1 gene.

Embodiment 274. The population of embodiments 271 or 272, wherein the indel is in the TRBC2 gene.

Embodiment 275. The population of embodiments 271 or 272, wherein the indel is in the TRAC gene.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1: Materials and Methods

Genomic DNA Isolation

HEK293_Cas9 transfected cells were harvested post-transfection at 24 hours. The gDNA was extracted from each well of a 96-well plate using 50 μL/well QuickExtract™ DNA Extraction Solution (Lucigen, Cat. QE09050) according to manufacturer's protocol. DNA samples were subjected to PCR and subsequent NGS analysis, as described herein.

Next-Generation Sequencing ("NGS") and Analysis for On-Target Cleavage Efficiency To quantitatively determine the efficiency of editing at the target location in the genome, deep sequencing was utilized to identify the presence of insertions and deletions introduced by gene editing. PCR primers were designed around the target site within the gene of interest (e.g. TRAC), and the genomic area of interest was amplified. Primer sequence design was done as is standard in the field.

Additional PCR was performed according to the manufacturer's protocols (Illumina) to add chemistry for sequencing. The amplicons were sequenced on an Illumina MiSeq instrument. The reads were aligned to the human reference genome (e.g., hg38) after eliminating those having low quality scores. Reads that overlapped the target region of interest were selected and the number of wild type reads versus the number of reads which contain an insertion or deletion ("indel") was calculated.

The editing percentage (e.g., the "editing efficiency" or "indel percent") is defined as the total number of sequence reads with insertions or deletions ("indels") over the total number of sequence reads, including wild type.

Example 2: TRAC Guide Design and Screening in HEK Cells

Human TRAC Guide Design

Initial guide selection was performed in silico using a human reference genome (e.g., hg38) and user defined genomic regions of interest (e.g., TRAC protein coding exons), for identifying PAMs in the regions of interest. For each identified PAM, analyses were performed and statistics reported. gRNA molecules were further selected and rank-ordered based on a number of criteria known in the art (e.g., GC content, predicted on-target activity, and potential off-target activity).

A total of 88 guide RNAs were designed toward TRAC (ENSG00000277734) targeting the protein exonic coding regions and intron 1. Guide sequences and corresponding genomic coordinates are provided (Table 2).

Guides were screened for editing efficiency in HEK293_Cas9 cells. The human embryonic kidney adenocarcinoma cell line HEK293 constitutively expressing Spy Cas9 ("HEK293_Cas9") was cultured in DMEM media supplemented with 10% fetal bovine serum. Cells were plated at a density of 10,000 cells/well in a 96-well plate about 24 hours prior to transfection (~70% confluent at time of transfection). Cells were transfected in duplicate with Lipofectamine RNAiMAX (ThermoFisher, Cat. 13778150) according to the manufacturer's protocol. Cells were transfected with a lipoplex containing individual guide (25 nM), trRNA (25 nM), Lipofectamine RNAiMAX (0.3 μL/well) and OptiMem. DNA isolation and NGS analysis were performed as described in Example 1. FIG. 1 and Table 5 show indel % at the TRAC locus by these guides in HEK293_Cas9 cells.

TABLE 5

TRAC guide editing in HEK293_Cas9 cells

| SEQ ID NO: | % Indels (Mean) | SD |
|---|---|---|
| 90 | 53.1 | 13 |
| 91 | 51.9 | 5.2 |
| 92 | 29.8 | 15.8 |
| 93 | 35.1 | 16.1 |
| 94 | 55.4 | 9 |
| 96 | 6.6 | 2.3 |
| 97 | 35.3 | 9.8 |
| 98 | 15.6 | 4.2 |
| 99 | 32 | 9.5 |
| 100 | 40 | 14.3 |
| 101 | 17 | 4.1 |
| 102 | 32.9 | 7.8 |
| 103 | 24.8 | 3.1 |
| 104 | 47.2 | 15.7 |
| 105 | 34.7 | 13.9 |

TABLE 5-continued

| TRAC guide editing in HEK293_Cas9 cells | | |
|---|---|---|
| SEQ ID NO: | % Indels (Mean) | SD |
| 106 | 27.4 | 3.8 |
| 107 | 54.9 | 17.8 |
| 108 | 28.2 | 7.9 |
| 109 | 54.4 | 14 |
| 110 | 52.9 | 9.5 |
| 111 | 22.6 | 5 |
| 112 | 46.8 | 15.3 |
| 113 | 41.6 | 10.8 |
| 114 | 0.4 | 0.1 |
| 115 | 26.4 | 9.4 |
| 116 | 22.8 | 3.3 |
| 117 | 8.9 | 1.8 |
| 118 | 0 | 0 |
| 119 | 5.3 | 1.1 |
| 120 | 0.4 | 0.1 |
| 121 | 0.2 | 0.1 |
| 122 | 1.2 | 0.6 |
| 123 | 2.2 | 0.4 |
| 124 | 0.3 | 0.1 |
| 125 | 0.1 | 0 |
| 126 | 0.1 | 0.1 |
| 127 | 0 | 0 |
| 128 | 0.4 | 0.4 |
| 129 | 1.1 | 0.3 |
| 130 | 1.6 | 0.7 |
| 131 | 0.2 | 0.1 |
| 132 | 0.4 | 0.1 |
| 133 | 2.5 | 0.5 |
| 134 | 0.5 | 0.2 |
| 135 | 0.7 | 0.3 |
| 136 | 0.1 | 0.1 |
| 137 | 0.1 | 0.1 |
| 138 | 0.5 | 0.2 |
| 139 | 0.5 | 0.1 |
| 140 | 0.3 | 0.1 |
| 141 | 0.1 | 0 |
| 142 | 0.4 | 0.1 |
| 143 | 0.4 | 0.1 |
| 144 | 1.3 | 0.8 |
| 145 | 0.2 | 0.1 |
| 146 | 0.1 | 0 |
| 147 | 0.1 | 0.1 |
| 148 | 2.5 | 1.2 |
| 149 | 3 | 1 |
| 150 | 0.2 | 0.1 |
| 151 | 0.7 | 0.4 |
| 152 | 0.2 | 0.1 |
| 153 | 0.7 | 0.1 |
| 154 | 0.3 | 0.1 |
| 155 | 0.1 | 0.1 |
| 156 | 0.1 | 0 |
| 157 | 0.1 | 0.1 |
| 158 | 0.1 | 0.1 |
| 159 | 0.2 | 0.1 |
| 160 | 0.1 | 0 |
| 161 | 0.7 | 0.2 |
| 162 | 0.1 | 0.1 |
| 163 | 0.7 | 0 |
| 164 | 0.1 | 0 |
| 165 | 0 | 0 |
| 166 | 0.3 | 0 |
| 167 | 0.3 | 0.3 |
| 168 | 0.1 | 0.1 |
| 169 | 0.5 | 0.2 |
| 170 | 0.2 | 0.1 |
| 171 | 0.2 | 0.1 |
| 172 | 0.2 | 0.1 |
| 173 | 0 | 0 |
| 174 | 0.1 | 0 |
| 175 | 0.1 | 0.1 |
| 176 | 0.1 | 0 |
| 177 | 0.1 | 0.1 |
| 178 | 0.1 | 0 |

Example 3: TRAC Guide Screening in Human CD3$^+$ T Cells

The 24 guides with the highest indel percent editing in HEK293_Cas9 cells from Example 2 were screened for editing efficiency and T-cell receptor (TCR) knockdown in human CD3$^+$ T cells. CD3$^+$ T cells are comprised of multiple T cell populations including CD4$^+$ T helper cells and CD8$^+$ cytotoxic T cells. These cells can be isolated from whole blood or from leuokopheresis samples. T cells can be modified to specifically target cancerous cells and to be less immunogenic, by engineering patient T cells using Cas9-mediated editing. This example describes a basic method used to deliver Cas9 RNP, for example, Cas9 RNP targeting TRAC, in T cells. Only the targeting crRNA in the RNP would need to be changed to adapt this protocol to a different T cell target (e.g., any of those provided herein).

Delivery of RNPs to T Cells

T cells were either obtained commercially (e.g. Human Peripheral Blood CD4$^+$CD45RA$^+$ T Cells, Frozen, Stem Cell Technology, Cat. 70029) or prepared internally from a leukopak. For internal preparation, T cells were first enriched from a leukopak using a commercially available kit (e.g., EasySep™ Human T Cell Isolation Kit, Stem Cell Technology). Enriched T cells were aliquoted and frozen down (at $5\times10^6$/vial) for future use. Vials were subsequently thawed as needed, and activated by addition of 3:1 ratio of CD3/CD28 beads (Dynabeads, Life Technologies) in T cell media (RPMI 1640, FBS, L-glutamine, non-essential amino acids, sodium pyruvate, HEPES buffer, 2-mercaptoethanol and optionally IL2). RNP was generated by pre-annealing individual crRNA and trRNA by mixing equivalent amounts of reagent and incubating at 95° C. for 2 min and cooling to room temperature. The dual guide (dgRNA) consisting of pre-annealed crRNA and trRNA, was incubated with Spy Cas9 protein to form a ribonucleoprotein (RNP) complex. CD3$^+$ T cells were transfected in triplicate with an RNP containing Spy Cas9 (10 nM), individual guide (10 nM) and tracer RNA (10 nM) nucleofected using the P3 Primary Cell 96-well Nucleofector™ Kit (Lonza, Cat. V4SP-3960) using the manufacturer's Amaxa™ 96-well Shuttle™ Protocol for Stimulated Human T Cells. T cell media was added to cells immediately post-nucleofection and cultured for 2 days or more.

Figure 2:
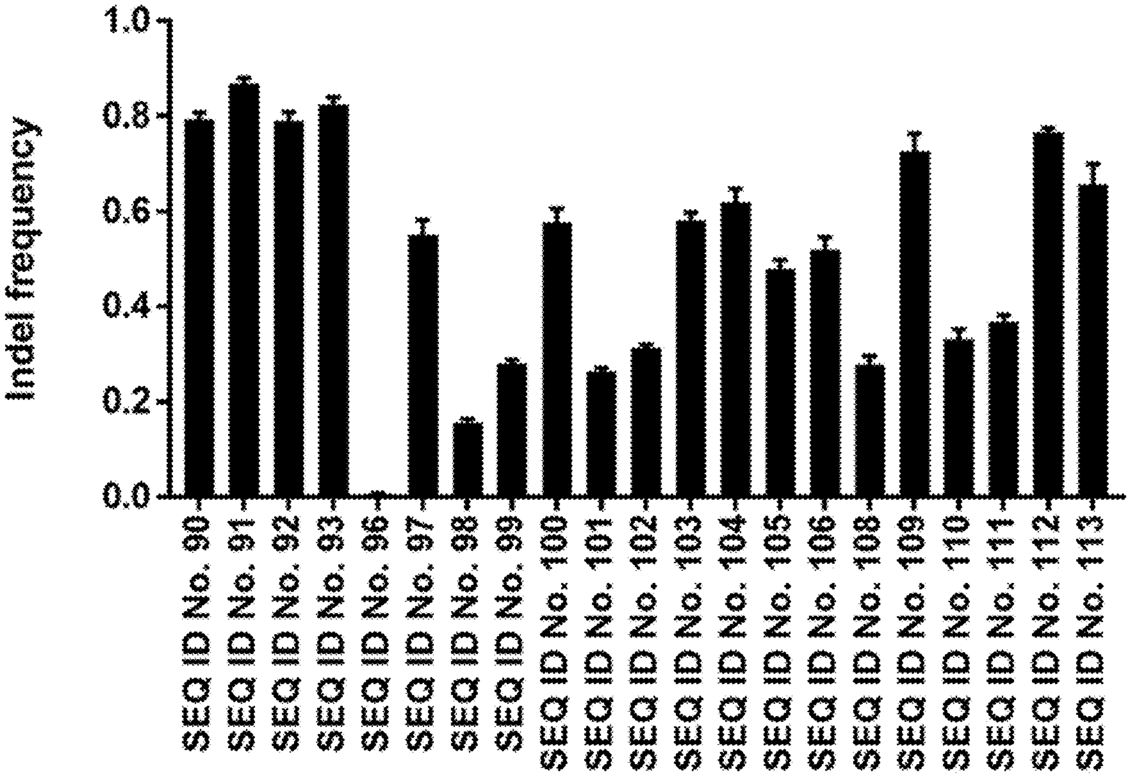
FIG. 2 shows the degree of TRAC editing in human $CD3^+$ T cells.

Two days post nucleofection, genomic DNA was prepared as described in Example 1 and NGS analysis performed. Table 6 and FIG. 2 show results for indel frequency following TRAC editing with various guides in CD3$^+$ T cells.

TABLE 6

| Indel frequency for TRAC editing in human CD3$^+$ T cells | | | |
|---|---|---|---|
| SEQ ID NO: | Indel Frequency | Standard Deviation | Sample Number (n) |
| 90 | 79.3% | 1.5% | 3 |
| 91 | 86.9% | 1.2% | 3 |
| 92 | 79.0% | 1.9% | 3 |
| 93 | 82.6% | 1.4% | 3 |
| 96 | 0.7% | 0.1% | 3 |
| 97 | 55.2% | 3.1% | 3 |
| 98 | 15.5% | 1.0% | 3 |
| 99 | 27.9% | 0.9% | 3 |
| 100 | 57.7% | 3.0% | 3 |
| 101 | 26.2% | 0.8% | 3 |
| 102 | 31.2% | 0.8% | 3 |
| 103 | 58.1% | 1.8% | 3 |
| 104 | 62.0% | 2.8% | 3 |
| 105 | 47.8% | 2.0% | 3 |

TABLE 6-continued

| Indel frequency for TRAC editing in human CD3+ T cells | | | |
|---|---|---|---|
| SEQ ID NO: | Indel Frequency | Standard Deviation | Sample Number (n) |
| 106 | 52.0% | 2.7% | 3 |
| 108 | 27.7% | 1.9% | 3 |
| 109 | 72.7% | 3.7% | 3 |
| 110 | 33.0% | 2.2% | 3 |
| 111 | 36.9% | 1.3% | 3 |
| 112 | 76.7% | 1.0% | 3 |
| 113 | 65.7% | 4.3% | 3 |

Flow Cytometric Analysis of TCR Expression

Figure 3:
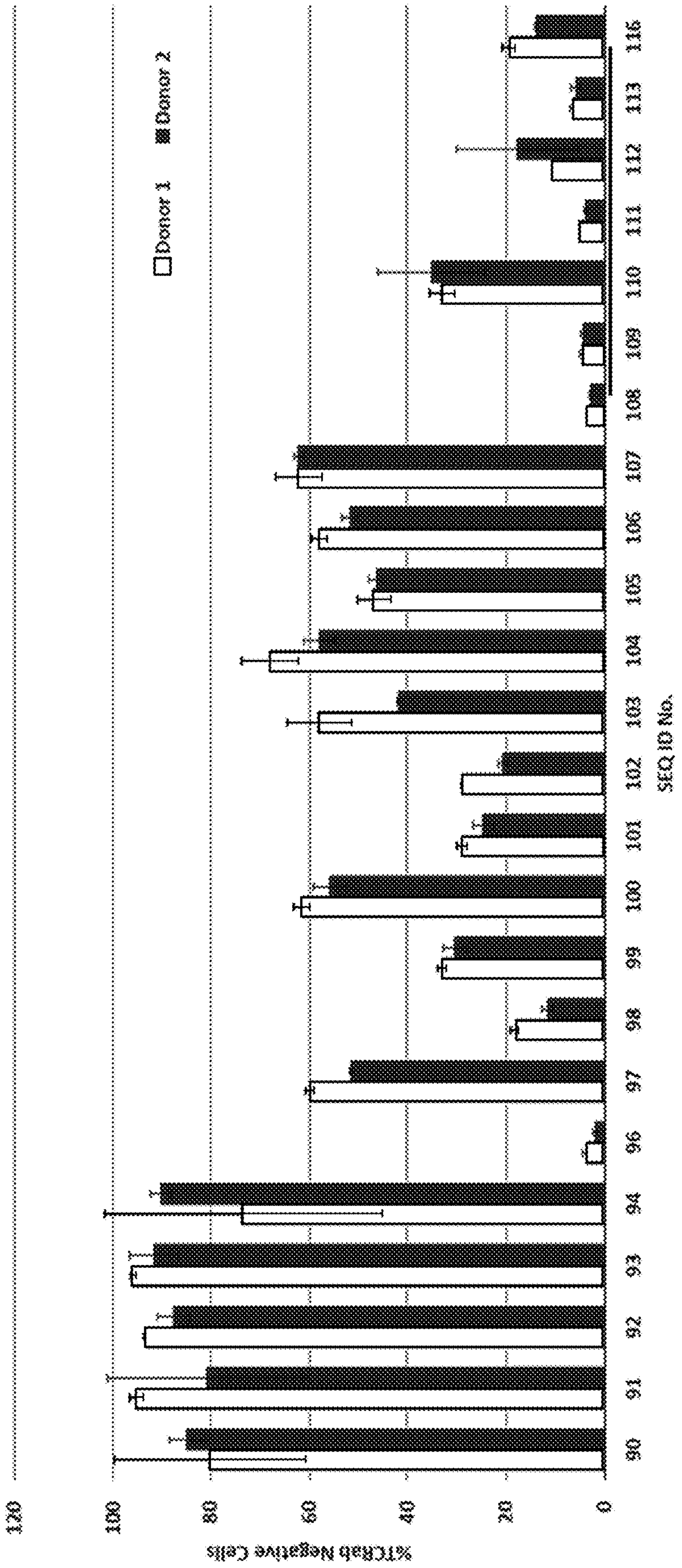
FIG. 3 shows the amount of TCR expression following TRAC editing in human $CD3^+$ T cells.

Expression of the TCR was measured 4 days post nucleofection. Cells were stained with fixable live dead dye (Thermo fisher L34975) and the TCR was detected using Alexa Fluor® 647 anti-human TCR α/β Antibody (Biolegend, Cat. 306714) Cells were incubated with 2 ul of antibody for at least 20 minutes one ice, analyzed by flow cytometery using, for example, Beckman Coulter CytoflexS). Data was analyzed using Flow Jo software. Live cell population was analyzed for TCR loss. The results are shown in Table 7 and FIG. 3.

TABLE 7

| TCR expression after TRAC editing in CD3+ T cells | | | | |
|---|---|---|---|---|
| SEQ ID NO: | Donor 1 - % TCR Negative | Donor 1 - Standard Deviation | Donor 2 - % TCR Negative | Donor 2 - Standard Deviation |
| 90 | 80.2 | 19.5 | 84.9 | 3.6 |
| 91 | 95.3 | 1.4 | 80.7 | 20.5 |
| 92 | 93.5 | 0.3 | 87.6 | 3.4 |
| 93 | 95.9 | 0.6 | 91.7 | 5 |
| 94 | 73.5 | 28.3 | 90.2 | 2.1 |
| 96 | 3.6 | 0.8 | 1.8 | 0.4 |
| 97 | 59.9 | 0.9 | 51.3 | 0.4 |
| 98 | 17.9 | 1.1 | 11.5 | 1.2 |
| 99 | 32.9 | 1.1 | 30.4 | 2.3 |
| 100 | 61.4 | 1.7 | 55.8 | 3.4 |
| 101 | 28.8 | 1.3 | 24.6 | 2 |
| 102 | 28.7 | 0.5 | 20.7 | 1 |
| 103 | 58.2 | 6.4 | 41.6 | 0.4 |
| 104 | 68 | 5.7 | 58 | 3.2 |
| 105 | 46.8 | 3.3 | 46.2 | 1.5 |
| 106 | 58 | 1.6 | 51.6 | 1.7 |
| 107 | 62.3 | 4.6 | 62.2 | 0.9 |
| 108 | 3.3 | 0.3 | 2.6 | 0.4 |
| 109 | 4.5 | 0.5 | 4.2 | 0.5 |
| 110 | 33.1 | 2.5 | 35.1 | 10.9 |
| 111 | 5.1 | 0.1 | 3.7 | 0.3 |
| 112 | 10.5 | 0.2 | 17.7 | 12.3 |
| 113 | 6.3 | 0.7 | 5.7 | 1 |
| 116 | 19.3 | 1.5 | 13.7 | 0.4 |

Example 4: TRBC Guide Design and Screening in HEK Cells

Human TRBC Guide Design

Initial guide selection for editing human TRBCJ (ENSG00000211751) and TRBC2 (ENSG00000211772) was as described in Example 2. A total of 89 guide RNAs were designed: 2 targeting TRBCJ only (SEQ ID NO: 11 and SEQ ID NO: 26), 2 targeting TRBC2 only (SEQ ID NO: 8) and 86 targeting both TRBCJ and TRBC2. Guides were designed to target the protein exonic coding regions. Guides and corresponding genomic coordinates are provided above (Table 1).

Figure 4A:
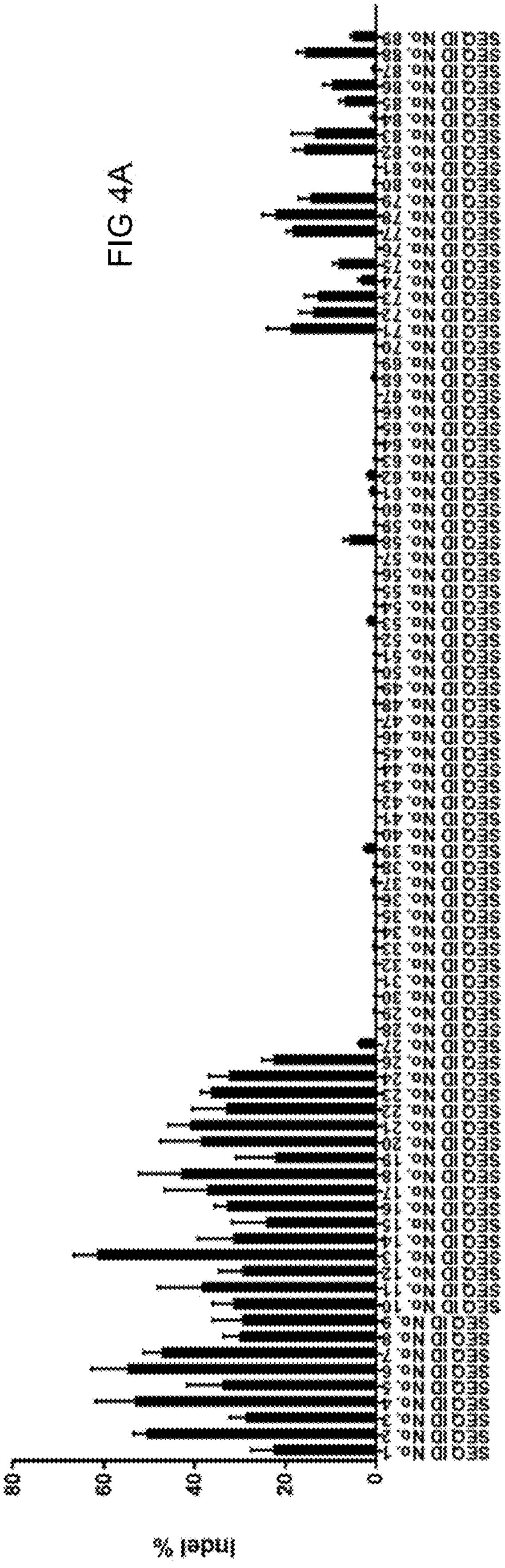
FIGS. 4A-B show the degree of TRBC editing in HEK-Cas9 cells.
Figure 4B:
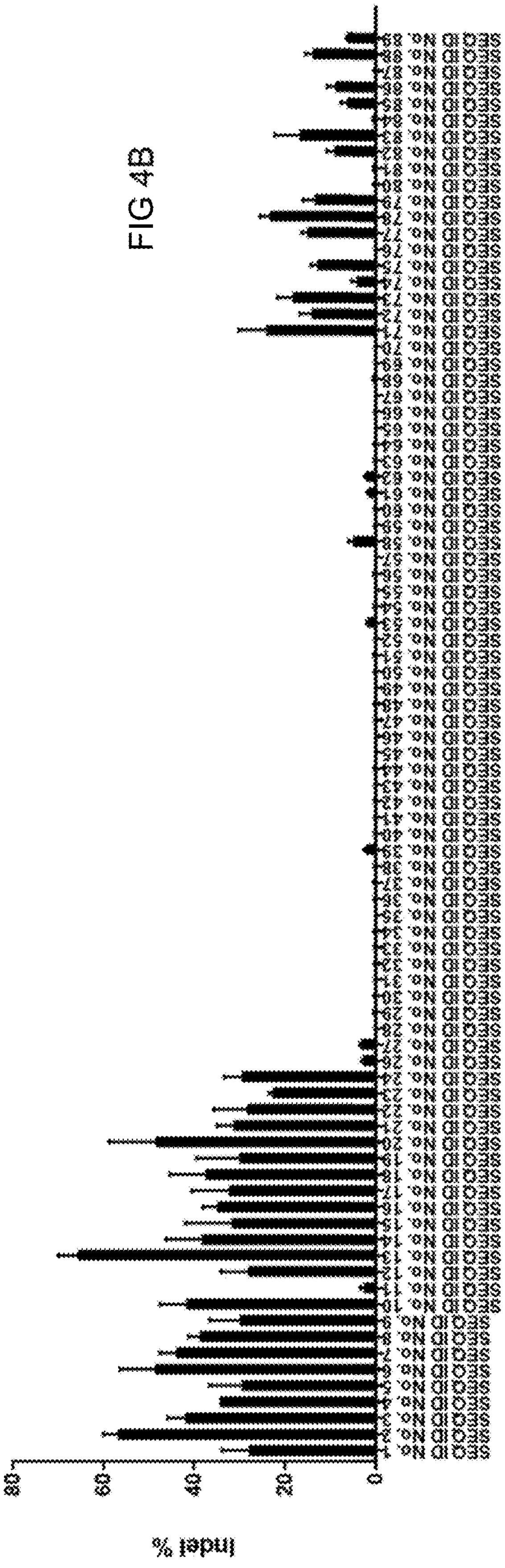

TRBC guides were screened for editing efficiency in HEK293_Cas9 cells. Transfection was performed as described in Example 2. DNA isolation and NGS analysis were performed as described in Example 1. FIGS. 4A and 4B and Table 8 show indel % at the TRBC1 and TRBC2 loci by these guides in HEK293_Cas9 cells.

TABLE 8

| TRBC guide editing in HEK293_Cas9 cells | | | | | | |
|---|---|---|---|---|---|---|
| SEQ ID NO: | TRBC1 Mean Indel % | TRBC1 SD | Number of values (n) | TRBC2 Mean Indel % | TRBC2 SD | Number of values (n) |
| 1 | 22.7 | 4.8 | 3 | 28.0 | 5.9 | 3 |
| 2 | 50.6 | 2.9 | 3 | 56.9 | 3.1 | 3 |
| 3 | 28.7 | 3.5 | 3 | 41.9 | 4 | 3 |
| 4 | 53.4 | 8.6 | 3 | 34.4 | NA | 1 |
| 5 | 33.9 | 7.7 | 3 | 29.5 | 7.1 | 3 |
| 6 | 54.8 | 8 | 3 | 48.7 | 7.7 | 3 |
| 7 | 47.3 | 4 | 3 | 43.9 | 3.8 | 3 |
| 8 | 30.2 | 3.5 | 3 | 38.6 | 2.5 | 3 |
| 9 | 29.5 | 6.4 | 3 | 30 | 6.5 | 3 |
| 10 | 31.5 | 4.6 | 3 | 41.7 | 5.9 | 3 |
| 11 | 38.4 | 9.7 | 3 | 2.6 | 0.8 | 3 |
| 12 | 29.6 | 5 | 3 | 28.1 | 6 | 3 |
| 13 | 61.7 | 4.9 | 3 | 65.7 | 4.4 | 3 |
| 14 | 31.5 | 7.8 | 3 | 38.3 | 8 | 3 |
| 15 | 24.2 | 7.5 | 3 | 31.7 | 10.3 | 3 |
| 16 | 33 | 2.6 | 3 | 34.9 | 3.2 | 3 |
| 17 | 37.4 | 9.3 | 3 | 32.3 | 8.2 | 3 |
| 18 | 43 | 9.4 | 3 | 37.6 | 7.9 | 3 |
| 19 | 22.2 | 8.6 | 3 | 30.2 | 9.3 | 3 |
| 20 | 38.7 | 8.9 | 3 | 48.5 | 10.4 | 3 |
| 21 | 40.9 | 5 | 3 | 31.3 | 3.6 | 3 |
| 22 | 33.1 | 7.5 | 3 | 28.3 | 7.4 | 3 |
| 23 | 36.4 | 2.2 | 3 | 22.7 | 0.8 | 3 |
| 24 | 32.6 | 4.2 | 3 | 29.5 | 3.8 | 3 |
| 26 | 22.5 | 2.6 | 3 | 2.9 | 0.3 | 3 |
| 27 | 3.7 | 0.2 | 3 | 3.2 | 0.3 | 3 |
| 28 | 0.1 | 0 | 3 | 0.1 | 0.1 | 3 |
| 29 | 0.3 | 0.1 | 3 | 0.4 | 0.2 | 3 |
| 30 | 0.2 | 0.1 | 3 | 0.3 | 0.2 | 3 |
| 31 | 0.1 | 0 | 3 | 0.2 | 0.1 | 3 |
| 32 | 0.2 | 0.1 | 3 | 0.2 | 0.1 | 3 |
| 33 | 0.4 | 0.1 | 3 | 0.2 | 0.1 | 3 |
| 34 | 0.4 | 0.1 | 3 | 0.3 | 0.1 | 3 |
| 35 | 0 | 0.1 | 3 | 0.1 | 0.1 | 3 |
| 36 | 0.3 | 0.1 | 3 | 0.3 | 0.1 | 3 |
| 37 | 0.8 | 0.1 | 3 | 0.5 | 0.2 | 3 |
| 38 | 0.3 | 0.1 | 3 | 0.3 | 0.1 | 3 |
| 39 | 2.2 | 0.4 | 3 | 2.2 | 0.4 | 3 |
| 40 | 0.1 | 0.1 | 3 | 0.2 | 0.1 | 3 |
| 41 | 0.1 | 0 | 3 | 0.2 | 0.1 | 3 |
| 42 | 0.1 | 0.1 | 3 | 0.2 | 0.1 | 3 |
| 43 | 0.2 | 0 | 3 | 0.1 | 0.1 | 3 |
| 44 | 0.2 | 0 | 3 | 0.3 | 0.1 | 3 |
| 45 | 0.1 | 0.1 | 3 | 0.1 | 0 | 3 |
| 46 | 0.1 | 0 | 3 | 0.1 | 0 | 3 |
| 47 | 0.1 | 0 | 3 | 0.2 | 0.1 | 3 |
| 48 | 0.2 | 0.2 | 3 | 0.3 | 0.1 | 3 |
| 49 | 0.1 | 0 | 3 | 0.1 | 0 | 3 |
| 50 | 0.3 | 0.1 | 3 | 0.2 | 0.1 | 3 |
| 51 | 0.4 | 0.1 | 3 | 0.4 | 0.1 | 3 |
| 52 | 0.2 | 0.1 | 3 | 0.1 | 0.1 | 3 |
| 53 | 1.6 | 0.2 | 3 | 1.8 | 0.2 | 3 |
| 54 | 0.2 | 0.1 | 3 | 0.3 | 0.1 | 3 |
| 55 | 0.1 | 0.1 | 3 | 0 | NA | 1 |
| 56 | 0.2 | 0.1 | 3 | 0.4 | 0.1 | 3 |
| 57 | 0.1 | 0 | 3 | 0.1 | 0 | 3 |
| 58 | 5.8 | 1.3 | 3 | 5 | 1.1 | 3 |
| 59 | 0.3 | 0.1 | 3 | 0.2 | 0.1 | 3 |
| 60 | 0.3 | 0.1 | 3 | 0.2 | 0.1 | 3 |
| 61 | 1 | 0.2 | 3 | 1.6 | 0.3 | 3 |
| 62 | 1.7 | 0.3 | 3 | 2.2 | 0.2 | 3 |
| 63 | 0.3 | 0.1 | 3 | 0.3 | 0.1 | 3 |
| 64 | 0.2 | 0.1 | 3 | 0.3 | 0.1 | 3 |
| 65 | 0.2 | 0 | 3 | 0.2 | 0 | 3 |
| 66 | 0.1 | 0.1 | 3 | 0.2 | 0.1 | 3 |

TABLE 8-continued

| TRBC guide editing in HEK293_Cas9 cells | | | | | | |
|---|---|---|---|---|---|---|
| SEQ ID NO: | TRBC1 Mean Indel % | TRBC1 SD | Number of values (n) | TRBC2 Mean Indel % | TRBC2 SD | Number of values (n) |
| 67 | 0.1 | 0 | 3 | 0.1 | 0.1 | 3 |
| 68 | 0.7 | 0.2 | 3 | 0.6 | 0.1 | 3 |
| 69 | 0 | 0.1 | 3 | 0.1 | 0.1 | 3 |
| 70 | 0.1 | 0.1 | 3 | 0.1 | 0.1 | 3 |
| 71 | 18.9 | 5.1 | 3 | 24.2 | 6 | 3 |
| 72 | 13.8 | 3 | 3 | 14.2 | 2.6 | 3 |
| 73 | 12.9 | 2.9 | 3 | 18.4 | 3.3 | 3 |
| 74 | 3.3 | 0.4 | 3 | 4.2 | 1.2 | 3 |
| 75 | 8.3 | 1.1 | 3 | 13 | 1.4 | 3 |
| 76 | 0.3 | 0 | 3 | 0.1 | 0.1 | 3 |
| 77 | 18.5 | 1.3 | 3 | 15.1 | 1.3 | 3 |
| 78 | 22.2 | 2.8 | 3 | 23.3 | 2.2 | 3 |
| 79 | 14.6 | 2.5 | 3 | 13.6 | 2.6 | 3 |
| 80 | 0.4 | 0.1 | 3 | 0.5 | 0.2 | 3 |
| 81 | 0.3 | 0.1 | 3 | 0.5 | 0.1 | 3 |
| 82 | 15.9 | 2.3 | 3 | 9.1 | 1.8 | 3 |
| 83 | 13.6 | 5 | 3 | 16.8 | 5.5 | 3 |
| 84 | 0.8 | 0.3 | 3 | 0.7 | 0.1 | 3 |
| 85 | 6.9 | 1.2 | 3 | 6.3 | 1.5 | 3 |
| 86 | 9.7 | 2 | 3 | 9 | 1.8 | 3 |
| 87 | 0.7 | 0.1 | 3 | 0.2 | 0.2 | 3 |
| 88 | 15.8 | 1.7 | 3 | 13.9 | 1.6 | 3 |
| 89 | 5 | 0.6 | 3 | 6.3 | 0.3 | 3 |

Example 5: TRBC Guide Screening in Human CD3+ T Cells

Figure 5:
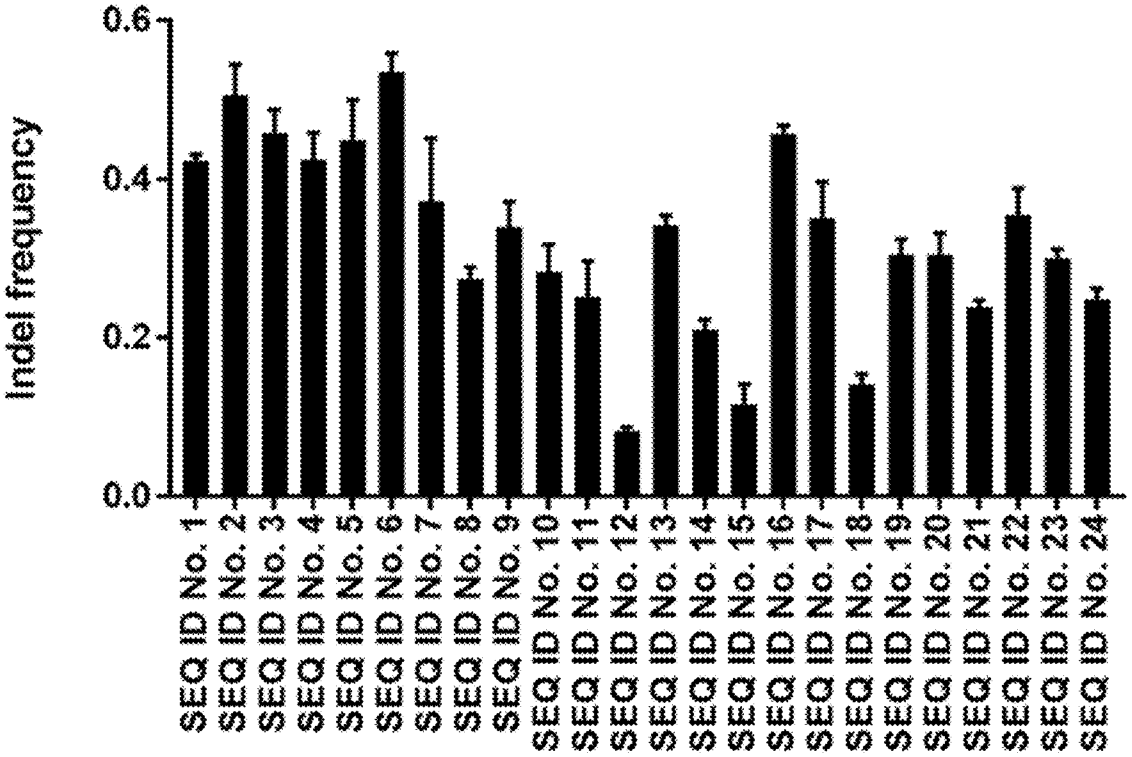
FIG. 5 shows the degree of TRBC editing in human $CD3^+$ T cells.
Figure 6:
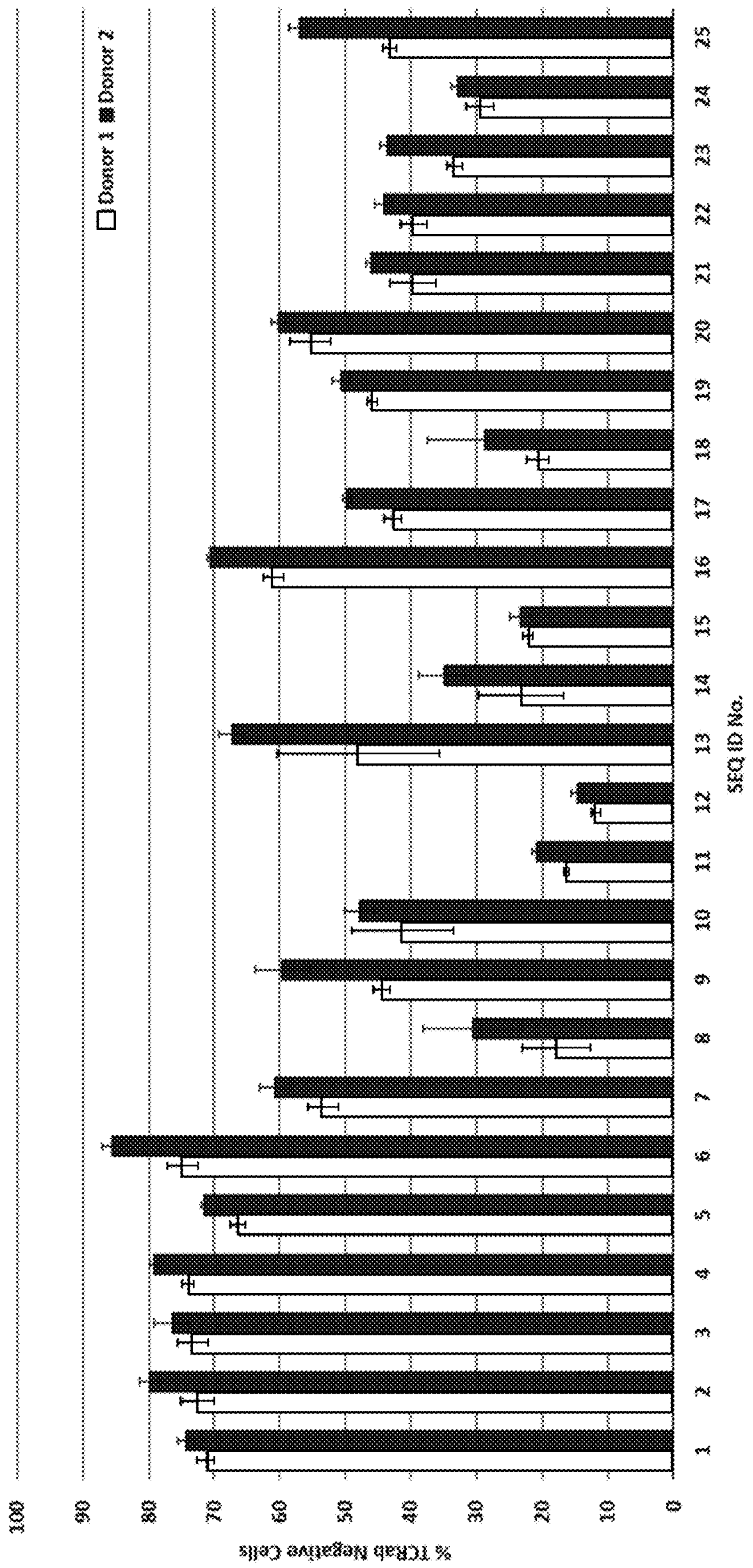
FIG. 6 shows the amount of TCR expression following TRBC editing in human CD3+ T cells.

TRBC guides with high indel percent editing in HEK293_Cas9 cells from Example 4 were screened for editing efficiency and T-cell receptor (TCR) expression in human CD3+ T cells. Nucleofection, editing analysis and TCR expression analysis were performed as in Example 3. Table 9 and FIG. 5 show results for indel frequency following TRBC editing with various guides in CD3+ T cells. Table 10 and FIG. 6 show TCR expression measurements (as % TCR negative cells) following TRBC editing in CD3+ T cells.

TABLE 9

| Indel Frequency at TRBC1 in CD3+ T cells | | | |
|---|---|---|---|
| SEQ ID NO: | Mean Indel frequency | Standard Deviation | Sample Number (n) |
| 1 | 42.40% | 0.80% | 3 |
| 2 | 50.50% | 3.90% | 3 |
| 3 | 45.80% | 3.00% | 3 |
| 4 | 42.50% | 3.40% | 3 |
| 5 | 45.00% | 5.00% | 3 |
| 6 | 53.50% | 2.40% | 3 |
| 7 | 37.30% | 7.90% | 3 |
| 8 | 27.40% | 1.50% | 3 |
| 9 | 34.00% | 3.20% | 3 |
| 10 | 28.20% | 3.50% | 3 |
| 11 | 25.10% | 4.60% | 3 |
| 12 | 8.30% | 0.40% | 3 |
| 13 | 34.20% | 1.20% | 3 |
| 14 | 21.00% | 1.30% | 3 |
| 15 | 11.60% | 2.50% | 3 |
| 16 | 45.70% | 1.00% | 3 |
| 17 | 35.10% | 4.60% | 3 |
| 18 | 14.10% | 1.30% | 3 |
| 19 | 30.40% | 2.10% | 3 |
| 20 | 30.50% | 2.70% | 3 |
| 21 | 23.80% | 0.90% | 3 |
| 22 | 35.50% | 3.40% | 3 |

TABLE 9-continued

| Indel Frequency at TRBC1 in CD3+ T cells | | | |
|---|---|---|---|
| SEQ ID NO: | Mean Indel frequency | Standard Deviation | Sample Number (n) |
| 23 | 30.00% | 1.10% | 3 |
| 24 | 24.80% | 1.40% | 3 |

TABLE 10

| TCR expression after TRBC editing in CD3+ T cells | | | | |
|---|---|---|---|---|
| SEQ ID NO: | Donor 1 - % TCR Negative | Donor 1 - Standard Deviation | Donor 2 - % TCR negative | Donor 2 - Standard Deviation |
| 1 | 71.2 | 1.4 | 74.4 | 1.3 |
| 2 | 72.4 | 2.6 | 79.9 | 1.5 |
| 3 | 73.3 | 2.3 | 76.4 | 2.8 |
| 4 | 74 | 0.9 | 79.2 | 0.7 |
| 5 | 66.4 | 1.1 | 71.5 | 0.5 |
| 6 | 75 | 2.2 | 85.7 | 1.4 |
| 7 | 53.5 | 2.2 | 60.7 | 2.3 |
| 8 | 18 | 5.1 | 30.6 | 7.6 |
| 9 | 44.4 | 1.3 | 59.6 | 4.1 |
| 10 | 41.2 | 7.9 | 47.9 | 2.3 |
| 11 | 16.3 | 0.3 | 20.9 | 0.7 |
| 12 | 11.8 | 0.7 | 14.6 | 1 |
| 13 | 48.2 | 12.3 | 67.2 | 2 |
| 14 | 23.3 | 6.5 | 34.8 | 3.9 |
| 15 | 22.1 | 0.8 | 23.3 | 1.6 |
| 16 | 60.8 | 1.7 | 70.5 | 0.5 |
| 17 | 42.8 | 1.4 | 49.7 | 0.7 |
| 18 | 20.6 | 1.8 | 28.7 | 8.7 |
| 19 | 45.9 | 0.8 | 50.7 | 1.4 |
| 20 | 55.3 | 3.2 | 60.2 | 1.1 |
| 21 | 39.7 | 3.4 | 46.1 | 0.8 |
| 22 | 39.6 | 2.1 | 44.1 | 1.4 |
| 23 | 33.5 | 1 | 43.6 | 1.1 |
| 24 | 29.5 | 2.1 | 32.8 | 1 |
| 25 | 43.2 | 1 | 57 | 1.5 |

Example 6: Off-Target Analysis of TRBC and TRAC Guides

Figure 7A:
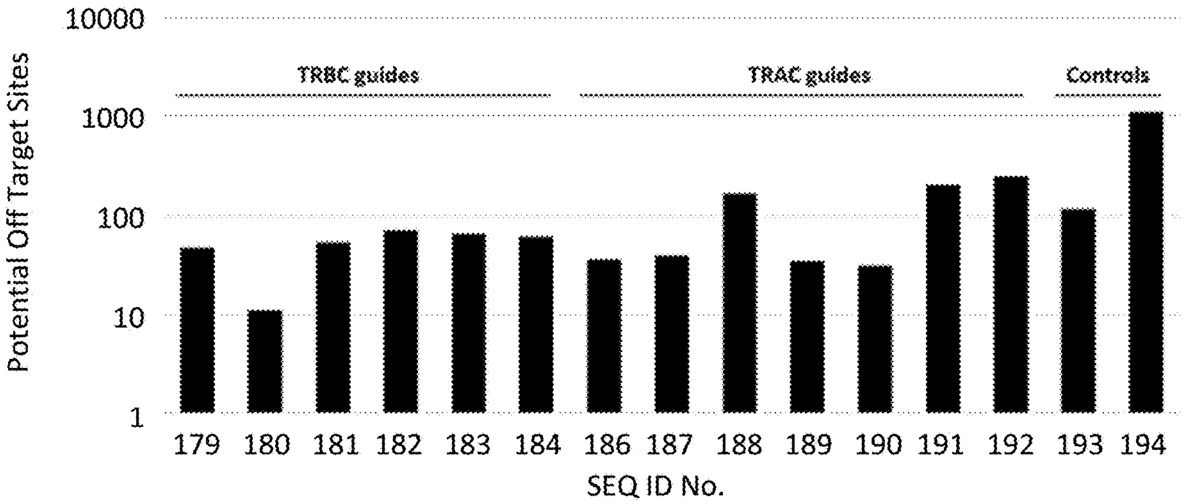
FIGS. 7A-B show biochemical off target analysis (measurement of potential off-target editing sites) for TRBC, TRAC and control guides (SEQ ID NOs: 193 and 194).

A biochemical method (See, e.g., Cameron et al., *Nature Methods.* 6, 600-606; 2017) was used to determine potential off-target genomic sites cleaved by Cas9 targeting TRAC, TRBC1 or TRBC2. Guides showing the most CD3 negative cells in Example 3 and Example 5 were tested for potential off-target genomic cleavage sites with this assay. In this experiment, 7 sgRNA targeting human TRAC, 6 sgRNA targeting TRBC and two control guides with known off-target profiles were screened using isolated HEK293_Cas genomic DNA. The number of potential off-target sites detected using an RNP concentration of 16 nM in the biochemical assay were plotted in FIG. 7A and shown in Table 11. The assay identified potential off-target sites for the sgRNAs tested.

TABLE 11

| Biochemical Off-Target Analysis | | |
|---|---|---|
| SEQ ID NO: | Target | Number of Sites |
| 179 | TRBC1/2 | 48 |
| 180 | TRBC1/2 | 11 |
| 181 | TRBC1/2 | 54 |
| 182 | TRBC1/2 | 72 |

TABLE 11-continued

| Biochemical Off-Target Analysis | | |
|---|---|---|
| SEQ ID NO: | Target | Number of Sites |
| 183 | TRBC1/2 | 65 |
| 184 | TRBC1/2 | 61 |
| 186 | TRAC | 36 |
| 187 | TRAC | 40 |
| 188 | TRAC | 168 |
| 189 | TRAC | 35 |
| 190 | TRAC | 31 |
| 191 | TRAC | 207 |
| 192 | TRAC | 253 |
| 193 | EMX1 | 118 |
| 194 | VEGFA | 1113 |

Targeted Sequencing for Validating Potential Off-Target Sites

In known off-target detection assays such as the biochemical method used above, a large number of potential off-target sites are typically recovered, by design, so as to "cast a wide net" for potential sites that can be validated in other contexts, e.g., in a primary cell of interest. For example, the biochemical method typically overrepresents the number of potential off-target sites as the assay utilizes purified high molecular weight genomic DNA free of the cell environment and is dependent on the dose of Cas9 RNP used. Accordingly, potential off-target sites identified by these methods may be validated using targeted sequencing of the identified potential off-target sites.

In one approach, Cas9 and a sgRNA of interest (e.g., a sgRNA having potential off-target sites for evaluation) are introduced to primary T cells. The T cells are then lysed and primers flanking the potential off-target site(s) are used to generate an amplicon for NGS analysis. Identification of indels at a certain level may validate potential off-target site, whereas the lack of indels found at the potential off-target site may indicate a false positive in the off-target assay that was utilized.

Figure 7B:
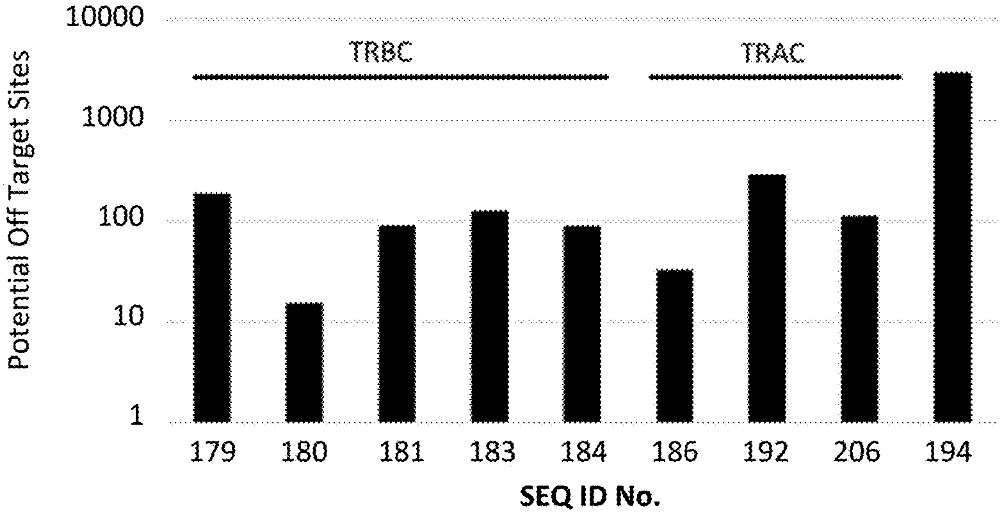

Guides showing on target indel activity were tested for potential off-target genomic cleavage sites with this assay. In this experiment, 5 sgRNAs targeting human TRBC1 or TRBC2 and 3 guides targeting human TRAC were screened using genomic DNA purified from pooled male human peripheral blood mononuclear cells (PBMCs) alongside a control guide, SEQ ID NO: 194 (VEGFA) with known off-target profiles. The number of potential off-target sites detected using a guide concentration of 64 nM in the biochemical assay are shown in FIG. 7B and Table 12.

TABLE 12

| 64 nM Off Target Analysis | | | |
|---|---|---|---|
| SEQ ID NO: of sgRNA | Target | Guide Sequence (SEQ ID NO:) | Off-target Site Count |
| 179 | TRBC1/2 | GGCUCUCGGAGAAUGACGAG (SEQ ID NO: 1) | 190 |
| 180 | TRBC1/2 | GGCCUCGGCGCUGACGAUCU (SEQ ID NO: 2) | 15 |
| 181 | TRBC1/2 | AUGACGAGUGGACCCAGGAU (SEQ ID NO: 3) | 92 |
| 183 | TRBC1/2 | UGAGGGUCUCGGCCACCUUC (SEQ ID NO: 5) | 127 |

TABLE 12-continued

| 64 nM Off Target Analysis | | | |
|---|---|---|---|
| SEQ ID NO: of sgRNA | Target | Guide Sequence (SEQ ID NO:) | Off-target Site Count |
| 184 | TRBC1/2 | AGAGAUCUCCCACACCCAAA (SEQ ID NO: 6) | 90 |
| 186 | TRAC | CUCUCAGCUGGUACACGGCA (SEQ ID NO: 90) | 32 |
| 192 | TRAC | UCAGGGUUCUGGAUAUCUGU (SEQ ID NO: 185) | 293 |
| 206 | TRAC | UAGGCAGACAGACUUGUCAC (SEQ ID NO: 214) | 114 |
| 194 | VEGFA | See Table 3 | 2945 |

Example 7: Using TRAC and TRBC Guides for Multiple Edits

Figure 8A:
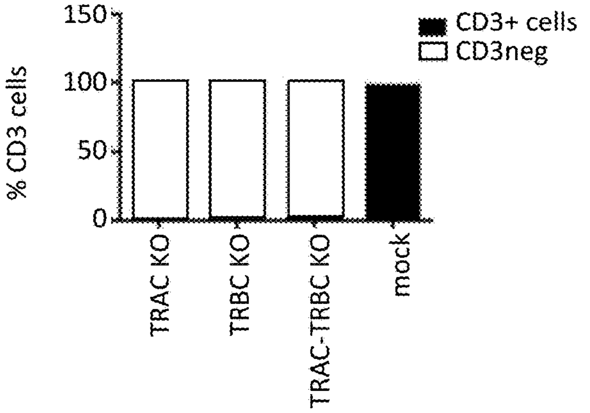
FIGS. 8A-D demonstrate knockout of the T-cell receptor and insertion of a TCR construct to produce cells with TCR edited T cells.

Guides were also tested for simultaneous editing of TRAC and TRBC loci. Peripheral blood mononuclear cells (PBMCs) from 3 different healthy donors were isolated from buffy coat using Lymphoprep™ (Stem Cell Technology) for density gradient centrifugation. These cells were activated and sorted using Dynabeads™ ClinExVivo™ CD3/CD28 (Invitrogen) following the manufacturer instructions. T cells were seeded at a concentration of 106 cells/ml in X-VIVO™ 15 Hematopoietic Serum-Free Culture Media (Lonza™) supplemented with 5% FBS and with IL7 and IL15 (5 ng/ml each). Two days after stimulation, T cells were electroporated as described in Example 3 simultaneously with a crRNA targeting TRAC and a crRNA targeting TRBC. Using cells from one donor, TRAC and TRBC guides were electroporated in isolation. At day 6 post stimulation, beads were detached and cells were seeded at a concentration of 1 million/ml in X-VIVO™ 15 supplemented with 5% FBS and with IL7 and IL15 (5 ng/ml each). TRAC and TRBC knockout efficiency at day 7 was assessed by evaluating the percentage of T cells devoid of the CD3 molecule by flow cytometry as shown in FIG. 8A and Table 13.

TABLE 13

| Efficiency of TCR knockdown | | | | | |
|---|---|---|---|---|---|
| SEQ | CD3+ | | CD3neg | | |
| ID NO: | Mean % | SD | Mean % | SD | Samples (n) |
| 95 | 1 | N/A | 98 | N/A | 1 |
| 6 | 1 | N/A | 99 | N/A | 1 |
| 6 and 95 | 2 | 1 | 98 | 1 | 3 |
| mock | 97 | 1 | 2 | 1 | 3 |

Simultaneous TRAC and TRBC Editing with Lentiviral Insertion of a TCR Gene.

Three days post stimulation, edited T cells were transduced with a lentiviral vector (LV) encoding a WT1-specific TCR derived from a healthy donor (HD1-TCR) randomly inserting the LV. Briefly, the TCR α and β chain genes were isolated, codon-optimized, cysteine-modified, and cloned in a LV under a bidirectional promoter. The DNA and amino acid sequences of the HD1 TCR α and β chain genes are given below. The alpha chain was cloned in antisense orientation under the minimal human CMV promoter and the beta chain in sense orientation under the PGK promoter.

Figure 8B:
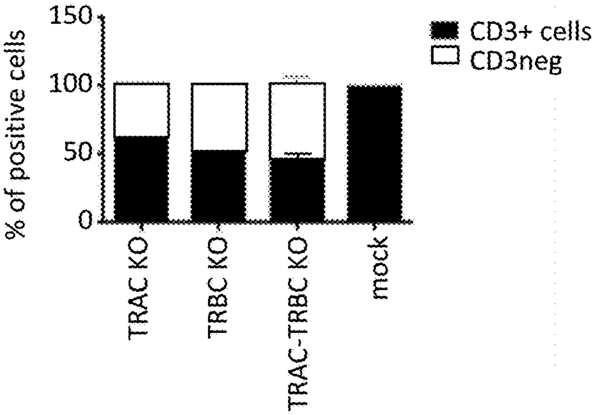
Figure 8C:
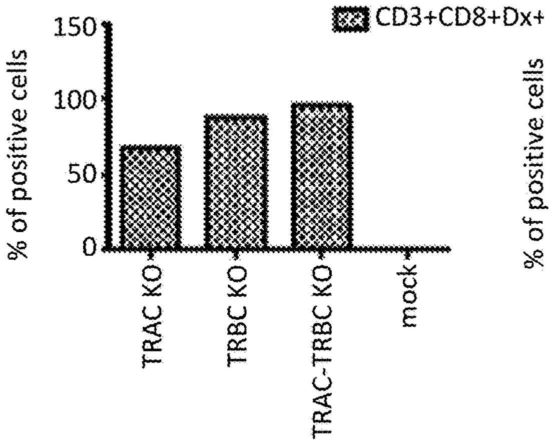
Figure 8D:
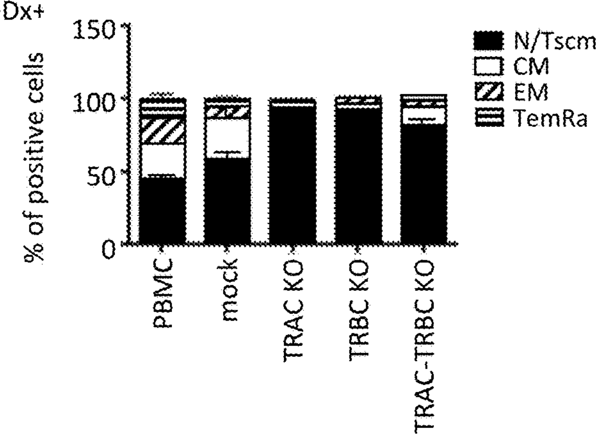
Figure 9A:
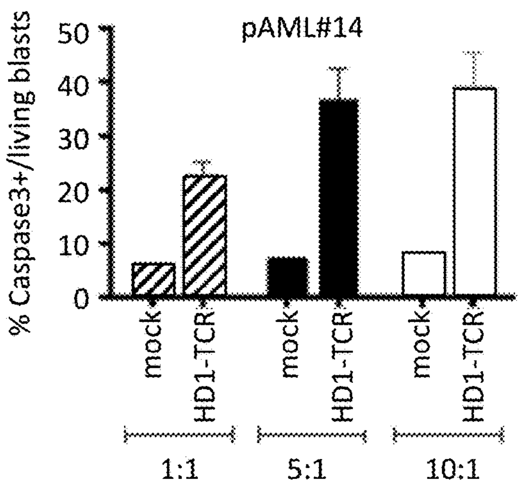
FIGS. 9A-D show the ability of T cells with a TCR insertion to kill primary AML blasts.
Figure 9B:
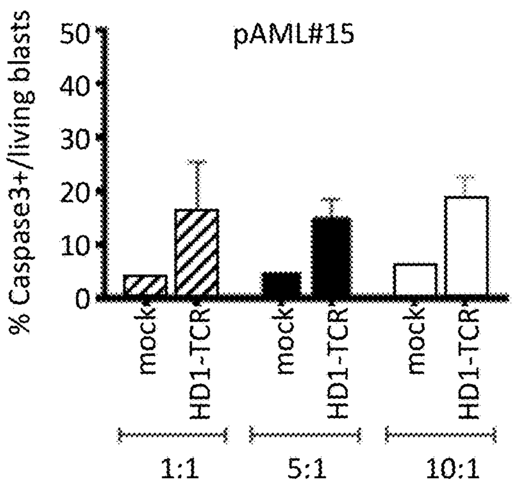
Figure 9C:
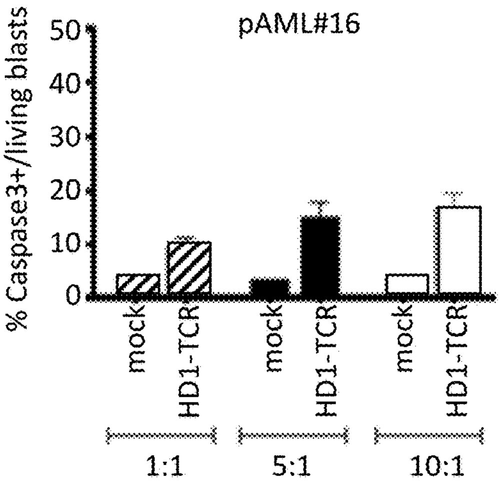
Figure 9D:
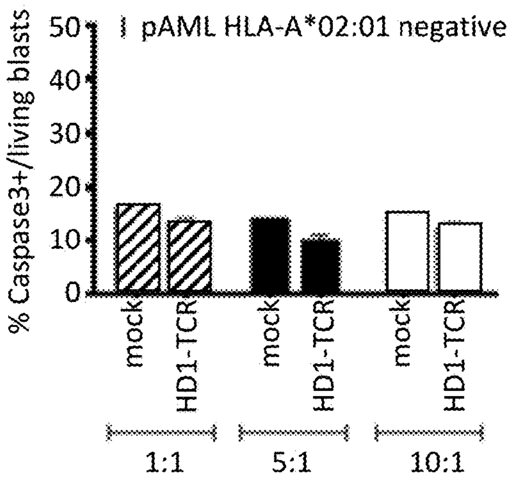

LVs were packaged by an integrase-competent third-generation construct and pseudotyped by the vescicular stomatitis virus (VSV) envelope. T lymphocytes were infected with the LV for 24 h. Afterwards, T cells were cultured at $10^6$ cells/ml and expanded. Two days after transduction, transduction efficiency was evaluated by determining the percentage of T cells expressing the specific VP gene (TRBV12-3/TRBV12-4) as well as the specific dextramer (epitope: VLDFAPPGA). At day 15 post stimulation, T cell phenotype was evaluated by cytofluorimetric analysis. FIG. 8B and Table 14 show that more than 45% of T cells expressed the CD3 molecule (mean±SEM=45.3±5.7). Percentage of WT1-specific $CD8^+$ T cells evaluated by measuring Dextramer positivity was greater than 95% (mean±SEM=95.3±0.7) Percentage of WT1-specific $CD8^+$ T cells evaluated by measuring Dextramer positivity was greater than 95% when SEQ ID NOs 6 and 95 were used (mean±SEM=95.3±0.7) (FIG. 8C, Table 14). T cell phenotype of the edited T cells was evaluated at dayl5 as shown in FIG. 8D and Table 15.

SEQ ID NO: 250: HD1 TCR α chain - DNA sequence
ATGGAAACCCTGCTGAAGGTGCTGAGCGGCACACTGCTGTGGCAGCTG

ACATGGGTCCGATCTCAGCAGCCTGTGCAGTCTCCTCAGGCCGTGATTCTGAGAG

AAGGCGAGGACGCCGTGATCAACTGCAGCAGCTCTAAGGCCCTGTACAGCGTGC

ACTGGTACAGACAGAAGCACGGCGAGGCCCCTGTGTTCCTGATGATCCTGCTGA

AAGGCGGCGAGCAGAAGGGCCACGAGAAGATCAGCGCCAGCTTCAACGAGAAG

AAGCAGCAGTCCAGCCTGTACCTGACAGCCAGCCAGCTGAGCTACAGCGGCACC

TACTTTTGTGGCACCGCCTGGATCAACGACTACAAGCTGTCTTTCGGAGCCGGCA

CCACAGTGACAGTGCGGGCCAATATTCAGAACCCCGATCCTGCCGTGTACCAGCT

GAGAGACAGCAAGAGCAGCGACAAGAGCGTGTGCCTGTTCACCGACTTCGACAG

CCAGACCAACGTGTCCCAGAGCAAGGACAGCGACGTGTACATCACCGATAAGTG

CGTGCTGGACATGCGGAGCATGGACTTCAAGAGCAACAGCGCCGTGGCCTGGTC

CAACAAGAGCGATTTCGCCTGCGCCAACGCCTTCAACAACAGCATTATCCCCGA

GGACACATTCTTCCCAAGTCCTGAGAGCAGCTGCGACGTGAAGCTGGTGGAAAA

GAGCTTCGAGACAGACACCAACCTGAACTTCCAGAACCTGAGCGTGATCGGCTT

CAGAATCCTGCTGCTCAAGGTGGCCGGCTTCAACCTGCTGATGACCCTGAGACTG

TGGTCCAGCTGA

SEQ ID NO: 251: HD1 TCR α chain - amino acid sequence
METLLKVLSGTLLWQLTWVRSQQPVQSPQAVILREGEDAVINCSSSKALYS

VHWYRQKHGEAPVFLMILLKGGEQKGHEKISASFNEKKQQSSLYLTASQLSYSGTYF

CGTAWINDYKLSFGAGTTVTVRANIQNPDPAVYQLRDSKSSDKSVCLFTDFDSQTNV

SQSKDSDVYITDKCVLDMRSMDFKSNSAVAWSNKSDFACANAFNNSIIPEDTFFPSPE

SSCDVKLVEKSFETDTNLNFQNLSVIGFRILLLKVAGFNLLMTLRLWSS*

SEQ ID NO: 252: HD1 TCR β chain - DNA sequence
ATGGGATCTTGGACACTGTGTTGCGTGTCCCTGTGCATCCTGGTGGCCA

AGCACACAGATGCCGGCGTGATCCAGTCTCCTAGACACGAAGTGACCGAGATGG

GCCAAGAAGTGACCCTGCGCTGCAAGCCTATCAGCGGCCACGATTACCTGTTCTG

GTACAGACAGACCATGATGAGAGGCCTGGAACTGCTGATCTACTTCAACAACAA

CGTGCCCATCGACGACAGCGGCATGCCCGAGGATAGATTCAGCGCCAAGATGCC

CAACGCCAGCTTCAGCACCCTGAAGATCCAGCCTAGCGAGCCCAGAGATAGCGC

CGTGTACTTCTGCGCCAGCAGAAAGACAGGCGGCTACAGCAATCAGCCCCAGCA

CTTTGGAGATGGCACCCGGCTGAGCATCCTGGAAGATCTGAAGAACGTGTTCCCA

CCTGAGGTGGCCGTGTTCGAGCCTTCTGAGGCCGAGATCAGCCACACACAGAAA

GCCACACTCGTGTGTCTGGCCACCGGCTTCTATCCCGATCACGTGGAACTGTCTT

GGTGGGTCAACGGCAAAGAGGTGCACAGCGGCGTCTGTACCGATCCTCAGCCTC

TGAAAGAGCAGCCCGCTCTGAACGACAGCAGATACTGCCTGAGCAGCAGACTGA

-continued

GAGTGTCCGCCACCTTCTGGCAGAACCCCAGAAACCACTTCAGATGCCAGGTGC

AGTTCTACGGCCTGAGCGAGAACGATGAGTGGACCCAGGATAGAGCCAAGCCTG

TGACACAGATCGTGTCTGCCGAAGCCTGGGGCAGAGCCGATTGTGGCTTTACCAG

CGAGAGCTACCAGCAGGGCGTGCTGTCTGCCACAATCCTGTACGAGATCCTGCTG

GGCAAAGCCACTCTGTACGCCGTGCTGGTGTCTGCCCTGGTGCTGATGGCCATGG

TCAAGCGGAAGGATAGCAGGGGCTGA

SEQ ID NO: 253: HD1 TCR β chain - amino acid sequence
MGSWTLCCVSLCILVAKHTDAGVIQSPRHEVTEMGQEVTLRCKPISGHDY

LFWYRQTMMRGLELLIYFNNNVPIDDSGMPEDRFSAKMPNASFSTLKIQPSEPRDSA

VYFCASRKTGGYSNQPQHFGDGTRLSILEDLKNVFPPEVAVFEPSEAEISHTQKATLV

CLATGFYPDHVELSWWVNGKEVHSGVCTDPQPLKEQPALNDSRYCLSSRLRVSATF

WQNPRNHFRCQVQFYGLSENDEWTQDRAKPVTQIVSAEAWGRADCGFTSESYQQG

VLSATILYEILLGKATLYAVLVSALVLMAMVKRKDSRG*

TABLE 14

Efficiency of TCR insertion in edited T cells

| SEQ ID NO: | CD3+ Mean % | CD3+ SD | CD3 neg Mean % | CD3 neg SD | CD3+CD8+Dx+ Mean % | CD3+CD8+Dx+ SD | Samples (n) |
|---|---|---|---|---|---|---|---|
| 95 | 62 | N/A | 39 | N/A | 68 | N/A | 1 |
| 6 | 51 | N/A | 49 | N/A | 88 | N/A | 1 |
| 6 and 95 | 45 | 10 | 55 | 10 | 95 | 1 | 3 |
| mock | 98 | 1 | 2 | 1 | 0 | 0 | 3 |

TABLE 15

Phenotype of TCR edited T cells

| SEQ ID NO | N/Tscm Mean | N/Tscm SD | CM Mean | CM SD | EM Mean | EM SD | TemRa Mean | TemRa SD | Samples (n) |
|---|---|---|---|---|---|---|---|---|---|
| PBMC | 44 | 4 | 25 | 5 | 19 | 3 | 12 | 5 | 3 |
| mock | 56 | 12 | 31 | 13 | 9 | 2 | 4 | 2 | 3 |
| 95 | 93 | N/A | 4 | N/A | 0 | N/A | 2 | N/A | 1 |
| 6 | 94 | N/A | 4 | N/A | 1 | N/A | 2 | N/A | 1 |
| 6 and 95 | 82 | 8 | 13 | 6 | 3 | 2 | 2 | 0 | 3 |

T cells with TRAC and TRBC edits and an LV HD1-TCR insertion were tested for ability to kill primary AML blasts. Edited T cells were magnetically sorted in order to enrich for WT1-CD8+ specific T cells using dextramer staining and magnetic sorting. Twenty-one days after the transduction, WT1-CD8+ T cells were co-cultured with primary AML blasts obtained from 3 different patients harboring the HLA-A*02:01 allele and, as control, with primary blasts not harboring the specific HLA allele. Co-cultures were seeded at different effector to target ratios (1:1; 5:1; 10:1). Upon 6 hours co-culture, expression of Caspase 3 in living target cells was used as read out. Results are shown in FIGS. 9A-D and Table 16. Induction of apoptosis in up to 43% of leukemic blasts expressing WT1 and harboring the HLA-A*02:01 (mean±SEM=31±6.6) was observed. No recognition was detectable against AML blasts not expressing the HLA-A*02:01 allele.

TABLE 16

AML killing

| Condition | E:F ratio | mock | HD1-TCR+ Mean % | SD |
|---|---|---|---|---|
| pAML#14 | 1:1 | 5.9 | 22.1 | 4.9 |
| | 5:1 | 6.7 | 36.1 | 10.9 |
| | 10:1 | 7.5 | 38.6 | 11.6 |
| pAML#15 | 1:1 | 3.6 | 15.7 | 16.9 |
| | 5:1 | 4.4 | 14.5 | 6.7 |
| | 10:1 | 5.3 | 18.1 | 8.1 |
| pAML#16 | 1:1 | 3.1 | 9.4 | 3.1 |
| | 5:1 | 3.1 | 14.7 | 5.5 |
| | 10:1 | 3.4 | 16.4 | 5.6 |
| pAML HLA-A*02:01 | 1:1 | 16.2 | 13.2 | 1.8 |
| | 5:1 | 13.8 | 9.8 | 2.2 |
| | 10:1 | 15.1 | 12.1 | 2.5 |

Example 8: Additional TRAC and TRBC Guides for Multiple Edits

Figure 10:
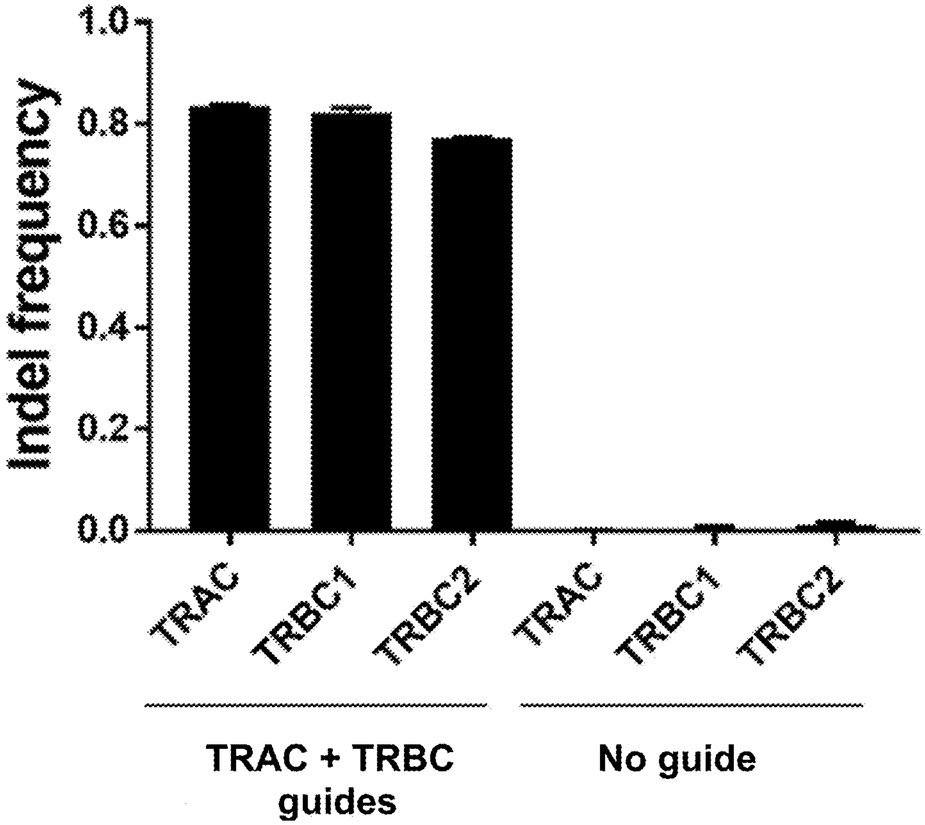
FIG. 10 demonstrates the editing frequency obtained by simultaneous editing of TRAC and TRBC loci using multiple dual guide RNAs.

Additional crRNAs were also tested for simultaneous editing of TRAC and TRBC loci. T cells were nucleofected with RNP containing SEQ ID NO: 185, RNP containing SEQ ID NO: 6, or a mixture of both RNP species. Procedures were carried out as in Example 3 except using BioWhittaker™ X-VIVO™ 15 Hematopoietic Serum-Free Culture Media (Lonza™, Cat. 04-418Q) supplemented with 5% FBS, 50 uM beta-mercaptoethanol, 10 mM N-Acetyl L-Cystine, 1× Penicillin-Streptomycin Solution (Corning, Cat. 30-002-CI) and optionally with IL7 (5 ng/ml), IL15 (5 ng/ml), and IL2 (200-500 U/ml). Seventeen days after nucleofection, T cells were harvested and analyzed by NGS. FIG. 10 and Table 17 show editing at each locus (as indel frequency) following the simultaneous nucleofection. Flow cytometry can also be used to test editing efficiency by measuring the portion of T cells expressing TCR proteins on their surface.

TABLE 17

| Editing with multiple guides | | | |
|---|---|---|---|
| Condition | Amplicon | Mean Indel Frequency | Std. Deviation |
| SEQ ID NO: | TRAC | 83.4% | 0.3% |
| 6 and SEQ | TRBC1 | 82.2% | 0.9% |
| ID NO: 185 | TRBC2 | 77.1% | 0.2% |
| No guide | TRAC | 0.1% | 0.1% |
| | TRBC1 | 0.4% | 0.6% |
| | TRBC2 | 1.0% | 0.7% |

Example 9

Figure 11A:
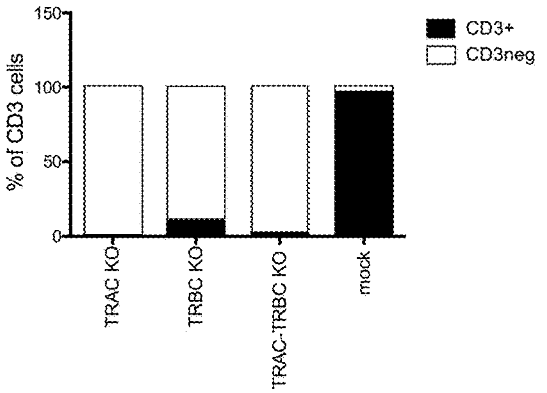
FIGS. 11A-D show the results of using TRAC and TRBC targeting crRNAs for combined editing.

An additional pair of TRAC and TRBC targeting crRNAs were tested for combined editing as described in Example 7. T cells were nucleofected with RNP containing SEQ ID NO: 95, RNP containing SEQ ID NO: 2, or a mixture of both RNP species. TRAC and TRBC knockout efficiency was assessed by evaluating the percentage of T cells devoid of the CD3 molecule by flow cytometry as shown in FIG. 11A and Table 18.

TABLE 18

| Efficiency of TCR knockdown | | | | | |
|---|---|---|---|---|---|
| SEQ | CD3+ | | CD3neg | | |
| ID NO: | Mean % | SD | Mean % | SD | Samples (n) |
| 95 | 0.5 | N/A | 99.5 | N/A | 1 |
| 2 | 10.2 | N/A | 89.3 | N/A | 1 |
| 2 and 95 | 1.8 | 1.0 | 98.1 | 1.0 | 3 |
| mock | 96.8 | N/A | 2.4 | N/A | 1 |

Figure 11B:
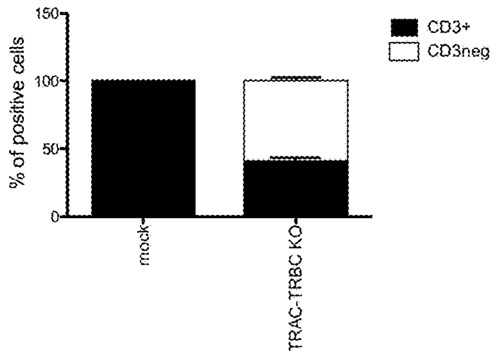
Figure 11C:
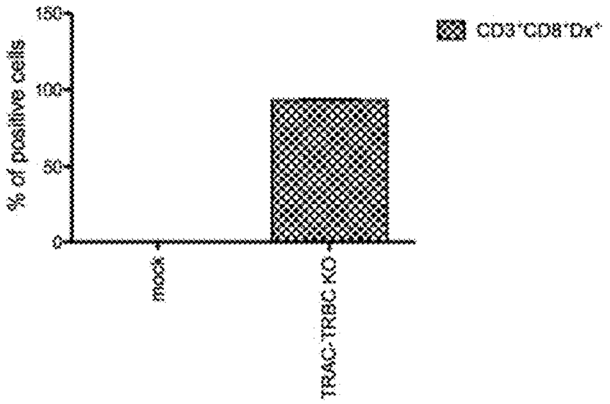
Figure 11D:
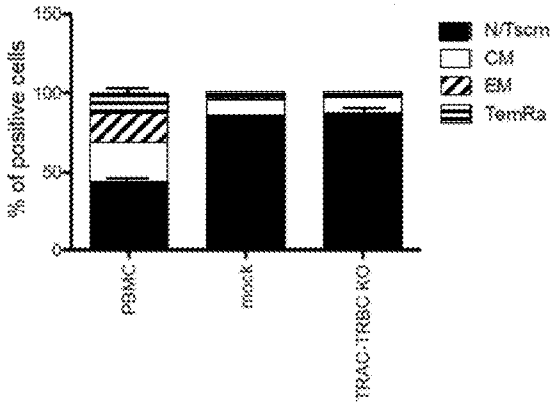

Following lentiviral transduction, T cell phenotype was evaluated by cytofluorimetric analysis as shown in FIG. 11B and Table 19. Percentage of WT1-specific $CD8^+$ T cells was evaluated by measuring Dextramer positivity (FIG. 11C, Table 19). T cell phenotype of the edited T cells is shown in FIG. 11D and Table 20.

TABLE 19

| Efficiency of TCR transduction in edited T cells | | | | | | | |
|---|---|---|---|---|---|---|---|
| | CD3+ | | CD3 neg | | CD3+CD8+Dx+ | | |
| SEQ ID NO: | Mean % | SD | Mean % | SD | Mean % | SD | Samples (n) |
| mock | 99.6 | N/A | 0.4 | N/A | 0 | N/A | 1 |
| 2 and 95 | 40.1 | 5.4 | 59.9 | 5.4 | 93 | 1 | 3 |

TABLE 20

| Phenotype of TCR edited T cells | | | | | | | | | |
|---|---|---|---|---|---|---|---|---|---|
| SEQ | N/Tscm | | CM | | EM | | TemRa | | |
| ID NO | Mean | SD | Mean | SD | Mean | SD | Mean | SD | Samples (n) |
| PBMC | 44 | 4 | 25 | 5 | 19 | 3 | 12 | 5 | 3 |
| mock | 86 | N/A | 10 | N/A | 1 | N/A | 3 | N/A | 1 |
| 2 and 95 | 89 | 4 | 8 | 3 | 1 | 0 | 3 | 1 | 3 |

The engineered cells of examples 7 and 9 combine a TRAC gRNA and a TRBC gRNA with a lentiviral vector that encodes a WT1-specific TCR having a TCR α chain of SEQ ID NO: 251 and a TCR β chain of SEQ ID NO: 253. The engineered cell can be altered by delivering a first and a second composition to the cell, and wherein the first composition comprises: (a) a guide RNA comprising a sequence chosen from: (i) a guide sequence selected from SEQ ID NOs: 1-89; (ii) at least 17, 18, 19, or 20 contiguous nucleotides of a sequence selected from SEQ ID NOs: 1-89; (iii) a guide sequence that is at least 99%, 98%, 97%, 96%, 95%, 94%, 93%, 92%, 91%, or 90% identical to a sequence selected from SEQ ID NOs: 1-89; (iv) a guide sequence comprising any one of SEQ ID NOs: 1-24; and (iv) a guide sequence comprising any one of SEQ ID NOs: 1-6; or (b) a nucleic acid encoding a guide RNA of (a.); and optionally (c) an RNA-guided DNA binding agent or a nucleic acid encoding an RNA-guided DNA binding agent; and wherein the second composition comprises a lentiviral vector that encodes a WT1-specific TCR having a TCR α chain of SEQ ID NO: 251 and a TCR β chain of SEQ ID NO: 253.

In some embodiments, the engineered cell can be altered by delivering a composition further comprising: (a) a guide RNA comprising a sequence chosen from: (i) a guide sequence selected from SEQ ID NOs: 90-178, 185, and 213-218; (ii) at least 17, 18, 19, or 20 contiguous nucleotides of a sequence selected from SEQ ID NOs: 90-178, 185, and 213-218; (iii) a guide sequence that is at least 99%, 98%, 97%, 96%, 95%, 94%, 93%, 92%, 91%, or 90% identical to a sequence selected from SEQ ID NOs: 90-178, 185, and 213-218; (iv) a guide sequence comprising any one of SEQ ID NOs: 90-113 and 213-218; and (iv) a guide sequence comprising any one of SEQ ID NOs: 90-95; or (b) a nucleic acid encoding a guide RNA of (a.).

Example 10. Editing with Single Guides

Examples below were performed by the following method unless noted otherwise in the examples.

Genomic DNA Isolation

T cells were harvested >48 hours post-nucleotransfection. DNA isolation was performed as described in Example 1. DNA samples were subjected to PCR and subsequent NGS analysis as described in Example 1.

Delivery of RNPs to T Cells

Healthy donor PBMCs or leukopaks were obtained commercially and T cells isolated by positive selection using the CD4/CD8 straight from Microbeads kit (Miltenyi Biotec) or by negative selection using the EasySep Human T-cell Isolation Kit (Stem Cell Technology, Catalog #17951) following the manufacturers protocol. T cells were cryopreserved in Cryostor CS10 freezing media (Catalog #07930) for future use. Upon thaw, T cells were rested overnight in base media (XVIVO15 supplemented with 2-mercaptoethanol, N-acetyl-cysteine and 5% human AB serum or FBS) supplemented with 200 U/mL IL2 (Peprotech) and 5 ng/mL each of IL7 and IL15. T cells were subsequently activated with T Cell TransAct (Miltenyi Biotec, 130-111-160) as recommended by manufacturer and cultured for 48-72 hours prior to electroporation.

The ribonucleoprotein (RNP) complex comprising a Cas9 protein and ggRNA was generated by first pre-annealing individual crRNA and trRNA by mixing equivalent amounts of reagent and incubating at 95° C. for 2 min and cooling to room temperature. Guide(s) in the RNP utilized crRNA and trRNA associated as a single RNA molecule (single guide RNA, sgRNA) or in two separate RNA molecules (dual guide RNA, dgRNA) that were previously annealed by incubating at 95° C. for 2 min followed by cooling to ambient temperature. RNPs targeting the TRAC or TRBC locus were complexed by mixing either SEQ ID NO: 186 (TRAC) or SEQ ID NO: 180 (TRBC1/2) with SpyCas9 at a 2:1 molar ratio to a final concentration of 20 uM Cas9-RNP. For electroporation, T cells were suspended at 5-20×$10^6$ cells/100 uL with TRAC and TRBC RNPs added as indicated to a final concentration of 2 μM RNP. T cells were nucleofected with RNP using the P3 Primary Cell 96-well Nucleofector™ Kit (Lonza, Cat. V4SP-3960) or Lonza 4D-Nucleofector X Unit (Catalog #: AAF-1002X) using Buffer P3 and manufacturer's pulse codes. Base media was added to cells immediately post electroporation and cells allowed to rest for at least 4 hours.

For select assays, cells were expanded using the G-Rex protocol. Briefly, after electroporation, transfer 1×10^6 cells in 1 ml of cytokine media in 1 well of a 24 well G-Rex and virus equivalent to MOI 3×10^5 to the well. After 24 h, make up the volume to 7 ml using cytokine media. Every 2-3 days, remove half the media (3.5 ml) without disturbing the cells and add 2× cytokine media. Harvest after on Day 11-13.

Cell Staining for Flow Cytometry

Four to 12 days after RNP nucleofection, edited T cells (200 ul/200,000 cells) were collected in a 96 well round bottom plate and spun down at 500 g for 5 minutes. Cells were then resuspended in an antibody mixture containing a combination of antibodies targeting CD3, CD4, CD8, CD45RO, CD45RA, CD27, CCR7, CD62L, and/or the TCR specific pMHC tetramer or TCR specific Vbeta chain antibody. The mixture was incubated for 45 minutes at room temperature in the dark. Samples were spun down at 500 g for 5 minutes, cell pellets collected, and resuspended in 1:10,000 DAPI (Biolegend—#422801) in FACS buffer. Flow cytometry was then performed using the cytoflex according to the manufacturer's instructions.

Single guides were also tested for individual and simultaneous editing at TRAC and TRBC loci in stimulated T cells. T cells were nucleofected with RNP containing guide SEQ ID NO: 180 targeting the TRBC1 and TRBC2 loci, RNP containing guide SEQ ID NO: 186 targeting TRAC, or a mixture of both RNP species at a 2:1 ratio of guide to Cas9. Two days post electroporation, T cells were passaged and lysates collected.

Figure 12A:
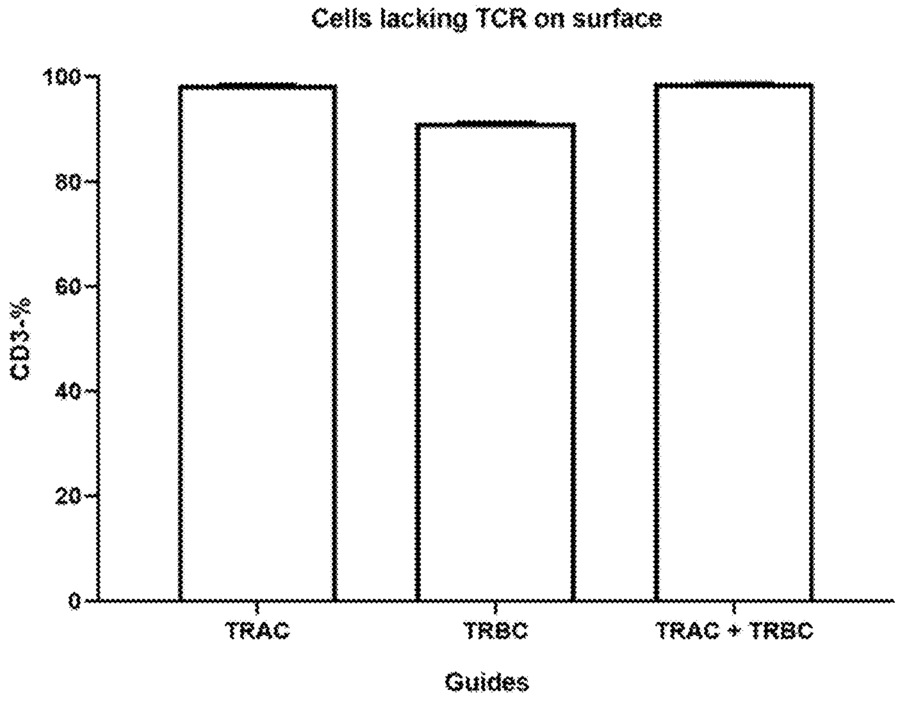
FIGS. 12A-B demonstrate the editing frequency obtained by simultaneous editing of TRAC and TRBC loci using multiple single guide RNAs.

Genomic DNA was prepared and NGS analysis performed as described in Example 1. Test samples were performed in triplicate, with a single mock sample. The knockdown efficiency of TCR surface expression for individual and simultaneous editing of TRAC and TRBC guides was assessed by flow cytometry targeting the presence or absence of CD3. The percentages of T cells devoid of the CD3 molecule are shown in Table 21 and FIG. 12A.

TABLE 21

| Edited CD3− cells in population | | | |
|---|---|---|---|
| Sample | Mean % CD3− | SD | n |
| TRAC RNP | 98.47 | 0.06 | 3 |
| TRBC RNP | 91.20 | 0.17 | 3 |
| TRAC/TRBC RNP | 95.83 | 5.05 | 3 |

Figure 12B:
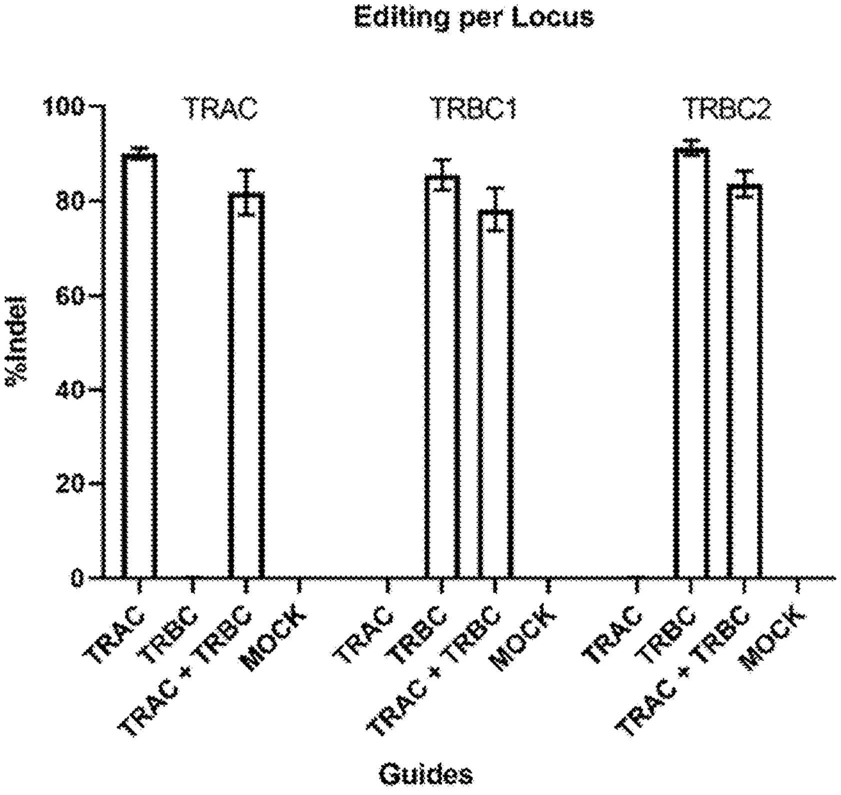

The indel frequency was assessed by NGS analysis following the individual and combinatorial editing of TRAC and TRBC in $CD3^-$ T cells. The percentage of guide editing in TRAC and TRBC are shown in Table 22 and FIG. 12B.

TABLE 22

| TRAC and TRBC guide editing in T cells | | | | | | | |
|---|---|---|---|---|---|---|---|
| SEQ ID NO: | TRAC Mean Indel % | TRAC SD | TRBC1 Mean Indel % | TRBC1 SD | TRBC2 Mean Indel % | TRBC2 SD | N |
| TRAC KO | 90 | 1.2 | 0.4 | 0 | 0.2 | 0.1 | 3 |
| TRBC KO | 0.2 | 0.1 | 85.4 | 3.2 | 91.2 | 1.5 | 3 |
| TRAC KO + TRBC KO | 81.8 | 4.7 | 78.2 | 4.4 | 83.6 | 2.7 | 3 |
| Mock | 0.2 | — | 0.2 | — | 0.1 | — | 1 |

Example 11. TRAC Guide Insertion Screen

Insertion of AAV Template into T Cells

The location of 12 guides targeting the TRAC locus was used to design an adenovirus-associated virus (AAV) template that would delete an 80 bp region of the TRAC locus to prevent cutting of the site after repair and preventing the guide/Cas9 from cutting the template. This would create a locus in which a TCR can be inserted into the TRAC locus. Using the homology arms with the 80 bp deletion, a construct was designed to insert the model TCR and the second to insert GFP with both driven by the EF1a promoter that were then synthesized by GenScript USA Inc. and inserted into a pUC19 vector with BglII restriction sites for subcloning into an AAV vector. AAV templates were designed with homology arms flanking TRAC guide cut sites to insert genes encoding TCRs or reporter molecules (ie. GFP) site-specifically in T cells.

T cell isolation and RNP nucleotransfection procedures were performed as described in Example 10. Ten minutes post electroporation, T cells were added to cytokine media at 1×$10^6$ cells/mL with AAV template added at a MOT of 3×$10^5$. Twenty-four hours post electroporation, cells were split and expanded for an additional 4-12 days in static culture or G-REX multiwell plates (Wilson Wolf Manufacturing) prior to use in functional assays or cryopreserved. Flow cytometry was performed.

TRAC Guide Insertion Screen

Figure 13A:
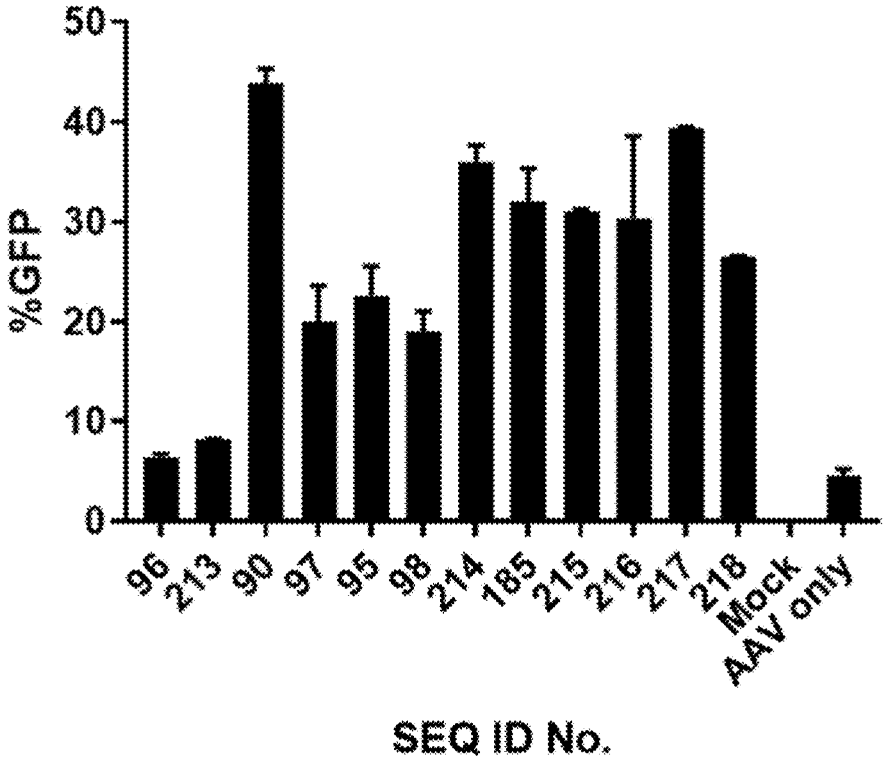
FIGS. 13A-B show degree of GFP insertion at the TRAC locus employing dual RNA guides and an AAV vector (AV9) with a gapped insertion template (FIG. 13A) and degree of TRAC knock out employing these dual RNA guides and AAV vector that are CD3− (FIG. 13B). A gapped insertion template (or simply gapped template) comprises two sequences that flank a "gap," i.e., a region in the corresponding target sequence not present in the gapped insertion template. The gapped insertion template is compatible with guides that target a site within the gap for cleavage and is useful for quantitatively comparing such guides regardless of whether they target the exact same cleavage site, provided that they both target a cleavage site within the gap.
Figure 13B:
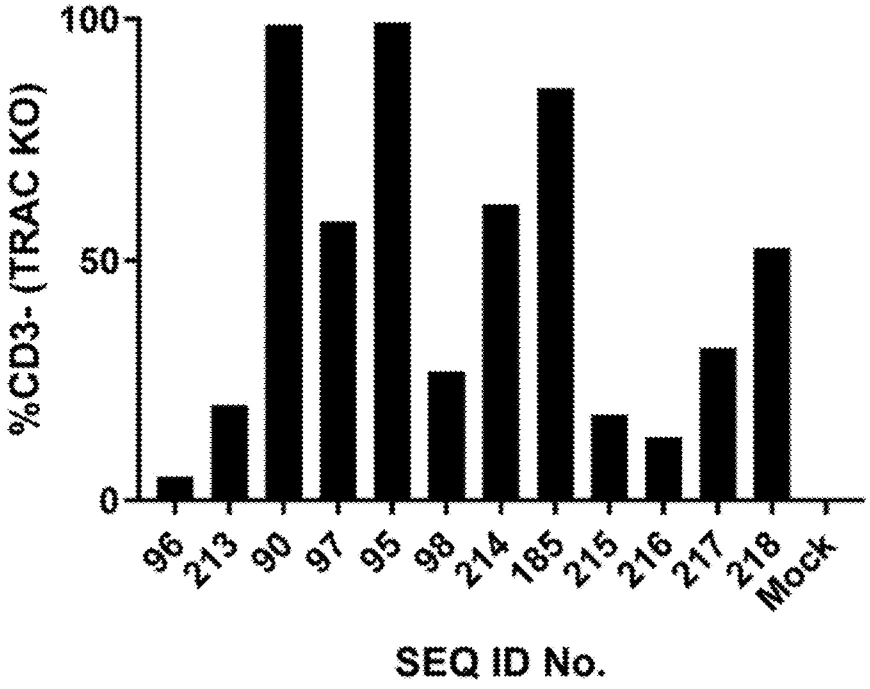

Dual guides targeting exon 1 of the TRAC locus were screened in T cells to evaluate insertion efficiency. The initial screen used an AAV-based insertion template (AV9) encoding a GFP reporter gene AV9 was designed with an 80 bp gap designed to cover the target sites of the guides listed in Table 23. AV9 is described in Table 37, below. T cells were nucleofected in duplicate with RNP containing a dual guide except for the AAV only and no RNP (mock) samples that were used as controls. Procedures for cell transduction with RNP were carried out as described in Example 10 with the exception that the guide to Cas9 ratio was 1:1. The insertion efficiency of the TRAC guides was determined by flow cytometry, as described in Example 10, to detect the fluorescence of GFP from the inserted construct as shown in Table 23 and FIG. 13A. The knockdown efficiency of TCR surface expression for editing by TRAC guides was assessed by flow cytometry targeting the presence or absence of CD3. The percentage of T cells devoid of the CD3 molecule are shown in Table 23 and FIG. 13B.

TABLE 23

Percent GFP expression of inserted guides

| Guide | GFP % | GFP % SD | % CD3− cells (n = 1) |
|---|---|---|---|
| 96 | 6.44 | 0.28 | 4.96 |
| 213 | 8.22 | 0.06 | 19.8 |
| 90 | 43.9 | 1.41 | 98.9 |
| 97 | 20.05 | 3.61 | 58.1 |
| 95 | 22.65 | 2.9 | 99.2 |
| 98 | 19.1 | 1.98 | 26.8 |
| 214 | 36.05 | 1.63 | 61.5 |
| 185 | 32.05 | 3.32 | 85.7 |
| 215 | 31 | 0.28 | 17.9 |
| 216 | 30.4 | 8.2 | 13.1 |
| 217 | 39.4 | 0.14 | 31.6 |
| 218 | 26.55 | 0.07 | 52.5 |
| Mock | 0 | 0 | 0.45 |
| AAV only | 4.52 | 0.72 | NA |

Example 12. Single Guide Screen for TRAC Insertion

Single guides targeting exon 1 of the TRAC locus were then screened in T cells to evaluate the insertion efficiency using AV9. Procedures for T cell preparation and RNP transduction were carried out in duplicate as described in Example 10 with the exception that the guide:Cas9 ratio was 1:1. AV9 was designed as described in Example 11 with the guides listed in Table 24. NGS indel analysis was conducted as described in Example 1.

Figure 14A:
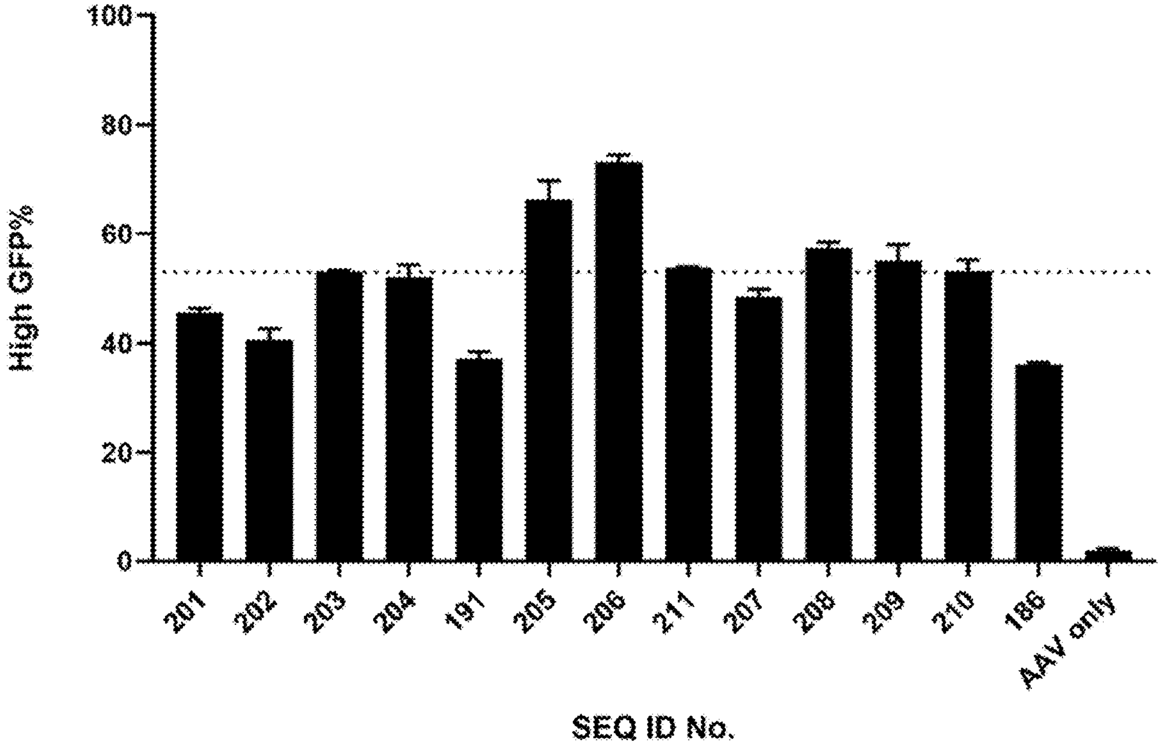
FIGS. 14A-14B show degree of GFP insertion at TRAC locus with sgRNA and gapped template AV9 (FIG. 14A), and percentage of cells engineered with these sgRNA and gapped template AV9 that are phenotypically CD3− (FIG. 14B).
Figure 14B:
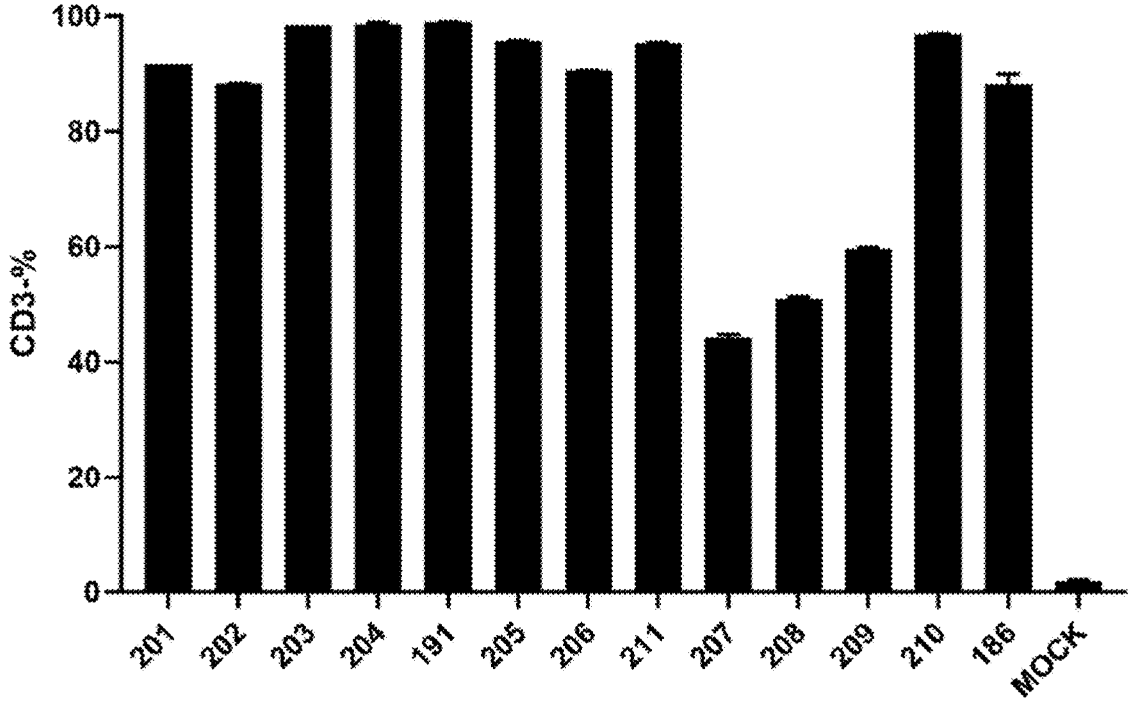

The insertion efficiency of the TRAC guides was determined by flow cytometry to detect the fluorescence of GFP from the inserted construct as shown in Table 24 and FIG. 14A. The knockout efficiency of TCR surface expression by TRAC guides was assessed by flow cytometry targeting the presence or absence of CD3. The percentage of T cells devoid of the CD3 molecule are shown in Table 24 and FIG. 14B. Editing efficiencies of chemically modified and unmodified guides were also assayed and found to have activity.

TABLE 24

Percentage of GFP positive cells

| Guide | % GFP (Mean) | % GFP SD | % CD3− cells | % CD3− cells SD |
|---|---|---|---|---|
| 201 | 45.65 | 0.78 | 88.85 | 0.21 |
| 202 | 40.65 | 2.05 | 89.10 | 0.42 |
| 203 | 53.05 | 0.21 | 96.15 | 0.21 |
| 204 | 51.95 | 2.33 | 95.70 | 0.71 |
| 191 | 37.15 | 1.34 | 95.95 | 0.21 |
| 205 | 66.35 | 3.46 | 93.50 | 0.71 |
| 206 | 73.15 | 1.34 | 93.25 | 0.78 |
| 211 | 53.75 | 0.21 | 92.55 | 0.21 |
| 207 | 48.45 | 1.34 | 62.25 | 0.64 |
| 208 | 57.35 | 1.06 | 71.50 | 0.14 |
| 209 | 55.00 | 2.97 | 72.15 | 1.91 |

TABLE 24-continued

Percentage of GFP positive cells

| Guide | % GFP (Mean) | % GFP SD | % CD3− cells | % CD3− cells SD |
|---|---|---|---|---|
| 210 | 53.15 | 2.05 | 93.70 | 0.28 |
| 186 | 36.15 | 0.35 | 85.50 | 0.57 |
| Mock | 1.88 | 0.41 | 0.63 | 0.01 |
| AAV only | 0.00 | 0.00 | 1.71 | 0.78 |

Example 13—Assessing Promoters and ITRs for Exogenous TCR Insertion and Expression

Engineering of Gene-Editing TCR-T Cells for Functional Assays

TCR insertion and subsequent surface expression was tested with a variety of promoters and two ITR lengths. T cell isolation and RNP transfection with guide SEQ ID NO: 185 were conducted as described in Examples 10 with the exception of using a 1:1 molar ratio of gRNA to SpyCas9. RNP transduction of AAV constructs containing TCR-C into T cells was conducted as described in Example 11. The AAV templates contained 500 bp homology arms corresponding to the 500 bp flanking each side of the SEQ ID NO: 185 cut site in the TRAC locus. Each AAV construct featured different combinations of promoters and ITRs as shown in Table 25. The edited T cells were tetramer stained for flow cytometric analysis as described in Example 11.

Figure 15A:
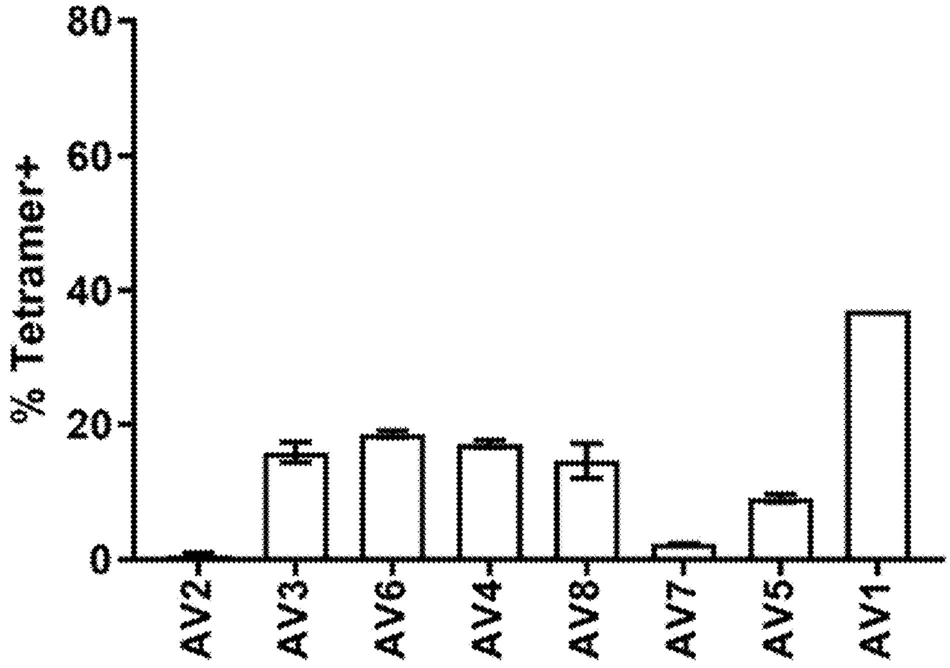
FIGS. 15A-B compare different promoter and inverted terminal repeat (ITR) lengths for TCR insertion as measured by positive tetramer stain (FIG. 15A) and mean fluorescence intensity (MFI) (FIG. 15B) during FACS analysis.
Figure 15B:
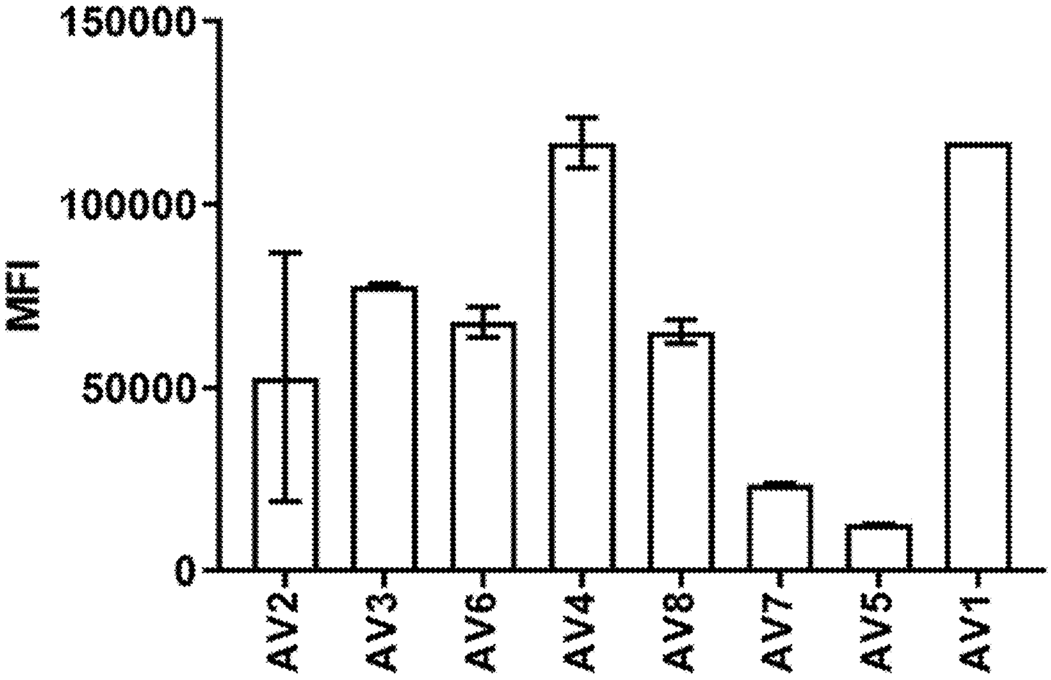

TCR-C insertion efficiency was evaluated by cytofluorimetric analysis assessing both T cell identity through the presence of CD3+ on the cell surface and the number of cells expressing the inserted TCR via to a tetramer of the TCR's specific ligand, the RMF peptide (see, e.g., US20160083449A1, the contents of which are hereby incorporated by reference). The percentage of CD3+ Tetramer+ cells is shown in Table 25 and FIG. 15A. Mean fluorescence intensity (MFI) of the for the tetramer stained T cells is shown in Table 25 and FIG. 15B.

TABLE 25

Promoters and ITRs for AAV templates
The sequence elements and sequences shown in this table are further defined in Table 37.

| AAV Template ID | Promoter | ITR length (bp) | % Tetramer+, CD3+ (Mean) | SD | Fluorescence intensity CD3+ (mean) | SD | n |
|---|---|---|---|---|---|---|---|
| AV2 | Ef1a - short | 145 | 0.48 | 0.48 | 52752 | 34002 | 2 |
| AV3 | MND-1 | 141 | 15.85 | 1.48 | 77704 | 646 | 2 |
| AV6 | MND-1 | 145 | 18.55 | 0.49 | 67845 | 4084 | 2 |
| AV4 | MND-2 | 141 | 17.10 | 0.57 | 116978 | 6798 | 2 |
| AV8 | MND-2 | 145 | 14.55 | 2.62 | 65281 | 3117 | 2 |
| AV5 | PGK | 135 | 2.35 | 0.03 | 23410 | 437 | 2 |
| AV7 | PGK | 146 | 9.01 | 0.57 | 12596 | 78 | 2 |
| AV1 | EF1a | 146 | 37 | — | 117223 | — | 1 |

Figures 16A, 16B, 16C:
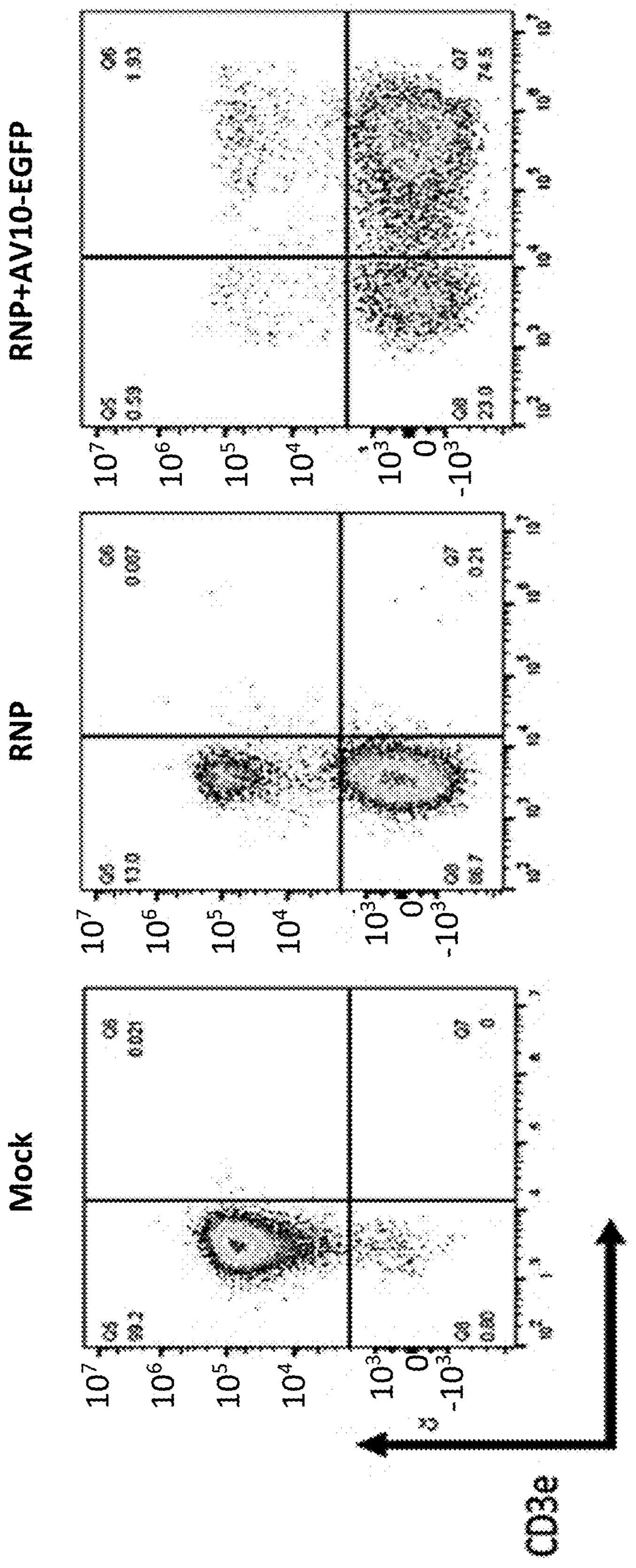
FIGS. 16A-C show the amount of GFP expression driven from the endogenous TRAC promoter in cells engineered by an insertion protocol with AAV insertion of a promoterless GFP construct at the TRAC locus.

Example 14: GFP Expression in Engineered T Cells Using Endogenous TRAC Promoter In another experiment, an AAV template (AV10) containing a P2A ribosomal skip site followed by a GFP reporter gene (ie. without an exogenous promoter) was inserted into exon 1 of the TRAC locus to determine if the endogenous TRAC promoter could drive GFP expression. T cells were nucleofected with RNP containing guide SEQ ID NO: 186 and transduced with AAV AV10 as described in Example 10. Control conditions included unedited T cells (Mock) and T cells which received RNP nucleofection but not AAV (RNP only). After 4-days of culture edited T cells were co-stained with APC-Cy7 conjugated anti-CD3e (Biolegend, 300318) for CD3 and analyzed by flow cytometry for GFP expression and TCR knockout as shown in Table 26 and FIGS. 16A-C.

TABLE 26

Percentage of edited CD3− and GFP positive cells in population.

| Sample | % CD3− | SD | % GFP+ | SD |
|---|---|---|---|---|
| AV10-GFP + RNP | 97.5 | 0.05 | 76.4 | 1.9 |
| RNP only | 86.7 | 2.05 | 1.1 | 0.0 |
| Mock | 0.8 | 0.04 | 0.0 | 0.0 |

Figure 17C:
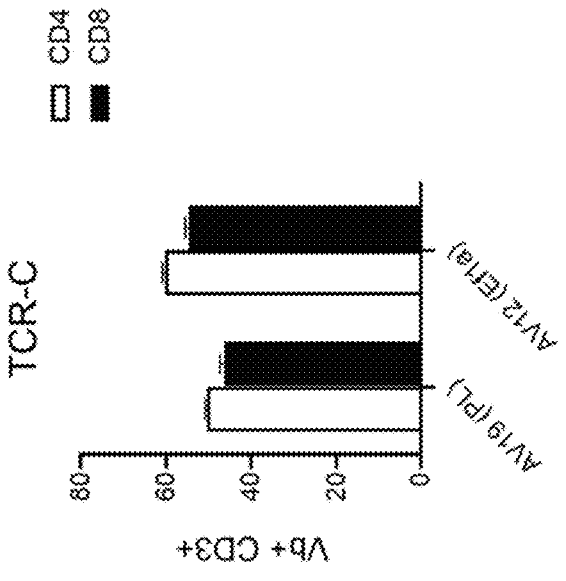
FIGS. 17A-C show insertion efficiency of TCR construct templates with and is without promoter sequences (PL—promoterless; EF1a—promoter EF1alpha or EF-1α) at the TRAC locus.
Figure 17B:
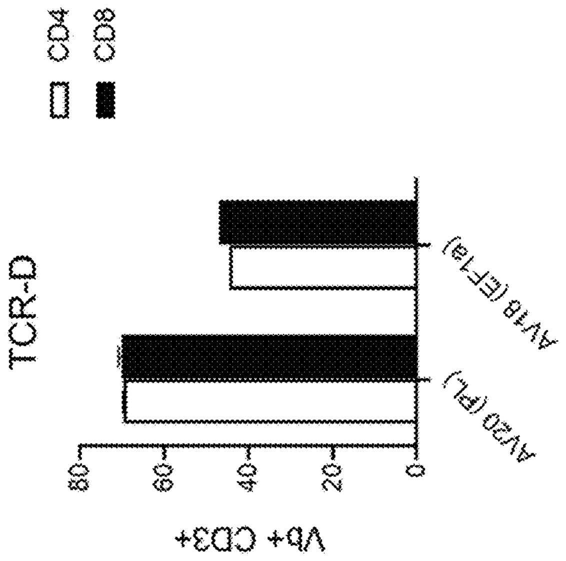
Figure 17A:
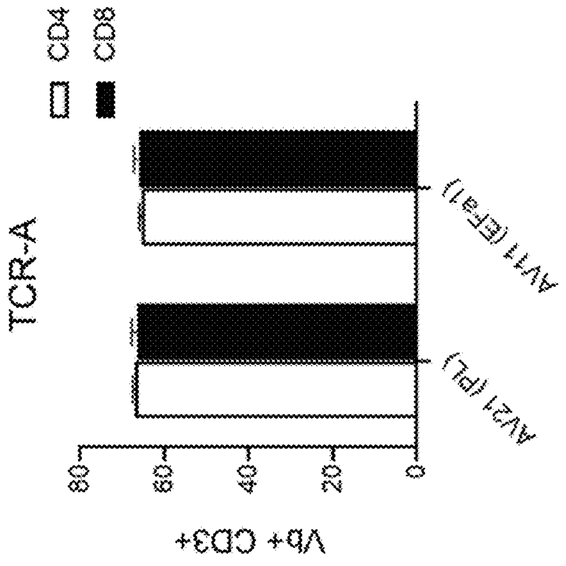

Example 15: TCR Expression in Engineered T Cells Using Endogenous and Exogenous TRAC Promoter In an additional experiment, AAV templates containing TCR-A, TCR-C, or TCR-D with or without an exogenous promoter were inserted into the TRAC locus to determine if the endogenous TRAC promoter could drive expression and function of the inserted TCRs. T cell transfection and AAV insertion were conducted in duplicate as described in Examples 10 and 11 respectively. T cells were nucleofected with RNP containing TRAC (SEQ ID NO: 186) and TRBC (guide SEQ ID NO: 180) with the RNP containing guide contained various AAV templates shown in Table 27. T cells expressing the inserted TCR were detected by flow cytometry using antibodies specific to the TCR Vbeta chain of the inserted TCR in CD4+ and CD8+ cells as shown in Table 27 and FIGS. 17A-C (anti-Vbeta8 for TCR-A, [Biolegend Cat #140104], Vbeta7.2 for TCR-D in FIG. 17B [Beckman Coulter, Cat #IM3604], and Vbeta17 for TCR-C shown in FIG. 17C [Beckman Coulter, Cat #IM2048]).

TABLE 27

Surface expression of engineered TCRs with and without exogenous promoters

| AAV template | TCR | Promoter | % CD4+ CD3+ Vb+ (mean) | SD | % CD8+ CD3+ Vb+ (mean) | SD |
|---|---|---|---|---|---|---|
| AV21 | TCR-A | Endogenous(PL) | 67.05 | 0.49 | 66.50 | 1.27 |
| AV11 | TCR-A | EF1a | 65.45 | 0.49 | 66.05 | 1.20 |
| AV20 | TCR-D | Endogenous(PL) | 69.85 | 0.07 | 70.25 | 0.64 |
| AV18 | TCR-D | EF1a | 44.60 | 0.00 | 47.00 | 0.00 |
| AV19 | TCR-C | Endogenous(PL) | 50.45 | 0.35 | 46.40 | 0.99 |
| AV12 | TCR-C | EF1a | 60.20 | 0.71 | 54.70 | 0.85 |

*PL—promoterless template construct

The sequence elements and sequences shown in this table are further defined in Table 37.

T-cell degranulation and cytokine release in response to the specific WT1 peptide antigen was performed to test the functionality of engineered effector T cells expressed from an endogenous promoter or exogenous TRAC promoter. Specifically, engineered T cells were assessed for upregulation of CD107a and expression of IL2 and IFNy after co-culture with peptide pulsed cells from the cancer cell lines OCI-AML3 (DSMZ, Cat. ACC 582). Briefly, 100,000 OCI-AML3 cells were pulsed in base media (Xvivo base media: No Cytokines+1 uL/mL GolgiPlug+0.7 uL/mL GolgiStop with 30 uL/mL CD107a APC/Cy7 (3 ul/well)) for 4-5 hours at 37 degrees with titrated amounts of the 9-mer peptides VLDFAPPGA (VLD) or RMFPNAPYL (RMF) peptide concentrations ranging from 0 to 5000 nM. Gene edited TCR+ T cells were suspended at 1×10^6 TCR inserted cells/ml in XVIVO15 base media containing for a final concentration of 30 ul/ml CD107a APC/Cyanine7 antibody (Biolegend), 1 ul/ml Golgiplug (BD) and 0.7 ul/ml Golgistop (BD) and added to the peptide pulsed target cells at a 1:1 Effector:Target (E:T)cell ratio. Co-cultures were incubated overnight at 37° C., and the cells stained for surface markers CD3, CD4, CD8 and the specific TCR beta chain of TCR-A or TCR-D, and incubated for 30 minutes. Following surface staining, cells were fixed and permeabilized using a commercially available kit (Invitrogen) for intracellular IFN-β and TNFα staining followed by a 30 minute incubation at room temperature. Following intracellular stain, cells were washed and analyzed by flow cytometry.

Figure 18A:
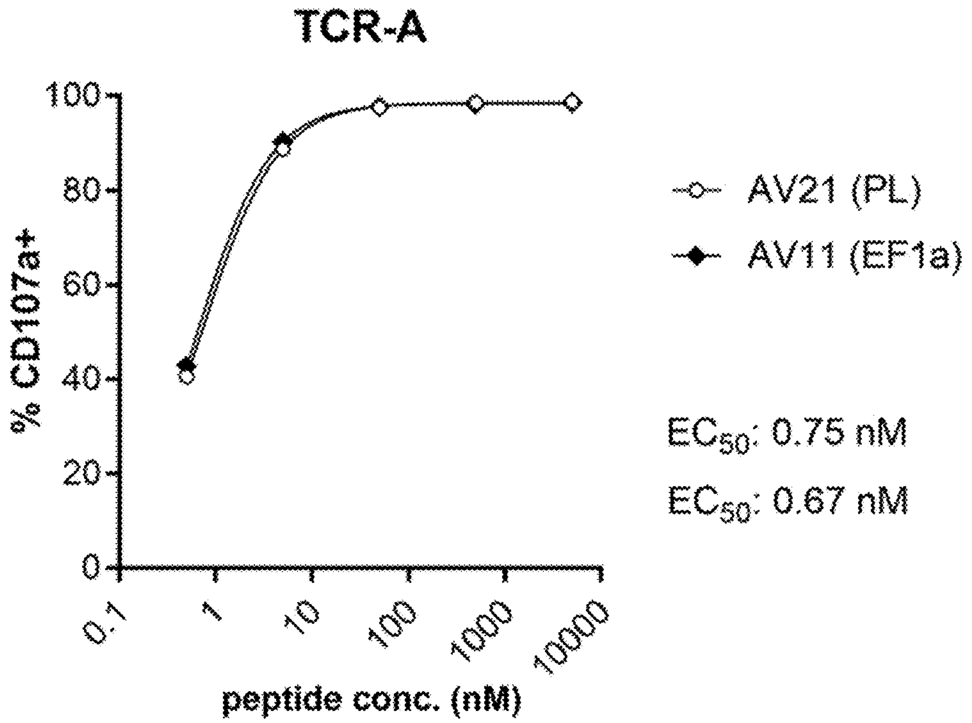
FIG. 18A-B measure degranulation in insertion transformants with & without promoters comprised in the transforming constructs using two different TCRs.
Figure 18B:
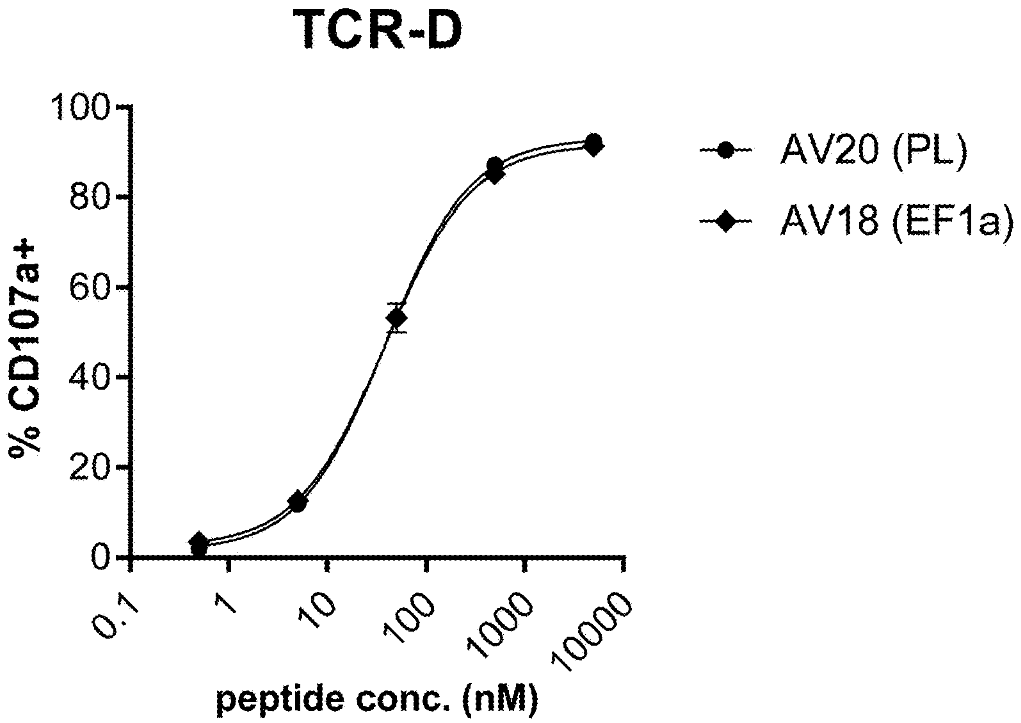
Figure 19A:
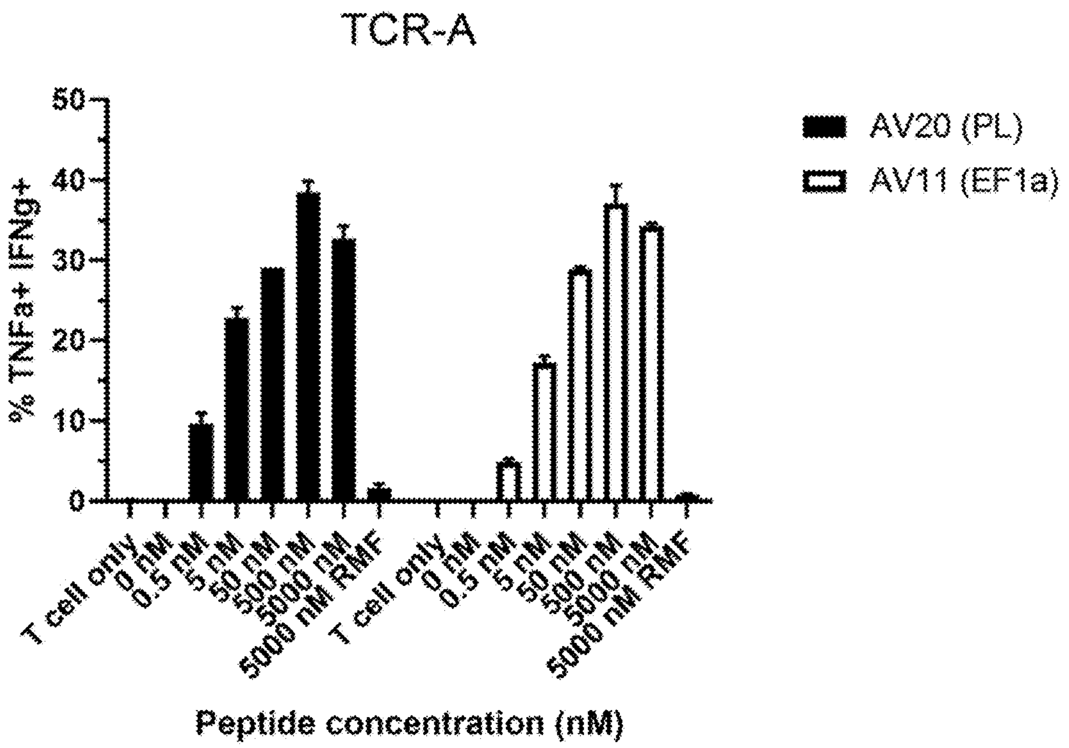
FIG. 19A-B measure interferon gamma expression in insertion transformants with & without promoters comprised in the transforming constructs using two different TCRs.
Figure 19B:
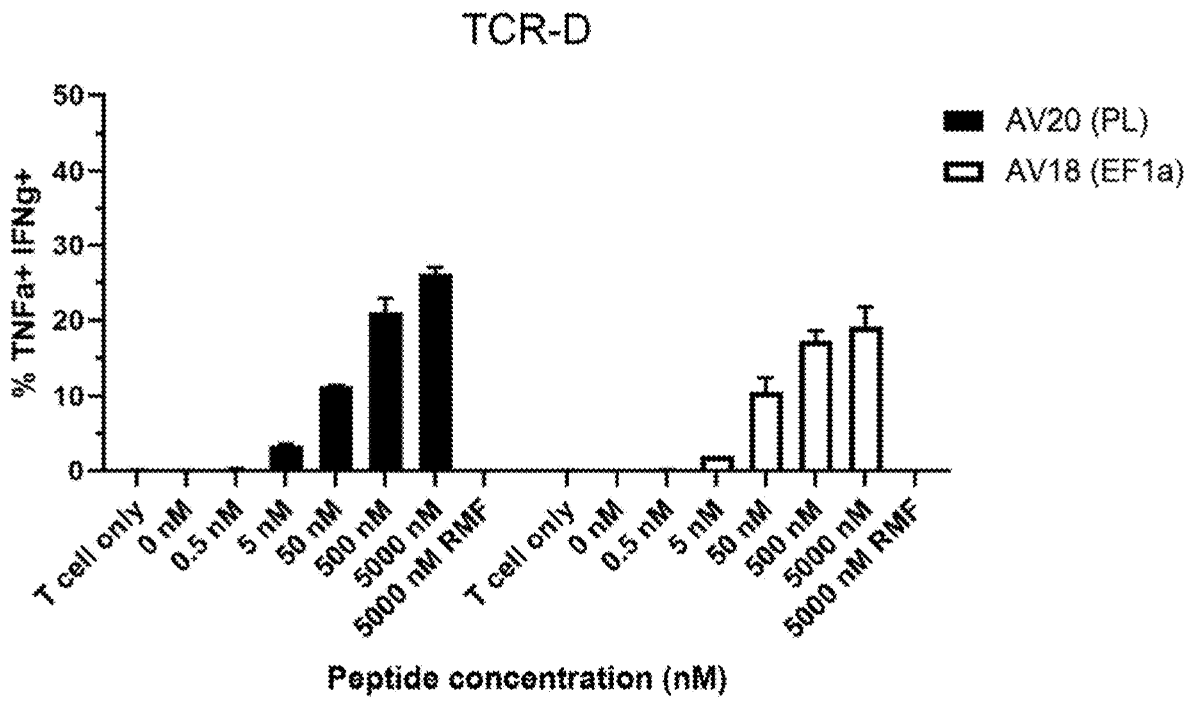

The impact of the EF1a (or EF-1α) and endogenous promoters on T cell killing and cytokine release was measured by the percentage of cells positive for CD107a, IFNy, and or TNFa present in each sample. The effector T cells with TCRs and promoter type are listed in Table 28. Flow cytometry results for the TCR+ T cells are shown in Table 28 and dose response curves for cells expressing TCR-A are shown in FIG. 18A (AV21 and AV11). The percentage of CD107a+ cells expressing TCR-D are shown in Table 28 and FIG. 18B (AV20 and AV18). The immune response elicited by the T cells was evaluated by measuring the percentage of TNF-alpha and interferon gamma as shown in Table 28 and FIGS. 19A-B.

TABLE 28

Degranulation and Interferon gamma response in engineered T cells expressing TCRs with and without exogenous promoters

| Construct | TCR | Promoter | Peptide Concentration | % CD107a+ | SD | % TNFa+ IFNg+ | SD |
|---|---|---|---|---|---|---|---|
| AV21 | TCR-A | Endogenous | 0 nM | 3.79 | 0.49 | 0.08 | 0.02 |
| | | | 0.5 nM | 40.55 | 0.35 | 9.66 | 1.34 |
| | | | 5 nM | 88.70 | 0.42 | 22.75 | 1.34 |
| | | | 50 nM | 97.55 | 0.07 | 29.10 | 0.00 |

TABLE 28-continued

Degranulation and Interferon gamma response in engineered T cells expressing TCRs with and without exogenous promoters

| Construct | TCR | Promoter | Peptide Concentration | % CD107a+ | SD | % TNFa+ IFNg+ | SD |
|---|---|---|---|---|---|---|---|
| | | | 500 nM | 98.55 | 0.07 | 38.55 | 1.34 |
| | | | 5000 nM | 98.65 | 0.35 | 32.80 | 1.56 |
| | | | 5000 nM RMF | 11.50 | 0.71 | 1.60 | 0.57 |
| AV11 | TCR-A | EF1a | 0 nM | 3.83 | 0.33 | 0.02 | 0.03 |
| | | | 0.5 nM | 42.85 | 0.07 | 4.92 | 0.40 |
| | | | 5 nM | 90.15 | 0.78 | 17.20 | 0.85 |
| | | | 50 nM | 97.65 | 0.21 | 28.90 | 0.28 |
| | | | 500 nM | 98.15 | 0.07 | 37.15 | 2.19 |
| | | | 5000 nM | 98.60 | 0.00 | 34.35 | 0.35 |
| | | | 5000 nM RMF | 11.45 | 0.21 | 0.83 | 0.11 |
| AV20 | TCR-D | Endogenous | 0 nM | 1.73 | 0.18 | 0.05 | 0.04 |
| | | | 0.5 nM | 2.16 | 0.19 | 0.21 | 0.08 |
| | | | 5 nM | 11.95 | 0.21 | 3.40 | 0.23 |
| | | | 50 nM | 53.30 | 0.85 | 11.35 | 0.07 |
| | | | 500 nM | 87.15 | 0.64 | 21.05 | 1.91 |
| | | | 5000 nM | 92.30 | 0.28 | 26.20 | 0.85 |
| | | | 5000 nM RMF | 1.82 | 0.13 | 0.01 | 0.01 |
| AV18 | TCR-D | EF1a | 0 nM | 2.56 | 0.11 | 0.01 | 0.02 |
| | | | 0.5 nM | 3.52 | 0.45 | 0.12 | 0.08 |
| | | | 5 nM | 12.70 | 1.98 | 2.12 | 0.00 |
| | | | 50 nM | 53.25 | 4.60 | 10.58 | 1.87 |
| | | | 500 nM | 85.10 | 2.40 | 17.25 | 1.34 |
| | | | 5000 nM | 91.35 | 1.63 | 19.15 | 2.62 |
| | | | 5000 nM RMF | 2.86 | 0.25 | 0.05 | 0.01 |

The sequence elements and sequences shown in this table are further defined in Table 37.

Figure 20A:
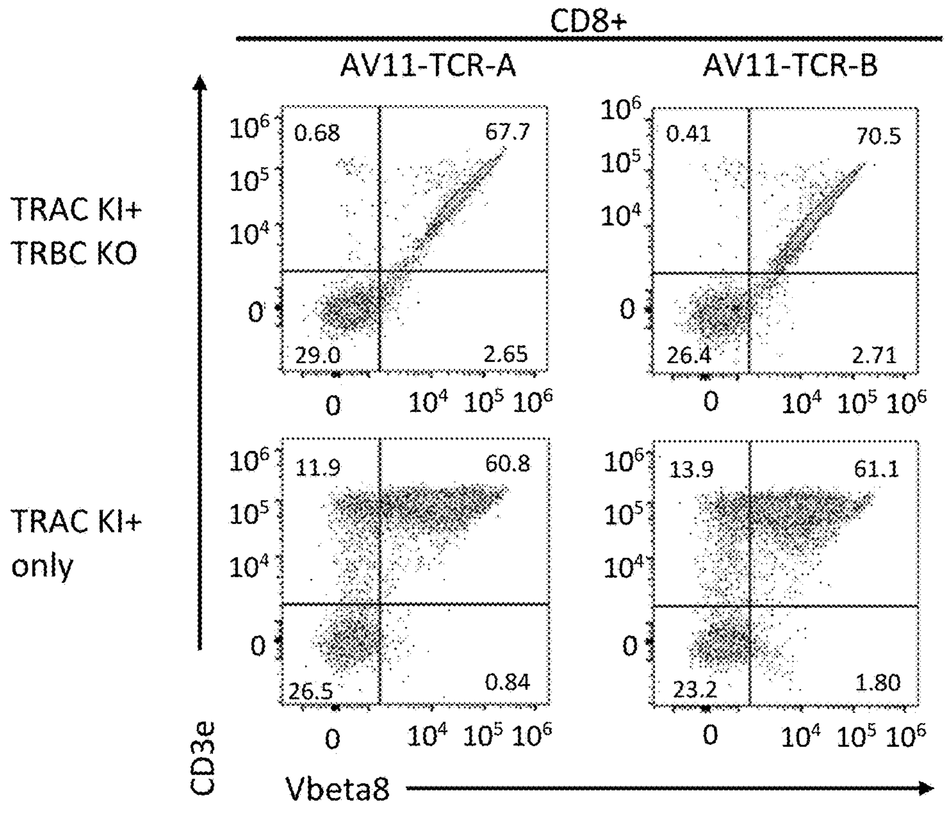
FIGS. 20A-B show surface presence of two TCR constructs, one with and one without Cys modifications.
Figure 20B:
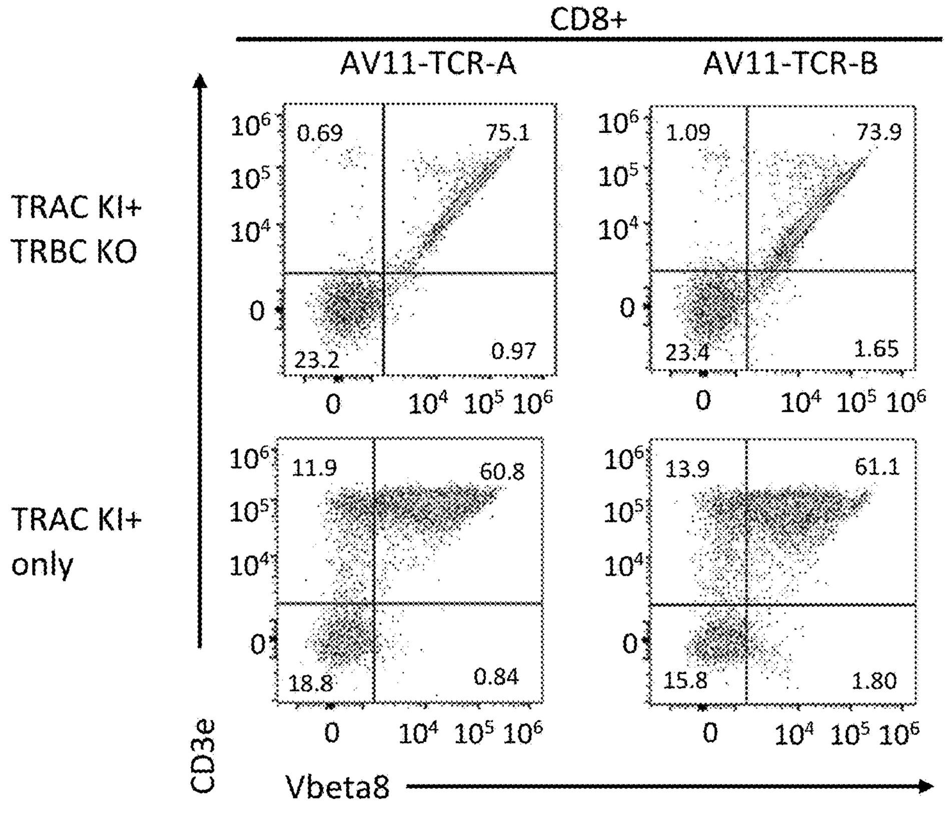
Figure 21A:
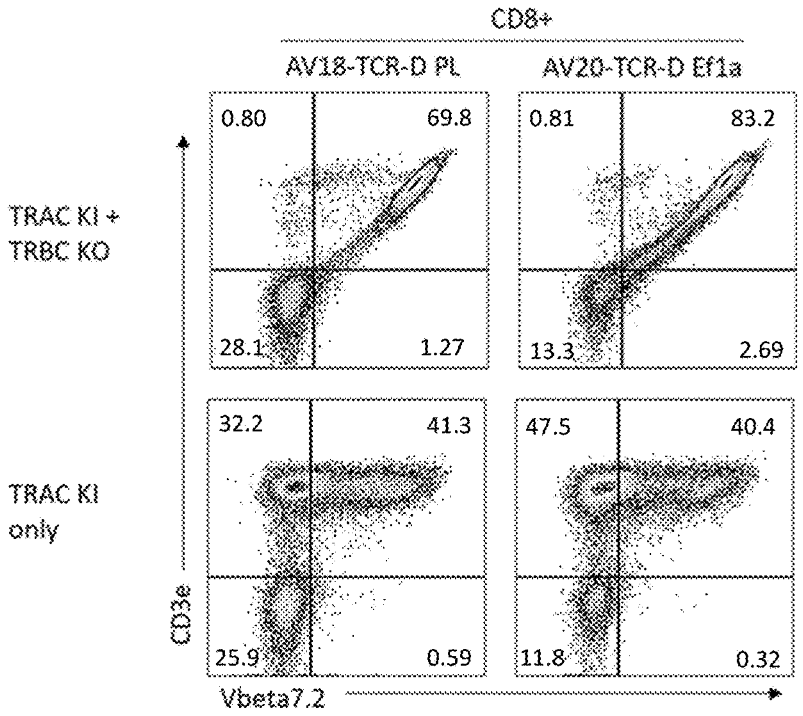
FIGS. 21A-D measure the degree of mispairing between TCR chains of the inserted constructs and endogenous TCR chains as measured by flow cytometry. The FACS data of FIG. 21A and FIG. 21B depict the fraction of engineered cells expressing the transgenic or mispaired TCRs, and the intensity of TCR expression in the engineered cells of FIG. 21A and FIG. 21B are graphed as MFI in FIG. 21C and FIG. 21D, respectively.
Figure 21B:
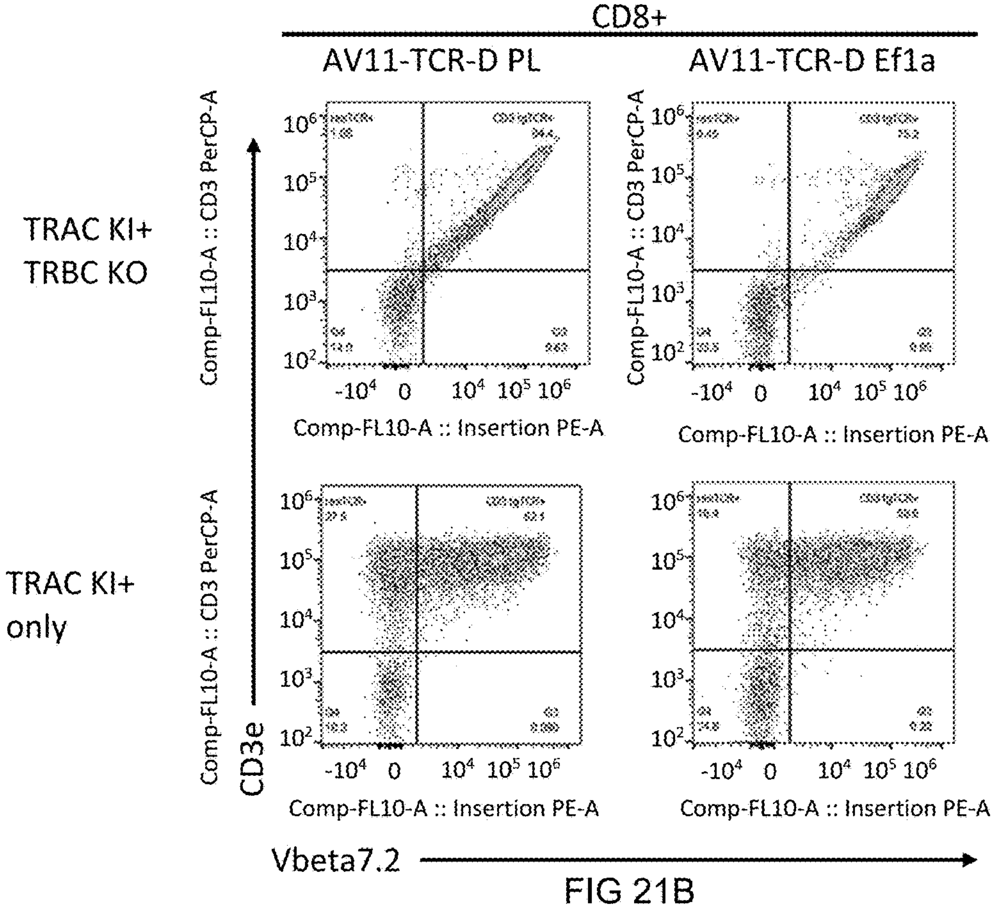
Figure 21C:
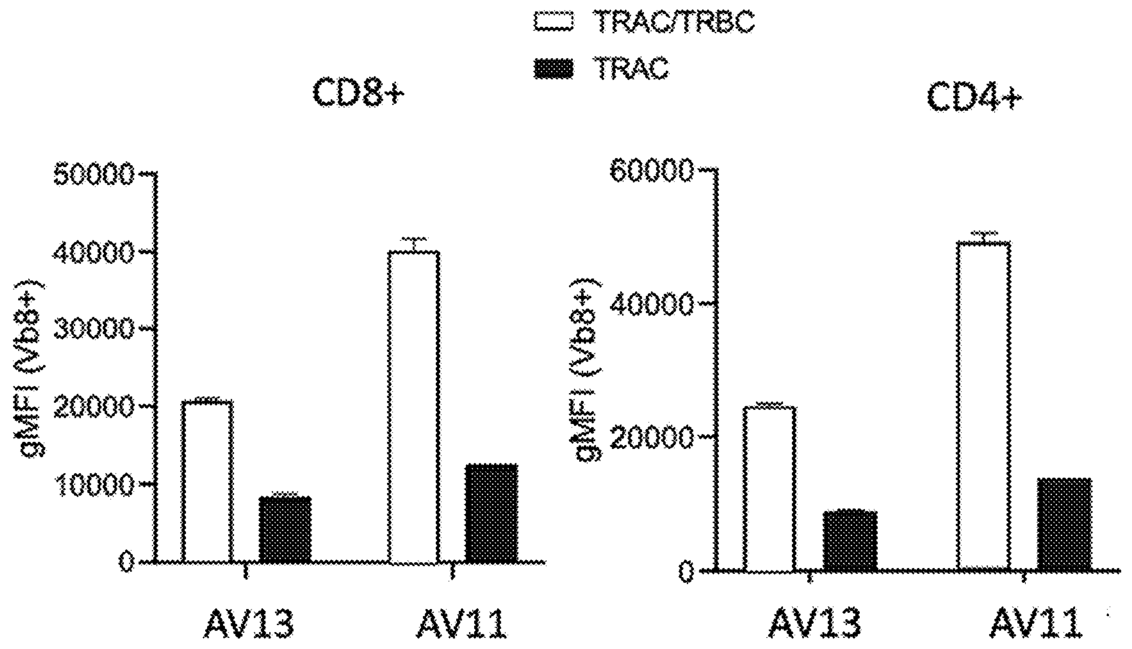
Figure 21D:
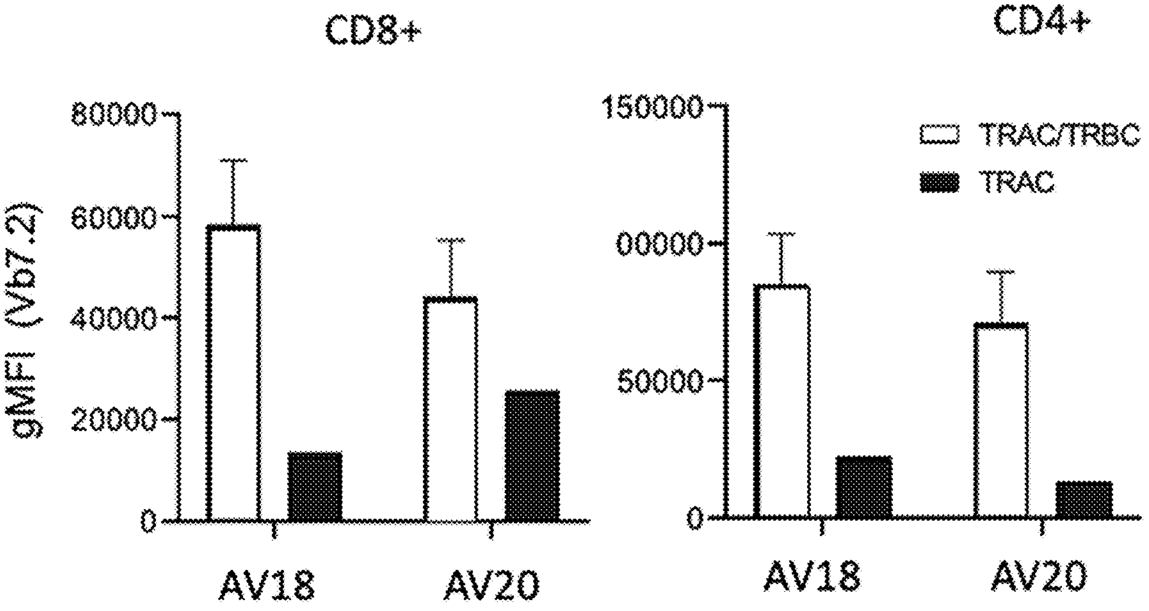

Example 16: Enhancing TCR Expression by Knockout of Both Endogenous Tcell Receptor Alpha and Beta Chains T cells were evaluated for surface expression of engineered TCR-A, TCR-B, or TCR-D comprising both the inserted alpha chain and inserted beta chain. Three conditions to increase pairing of inserted alpha and beta chains were tested: (1) the addition of cysteine residues that may form cysteine bridges to associate the inserted alpha and beta chains; (2) expression from the endogenous TRAC promoter or from and exogenous promoter and (3) the disruption of endogenous copies of TRAC, TRBC1 and TRBC2. T cell transfection and AAV transduction were conducted as described in Example 10. TCRs were inserted via AAV templates AV11, AV13, AV18, or AV20 with either RNP targeting only the TRAC locus or RNP targeting both the TRAC, TRBC1, and TRBC2 loci, as described above. Post transfection, T cells were expanded as described in Example 10. Nine days post cell expansion, edited T cells were co-stained with anti-CD3e and an appropriate V-beta reagent (PE) to identify engineered TCRs via flow cytometry. The percentage of TCR-A and TCR-B CD3+Vb7.2+ cells for each condition is shown in Table 29. FIGS. 20A and 20B plot a representative example of surface expression of engineered TCR-A and TCR-B CD3+Vb7.2+ cells for the data in Table 29. Surface expression of engineered TCR-A and TCR-B in the CD8+ and CD4+ cell populations was also measured as shown in Table 29 and FIG. 21C.

TABLE 29

Assessment of expression of engineered TCR-A and TCR-B comprising both inserted alpha and beta chains

| | | CD8+ | | | | CD4+ | | | |
|---|---|---|---|---|---|---|---|---|---|
| Sample | RNP | Mean CD3+ % Vb+ | SD | Vb MFI | SD | Mean CD3+ % Vb+ | SD | Vb MFI | SD |
| AV13- | TRAC | 62.2 | 1.56 | 8487 | 290` | 68.85 | 0.64 | 8947 | 291 |
| TCR-B | TRAC + | 69.05 | 2.05 | 20709 | 443.36 | 75.35 | 2.05 | 24521 | 492 |
| (with cys) | TRBC | | | | | | | | |
| AV11- | TRAC | 60.8 | nd | 12520 | nd | 69.3 | nd | 13782 | nd |
| TCR-A | TRAC + | 67.55 | 0.21 | 40104 | 2203 | 74.75 | 0.50 | 49273 | 1743 |
| (no cys) | TRBC | | | | | | | | |

The percentage of AV20-TCR-D and AV18-TCR-D CD3+ Vb7.2+ cells using the endogenous or exogenous promoter is shown in Table 30. Surface expression of engineered TCR-D in the CD8+ and CD4+ cell populations was measured as shown in Table 30 and FIGS. 21A-D.

TABLE 30

| Assessment of expression of engineered TCR-D comprising both inserted alpha and beta chains | | | | | | | | | |
|---|---|---|---|---|---|---|---|---|---|
| | | CD8+ | | | | CD4+ | | | |
| Sample | RNP | CD3+ % Vb+ | SD | Vb MFI | SD | CD3+ % Vb+ | SD | Vb MFI | SD |
| AV18- | TRAC | 41.3 | nd | 13586 | nd | 58.6 | nd | 22324 | nd |
| TCR-D | TRAC + TRBC | 71.4 | 1.6 | 58469 | 12479 | 74.05 | 1.15 | 85360 | 18034 |
| AV20- | TRAC | 40.4 | nd | 25613 | nd | 62.1 | nd | 13406 | nd |
| TCR-E | TRAC + TRBC | 83.5 | 0.3 | 44342 | 11035 | 84.1 | 0.3 | 71007 | 18790 |

Figure 22:
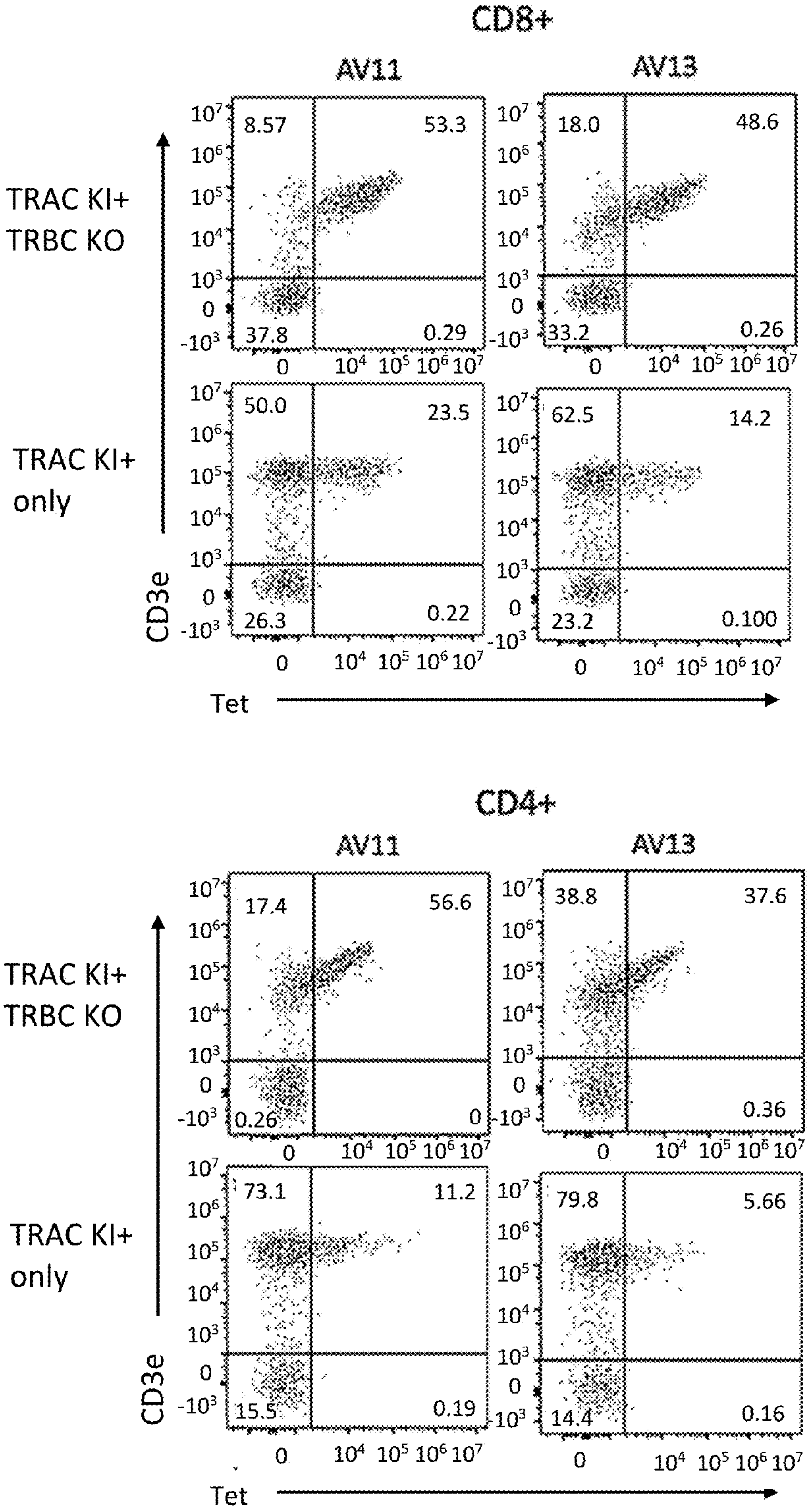
FIG. 22 measures the degree of mispairing between TCR chains of inserted constructs and endogenous TCR chains in CD8+ or CD4+ cells as measured by flow cytometry.
Figure 23:
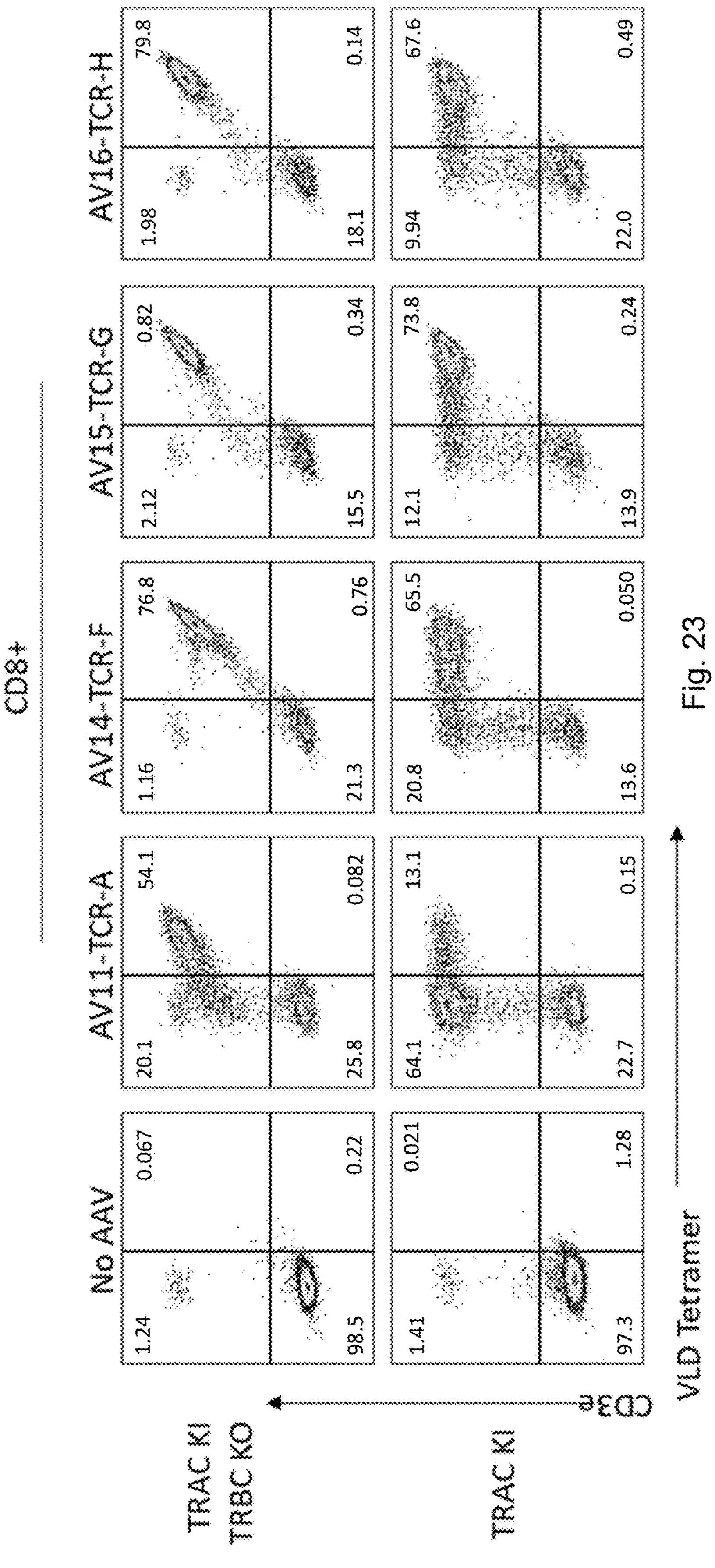
FIG. 23 shows VLD (Wilms' tumor antigen) tetramer staining for four different versions of the TCR with and without knockout of TRBC, indicating the degree of mispairing for the WT1-TCR engineered CD8+ cells.
Figure 24:
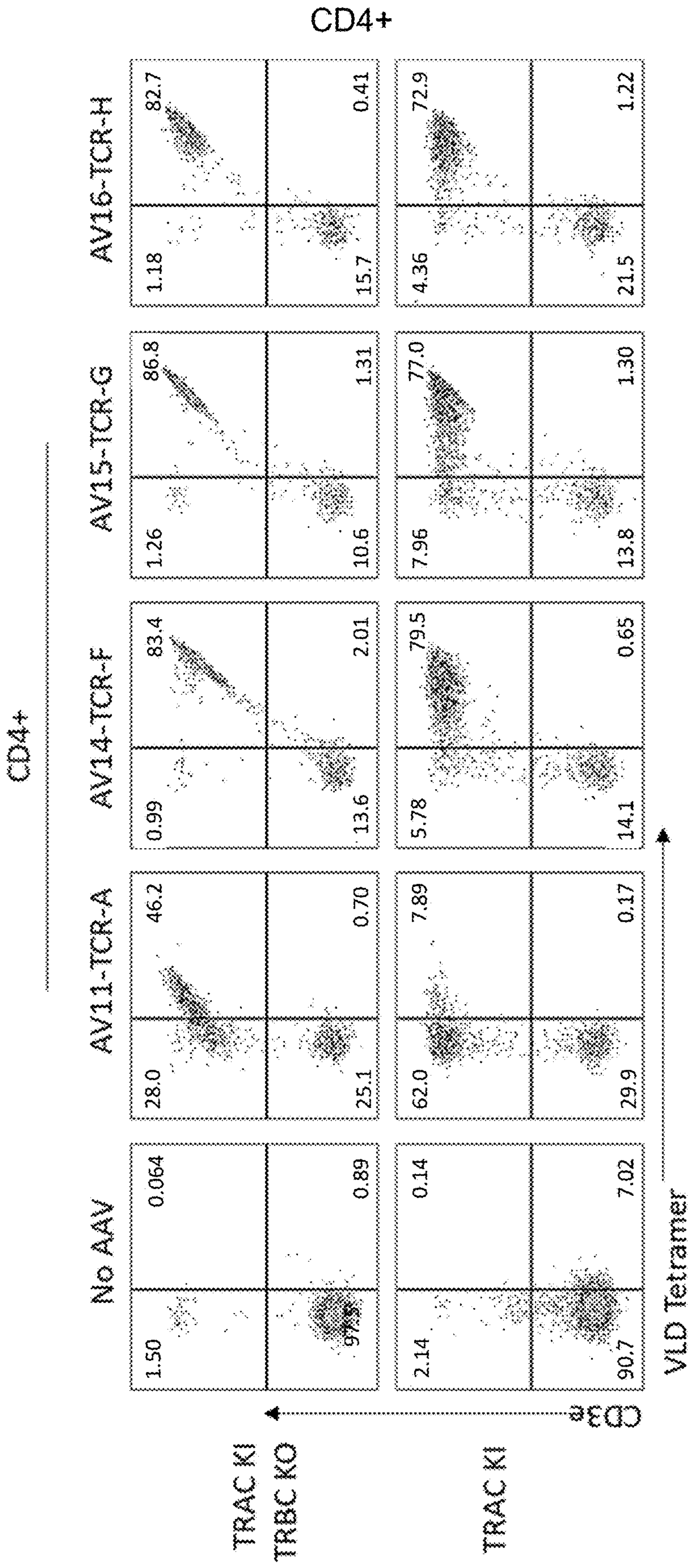
FIG. 24 shows VLD (Wilms' tumor antigen) tetramer staining for four different TCRs with and without knockout of TRBC, indicating the degree of mispairing for the WT1-TCR engineered CD4+ cells.
Figure 25:
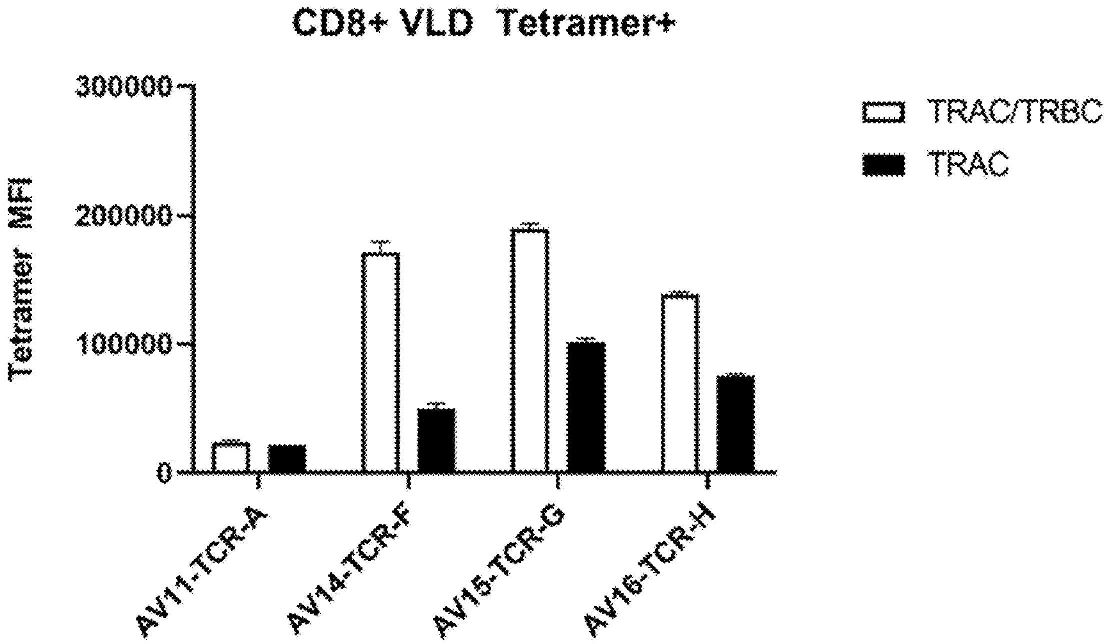
FIG. 25 show the intensity of TCR expression in $CD8^+$ cells with four TCR constructs inserted in the TRAC locus along with knockout of TRBC as measured by the MFI of the tetramer stain.
Figure 26:
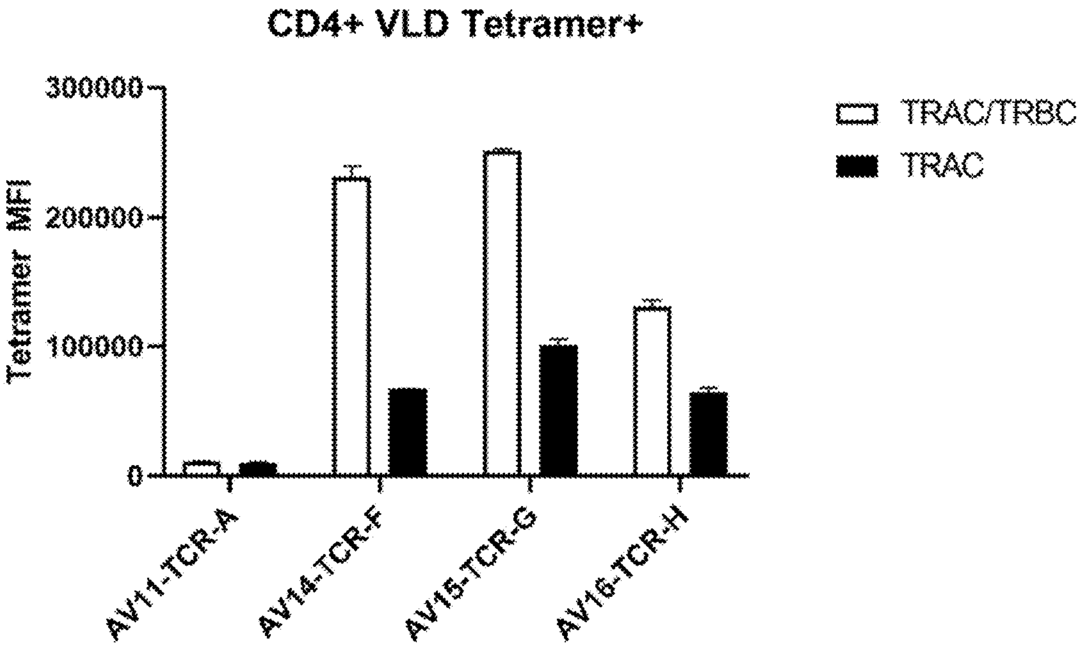
FIG. 26 show the intensity of TCR expression in $CD4^+$ cells with four TCR constructs inserted in the TRAC locus along with knockout of TRBC as measured by the MFI of the tetramer stain.
Figure 27A:
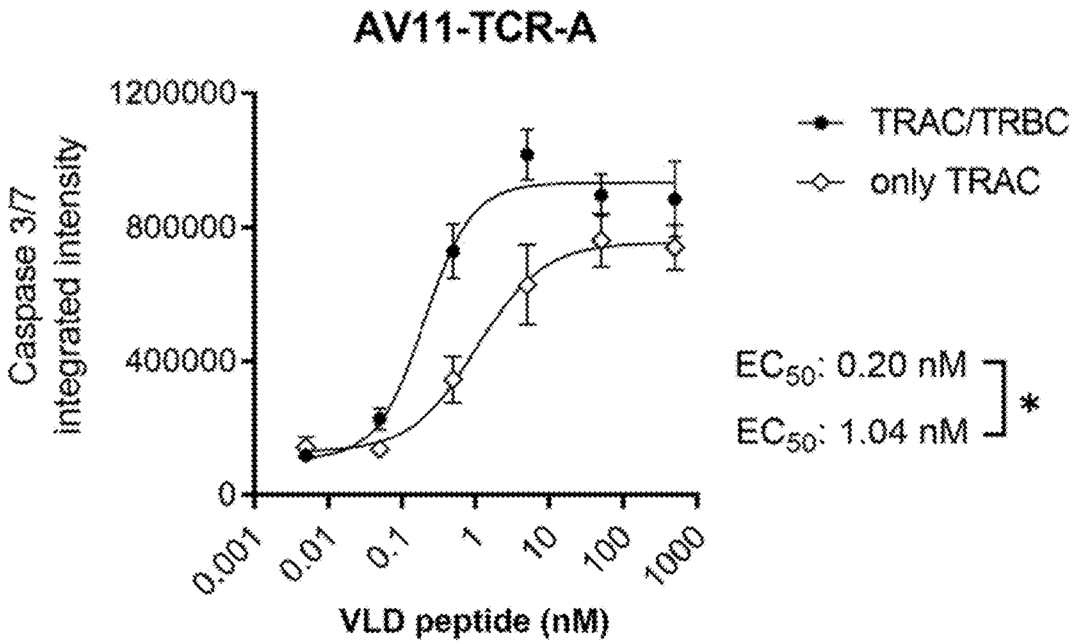
FIGS. 27A-C show the cytotoxicity of T cells containing inserted transgenic TCR (AV11-TCR-A, AV13-TCR-B, AV12-TCR-C) that are also TRAC/TRBC double knockouts or TRAC single knockouts. Cytotoxicity was measured by measuring the florescence from apoptotic cells in response to Caspase 3/7 apoptotic cells after 6 hours.
Figure 27B:
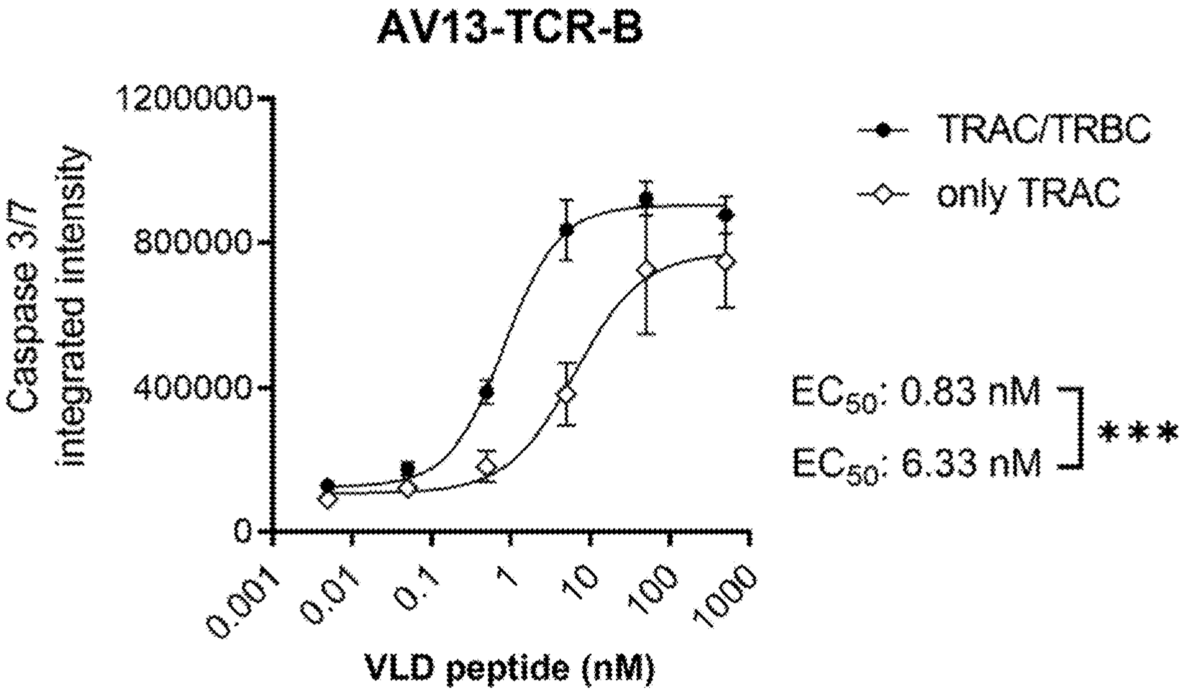
Figure 27C:
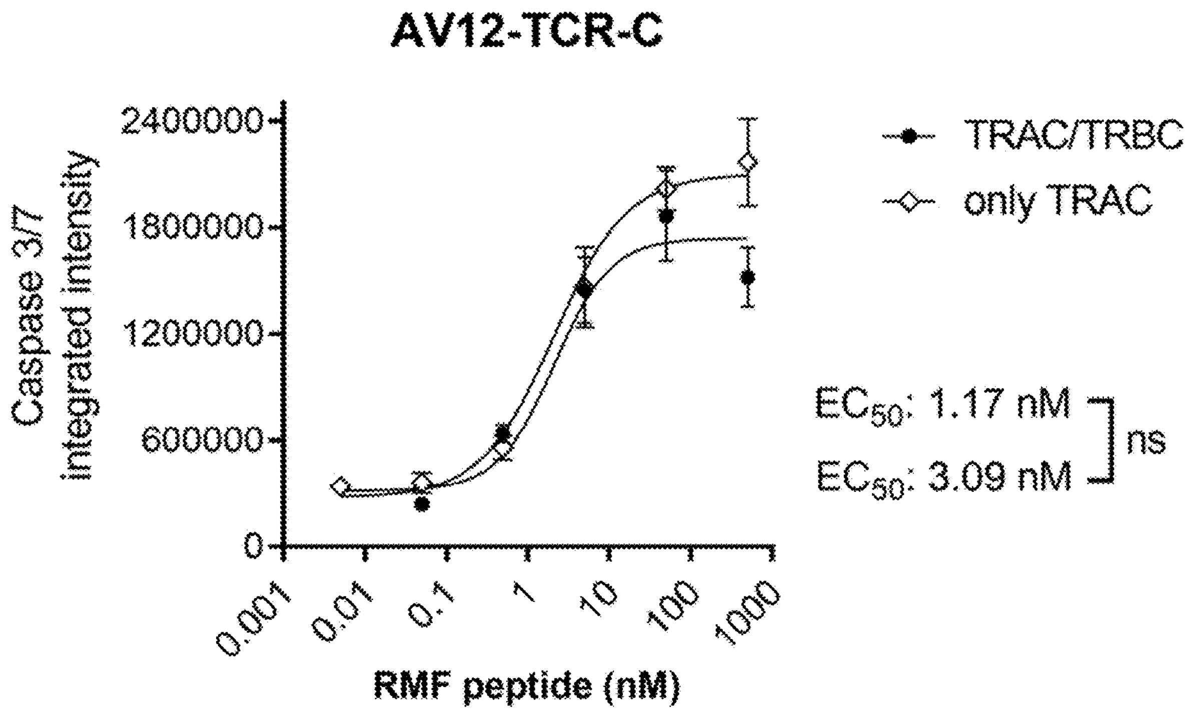
Figure 28A:
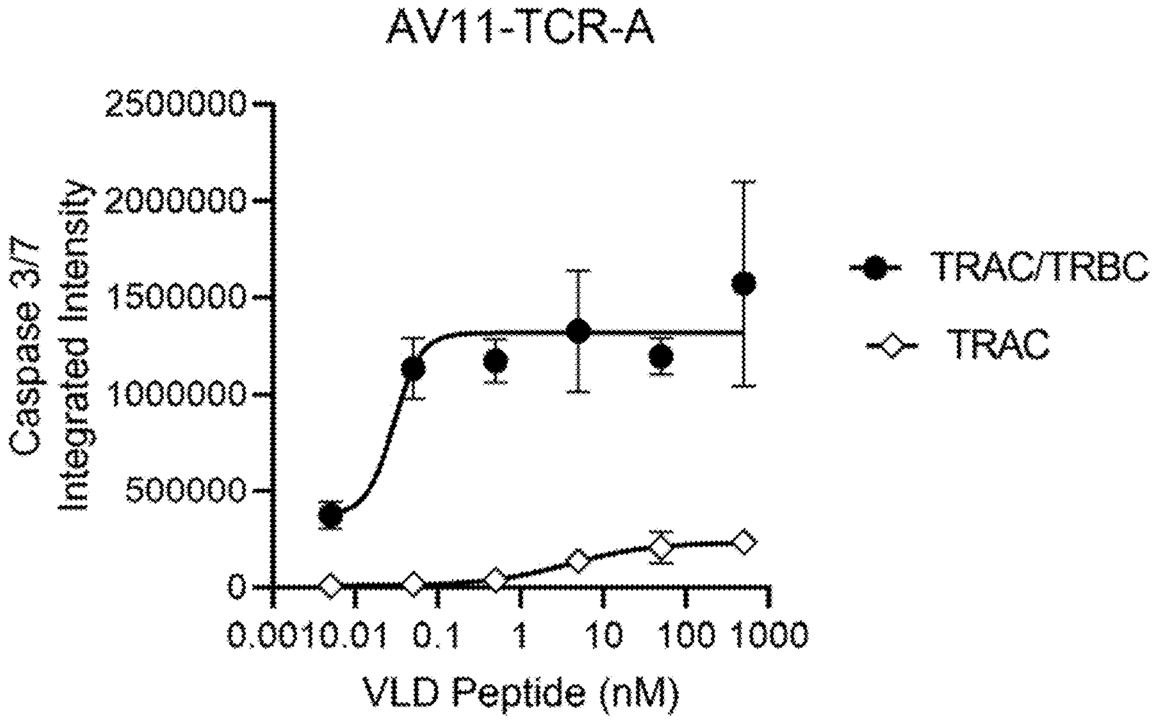
FIGS. 28A-D show the cytotoxicity of T cells containing inserted transgenic TCR (AV11-TCR-A, AV14-TCR-F, AV15-TCR-G, AV16-TCR-H) that are also TRAC/TRBC double knockouts or TRAC single knockouts. Cytotoxicity was measured by measuring the florescence from apoptotic cells in response to Caspase 3/7 apoptotic cells after 6 hours.
Figure 28B:
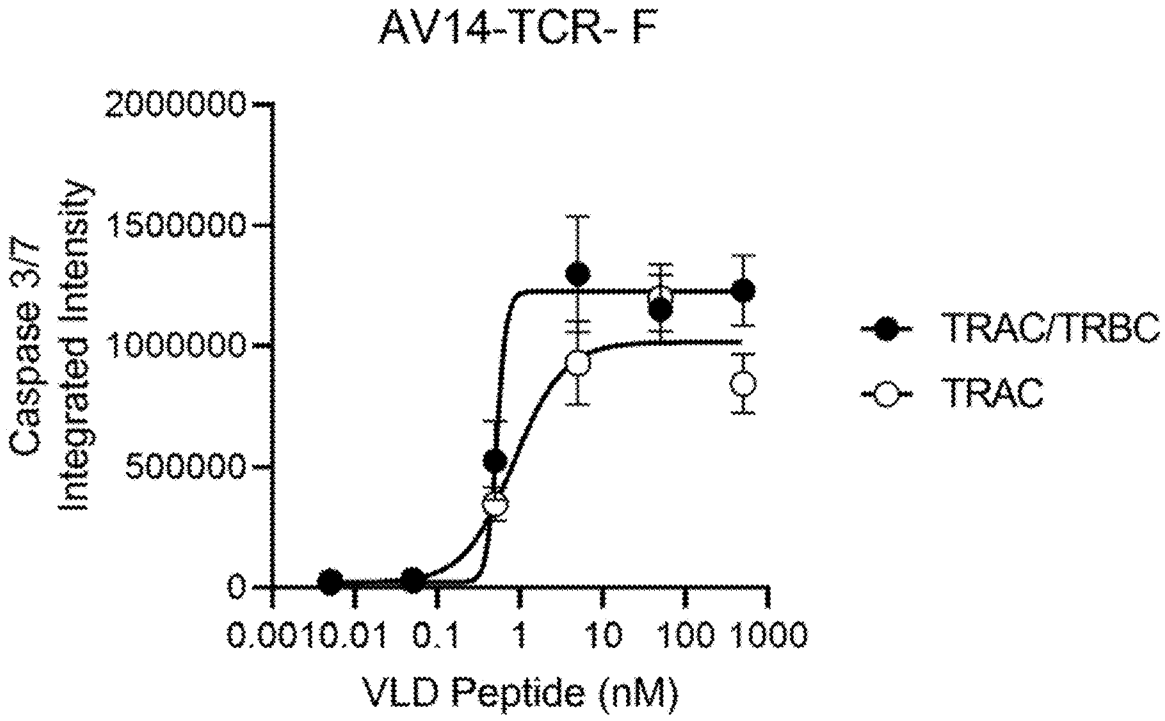
Figure 28C:
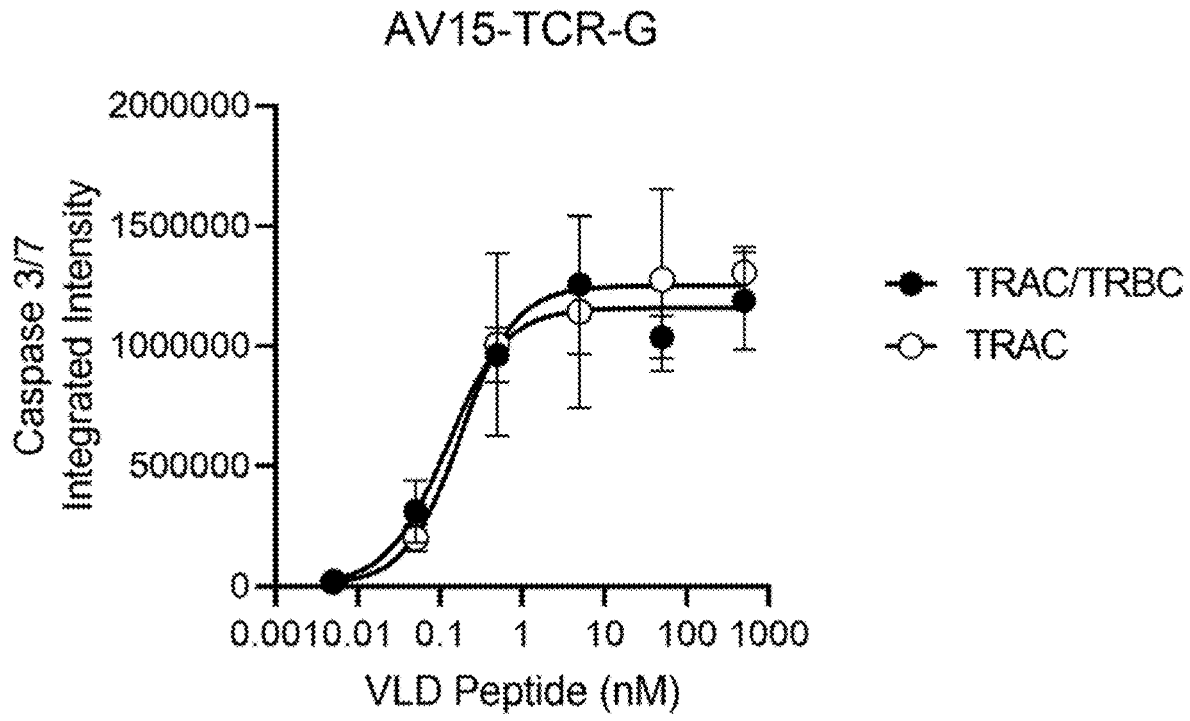
Figure 28D:
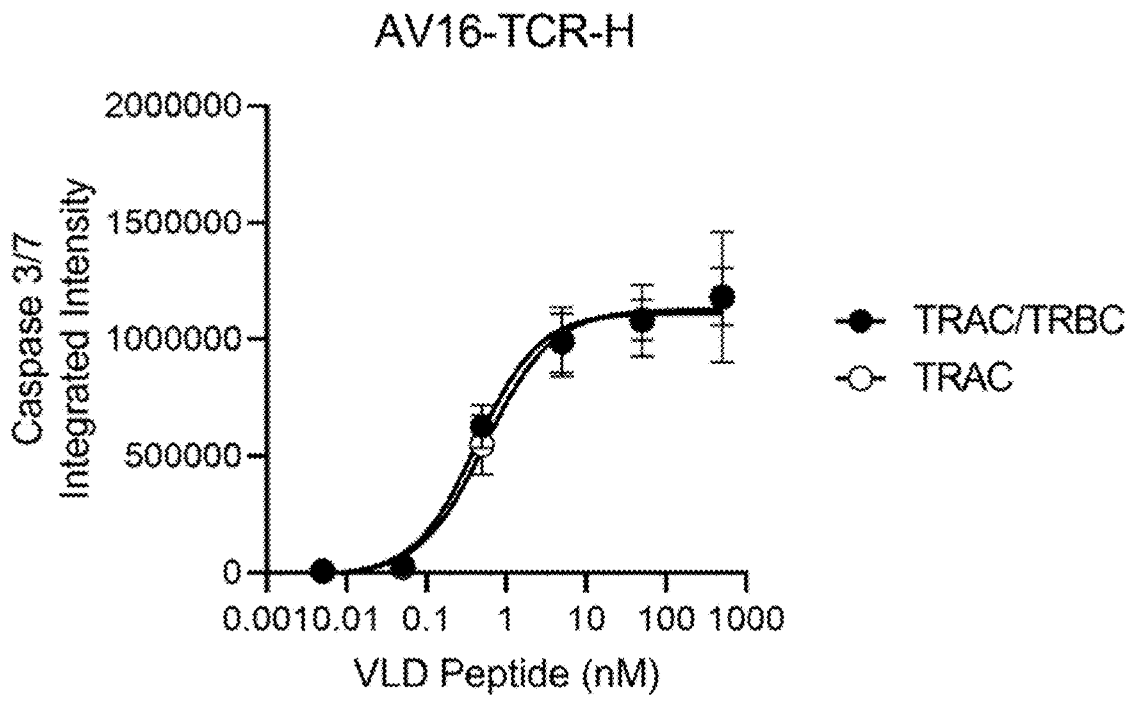
Figure 29A:
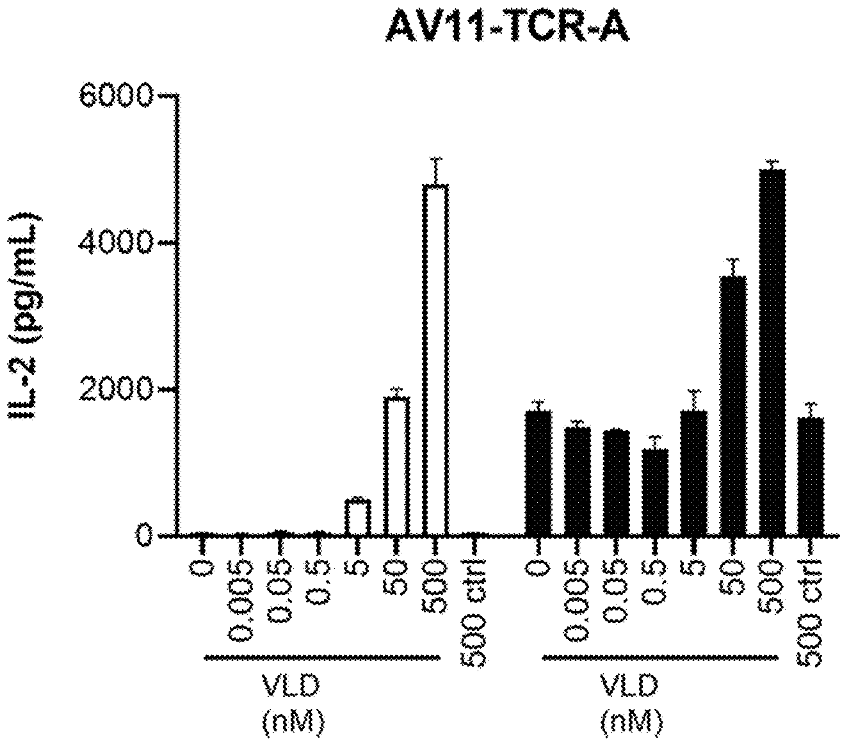
FIGS. 29A-G show the level of peptide-specific IL-2 secretion from T cells containing inserted transgenic TCR (AV11-TCR-A, AV13-TCR-B, AV12-TCR-C, AV14-TCR-F, AV15-TCR-G, AV16-TCR-H) that are also TRAC/TRBC double knockouts or TRAC single knockouts; as measured by ELISA.
Figure 29B:
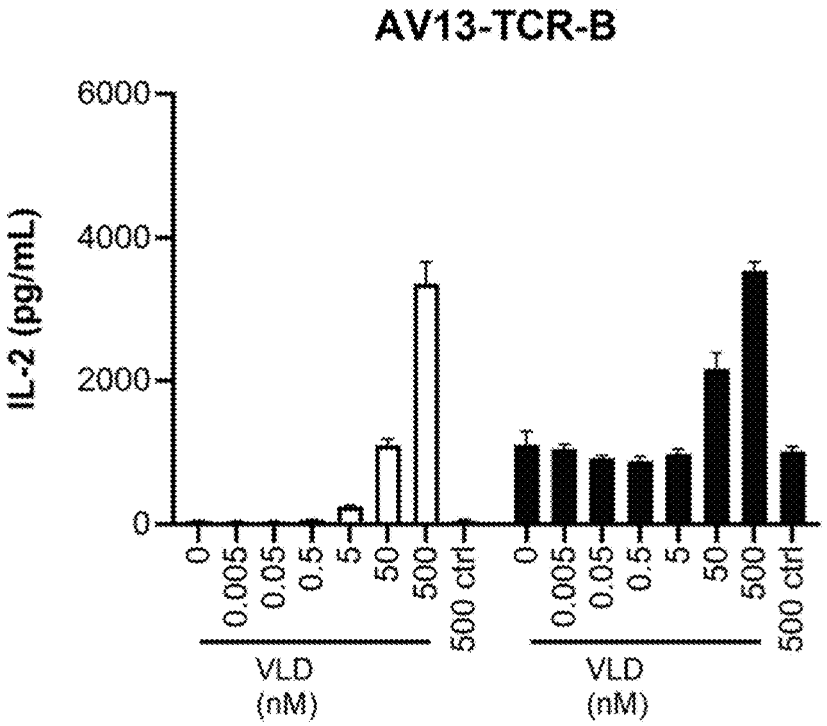
Figure 29C:
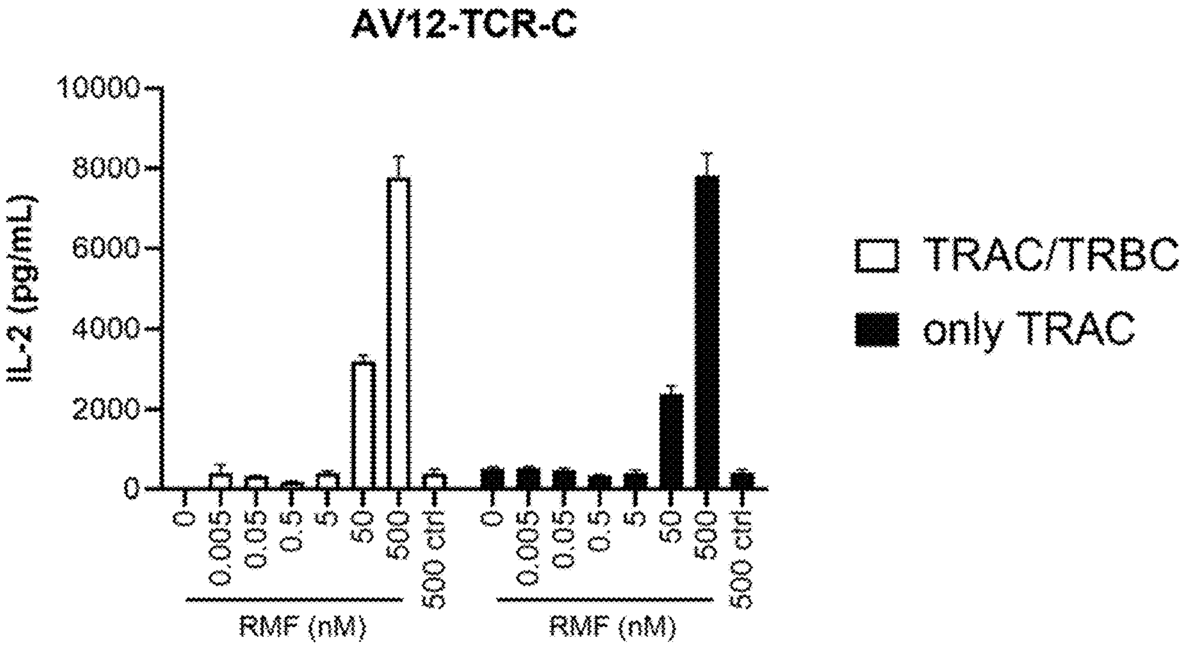
Figure 29D:
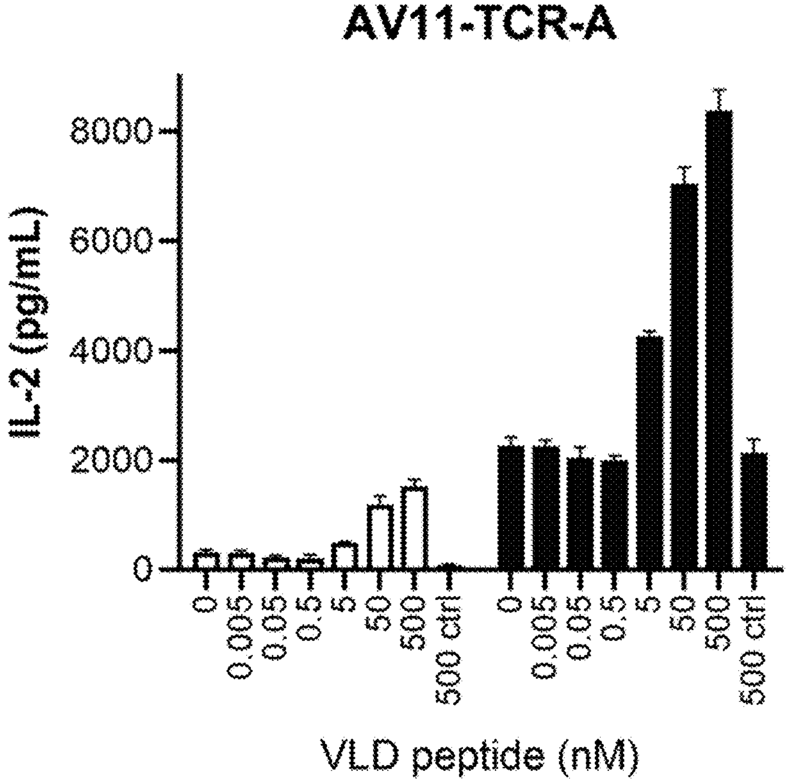
Figure 29E:
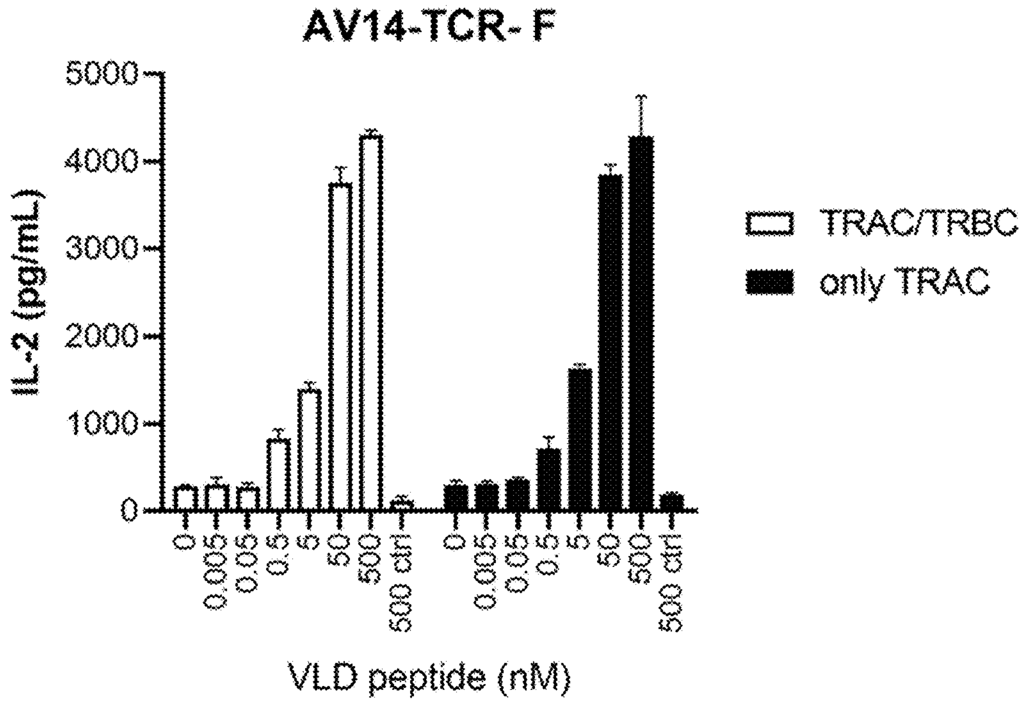
Figure 29F:
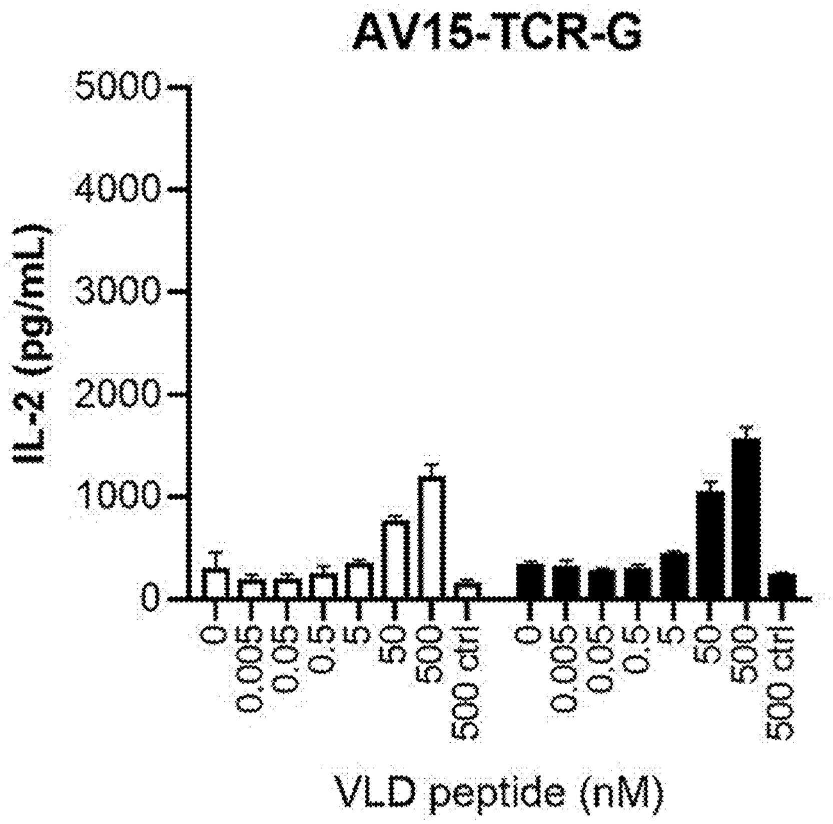
Figure 29G:
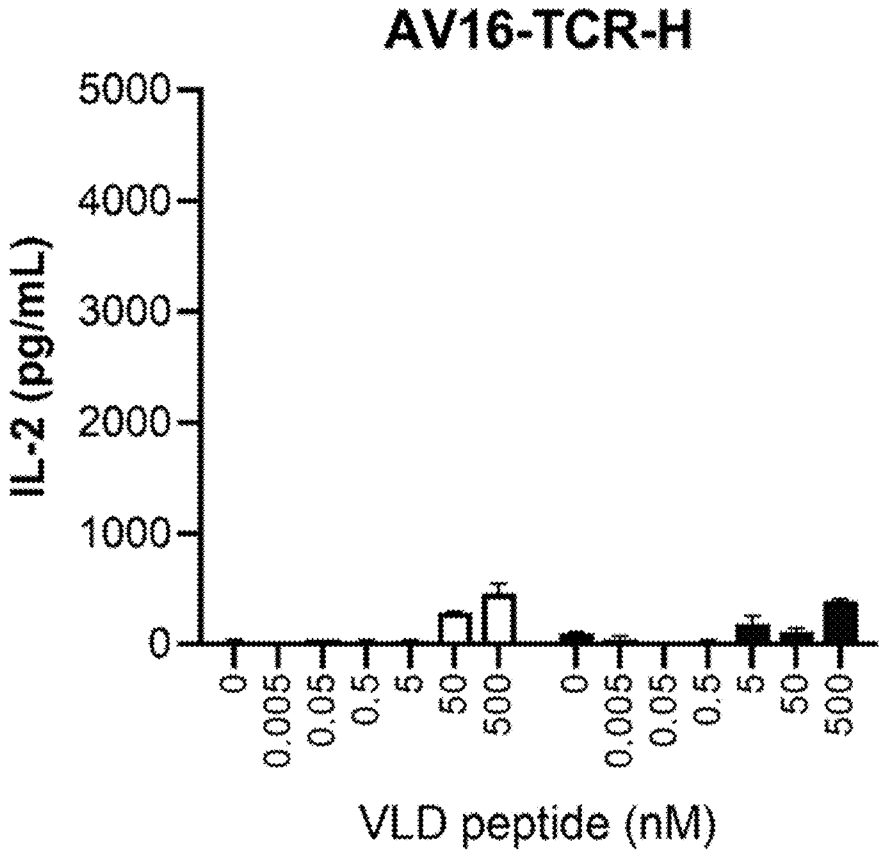
Figure 30A:
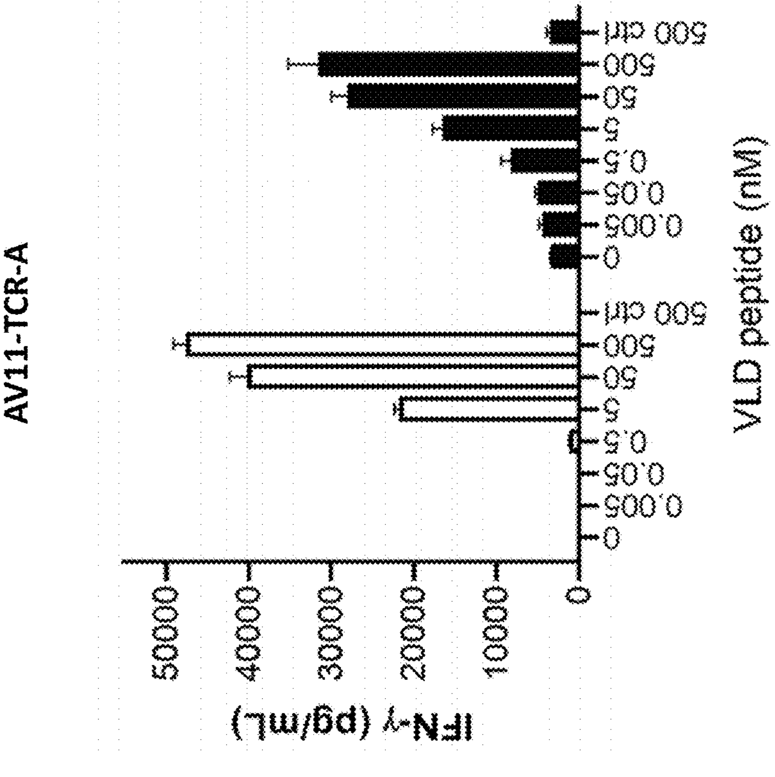
FIGS. 30A-D show the level of peptide-specific IFN-γ secretion from T-cells containing inserted transgenic TCR (AV11-TCR-A, AV14-TCR-F, AV15-TCR-G, AV16-TCR-H) that are also TRAC/TRBC double knockouts or TRAC single knockouts; as measured by ELISA.
Figure 30B:
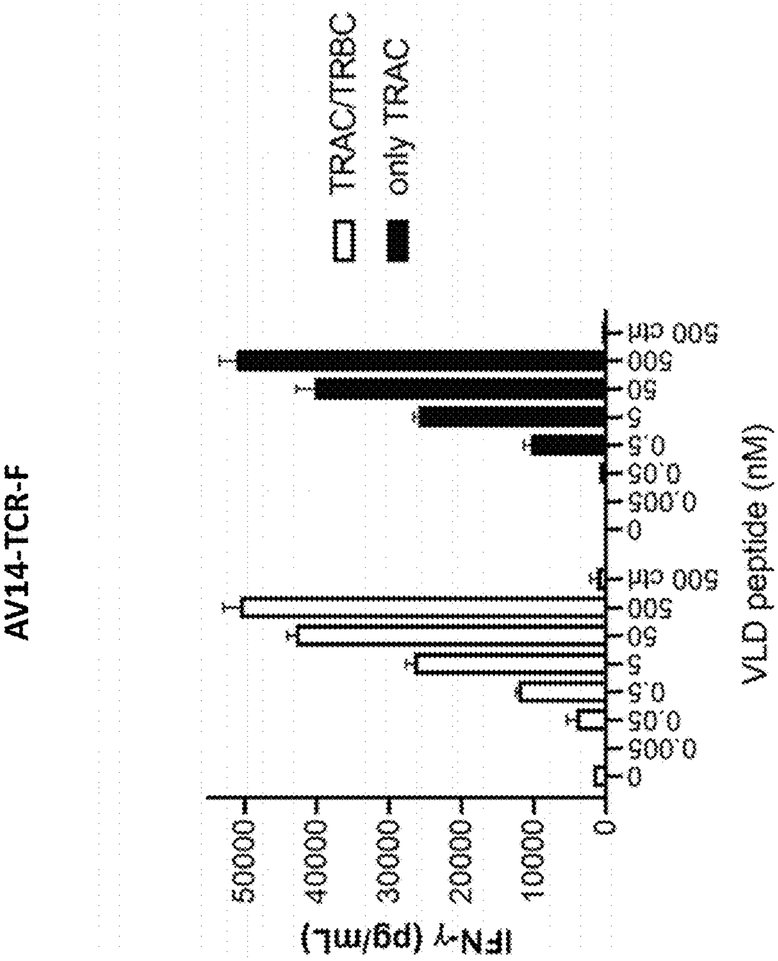
Figure 30D:
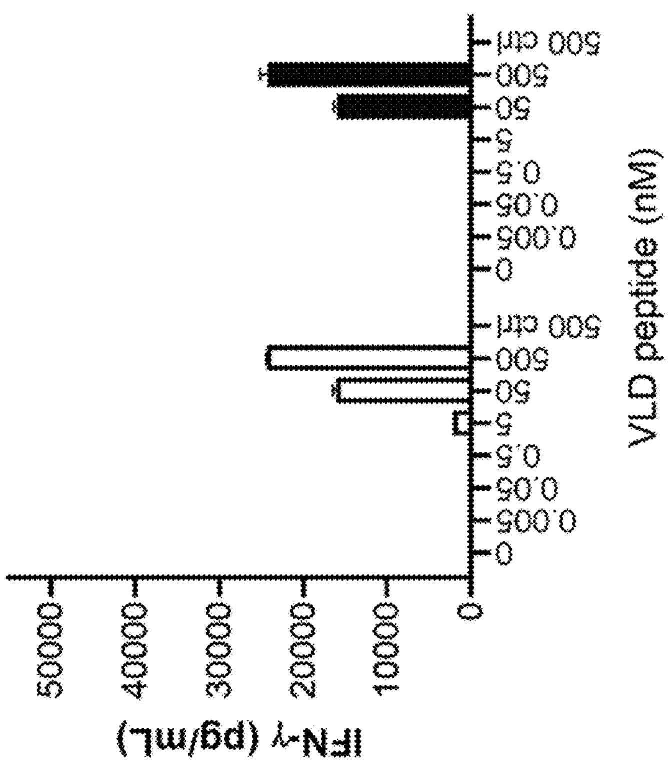
Figure 30C:
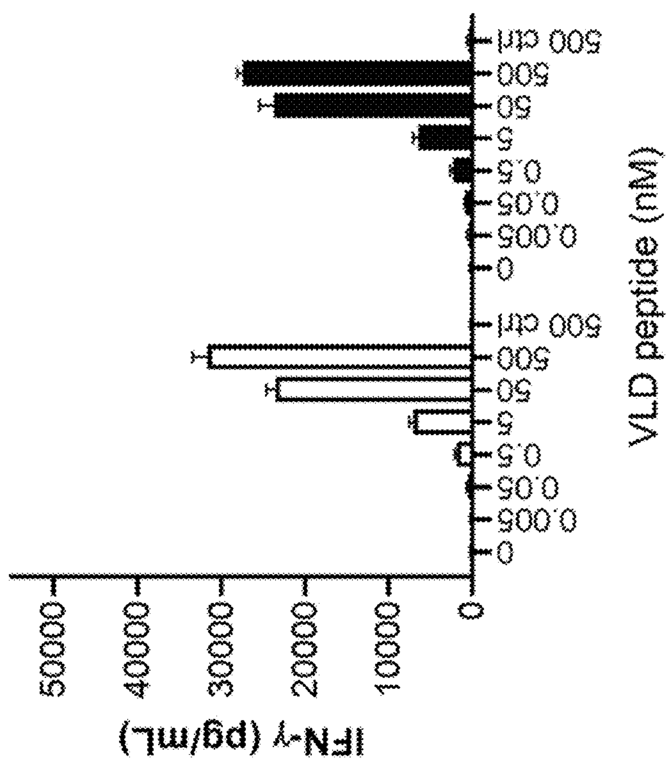

Example 17: Impact of TRBC Knockout on Pairing Alpha and Beta Chains from Additional TCRs T cells were evaluated with additional engineered TCRs for the impact of endogenous beta chains on pairing of both the inserted alpha chain and inserted beta chain. The experiment was performed as described herein except tetramer staining was used to measure MFI and the AAV inserts in Table 31 were used for transduction. Nine days post cell expansion, edited T cells were co-stained with VLD-Tetramer, an orthogonal method to V-beta staining, to identify cells with TCR surface expression by flow cytometry as shown in Table 31 and data from representative experiments are shown in FIGS. 22, 23, and 24. The mean fluorescence intensity (MFI) was also determined by flow cytometry as shown in Table 31 and FIGS. 25 and 26.

TABLE 31

| Surface TCR expression in engineered T cells | | | | | | | | | |
|---|---|---|---|---|---|---|---|---|---|
| | | CD8+ | | | | CD4+ | | | |
| Sample | RNP | Mean % Tetramer+ | SD | Mean Tetramer MFI | SD | Mean % Tetramer+ | SD | Mean Tetramer MFI | SD |
| AV11- | TRAC | 12.65 | 0.6 | 21853.5 | 12 | 7.6 | 0.4 | 10064.5 | 634 |
| TCR-A | TRAC + TRBC | 51.2 | 3.9 | 23697 | 1605 | 48 | 2.5 | 11332 | 387 |
| AV14- | TRAC | 61.05 | 6.2 | 50097 | 3828 | 78.9 | 0.8 | 67332.5 | 1379 |
| TCR-F | TRAC + TRBC | 76.6 | 0.3 | 171770 | 7974. | 81.8 | 2.3 | 231348 | 8432 |
| AV15- | TRAC | 73.6 | 0.3 | 101676 | 2594 | 77.55 | 0.77 | 101366 | 4317 |
| TCR-G | TRAC + TRBC | 81.9 | 0.1 | 190002 | 3919 | 85.35 | 2.05 | 251084 | 1569 |
| AV16- | TRAC | 68.85 | 1.8 | 75226.5 | 1704 | 71.65 | 1.8 | 64255 | 3921 |
| TCR-H | TRAC + TRBC | 77.1 | 3.8 | 138847 | 1916 | 80.25 | 3.5 | 131127 | 5313 |
| RNP | TRAC | 0.0555 | 0.05 | n.a | n.a | 0.112 | 0.04 | n.a | n.a |
| only | TRAC + TRBC | 0.052 | 0.02 | n.a | n.a | 0.107 | 0.06 | n.a | n.a |

Example 18—Engineered T Cell Cytotoxicity and Cytokine Release

Engineered T cells were assayed for cytotoxicity and cytokine response through the measurement of apoptosis in target cells and the measurement of cytokines released into growth media, respectively. T cells were engineered as described herein using the AAV template sequences described in Table 32 with either RNP targeting only the TRAC locus or RNP targeting both the TRAC and TRBC loci. The HLA-02.01 positive T2 cell line target cells were pulsed and co-cultured with edited T cells as described in Example 15 except the cell ratio of TCR+ T cells was 2.5:1 E:T. Caspase 3/7 red reagent (Essen Bioscience) was added to each well at a final concentration of 2 μM. The Incucyte Live Cell Analysis System (Essen Bioscience) and Incucyte S3 analysis software (version 2018B) was used to quantify red florescence from Caspase 3/7 apoptotic cells after 6 hours. After 24 hours supernatants from each well were harvested and IL2 and IFN-γ cytokine release was quantified by ELISA using the Duoset ELISA kit (R&D Systems) following the manufacturers protocol. Mean Caspase 3/7 integrated intensity is shown in Tables 32 and 33 and FIGS. 27A-C and 28A-D. Cytokine release is shown in Tables 34AD and FIGS. 29A-G and 30A-D.

TABLE 32

| Cytotoxicity | | | | | |
|---|---|---|---|---|---|
| | | TRAC/TRBC | | only TRAC | |
| Sample | peptide (nM) | Mean Caspase 3/7 integrated intensity | SD | Mean Caspase 3/7 integrated intensity | SD |
| AV11- | 0 nM VLD | 92,634 | 7,107 | 132,075 | 37,266 |
| TCR-A | 0.005 nM VLD | 116,733 | 25,315 | 141,590 | 71,782 |

TABLE 32-continued

Cytotoxicity

| Sample | peptide (nM) | TRAC/TRBC Mean Caspase 3/7 integrated intensity | TRAC/TRBC SD | only TRAC Mean Caspase 3/7 integrated intensity | only TRAC SD |
|---|---|---|---|---|---|
| | 0.05 nM VLD | 227,475 | 69,325 | 135,336 | 36,246 |
| | 0.5 nM VLD | 729,355 | 193,569 | 345,431 | 43,799 |
| | 5 nM VLD | 1,017,766 | 174,286 | 629,094 | 151,367 |
| | 50 nM VLD | 897,413 | 122,632 | 762,373 | 59,142 |
| | 500 nM VLD | 885,460 | 225,388 | 741,203 | 77,370 |
| | 500 nM RMF | 98,877 | 12,254 | 121,279 | 7,212 |
| AV13-TCR-B | 0 nM VLD | 97,684 | 21,060 | 93,536 | 19,338 |
| | 0.005 nM VLD | 126,983 | 7,518 | 88,855 | 42,431 |
| | 0.05 nM VLD | 174,492 | 11,465 | 119,259 | 14,122 |
| | 0.5 nM VLD | 388,825 | 71,913 | 180,269 | 23,378 |
| | 5 nM VLD | 835,068 | 86,910 | 382,323 | 94,136 |
| | 50 nM VLD | 922,968 | 49,804 | 724,521 | 280,318 |
| | 500 nM VLD | 876,706 | 57,316 | 748,140 | 249,718 |
| | 500 nM RMF | 78,919 | 21,138 | 81,044 | 8,512 |
| AV12-TCR-C | 0 nM RMF | 279,375 | 93,562 | 276,204 | 65,787 |
| | 0.05 nM RMF | 238,879 | 17,971 | 360,532 | 63,189 |
| | 0.5 nM RMF | 639,925 | 37,882 | 560,793 | 134,482 |
| | 5 nM RMF | 1,446,931 | 341,193 | 1,463,030 | 193,719 |
| | 50 nM RMF | 1,864,716 | 569,777 | 2,020,037 | 65,722 |
| | 500 nM RMF | 1,519,652 | 256,405 | 2,168,849 | 391,750 |
| | 500 nM VLD | 218,526 | 35,777 | 330,230 | 34,681 |

TABLE 33

Cytotoxicity

| Sample | peptide (nM) | TRAC/TRBC Mean Caspase 3/7 integrated intensity | TRAC/TRBC SD | TRAC only Mean Caspase 3/7 integrated intensity | TRAC only SD |
|---|---|---|---|---|---|
| AV11-TCR-A | 0 nM VLD | 381,416 | 143,786 | 9,042 | 413 |
| | 0.005 nM VLD | 374,092 | 69,482 | 9,184 | 1,881 |
| | 0.05 nM VLD | 1,134,226 | 154,362 | 16,907 | 5,212 |
| | 0.5 nM VLD | 1,173,265 | 110,362 | 38,844 | 19,238 |
| | 5 nM VLD | 1,325,404 | 313,592 | 137,374 | 35,354 |
| | 50 nM VLD | 1,197,360 | 92,955 | 207,010 | 81,220 |
| | 500 nM VLD | 1,571,735 | 526,514 | 233,358 | 55,713 |
| | 500 nM RMF | 280,465 | 54,951 | 7,342 | 1,113 |
| AV14-TCR-F | 0 nM VLD | 21,702 | 8,974 | 18,238 | 3,665 |
| | 0.005 nM VLD | 17,809 | 2,730 | 24,480 | 7,844 |
| | 0.05 nM VLD | 25,664 | 9,946 | 31,096 | 6,502 |
| | 0.5 nM VLD | 528,157 | 163,446 | 346,541 | 71,382 |
| | 5 nM VLD | 1,297,535 | 240,491 | 930,724 | 169,903 |
| | 50 nM VLD | 1,150,859 | 143,371 | 1,198,605 | 138,751 |
| | 500 nM VLD | 1,228,755 | 146,056 | 845,589 | 119,495 |
| | 500 nM RMF | 8,578 | 1,615 | 9,659 | 2,534 |

TABLE 33-continued

Cytotoxicity

| Sample | peptide (nM) | TRAC/TRBC Mean Caspase 3/7 integrated intensity | TRAC/TRBC SD | TRAC only Mean Caspase 3/7 integrated intensity | TRAC only SD |
|---|---|---|---|---|---|
| AV15-TCR-G | 0 nM VLD | 12,408 | 4,254 | 12,182 | 2,841 |
| | 0.005 nM VLD | 20,974 | 7,838 | 21,046 | 12,983 |
| | 0.05 nM VLD | 310,566 | 130,784 | 199,014 | 55,935 |
| | 0.5 nM VLD | 963,870 | 113,005 | 1,007,001 | 378,833 |
| | 5 nM VLD | 1,255,083 | 289,237 | 1,143,162 | 399,176 |
| | 50 nM VLD | 1,037,328 | 87,408 | 1,276,265 | 379,466 |
| | 500 nM VLD | 1,187,161 | 202,415 | 1,305,422 | 104,837 |
| | 500 nM RMF | 6,795 | 1,439 | 4,949 | 1,238 |
| AV16-TCR-H | 0 nM VLD | 7,388 | 1,738 | 6,560 | 1,298 |
| | 0.005 nM VLD | 9,815 | 1,987 | 7,651 | 4,159 |
| | 0.05 nM VLD | 32,360 | 3,457 | 23,556 | 6,335 |
| | 0.5 nM VLD | 627,805 | 91,413 | 549,651 | 126,913 |
| | 5 nM VLD | 983,752 | 124,769 | 991,625 | 147,487 |
| | 50 nM VLD | 1,080,676 | 152,098 | 1,082,346 | 86,963 |
| | 500 nM VLD | 1,181,699 | 122,175 | 1,180,497 | 276,768 |
| | 500 nM RMF | 3,889 | 3,101 | 4,189 | 944 |

TABLE 34A

IL2 Cytokine release

| Construct | peptide (nM) | IL2 TRAC/TRBC Mean (pg/ml) | IL2 TRAC/TRBC SD (pg/ml) | IL2 TRAC/TRBC N | IL2 only TRAC Mean (pg/ml) | IL2 only TRAC SD (pg/ml) | IL2 only TRAC N |
|---|---|---|---|---|---|---|---|
| AV11-TCR-A | 0 nM VLD | 46 | 3 | 3 | 1,715 | 119 | 3 |
| | 0.005 nM VLD | 34 | 3 | 3 | 1,490 | 79 | 3 |
| | 0.05 nM VLD | 52 | 19 | 3 | 1,436 | 18 | 3 |
| | 0.5 nM VLD | 50 | 10 | 3 | 1,186 | 170 | 3 |
| | 5 nM VLD | 506 | 29 | 3 | 1,713 | 264 | 3 |
| | 50 nM VLD | 1,902 | 104 | 3 | 3,554 | 223 | 3 |
| | 500 nM VLD | 4,804 | 345 | 3 | 5,003 | 112 | 3 |
| | 500 nM RMF | 46 | 3 | 3 | 1,615 | 194 | 3 |
| AV13-TCR-B | 0 nM VLD | 46 | 3 | 3 | 1,109 | 181 | 3 |
| | 0.005 nM VLD | 42 | 2 | 3 | 1,048 | 60 | 3 |
| | 0.05 nM VLD | 39 | 5 | 3 | 913 | 44 | 3 |
| | 0.5 nM VLD | 55 | 10 | 3 | 868 | 73 | 3 |
| | 5 nM VLD | 248 | 17 | 3 | 976 | 66 | 3 |
| | 50 nM VLD | 1,095 | 90 | 3 | 2,160 | 240 | 3 |
| | 500 nM VLD | 3,363 | 303 | 3 | 3,547 | 121 | 3 |
| | 500 nM RMF | 51 | 18 | 3 | 1,011 | 64 | 3 |
| AV12-TCR-C | 0 nM RMF | n.d. | n.d. | n.d. | 498 | 49 | 3 |
| | 0.05 nM RMF | 398 | 210 | 3 | 511 | 40 | 3 |
| | 0.5 nM RMF | 320 | 15 | 2 | 481 | 42 | 3 |
| | 5 nM RMF | 182 | 17 | 3 | 333 | 19 | 3 |
| | 50 nM RMF | 392 | 56 | 3 | 396 | 79 | 3 |
| | 500 nM RMF | 3,193 | 165 | 3 | 2,386 | 207 | 3 |
| | 500 nM VLD | 7,776 | 539 | 3 | 7,830 | 557 | 3 |
| | 0 nM VLD | 378 | 113 | 3 | 415 | 66 | 3 |

TABLE 34B

Inteferon-gamma release

| Construct | Peptide (nM) | TRAC/TRBC Mean (pg/ml) | TRAC/TRBC SD (pg/ml) | TRAC/TRBC N | only TRAC Mean (pg/ml) | only TRAC SD (pg/ml) | only TRAC N |
|---|---|---|---|---|---|---|---|
| AV11-TCR-A | 0 nM VLD | <LLOD* | <LLOD | 3 | 1.313 | 446 | 3 |
| | 0.005 nM VLD | <LLOD | <LLOD | 3 | 904 | 243 | 3 |
| | 0.05 nM VLD | <LLOD | <LLOD | 3 | 731 | 68 | 3 |
| | 0.5 nM VLD | <LLOD | <LLOD | 3 | 1,442 | 148 | 3 |

TABLE 34B-continued

| Inteferon-gamma release | | | | | | | |
|---|---|---|---|---|---|---|---|
| | | TRAC/TRBC | | | only TRAC | | |
| Construct | Peptide (nM) | Mean (pg/ml) | SD (pg/ml) | N | Mean (pg/ml) | SD (pg/ml) | N |
| | 5 nM VLD | 7,361 | 399 | 3 | 4,323 | 332 | 3 |
| | 50 nM VLD | 15,845 | 1,783 | 3 | 9,221 | 381 | 3 |
| | 500 nM VLD | 25,242 | 3,021 | 3 | 11,558 | 407 | 3 |
| | 500 nM RMF | <LLOD | <LLOD | 3 | 1,656 | 115 | 3 |
| AV13-TCR-B | 0 nM VLD | <LLOD | <LLOD | 3 | 406 | 75 | 3 |
| | 0.005 nM VLD | <LLOD | <LLOD | 3 | 265 | 36 | 3 |
| | 0.05 nM VLD | <LLOD | <LLOD | 3 | 981 | 896 | 3 |
| | 0.5 nM VLD | <LLOD | <LLOD | 3 | 471 | 140 | 3 |
| | 5 nM VLD | 4,643 | 154 | 3 | 1,865 | 183 | 3 |
| | 50 nM VLD | 11,273 | 643 | 3 | 3,645 | 184 | 3 |
| | 500 nM VLD | 19,868 | 1,925 | 3 | 6,476 | 434 | 3 |
| | 500 nM RMF | <LLOD | <LLOD | 3 | 648 | 199 | 3 |
| AV12-TCR-C | 0 nM RMF | n.d. | n.d | n.d | 1,243 | 92 | 3 |
| | 0.05 nM RMF | <LLOD | <LLOD | 3 | 839 | 144 | 3 |
| | 0.5 nM RMF | <LLOD | <LLOD | 2 | 1,151 | 93 | 3 |
| | 5 nM RMF | <LLOD | <LLOD | 3 | 1,181 | 96 | 3 |
| | 50 nM RMF | 4,643 | 154 | 3 | 2,434 | 26 | 3 |
| | 500 nM RMF | 11,273 | 643 | 3 | 5,302 | 723 | 3 |
| | 500 nM VLD | 19,868 | 1,925 | 3 | 16,247 | 192 | 3 |
| | 0 nM VLD | <LLOD | <LLOD | 3 | 1,058 | 93 | 3 |

*LLOD indicates that the reading is below the level of detection in the particular assay used.

TABLE 34C

| IL2 Cytokine release | | | | | | | |
|---|---|---|---|---|---|---|---|
| | | TRAC/TRBC | | | TRAC only | | |
| TCR | peptide (nM) | Mean (pg/ml) | SD (pg/ml) | N | Mean (pg/ml) | SD (pg/ml) | N |
| AV11-TCR-A | 0 nM VLD | 314 | 46 | 3 | 2.259 | 156 | 3 |
| | 0.005 nM VLD | 304 | 42 | 3 | 2,247 | 122 | 3 |
| | 0.05 nM VLD | 227 | 29 | 3 | 2,046 | 188 | 3 |
| | 0.5 nM VLD | 200 | 63 | 3 | 2,007 | 73 | 3 |
| | 5 nM VLD | 494 | 15 | 3 | 4,266 | 96 | 3 |
| | 50 nM VLD | 1,182 | 157 | 3 | 7,062 | 283 | 3 |
| | 500 nM VLD | 1,511 | 141 | 3 | 8,375 | 385 | 3 |
| | 500 nM RMF | 81 | 19 | 3 | 2,135 | 245 | 3 |
| AV16-TCR-H | 0 nM VLD | 17 | 21 | 2 | 102 | 9 | 2 |
| | 0.005 nM VLD | 15 | 0 | 1 | 44 | 27 | 3 |
| | 0.05 nM VLD | 40 | 0 | 1 | 2 | 0 | 1 |
| | 0.5 nM VLD | 17 | 17 | 2 | 23 | 11 | 3 |
| | 5 nM VLD | 30 | 6 | 2 | 175 | 79 | 2 |
| | 50 nM VLD | 286 | 8 | 2 | 111 | 32 | 3 |
| | 500 nM VLD | 455 | 90 | 3 | 387 | 17 | 3 |
| | 500 nM RMF | n/a | n/a | n/a | n/a | n/a | n/a |
| AV15-TCR-G | 0 nM VLD | 306 | 144 | 3 | 338 | 28 | 3 |
| | 0.005 nM VLD | 196 | 40 | 3 | 326 | 49 | 3 |
| | 0.05 nM VLD | 198 | 42 | 3 | 284 | 14 | 3 |
| | 0.5 nM VLD | 248 | 72 | 3 | 305 | 26 | 3 |
| | 5 nM VLD | 351 | 27 | 3 | 442 | 21 | 3 |
| | 50 nM VLD | 764 | 47 | 3 | 1,053 | 89 | 3 |
| | 500 nM VLD | 1,203 | 111 | 3 | 1,566 | 112 | 3 |
| | 500 nM RMF | 157 | 29 | 3 | 242 | 10 | 3 |
| AV14-TCR-F | 0 nM VLD | 283 | 16 | 3 | 295 | 55 | 3 |
| | 0.005 nM VLD | 303 | 84 | 3 | 316 | 24 | 3 |
| | 0.05 nM VLD | 274 | 46 | 3 | 361 | 25 | 3 |
| | 0.5 nM VLD | 836 | 103 | 3 | 724 | 129 | 3 |
| | 5 nM VLD | 1,406 | 69 | 3 | 1,634 | 51 | 3 |
| | 50 nM VLD | 3,755 | 180 | 3 | 3,850 | 116 | 3 |
| | 500 nM VLD | 4,301 | 57 | 3 | 4,289 | 459 | 3 |
| | 500 nM RMF | 117 | 53 | 3 | 190 | 19 | 2 |

TABLE 34D

| Inteferon-gamma release | | | | | | | |
|---|---|---|---|---|---|---|---|
| | | TRAC/TRBC | | | only TRAC | | |
| TCR | peptide (nM) | Mean | SD | N | Mean | SD | N |
| AV11-TCR-A | 0 nM VLD | <LLOD | <LLOD | 3 | 3,491 | 108 | 3 |
| | 0.005 nM VLD | <LLOD | <LLOD | 3 | 4,489 | 444 | 3 |
| | 0.05 nM VLD | <LLOD | <LLOD | 3 | 5,126 | 262 | 3 |
| | 0.5 nM VLD | 1,257 | 23 | 3 | 8,284 | 1,195 | 3 |
| | 5 nM VLD | 21,739 | 653 | 3 | 16,572 | 1,237 | 3 |
| | 50 nM VLD | 40,200 | 2,121 | 3 | 28,080 | 1,871 | 3 |
| | 500 nM VLD | 47,628 | 1,520 | 3 | 31,541 | 3,672 | 3 |
| | 500 nM RMF | 0 | 0 | 3 | 3,590 | 389 | 3 |
| AV16-TCR-H | 0 nM VLD | <LLOD | <LLOD | 3 | <LLOD | <LLOD | 3 |
| | 0.005 nM VLD | <LLOD | <LLOD | 3 | <LLOD | <LLOD | 3 |
| | 0.05 nM VLD | <LLOD | <LLOD | 3 | <LLOD | <LLOD | 3 |
| | 0.5 nM VLD | <LLOD | <LLOD | 3 | <LLOD | <LLOD | 3 |
| | 5 nM VLD | <LLOD | <LLOD | 3 | <LLOD | <LLOD | 3 |
| | 50 nM VLD | 16,058 | 422 | 3 | 15,923 | 427 | 3 |
| | 500 nM VLD | 24,426 | 61 | 3 | 24,319 | 849 | 3 |
| | 500 nM RMF | <LLOD | <LLOD | 3 | <LLOD | <LLOD | 3 |
| AV15-TCR-G | 0 nM VLD | 219 | 15 | 3 | 260 | 33 | 3 |
| | 0.005 nM VLD | 219 | 56 | 3 | 429 | 196 | 3 |
| | 0.05 nM VLD | 549 | 102 | 3 | 854 | 54 | 3 |
| | 0.5 nM VLD | 1,850 | 258 | 3 | 2,265 | 391 | 3 |
| | 5 nM VLD | 7,034 | 497 | 3 | 6,424 | 616 | 3 |
| | 50 nM VLD | 23,558 | 1,135 | 3 | 23,733 | 1,748 | 3 |
| | 500 nM VLD | 31,629 | 1,790 | 3 | 27,473 | 663 | 3 |
| | 500 nM RMF | 235 | 33 | 3 | 416 | 199 | 3 |
| AV14-TCR-F | 0 nM VLD | <LLOD | <LLOD | 3 | <LLOD | <LLOD | 3 |
| | 0.005 nM VLD | <LLOD | <LLOD | 3 | <LLOD | <LLOD | 3 |
| | 0.05 nM VLD | 4,088 | 1,334 | 3 | <LLOD | <LLOD | 3 |
| | 0.5 nM VLD | 12,141 | 321 | 3 | 10,419 | 934 | 3 |
| | 5 nM VLD | 26,510 | 1,161 | 3 | 25,934 | 611 | 3 |
| | 50 nM VLD | 42,858 | 1,197 | 3 | 40,326 | 2,516 | 3 |
| | 500 nM VLD | 50,607 | 2,350 | 3 | 51,106 | 2,385 | 3 |
| | 500 nM RMF | 1,230 | 938 | 3 | <LLOD | <LLOD | 3 |

Example 19: Engineered T Cell Cytotoxicity as Assayed by CD107a Degranulation and Intracellular Cytokine Staining (ICS)

Figure 31A:
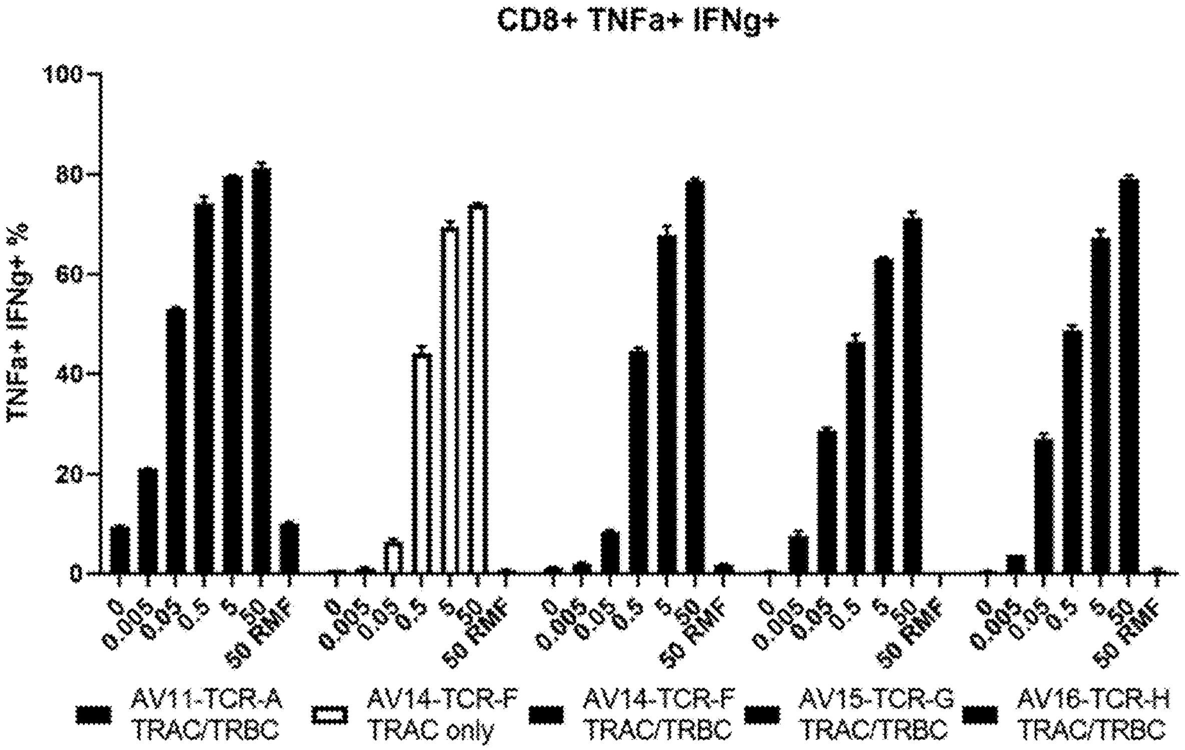
FIGS. 31A-B show the level of peptide-specific IFN-γ staining in $CD4^+$ and $CD8^+$ T-cells containing inserted transgenic (AV11-TCR-A, AV14-TCR-F, AV15-TCR-G, AV16-TCR-H) that are also TRAC/TRBC double knockouts or TRAC single knockouts.
Figure 31B:
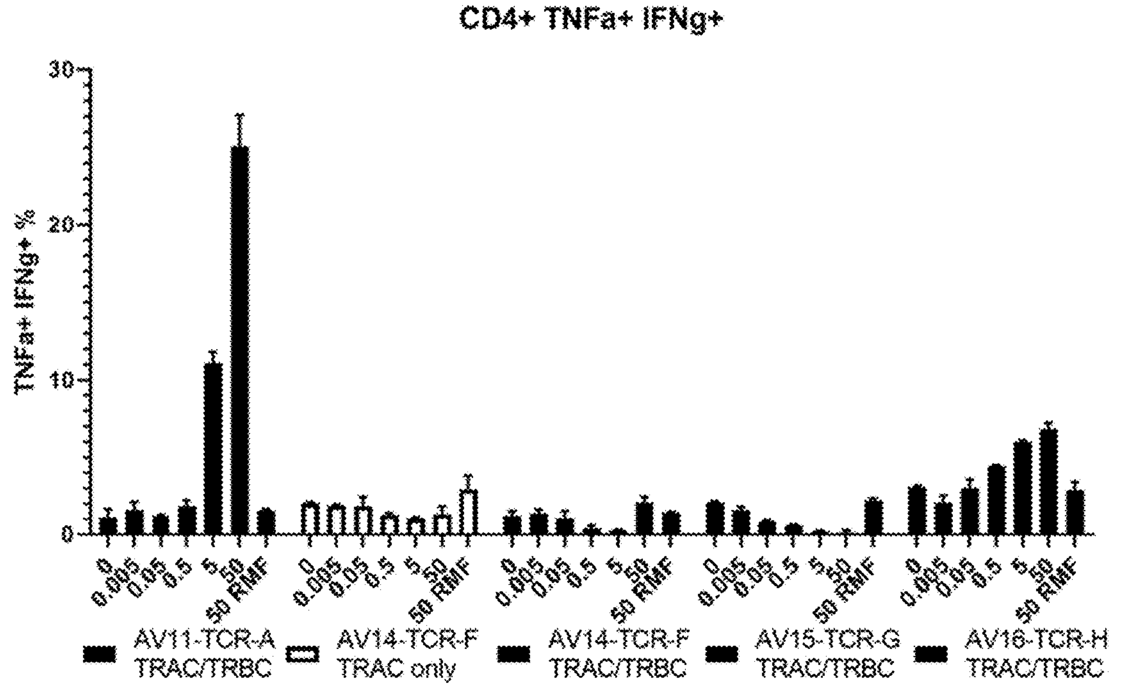
Figure 32A:
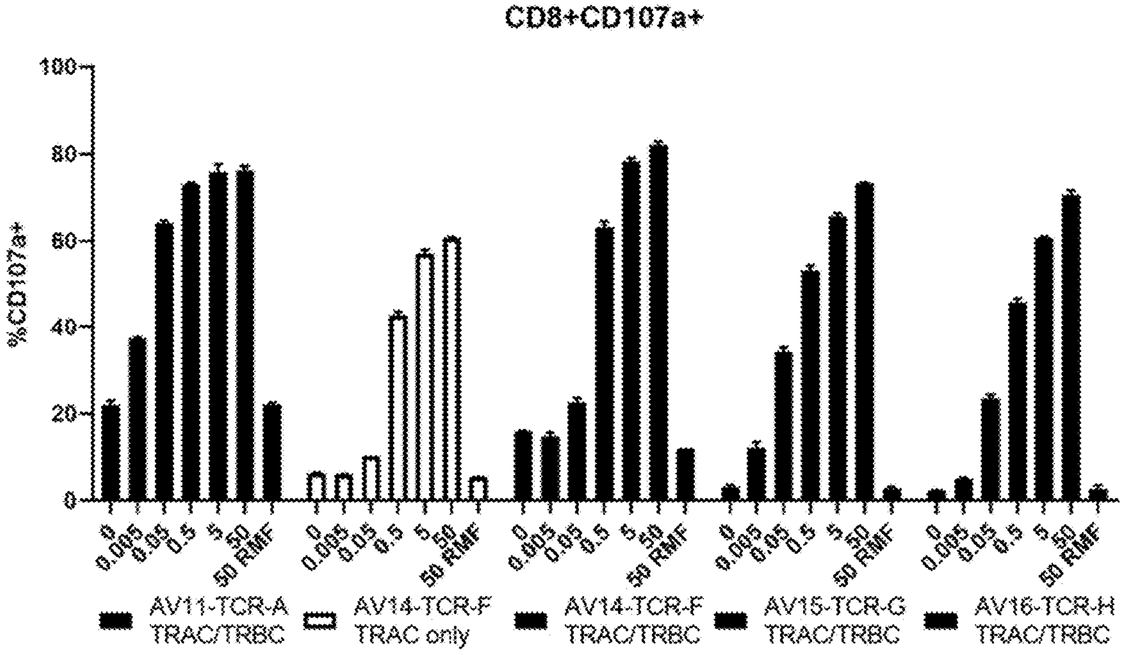
FIGS. 32A-B show the results of a CD107a degranulation assay demonstrating the extent of alloreactivity of $CD4^+$ and $CD8^+$ cells with a transgenic TCR in the TRAC locus wherein the native TRAC is knocked out and in the presence or absence of TRBC knockout. (AV11-TCR-A, AV14-TCR-F, AV15-TCR-G, AV16-TCR-H).
Figure 32B:
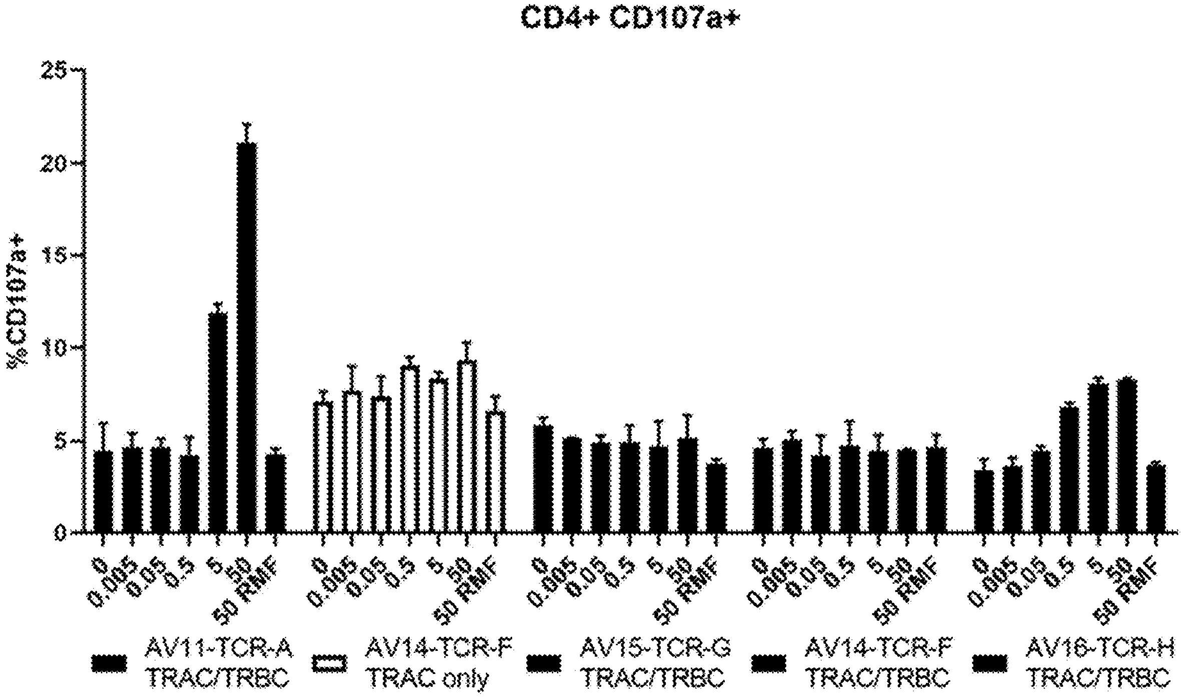

Engineered T cells were also assessed for cytotoxicity and cytokine response through the measurement of CD107a and intracellular cytokine staining, respectively. T cells were engineered as described in Example 18 using the AAV template sequences described in Table 35 with RNP targeting the TRAC locus only or both the TRAC and TRBC loci. HLA-02.01 positive T2 cell line were pulsed as described in Example 18 except edited TCR+ T cells were added to the peptide pulsed target cells at a 1:1 E:T cell ratio. Co-cultures were incubated overnight at 37 C, and the cells stained for surface markers CD3, CD4, CD8 and the specific TCR beta chain or tetramer. Following surface staining, cells were fixed and permeabilized for intracellular IFN-γ and TNFα staining using a commercially available kit (Invitrogen). The immune response elicited to TCR expression is shown in Table 35A and FIGS. 31A-B. Cytotoxicity resulting from expressed TCRs with and with TRBC knockout was evaluated by measuring CD107a in engineered T cells as shown in Table 35B and FIG. 32A-B.

TABLE 35A

| Intracellular cytokine staining | | | | | | | |
|---|---|---|---|---|---|---|---|
| | VLD | CD8+TNFa+ IFNg+ | | | CD4+TNFa+ IFNg+ | | |
| Sample Name | peptide (nM) | Mean % cells | SD | N | Mean % cells | SD | N |
| AV11- | 0 | 9.4 | 0.2 | 2 | 1.1 | 0.5 | 2 |
| TCR-A | 0.005 | 21.0 | 0.1 | 2 | 1.6 | 0.5 | 2 |
| TRAC/ | 0.05 | 53.0 | 0.4 | 2 | 1.2 | 0.1 | 2 |
| TRBC | 0.5 | 74.3 | 1.3 | 2 | 1.8 | 0.4 | 2 |
| | 5 | 79.8 | 0.1 | 2 | 11.1 | 0.7 | 2 |
| | 50 | 81.3 | 1.0 | 2 | 25.1 | 2.0 | 2 |
| | 50 RMF | 10.0 | 0.3 | 2 | 1.6 | 0.1 | 2 |
| AV14- | 0 | 0.8 | 0.0 | 2 | 2.0 | 0.0 | 2 |
| TCR-F | 0.005 | 1.0 | 0.2 | 2 | 1.9 | 0.0 | 2 |
| TRAC | 0.05 | 6.4 | 0.6 | 2 | 1.9 | 0.6 | 2 |
| only | 0.5 | 44.1 | 1.5 | 2 | 1.3 | 0.1 | 2 |
| | 5 | 69.6 | 1.0 | 2 | 1.0 | 0.1 | 2 |
| | 50 | 74.1 | 0.2 | 2 | 1.3 | 0.5 | 2 |
| | 50 RMF | 0.7 | 0.1 | 2 | 2.9 | 0.9 | 2 |
| AV14- | 0 | 1.3 | 0.0 | 2 | 1.2 | 0.3 | 2 |
| TCR-F | 0.005 | 1.9 | 0.3 | 2 | 1.4 | 0.3 | 2 |
| TRAC/ | 0.05 | 8.5 | 0.3 | 2 | 1.1 | 0.5 | 2 |
| TRBC | 0.5 | 44.6 | 0.6 | 2 | 0.4 | 0.2 | 2 |
| | 5 | 68.0 | 1.8 | 2 | 0.3 | 0.0 | 2 |
| | 50 | 78.7 | 0.4 | 2 | 2.1 | 0.4 | 2 |
| | 50 RMF | 1.8 | 0.1 | 2 | 1.5 | 0.0 | 2 |
| AV15- | 0 | 0.4 | 0.1 | 2 | 2.1 | 0.1 | 2 |
| TCR-G | 0.005 | 7.6 | 0.9 | 2 | 1.6 | 0.2 | 2 |
| TRAC/ | 0.05 | 28.7 | 0.6 | 2 | 0.9 | 0.0 | 2 |
| TRBC | 0.5 | 46.5 | 1.3 | 2 | 0.6 | 0.0 | 2 |
| | 5 | 63.1 | 0.4 | 2 | 0.2 | 0.0 | 2 |
| | 50 | 71.4 | 1.2 | 2 | 0.1 | 0.1 | 2 |
| | 50 RMF | 0.4 | 0.0 | 2 | 2.2 | 0.1 | 2 |
| AV16- | 0 | 0.5 | 0.1 | 2 | 3.1 | 0.1 | 2 |
| TCR-H | 0.005 | 3.7 | 0.0 | 2 | 2.1 | 0.5 | 2 |
| TRAC/ | 0.05 | 27.1 | 1.0 | 2 | 3.0 | 0.6 | 2 |
| TRBC | 0.5 | 48.7 | 1.0 | 2 | 4.4 | 0.1 | 2 |
| | 5 | 67.5 | 1.5 | 2 | 6.0 | 0.1 | 2 |
| | 50 | 79.2 | 0.6 | 2 | 6.9 | 0.4 | 2 |
| | 50 RMF | 0.6 | 0.4 | 2 | 2.9 | 0.5 | 2 |

TABLE 35B

| CD107a degranulation | | | | | | | |
|---|---|---|---|---|---|---|---|
| | VLD | CD8+ CD107a+ | | | CD4+ CD107a+ | | |
| Sample Name | peptide (nM) | Mean % cells | SD | N | Mean % cells | SD | N |
| AV11- | 0 | 21.95 | 1.06 | 2 | 4.45 | 1.51 | 2 |
| TCR-A | 0.005 | 37.30 | 0.28 | 2 | 4.64 | 0.78 | 2 |
| TRAC/ | 0.05 | 64.10 | 0.57 | 2 | 4.68 | 0.44 | 2 |

TABLE 35B-continued

| CD107a degranulation | | | | | | | |
|---|---|---|---|---|---|---|---|
| | VLD | CD8+ CD107a+ | | | CD4+ CD107a+ | | |
| Sample Name | peptide (nM) | Mean % cells | SD | N | Mean % cells | SD | N |
| TRBC | 0.5 | 73.05 | 0.35 | 2 | 4.23 | 0.96 | 2 |
| | 5 | 75.80 | 1.84 | 2 | 11.85 | 0.49 | 2 |
| | 50 | 76.20 | 0.99 | 2 | 21.10 | 0.99 | 2 |
| | 50 RMF | 22.05 | 0.49 | 2 | 4.30 | 0.28 | 2 |
| AV14- | 0 | 6.33 | 0.03 | 2 | 7.14 | 0.52 | 2 |
| TCR-F | 0.005 | 5.93 | 0.13 | 2 | 7.73 | 1.29 | 2 |
| TRAC | 0.05 | 10.30 | 0.00 | 2 | 7.39 | 1.10 | 2 |
| only | 0.5 | 42.75 | 0.78 | 2 | 9.08 | 0.46 | 2 |
| | 5 | 57.05 | 0.92 | 2 | 8.35 | 0.36 | 2 |
| | 50 | 60.75 | 0.07 | 2 | 9.38 | 0.88 | 2 |
| | 50 RMF | 5.42 | 0.02 | 2 | 6.63 | 0.76 | 2 |
| AV14- | 0 | 15.90 | 0.14 | 2 | 5.84 | 0.41 | 2 |
| TCR-F | 0.005 | 14.75 | 0.92 | 2 | 5.14 | 0.03 | 2 |
| TRAC/ | 0.05 | 22.55 | 1.06 | 2 | 4.89 | 0.40 | 2 |
| TRBC | 0.5 | 63.15 | 1.34 | 2 | 4.94 | 0.90 | 2 |
| | 5 | 78.25 | 0.78 | 2 | 4.71 | 1.35 | 2 |
| | 50 | 82.05 | 0.78 | 2 | 5.14 | 1.26 | 2 |
| | 50 RMF | 12.00 | 0.00 | 2 | 3.78 | 0.23 | 2 |
| AV15- | 0 | 3.15 | 0.40 | 2 | 4.62 | 0.47 | 2 |
| TCR-G | 0.005 | 12.15 | 1.34 | 2 | 5.06 | 0.47 | 2 |
| TRAC/ | 0.05 | 34.25 | 1.06 | 2 | 4.23 | 1.06 | 2 |
| TRBC | 0.5 | 53.30 | 0.99 | 2 | 4.74 | 1.32 | 2 |
| | 5 | 65.75 | 0.64 | 2 | 4.44 | 0.88 | 2 |
| | 50 | 73.25 | 0.21 | 2 | 4.52 | 0.05 | 2 |
| AV16- | 50 RMF | 2.82 | 0.37 | 2 | 4.67 | 0.65 | 2 |
| TCR-H | 0 | 2.29 | 0.07 | 2 | 3.42 | 0.60 | 2 |
| TRAC/ | 0.005 | 5.05 | 0.17 | 2 | 3.63 | 0.46 | 2 |
| TRBC | 0.05 | 23.60 | 0.85 | 2 | 4.48 | 0.24 | 2 |
| | 0.5 | 45.65 | 0.92 | 2 | 6.82 | 0.24 | 2 |
| | 5 | 60.70 | 0.28 | 2 | 8.09 | 0.30 | 2 |
| | 50 | 70.55 | 1.06 | 2 | 8.28 | 0.08 | 2 |
| | 50 RMF | 2.64 | 0.84 | 2 | 3.70 | 0.15 | 2 |

Example 20: Alloreactivity Assay

Figures 33A, 33B:
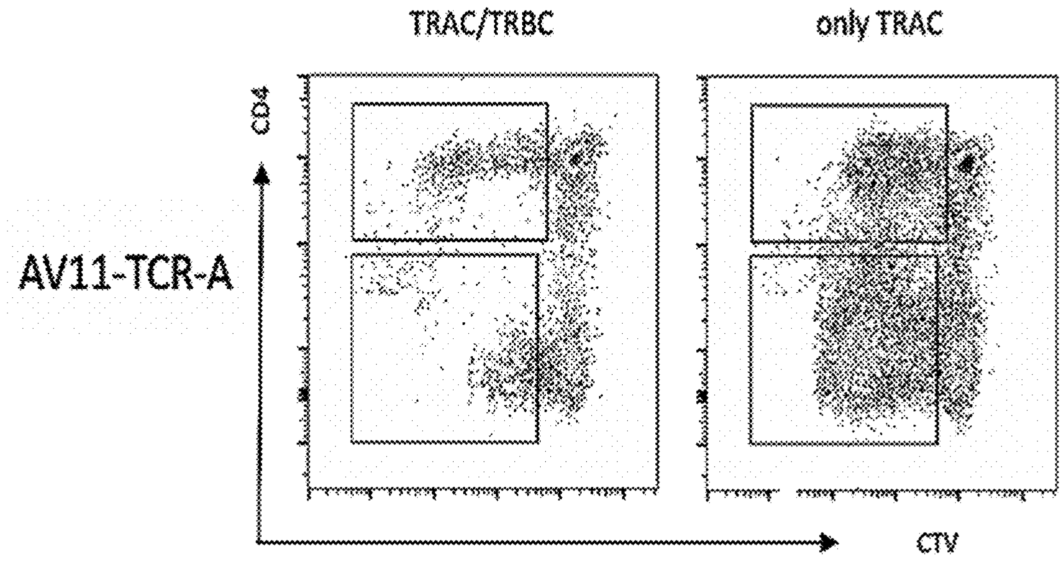
FIGS. 33A-D show the results of a mixed lymphocyte reaction demonstrating the extent of alloreactivity of $CD4^+$ and $CD8^+$ cells with a transgenic TCR in the TRAC locus wherein the native TRAC is knocked out and in the presence or absence of TRBC knockout. CTV, CellTrace Violet (ThermoFisher).
Figure 33C:
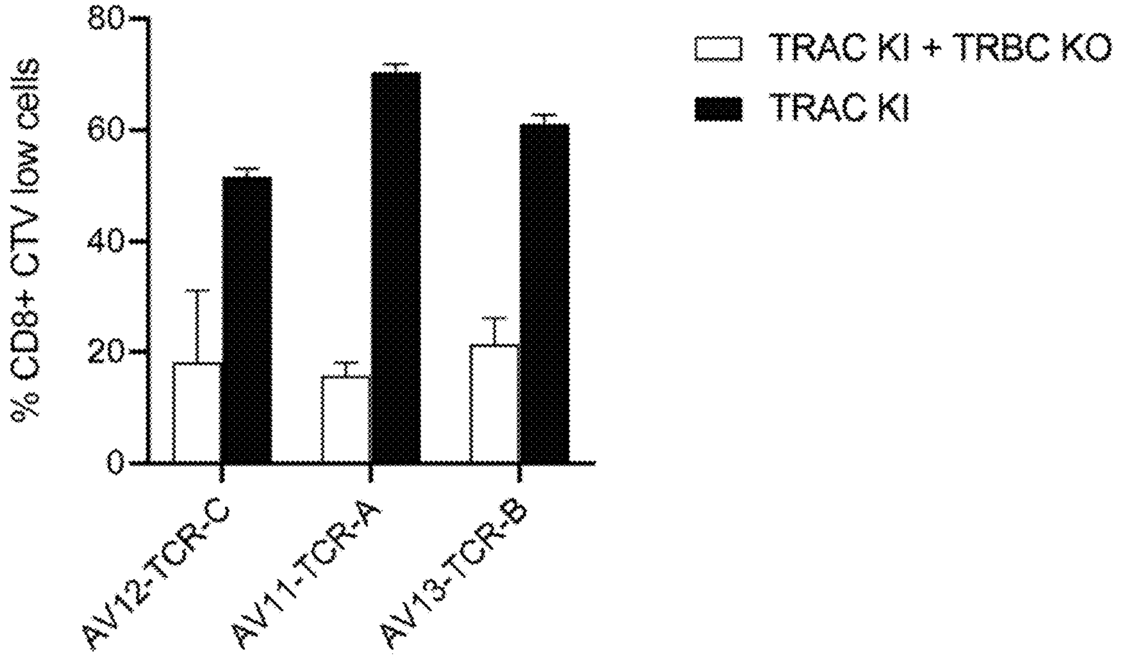
Figure 33D:
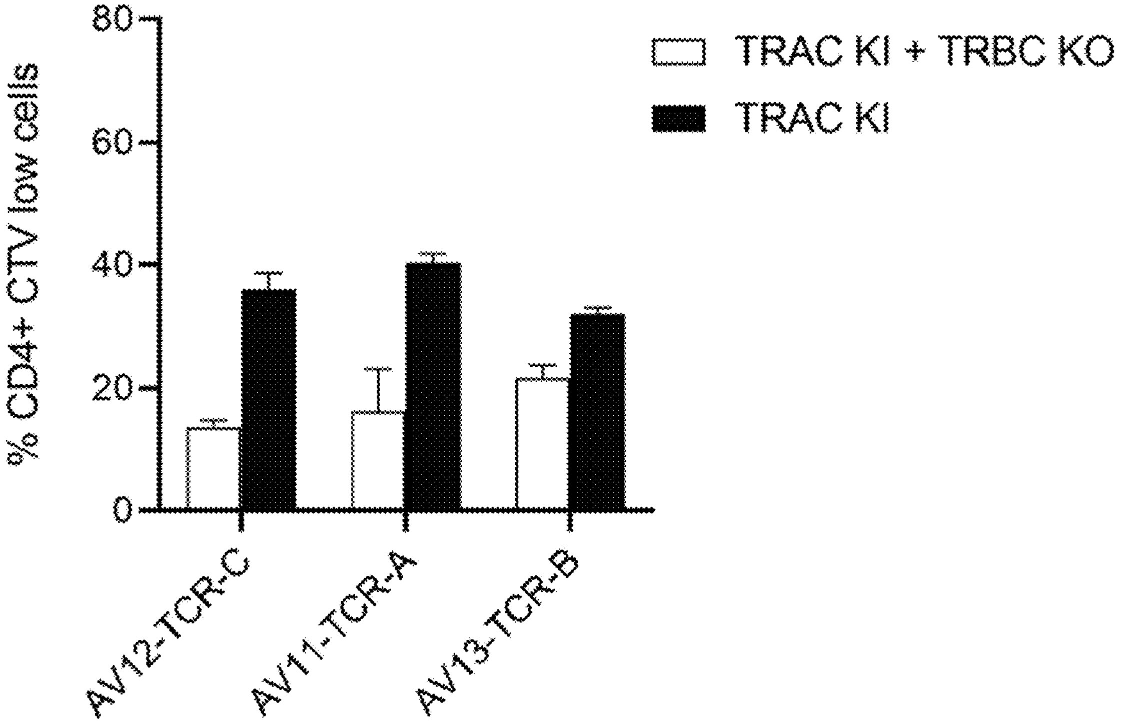

Engineered T cells prepared in Example 18 were also assayed for non-specific reactivity to antigen presenting cells in a mixed lymphocyte reaction (MLR) suppression assay. Engineered T cells were labelled with CellTrace Violet (Invitrogen), according to manufacturer's instructions. Allogeneic PBMCs were depleted of CD3+ cells using MACS (Miltenyi) and used to stimulate the CTV-labelled T cells. Specifically, $5\times10^4$ T cells were plated with $3\times10^4$ CD3-depleted allogeneic PBMCs in a 96-well U-bottom plate (Corning). Five days later, the cells were harvested, stained with anti-CD4 and analyzed by flow cytometry. The degree of proliferation was quantified by dilution of the CellTrace Violet dye. Roswell Park Memorial Institute 1640 media (RPMI; Corning) with glutamine was supplemented with 10% FBS, 1× GlutaMAX, 10 mM HEPES, 1× Penicillin/streptomycin, 1 mM sodium pyruvate, 50 uM 2-ME, and 1× non-essential amino acids was used throughout the MLR assay. The mean percentage of cells staining with low levels of CellTrace Violet (CTV), i.e. cells with high proliferation, is shown in Table 36 and FIGS. 33A-B. FIGS. 33A and 33B show gating used to assay CTV levels. Cells treated with TRBC RNP showed less proliferation than cells not treated with TRBC RNP in both CD4+ and CD4− (CD8+) cells for each inserted TCR tested as shown in Table 36 and FIGS. 33C and 33D.

TABLE 36

| Proliferation in response to allogeneic PBMCs | | | | | | | |
|---|---|---|---|---|---|---|---|
| | | TRAC RNP + TRBC RNP | | | TRAC RNP | | |
| T Cell Type | Sample Name | Mean % CTV low cells | SD | n | Mean % CTV low cells | SD | n |
| CD4– | AV12-TCR-C | 18% | 13% | 3 | 52% | 2% | 3 |
| | AV11-TCR-A | 16% | 3% | 3 | 70% | 2% | 3 |
| | AV13-TCR-B | 21% | 5% | 3 | 61% | 2% | 3 |
| CD4+ | AV12-TCR-C | 14% | 1% | 3 | 36% | 3% | 3 |
| | AV11-TCR-A | 16% | 7% | 3 | 40% | 2% | 3 |
| | AV13-TCR-B | 22% | 2% | 3 | 32% | 1% | 3 |

Table 37—Nucleic Acid Templates. Note, all templates delivered as ssAAV and comprise AAV2 5' and 3' ITRs. Homology arms are as described above. Many additionally comprise one or more promoter, cleavage, or polyA sequences, as set forth below. An "*" indicates a stop codon, below.

TABLE 37

| Template | Trans-gene | Promoter or (Promoter-less/Peptide) | TCR ORF Config-uration | PolyA |
|---|---|---|---|---|
| AV1 (SEQ ID NO: 613) | TCR-C | EF1a | β-P2A-α-* | bGH |
| AV2 (SEQ ID NO: 614) | TCR-C | Ef1a - short | β-P2A-α-* | bGH |
| AV3 (SEQ ID NO: 615) | TCR-C | MND-1 | β-P2A-α-* | bGH |
| AV4 (SEQ ID NO: 616) | TCR-C | MND-2 | β-P2A-α-* | bGH |
| AV5 (SEQ ID NO: 617) | TCR-C | PGK | β-P2A-α-* | bGH |
| AV6 (SEQ ID NO: 618) | TCR-C | MND-1 | β-P2A-α-* | bGH |
| AV7 (SEQ ID NO: 619) | TCR-C | PGK | β-P2A-α-* | bGH |
| AV8 (SEQ ID NO: 620) | TCR-C | MND-2 | β-P2A-α-* | bGH |
| AV9 (SEQ ID NO: 621) | EGFP | EF1a | n/a | SV40 |
| AV10 (SEQ ID NO: 622) | EGFP | (T2A) | n/a | bGH |
| AV11 (SEQ ID NO: 623) | TCR-A | EF1a | β-P2A-α-* | bGH |
| AV12 (SEQ ID NO: 624) | TCR-C | EF1a | β-P2A-α-* | bGH |
| AV13 (SEQ ID NO: 625) | TCR-B | EF1a | β-P2A-α-* | bGH |
| AV14 (SEQ ID NO: 626) | TCR-F | EF1a | β-P2A-α-* | bGH |
| AV15 (SEQ ID NO: 627) | TCR-G | EF1a | β-P2A-α-* | bGH |
| AV16 (SEQ ID NO: 628) | TCR-H | EF1a | β-P2A-α-* | bGH |
| AV18 (SEQ ID NO: 629) | TCR-D | EF1a | β-P2A-α-* | bGH |
| AV19 (SEQ ID NO: 630) | TCR-C | (T2A) | β-P2A-α-* | bGH |
| AV20 (SEQ ID NO: 631) | TCR-E | (T2A) | β-P2A-α-* | bGH |
| AV21 (SEQ ID NO: 632) | TCR-B | (T2A) | β-P2A-α-* | bGH |

The elements of the templates defined in Table 37 are defined according to the following sequences as follows: EF1a (SEQ ID NO: 603); EF1 (SEQ ID NO: 604); MND-1 (SEQ ID NO: 605); MND-2 (SEQ ID NO: 606); PGK (SEQ ID NO: 607); T2A (SEQ ID NO: 608); P2A (SEQ ID NO: 609); EGFP (SEQ ID NO: 610); SV40 Poly A (SEQ ID NO: 611); bGH PolyA (SEQ ID NO: 612)

What is claimed is:

1. A method of reducing the expression of an endogenous T cell receptor and inserting a heterologous immunological receptor at the TRAC locus, comprising delivering to a cell: (a) a TRAC guide RNA and a TRBC1/2 guide RNA; (b) an RNA-guided DNA binding agent, or a nucleic acid encoding an RNA-guided DNA binding agent; and (c) a nucleic acid encoding the heterologous immunological receptor, wherein the TRAC guide RNA comprises:

i) a guide sequence that is SEQ ID NO: 90; or ii) a guide sequence that is SEQ ID NO: 185; or iii) a guide sequence that is SEQ ID NO: 214.

2. The method of claim 1, wherein the nucleic acid encoding the heterologous immunological receptor is flanked by sequences homologous to the TRAC locus.

3. The method of claim 1, wherein the TRAC guide RNA comprises a guide sequence that is SEQ ID NO: 90.

4. The method of claim 1, wherein the TRAC guide RNA comprises a guide sequence that is SEQ ID NO: 90 and the TRBC1/2 guide RNA comprises a guide sequence that is SEQ ID NO: 2.

5. The method of claim 1, wherein the heterologous immunological receptor is a heterologous T-cell receptor.

6. The method of claim 5, wherein the heterologous T-cell receptor recognizes a cancer antigen.

7. The method of claim 6, wherein the heterologous T-cell receptor is a WT1-specific T-cell receptor that recognizes WT1 or a fragment thereof.

8. The method of claim 1, wherein the heterologous immunological receptor is a chimeric antigen receptor.

9. The method of claim 8, wherein the chimeric antigen receptor recognizes a cancer antigen.

10. The method of claim 1, wherein the RNA-guided DNA binding agent is Cas9.

11. The method of claim 1, wherein the TRAC guide RNA and the TRBC1/2 guide RNA, the RNA-guided DNA binding agent or the nucleic acid encoding the RNA-guided DNA binding agent, and the nucleic acid encoding the heterologous immunological receptor are delivered to the cell via a vector, via transfection, via a lipid nanoparticle, or via microinjection.

12. The method of claim 1, wherein the TRAC guide RNA comprises SEQ ID NO: 186.

13. The method of claim 1, wherein the TRAC guide RNA comprises SEQ ID NO: 203.

14. The method of claim 1, wherein the TRAC guide RNA comprises a guide sequence that is SEQ ID NO: 185.

15. The method of claim 1, wherein the TRAC guide RNA comprises a guide sequence that is SEQ ID NO: 214.

16. The method of claim 1, wherein the TRBC1/2 guide RNA comprises a guide sequence that is SEQ ID NO: 2, a guide sequence that is 95% or 90% identical to SEQ ID NO: 2, or a guide sequence that is 18 or 19 contiguous nucleotides of SEQ ID NO: 2.

17. A method of reducing the expression of an endogenous T cell receptor and inserting a heterologous immunological receptor at the TRAC locus, comprising delivering to a cell: (a) a TRAC guide RNA; (b) an RNA-guided DNA binding agent, or a nucleic acid encoding an RNA-guided DNA binding agent; and (c) a nucleic acid encoding the heterologous immunological receptor, wherein the TRAC guide RNA comprises:

i) a guide sequence that is SEQ ID NO: 90; or ii) a guide sequence that is SEQ ID NO: 185; or iii) a guide sequence that is SEQ ID NO: 214.

18. The method of claim 17, wherein the nucleic acid encoding the heterologous immunological receptor is flanked by sequences homologous to the TRAC locus.

19. The method of claim 17, wherein the TRAC guide RNA comprises a guide sequence that is SEQ ID NO: 90.

20. The method of claim 17, wherein the TRAC guide RNA comprises a guide sequence that is SEQ ID NO: 185.

21. The method of claim 17, wherein the TRAC guide RNA comprises a guide sequence that is SEQ ID NO: 214.

22. The method of claim 17, wherein the TRAC guide RNA comprises SEQ ID NO: 186.

23. The method of claim 17, wherein the TRAC guide RNA comprises SEQ ID NO: 203.

24. The method of claim 17, wherein the heterologous immunological receptor is a heterologous T-cell receptor.

25. The method of claim 24, wherein the heterologous T-cell receptor recognizes a cancer antigen.

26. The method of claim 25, wherein the heterologous T-cell receptor is a WT1-specific T-cell receptor that recognizes WT1 or a fragment thereof.

27. The method of claim 17, wherein the heterologous immunological receptor is a chimeric antigen receptor.

28. The method of claim 27, wherein the chimeric antigen receptor recognizes a cancer antigen.

29. The method of claim 17, wherein the RNA-guided DNA binding agent is Cas9.

30. The method of claim 17, wherein the TRAC guide RNA, the RNA-guided DNA binding agent or the nucleic acid encoding the RNA-guided DNA binding agent, and the nucleic acid encoding the heterologous immunological receptor are delivered to the cell via a vector, via transfection, via a lipid nanoparticle, or via microinjection.

* * * * *

SEQUENCE LISTING

```
<160> NUMBER OF SEQ ID NOS: 632

<210> SEQ ID NO 1
<211> LENGTH: 20
<212> TYPE: RNA
<213> ORGANISM: Homo sapiens

<400> SEQUENCE: 1

ggcucucgga gaaugacgag                                                 20


<210> SEQ ID NO 2
<211> LENGTH: 20
<212> TYPE: RNA
<213> ORGANISM: Homo sapiens

<400> SEQUENCE: 2

ggccucggcg cugacgaucu                                                 20


<210> SEQ ID NO 3
<211> LENGTH: 20
<212> TYPE: RNA
<213> ORGANISM: Homo sapiens

<400> SEQUENCE: 3

augacgagug gacccaggau                                                 20


<210> SEQ ID NO 4
<211> LENGTH: 20
<212> TYPE: RNA
<213> ORGANISM: Homo sapiens

<400> SEQUENCE: 4

agaagguggc cgagacccuc                                                 20
```

-continued

```
<210> SEQ ID NO 5
<211> LENGTH: 20
<212> TYPE: RNA
<213> ORGANISM: Homo sapiens

<400> SEQUENCE: 5

ugagggucuc ggccaccuuc                                           20

<210> SEQ ID NO 6
<211> LENGTH: 20
<212> TYPE: RNA
<213> ORGANISM: Homo sapiens

<400> SEQUENCE: 6

agagaucucc cacacccaaa                                           20

<210> SEQ ID NO 7
<211> LENGTH: 20
<212> TYPE: RNA
<213> ORGANISM: Homo sapiens

<400> SEQUENCE: 7

uggcucaaac acagcgaccu                                           20

<210> SEQ ID NO 8
<211> LENGTH: 20
<212> TYPE: RNA
<213> ORGANISM: Homo sapiens

<400> SEQUENCE: 8

ggcgcugacg aucuggguga                                           20

<210> SEQ ID NO 9
<211> LENGTH: 20
<212> TYPE: RNA
<213> ORGANISM: Homo sapiens

<400> SEQUENCE: 9

uggcagacag gaccccuugc                                           20

<210> SEQ ID NO 10
<211> LENGTH: 20
<212> TYPE: RNA
<213> ORGANISM: Homo sapiens

<400> SEQUENCE: 10

ugacgagugg acccaggaua                                           20

<210> SEQ ID NO 11
<211> LENGTH: 20
<212> TYPE: RNA
<213> ORGANISM: Homo sapiens

<400> SEQUENCE: 11

agacaggacc ccuugcuggu                                           20

<210> SEQ ID NO 12
<211> LENGTH: 20
<212> TYPE: RNA
<213> ORGANISM: Homo sapiens

<400> SEQUENCE: 12

uugacagcgg aagugguugc                                           20
```

<210> SEQ ID NO 13
<211> LENGTH: 20
<212> TYPE: RNA
<213> ORGANISM: Homo sapiens

<400> SEQUENCE: 13
cguagaacug gacuugacag 20

<210> SEQ ID NO 14
<211> LENGTH: 20
<212> TYPE: RNA
<213> ORGANISM: Homo sapiens

<400> SEQUENCE: 14
cgcugucaag uccaguucua 20

<210> SEQ ID NO 15
<211> LENGTH: 20
<212> TYPE: RNA
<213> ORGANISM: Homo sapiens

<400> SEQUENCE: 15
acuggacuug acagcggaag 20

<210> SEQ ID NO 16
<211> LENGTH: 20
<212> TYPE: RNA
<213> ORGANISM: Homo sapiens

<400> SEQUENCE: 16
guugcggggg uucugccaga 20

<210> SEQ ID NO 17
<211> LENGTH: 20
<212> TYPE: RNA
<213> ORGANISM: Homo sapiens

<400> SEQUENCE: 17
cugccugagc agccgccuga 20

<210> SEQ ID NO 18
<211> LENGTH: 20
<212> TYPE: RNA
<213> ORGANISM: Homo sapiens

<400> SEQUENCE: 18
gacagcggaa gugguugcgg 20

<210> SEQ ID NO 19
<211> LENGTH: 20
<212> TYPE: RNA
<213> ORGANISM: Homo sapiens

<400> SEQUENCE: 19
ccacucaccu gcucuacccc 20

<210> SEQ ID NO 20
<211> LENGTH: 20
<212> TYPE: RNA
<213> ORGANISM: Homo sapiens

<400> SEQUENCE: 20
gcugucaagu ccaguucuac 20

<210> SEQ ID NO 21
<211> LENGTH: 20
<212> TYPE: RNA
<213> ORGANISM: Homo sapiens

<400> SEQUENCE: 21
acacuggugu gccuggccac 20

<210> SEQ ID NO 22
<211> LENGTH: 20
<212> TYPE: RNA
<213> ORGANISM: Homo sapiens

<400> SEQUENCE: 22
agacccucag gcggcugcuc 20

<210> SEQ ID NO 23
<211> LENGTH: 20
<212> TYPE: RNA
<213> ORGANISM: Homo sapiens

<400> SEQUENCE: 23
augggaagga ggugcacagu 20

<210> SEQ ID NO 24
<211> LENGTH: 20
<212> TYPE: RNA
<213> ORGANISM: Homo sapiens

<400> SEQUENCE: 24
agggcgggcu gcuccuugag 20

<210> SEQ ID NO 25
<211> LENGTH: 20
<212> TYPE: RNA
<213> ORGANISM: Homo sapiens

<400> SEQUENCE: 25
ucccuagcaa gaucucauag 20

<210> SEQ ID NO 26
<211> LENGTH: 20
<212> TYPE: RNA
<213> ORGANISM: Homo sapiens

<400> SEQUENCE: 26
ggugcacagu ggggucagca 20

<210> SEQ ID NO 27
<211> LENGTH: 20
<212> TYPE: RNA
<213> ORGANISM: Homo sapiens

<400> SEQUENCE: 27
ccagcucagc uccacguggu 20

<210> SEQ ID NO 28
<211> LENGTH: 20
<212> TYPE: RNA
<213> ORGANISM: Homo sapiens

<400> SEQUENCE: 28
ccgcaaccac uuccgcuguc 20

<210> SEQ ID NO 29
<211> LENGTH: 20
<212> TYPE: RNA
<213> ORGANISM: Homo sapiens

<400> SEQUENCE: 29
guccacucgu cauucuccga 20

<210> SEQ ID NO 30
<211> LENGTH: 20
<212> TYPE: RNA
<213> ORGANISM: Homo sapiens

<400> SEQUENCE: 30
gcccguagaa cuggacuuga 20

<210> SEQ ID NO 31
<211> LENGTH: 20
<212> TYPE: RNA
<213> ORGANISM: Homo sapiens

<400> SEQUENCE: 31
ucacccagau cgucagcgcc 20

<210> SEQ ID NO 32
<211> LENGTH: 20
<212> TYPE: RNA
<213> ORGANISM: Homo sapiens

<400> SEQUENCE: 32
ggguccacuc gucauucucc 20

<210> SEQ ID NO 33
<211> LENGTH: 20
<212> TYPE: RNA
<213> ORGANISM: Homo sapiens

<400> SEQUENCE: 33
uccaguucua cgggcucucg 20

<210> SEQ ID NO 34
<211> LENGTH: 20
<212> TYPE: RNA
<213> ORGANISM: Homo sapiens

<400> SEQUENCE: 34
cggagaauga cgaguggacc 20

<210> SEQ ID NO 35
<211> LENGTH: 20
<212> TYPE: RNA
<213> ORGANISM: Homo sapiens

<400> SEQUENCE: 35
accacuuccg cugucaaguc 20

<210> SEQ ID NO 36
<211> LENGTH: 20
<212> TYPE: RNA
<213> ORGANISM: Homo sapiens

<400> SEQUENCE: 36
aaugacgagu ggacccagga 20

<210> SEQ ID NO 37
<211> LENGTH: 20
<212> TYPE: RNA
<213> ORGANISM: Homo sapiens

<400> SEQUENCE: 37
acgggcucuc ggagaaugac 20

<210> SEQ ID NO 38
<211> LENGTH: 20
<212> TYPE: RNA
<213> ORGANISM: Homo sapiens

<400> SEQUENCE: 38
gacuccagau acugccugag 20

<210> SEQ ID NO 39
<211> LENGTH: 20
<212> TYPE: RNA
<213> ORGANISM: Homo sapiens

<400> SEQUENCE: 39
cgcuguguuu gagccaucag 20

<210> SEQ ID NO 40
<211> LENGTH: 20
<212> TYPE: RNA
<213> ORGANISM: Homo sapiens

<400> SEQUENCE: 40
agaacuggac uugacagcgg 20

<210> SEQ ID NO 41
<211> LENGTH: 20
<212> TYPE: RNA
<213> ORGANISM: Homo sapiens

<400> SEQUENCE: 41
gagacccuca ggcggcugcu 20

<210> SEQ ID NO 42
<211> LENGTH: 20
<212> TYPE: RNA
<213> ORGANISM: Homo sapiens

<400> SEQUENCE: 42
cgucauucuc cgagagcccg 20

<210> SEQ ID NO 43
<211> LENGTH: 20
<212> TYPE: RNA
<213> ORGANISM: Homo sapiens

<400> SEQUENCE: 43
cagcccgccc ucaaugacuc 20

<210> SEQ ID NO 44
<211> LENGTH: 20
<212> TYPE: RNA
<213> ORGANISM: Homo sapiens

<400> SEQUENCE: 44
ggcugcucag gcaguaucug 20

<210> SEQ ID NO 45
<211> LENGTH: 20
<212> TYPE: RNA
<213> ORGANISM: Homo sapiens

<400> SEQUENCE: 45
agugguugcg gggguucugc 20

<210> SEQ ID NO 46
<211> LENGTH: 20
<212> TYPE: RNA
<213> ORGANISM: Homo sapiens

<400> SEQUENCE: 46
ggucgcugug uuugagccau 20

<210> SEQ ID NO 47
<211> LENGTH: 20
<212> TYPE: RNA
<213> ORGANISM: Homo sapiens

<400> SEQUENCE: 47
gaucucauag aggauggugg 20

<210> SEQ ID NO 48
<211> LENGTH: 20
<212> TYPE: RNA
<213> ORGANISM: Homo sapiens

<400> SEQUENCE: 48
uguuugagcc aucagaagca 20

<210> SEQ ID NO 49
<211> LENGTH: 20
<212> TYPE: RNA
<213> ORGANISM: Homo sapiens

<400> SEQUENCE: 49
uacugccuga gcagccgccu 20

<210> SEQ ID NO 50
<211> LENGTH: 20
<212> TYPE: RNA
<213> ORGANISM: Homo sapiens

<400> SEQUENCE: 50
acccgcagcc ccucaaggag 20

<210> SEQ ID NO 51
<211> LENGTH: 20
<212> TYPE: RNA
<213> ORGANISM: Homo sapiens

<400> SEQUENCE: 51
aggcaguauc uggagucauu 20

<210> SEQ ID NO 52
<211> LENGTH: 20
<212> TYPE: RNA

-continued

<213> ORGANISM: Homo sapiens

<400> SEQUENCE: 52
uguguuugag ccaucagaag                                                     20

<210> SEQ ID NO 53
<211> LENGTH: 20
<212> TYPE: RNA
<213> ORGANISM: Homo sapiens

<400> SEQUENCE: 53
gguugcgggg guucugccag                                                     20

<210> SEQ ID NO 54
<211> LENGTH: 20
<212> TYPE: RNA
<213> ORGANISM: Homo sapiens

<400> SEQUENCE: 54
gggucucggc caccuucugg                                                     20

<210> SEQ ID NO 55
<211> LENGTH: 20
<212> TYPE: RNA
<213> ORGANISM: Homo sapiens

<400> SEQUENCE: 55
cagaaggugg ccgagacccu                                                     20

<210> SEQ ID NO 56
<211> LENGTH: 20
<212> TYPE: RNA
<213> ORGANISM: Homo sapiens

<400> SEQUENCE: 56
cgccgaggcc ugggguagag                                                     20

<210> SEQ ID NO 57
<211> LENGTH: 20
<212> TYPE: RNA
<213> ORGANISM: Homo sapiens

<400> SEQUENCE: 57
gguucugcca gaagguggcc                                                     20

<210> SEQ ID NO 58
<211> LENGTH: 20
<212> TYPE: RNA
<213> ORGANISM: Homo sapiens

<400> SEQUENCE: 58
cagagaucuc ccacacccaa                                                     20

<210> SEQ ID NO 59
<211> LENGTH: 20
<212> TYPE: RNA
<213> ORGANISM: Homo sapiens

<400> SEQUENCE: 59
uugagggcgg gcugcuccuu                                                     20

<210> SEQ ID NO 60
<211> LENGTH: 20

-continued

<212> TYPE: RNA
<213> ORGANISM: Homo sapiens

<400> SEQUENCE: 60
aagccugugg ccaggcacac 20

<210> SEQ ID NO 61
<211> LENGTH: 20
<212> TYPE: RNA
<213> ORGANISM: Homo sapiens

<400> SEQUENCE: 61
cagcgccgag gccuggggua 20

<210> SEQ ID NO 62
<211> LENGTH: 20
<212> TYPE: RNA
<213> ORGANISM: Homo sapiens

<400> SEQUENCE: 62
cccacucacc ugcucuaccc 20

<210> SEQ ID NO 63
<211> LENGTH: 20
<212> TYPE: RNA
<213> ORGANISM: Homo sapiens

<400> SEQUENCE: 63
ugucugccac cauccucuau 20

<210> SEQ ID NO 64
<211> LENGTH: 20
<212> TYPE: RNA
<213> ORGANISM: Homo sapiens

<400> SEQUENCE: 64
ugcuucugau ggcucaaaca 20

<210> SEQ ID NO 65
<211> LENGTH: 20
<212> TYPE: RNA
<213> ORGANISM: Homo sapiens

<400> SEQUENCE: 65
uucccauuca cccaccagcu 20

<210> SEQ ID NO 66
<211> LENGTH: 20
<212> TYPE: RNA
<213> ORGANISM: Homo sapiens

<400> SEQUENCE: 66
gucagcgccg aggccugggg 20

<210> SEQ ID NO 67
<211> LENGTH: 20
<212> TYPE: RNA
<213> ORGANISM: Homo sapiens

<400> SEQUENCE: 67
cccucaggcg gcugcucagg 20

<210> SEQ ID NO 68

<211> LENGTH: 20
<212> TYPE: RNA
<213> ORGANISM: Homo sapiens

<400> SEQUENCE: 68
aaugacucca gauacugccu 20

<210> SEQ ID NO 69
<211> LENGTH: 20
<212> TYPE: RNA
<213> ORGANISM: Homo sapiens

<400> SEQUENCE: 69
cacacuggug ugccuggcca 20

<210> SEQ ID NO 70
<211> LENGTH: 20
<212> TYPE: RNA
<213> ORGANISM: Homo sapiens

<400> SEQUENCE: 70
ucauagagga ugguggcaga 20

<210> SEQ ID NO 71
<211> LENGTH: 20
<212> TYPE: RNA
<213> ORGANISM: Homo sapiens

<400> SEQUENCE: 71
cacccagauc gucagcgccg 20

<210> SEQ ID NO 72
<211> LENGTH: 20
<212> TYPE: RNA
<213> ORGANISM: Homo sapiens

<400> SEQUENCE: 72
ugacagcgga agugguugcg 20

<210> SEQ ID NO 73
<211> LENGTH: 20
<212> TYPE: RNA
<213> ORGANISM: Homo sapiens

<400> SEQUENCE: 73
ucuccgagag cccguagaac 20

<210> SEQ ID NO 74
<211> LENGTH: 20
<212> TYPE: RNA
<213> ORGANISM: Homo sapiens

<400> SEQUENCE: 74
aguccaguuc uacgggcucu 20

<210> SEQ ID NO 75
<211> LENGTH: 20
<212> TYPE: RNA
<213> ORGANISM: Homo sapiens

<400> SEQUENCE: 75
aucgucagcg ccgaggccug 20

<210> SEQ ID NO 76
<211> LENGTH: 20
<212> TYPE: RNA
<213> ORGANISM: Homo sapiens

<400> SEQUENCE: 76
aaggaggugc acaguggggu 20

<210> SEQ ID NO 77
<211> LENGTH: 20
<212> TYPE: RNA
<213> ORGANISM: Homo sapiens

<400> SEQUENCE: 77
uaucuggagu cauugagggc 20

<210> SEQ ID NO 78
<211> LENGTH: 20
<212> TYPE: RNA
<213> ORGANISM: Homo sapiens

<400> SEQUENCE: 78
gcggggguuc ugccagaagg 20

<210> SEQ ID NO 79
<211> LENGTH: 20
<212> TYPE: RNA
<213> ORGANISM: Homo sapiens

<400> SEQUENCE: 79
cuugacagcg gaagugguug 20

<210> SEQ ID NO 80
<211> LENGTH: 20
<212> TYPE: RNA
<213> ORGANISM: Homo sapiens

<400> SEQUENCE: 80
guguggccuu uugggugugg 20

<210> SEQ ID NO 81
<211> LENGTH: 20
<212> TYPE: RNA
<213> ORGANISM: Homo sapiens

<400> SEQUENCE: 81
gaucgucagc gccgaggccu 20

<210> SEQ ID NO 82
<211> LENGTH: 20
<212> TYPE: RNA
<213> ORGANISM: Homo sapiens

<400> SEQUENCE: 82
uguggccagg cacaccagug 20

<210> SEQ ID NO 83
<211> LENGTH: 20
<212> TYPE: RNA
<213> ORGANISM: Homo sapiens

<400> SEQUENCE: 83
aggccucggc gcugacgauc 20

<210> SEQ ID NO 84
<211> LENGTH: 20
<212> TYPE: RNA
<213> ORGANISM: Homo sapiens

<400> SEQUENCE: 84
gugaauggga aggaggugca 20

<210> SEQ ID NO 85
<211> LENGTH: 20
<212> TYPE: RNA
<213> ORGANISM: Homo sapiens

<400> SEQUENCE: 85
gcggcugcuc aggcaguauc 20

<210> SEQ ID NO 86
<211> LENGTH: 20
<212> TYPE: RNA
<213> ORGANISM: Homo sapiens

<400> SEQUENCE: 86
acugccugag cagccgccug 20

<210> SEQ ID NO 87
<211> LENGTH: 20
<212> TYPE: RNA
<213> ORGANISM: Homo sapiens

<400> SEQUENCE: 87
aaaggccaca cuggugugcc 20

<210> SEQ ID NO 88
<211> LENGTH: 20
<212> TYPE: RNA
<213> ORGANISM: Homo sapiens

<400> SEQUENCE: 88
ugagggcggg cugcuccuug 20

<210> SEQ ID NO 89
<211> LENGTH: 20
<212> TYPE: RNA
<213> ORGANISM: Homo sapiens

<400> SEQUENCE: 89
gagcagccgc cugagggucu 20

<210> SEQ ID NO 90
<211> LENGTH: 20
<212> TYPE: RNA
<213> ORGANISM: Homo sapiens

<400> SEQUENCE: 90
cucucagcug guacacggca 20

<210> SEQ ID NO 91
<211> LENGTH: 20
<212> TYPE: RNA
<213> ORGANISM: Homo sapiens

<400> SEQUENCE: 91
uucggaaccc aaucacugac 20

<210> SEQ ID NO 92
<211> LENGTH: 20
<212> TYPE: RNA
<213> ORGANISM: Homo sapiens

<400> SEQUENCE: 92
uaaacccggc cacuuucagg 20

<210> SEQ ID NO 93
<211> LENGTH: 20
<212> TYPE: RNA
<213> ORGANISM: Homo sapiens

<400> SEQUENCE: 93
gauuaaaccc ggccacuuuc 20

<210> SEQ ID NO 94
<211> LENGTH: 20
<212> TYPE: RNA
<213> ORGANISM: Homo sapiens

<400> SEQUENCE: 94
cgucaugagc agauuaaacc 20

<210> SEQ ID NO 95
<211> LENGTH: 20
<212> TYPE: RNA
<213> ORGANISM: Homo sapiens

<400> SEQUENCE: 95
agagucucuc agcugguaca 20

<210> SEQ ID NO 96
<211> LENGTH: 20
<212> TYPE: RNA
<213> ORGANISM: Homo sapiens

<400> SEQUENCE: 96
acacggcagg gucaggguuc 20

<210> SEQ ID NO 97
<211> LENGTH: 20
<212> TYPE: RNA
<213> ORGANISM: Homo sapiens

<400> SEQUENCE: 97
ucucucagcu gguacacggc 20

<210> SEQ ID NO 98
<211> LENGTH: 20
<212> TYPE: RNA
<213> ORGANISM: Homo sapiens

<400> SEQUENCE: 98
uggauuuaga gucucucagc 20

<210> SEQ ID NO 99
<211> LENGTH: 20
<212> TYPE: RNA
<213> ORGANISM: Homo sapiens

<400> SEQUENCE: 99
gagaaucaaa aucggugaau 20

<210> SEQ ID NO 100
<211> LENGTH: 20
<212> TYPE: RNA
<213> ORGANISM: Homo sapiens

<400> SEQUENCE: 100
acaaaacugu gcuagacaug 20

<210> SEQ ID NO 101
<211> LENGTH: 20
<212> TYPE: RNA
<213> ORGANISM: Homo sapiens

<400> SEQUENCE: 101
ugugcuagac augaggucua 20

<210> SEQ ID NO 102
<211> LENGTH: 20
<212> TYPE: RNA
<213> ORGANISM: Homo sapiens

<400> SEQUENCE: 102
gcaccaaagc ugcccuuacc 20

<210> SEQ ID NO 103
<211> LENGTH: 20
<212> TYPE: RNA
<213> ORGANISM: Homo sapiens

<400> SEQUENCE: 103
aaguuccugu gaugucaagc 20

<210> SEQ ID NO 104
<211> LENGTH: 20
<212> TYPE: RNA
<213> ORGANISM: Homo sapiens

<400> SEQUENCE: 104
cucgaccagc uugacaucac 20

<210> SEQ ID NO 105
<211> LENGTH: 20
<212> TYPE: RNA
<213> ORGANISM: Homo sapiens

<400> SEQUENCE: 105
auccuccucc ugaaaguggc 20

<210> SEQ ID NO 106
<211> LENGTH: 20
<212> TYPE: RNA
<213> ORGANISM: Homo sapiens

<400> SEQUENCE: 106
acccggccac uuucaggagg 20

<210> SEQ ID NO 107
<211> LENGTH: 20
<212> TYPE: RNA
<213> ORGANISM: Homo sapiens

<400> SEQUENCE: 107
uuaaucugcu caugacgcug 20

<210> SEQ ID NO 108
<211> LENGTH: 20
<212> TYPE: RNA
<213> ORGANISM: Homo sapiens

<400> SEQUENCE: 108
acacggauga acaauaaggc 20

<210> SEQ ID NO 109
<211> LENGTH: 20
<212> TYPE: RNA
<213> ORGANISM: Homo sapiens

<400> SEQUENCE: 109
acuuacacgg augaacaaua 20

<210> SEQ ID NO 110
<211> LENGTH: 20
<212> TYPE: RNA
<213> ORGANISM: Homo sapiens

<400> SEQUENCE: 110
gcugguacac ggcaggguca 20

<210> SEQ ID NO 111
<211> LENGTH: 20
<212> TYPE: RNA
<213> ORGANISM: Homo sapiens

<400> SEQUENCE: 111
ggaagcuaca uaccuacauu 20

<210> SEQ ID NO 112
<211> LENGTH: 20
<212> TYPE: RNA
<213> ORGANISM: Homo sapiens

<400> SEQUENCE: 112
uccucacugu gugcaucagg 20

<210> SEQ ID NO 113
<211> LENGTH: 20
<212> TYPE: RNA
<213> ORGANISM: Homo sapiens

<400> SEQUENCE: 113
cugguuccuc uuccaaaugu 20

<210> SEQ ID NO 114
<211> LENGTH: 20
<212> TYPE: RNA
<213> ORGANISM: Homo sapiens

<400> SEQUENCE: 114
aaagucagau uuguugcucc 20

<210> SEQ ID NO 115
<211> LENGTH: 20
<212> TYPE: RNA
<213> ORGANISM: Homo sapiens

<400> SEQUENCE: 115
uucaaaaccu gucagugauu 20

<210> SEQ ID NO 116
<211> LENGTH: 20
<212> TYPE: RNA
<213> ORGANISM: Homo sapiens

<400> SEQUENCE: 116
ugcucaugac gcugcggcug 20

<210> SEQ ID NO 117
<211> LENGTH: 20
<212> TYPE: RNA
<213> ORGANISM: Homo sapiens

<400> SEQUENCE: 117
ucaaggcccc ucaccucagc 20

<210> SEQ ID NO 118
<211> LENGTH: 20
<212> TYPE: RNA
<213> ORGANISM: Homo sapiens

<400> SEQUENCE: 118
ggcguuugca caugcaaagu 20

<210> SEQ ID NO 119
<211> LENGTH: 20
<212> TYPE: RNA
<213> ORGANISM: Homo sapiens

<400> SEQUENCE: 119
gaccacagcc gcagcgucau 20

<210> SEQ ID NO 120
<211> LENGTH: 20
<212> TYPE: RNA
<213> ORGANISM: Homo sapiens

<400> SEQUENCE: 120
augacgcugc ggcugugguc 20

<210> SEQ ID NO 121
<211> LENGTH: 20
<212> TYPE: RNA
<213> ORGANISM: Homo sapiens

<400> SEQUENCE: 121
auucggaacc caaucacuga 20

<210> SEQ ID NO 122
<211> LENGTH: 20
<212> TYPE: RNA
<213> ORGANISM: Homo sapiens

<400> SEQUENCE: 122
aacccggcca cuuucaggag 20

<210> SEQ ID NO 123
<211> LENGTH: 20
<212> TYPE: RNA
<213> ORGANISM: Homo sapiens

<400> SEQUENCE: 123
uuaaacccgg ccacuuucag 20

<210> SEQ ID NO 124
<211> LENGTH: 20
<212> TYPE: RNA
<213> ORGANISM: Homo sapiens

<400> SEQUENCE: 124
agauuuguug cuccaggcca 20

<210> SEQ ID NO 125
<211> LENGTH: 20
<212> TYPE: RNA
<213> ORGANISM: Homo sapiens

<400> SEQUENCE: 125
ugagaaucaa aaucggugaa 20

<210> SEQ ID NO 126
<211> LENGTH: 20
<212> TYPE: RNA
<213> ORGANISM: Homo sapiens

<400> SEQUENCE: 126
gaugucaagc uggucgagaa 20

<210> SEQ ID NO 127
<211> LENGTH: 20
<212> TYPE: RNA
<213> ORGANISM: Homo sapiens

<400> SEQUENCE: 127
guuucaaagc uuuucucgac 20

<210> SEQ ID NO 128
<211> LENGTH: 20
<212> TYPE: RNA
<213> ORGANISM: Homo sapiens

<400> SEQUENCE: 128
ugaaggcguu ugcacaugca 20

<210> SEQ ID NO 129
<211> LENGTH: 20
<212> TYPE: RNA
<213> ORGANISM: Homo sapiens

<400> SEQUENCE: 129
acccugaccc ugccguguac 20

<210> SEQ ID NO 130
<211> LENGTH: 20
<212> TYPE: RNA
<213> ORGANISM: Homo sapiens

<400> SEQUENCE: 130
agcuucaagg ccccucaccu 20

<210> SEQ ID NO 131
<211> LENGTH: 20
<212> TYPE: RNA

<213> ORGANISM: Homo sapiens

<400> SEQUENCE: 131
guuccgaauc cuccuccuga 20

<210> SEQ ID NO 132
<211> LENGTH: 20
<212> TYPE: RNA
<213> ORGANISM: Homo sapiens

<400> SEQUENCE: 132
agauuaaacc cggccacuuu 20

<210> SEQ ID NO 133
<211> LENGTH: 20
<212> TYPE: RNA
<213> ORGANISM: Homo sapiens

<400> SEQUENCE: 133
cccugccgug uaccagcuga 20

<210> SEQ ID NO 134
<211> LENGTH: 20
<212> TYPE: RNA
<213> ORGANISM: Homo sapiens

<400> SEQUENCE: 134
ucacuggauu uagagucucu 20

<210> SEQ ID NO 135
<211> LENGTH: 20
<212> TYPE: RNA
<213> ORGANISM: Homo sapiens

<400> SEQUENCE: 135
uacuuacacg gaugaacaau 20

<210> SEQ ID NO 136
<211> LENGTH: 20
<212> TYPE: RNA
<213> ORGANISM: Homo sapiens

<400> SEQUENCE: 136
uaucacagac aaaacugugc 20

<210> SEQ ID NO 137
<211> LENGTH: 20
<212> TYPE: RNA
<213> ORGANISM: Homo sapiens

<400> SEQUENCE: 137
ccacagcacu guugcucuug 20

<210> SEQ ID NO 138
<211> LENGTH: 20
<212> TYPE: RNA
<213> ORGANISM: Homo sapiens

<400> SEQUENCE: 138
ccugugaugu caagcugguc 20

<210> SEQ ID NO 139
<211> LENGTH: 20

<212> TYPE: RNA
<213> ORGANISM: Homo sapiens

<400> SEQUENCE: 139
acaugagguc uauggacuuc 20

<210> SEQ ID NO 140
<211> LENGTH: 20
<212> TYPE: RNA
<213> ORGANISM: Homo sapiens

<400> SEQUENCE: 140
acuguugcuc uugaagucca 20

<210> SEQ ID NO 141
<211> LENGTH: 20
<212> TYPE: RNA
<213> ORGANISM: Homo sapiens

<400> SEQUENCE: 141
agcuacauac cuacauuugg 20

<210> SEQ ID NO 142
<211> LENGTH: 20
<212> TYPE: RNA
<213> ORGANISM: Homo sapiens

<400> SEQUENCE: 142
uagaaaguuc cugugauguc 20

<210> SEQ ID NO 143
<211> LENGTH: 20
<212> TYPE: RNA
<213> ORGANISM: Homo sapiens

<400> SEQUENCE: 143
ucacugugug caucaggagg 20

<210> SEQ ID NO 144
<211> LENGTH: 20
<212> TYPE: RNA
<213> ORGANISM: Homo sapiens

<400> SEQUENCE: 144
gacaaaacug ugcuagacau 20

<210> SEQ ID NO 145
<211> LENGTH: 20
<212> TYPE: RNA
<213> ORGANISM: Homo sapiens

<400> SEQUENCE: 145
cuucaacaac agcauuauuc 20

<210> SEQ ID NO 146
<211> LENGTH: 20
<212> TYPE: RNA
<213> ORGANISM: Homo sapiens

<400> SEQUENCE: 146
caacaacagc auuauuccag 20

<210> SEQ ID NO 147

<211> LENGTH: 20
<212> TYPE: RNA
<213> ORGANISM: Homo sapiens

<400> SEQUENCE: 147
ucucaaacaa augugucaca 20

<210> SEQ ID NO 148
<211> LENGTH: 20
<212> TYPE: RNA
<213> ORGANISM: Homo sapiens

<400> SEQUENCE: 148
augaggucua uggacuucaa 20

<210> SEQ ID NO 149
<211> LENGTH: 20
<212> TYPE: RNA
<213> ORGANISM: Homo sapiens

<400> SEQUENCE: 149
gacccugccg uguaccagcu 20

<210> SEQ ID NO 150
<211> LENGTH: 20
<212> TYPE: RNA
<213> ORGANISM: Homo sapiens

<400> SEQUENCE: 150
ccccugucuu accuguuuca 20

<210> SEQ ID NO 151
<211> LENGTH: 20
<212> TYPE: RNA
<213> ORGANISM: Homo sapiens

<400> SEQUENCE: 151
agcaacagug cuguggccug 20

<210> SEQ ID NO 152
<211> LENGTH: 20
<212> TYPE: RNA
<213> ORGANISM: Homo sapiens

<400> SEQUENCE: 152
cuacauaccu acauuuggaa 20

<210> SEQ ID NO 153
<211> LENGTH: 20
<212> TYPE: RNA
<213> ORGANISM: Homo sapiens

<400> SEQUENCE: 153
acuuugugac acauuuguuu 20

<210> SEQ ID NO 154
<211> LENGTH: 20
<212> TYPE: RNA
<213> ORGANISM: Homo sapiens

<400> SEQUENCE: 154
aucacagaca aaacugugcu 20

<210> SEQ ID NO 155
<211> LENGTH: 20
<212> TYPE: RNA
<213> ORGANISM: Homo sapiens

<400> SEQUENCE: 155
uucaacaaca gcauuauucc 20

<210> SEQ ID NO 156
<211> LENGTH: 20
<212> TYPE: RNA
<213> ORGANISM: Homo sapiens

<400> SEQUENCE: 156
caugaggucu auggacuuca 20

<210> SEQ ID NO 157
<211> LENGTH: 20
<212> TYPE: RNA
<213> ORGANISM: Homo sapiens

<400> SEQUENCE: 157
gcuacauacc uacauuugga 20

<210> SEQ ID NO 158
<211> LENGTH: 20
<212> TYPE: RNA
<213> ORGANISM: Homo sapiens

<400> SEQUENCE: 158
cucuuguccc acagauaucc 20

<210> SEQ ID NO 159
<211> LENGTH: 20
<212> TYPE: RNA
<213> ORGANISM: Homo sapiens

<400> SEQUENCE: 159
gauucugaug uguauaucac 20

<210> SEQ ID NO 160
<211> LENGTH: 20
<212> TYPE: RNA
<213> ORGANISM: Homo sapiens

<400> SEQUENCE: 160
cugugauguc aagcuggucg 20

<210> SEQ ID NO 161
<211> LENGTH: 20
<212> TYPE: RNA
<213> ORGANISM: Homo sapiens

<400> SEQUENCE: 161
ccugccgugu accagcugag 20

<210> SEQ ID NO 162
<211> LENGTH: 20
<212> TYPE: RNA
<213> ORGANISM: Homo sapiens

<400> SEQUENCE: 162
acauaccuac auuuggaaga 20

<210> SEQ ID NO 163
<211> LENGTH: 20
<212> TYPE: RNA
<213> ORGANISM: Homo sapiens

<400> SEQUENCE: 163
ccucacugug ugcaucagga 20

<210> SEQ ID NO 164
<211> LENGTH: 20
<212> TYPE: RNA
<213> ORGANISM: Homo sapiens

<400> SEQUENCE: 164
acaaaugugu cacaaaguaa 20

<210> SEQ ID NO 165
<211> LENGTH: 20
<212> TYPE: RNA
<213> ORGANISM: Homo sapiens

<400> SEQUENCE: 165
gagcaacagu gcuguggccu 20

<210> SEQ ID NO 166
<211> LENGTH: 20
<212> TYPE: RNA
<213> ORGANISM: Homo sapiens

<400> SEQUENCE: 166
ucgaccagcu ugacaucaca 20

<210> SEQ ID NO 167
<211> LENGTH: 20
<212> TYPE: RNA
<213> ORGANISM: Homo sapiens

<400> SEQUENCE: 167
auuaaacccg gccacuuuca 20

<210> SEQ ID NO 168
<211> LENGTH: 20
<212> TYPE: RNA
<213> ORGANISM: Homo sapiens

<400> SEQUENCE: 168
cacggcaggg ucaggguucu 20

<210> SEQ ID NO 169
<211> LENGTH: 20
<212> TYPE: RNA
<213> ORGANISM: Homo sapiens

<400> SEQUENCE: 169
aaacccggcc acuuucagga 20

<210> SEQ ID NO 170
<211> LENGTH: 20
<212> TYPE: RNA
<213> ORGANISM: Homo sapiens

<400> SEQUENCE: 170
caaggccccu caccucagcu 20

<210> SEQ ID NO 171
<211> LENGTH: 20
<212> TYPE: RNA
<213> ORGANISM: Homo sapiens

<400> SEQUENCE: 171
cccggccacu uucaggagga 20

<210> SEQ ID NO 172
<211> LENGTH: 20
<212> TYPE: RNA
<213> ORGANISM: Homo sapiens

<400> SEQUENCE: 172
cauuucuaua auacuuacac 20

<210> SEQ ID NO 173
<211> LENGTH: 20
<212> TYPE: RNA
<213> ORGANISM: Homo sapiens

<400> SEQUENCE: 173
acagccgcag cgucaugagc 20

<210> SEQ ID NO 174
<211> LENGTH: 20
<212> TYPE: RNA
<213> ORGANISM: Homo sapiens

<400> SEQUENCE: 174
aucaaaaucg gugaauaggc 20

<210> SEQ ID NO 175
<211> LENGTH: 20
<212> TYPE: RNA
<213> ORGANISM: Homo sapiens

<400> SEQUENCE: 175
gcguuugcac augcaaaguc 20

<210> SEQ ID NO 176
<211> LENGTH: 20
<212> TYPE: RNA
<213> ORGANISM: Homo sapiens

<400> SEQUENCE: 176
cuguugcucu ugaaguccau 20

<210> SEQ ID NO 177
<211> LENGTH: 20
<212> TYPE: RNA
<213> ORGANISM: Homo sapiens

<400> SEQUENCE: 177
aaaucgguga auaggcagac 20

<210> SEQ ID NO 178
<211> LENGTH: 20
<212> TYPE: RNA
<213> ORGANISM: Homo sapiens

<400> SEQUENCE: 178
uugucuguga uauacacauc 20

<210> SEQ ID NO 179
<211> LENGTH: 100
<212> TYPE: RNA
<213> ORGANISM: Artificial Sequence
<220> FEATURE:
<223> OTHER INFORMATION: sgRNA sequence

<400> SEQUENCE: 179
ggcucucgga gaaugacgag guuuuagagc uagaaauagc aaguuaaaau aaggcuaguc 60
cguuaucaac uugaaaaagu ggcaccgagu cggugcuuuu 100

<210> SEQ ID NO 180
<211> LENGTH: 100
<212> TYPE: RNA
<213> ORGANISM: Artificial Sequence
<220> FEATURE:
<223> OTHER INFORMATION: sgRNA sequence

<400> SEQUENCE: 180
ggccucggcg cugacgaucu guuuuagagc uagaaauagc aaguuaaaau aaggcuaguc 60
cguuaucaac uugaaaaagu ggcaccgagu cggugcuuuu 100

<210> SEQ ID NO 181
<211> LENGTH: 100
<212> TYPE: RNA
<213> ORGANISM: Artificial Sequence
<220> FEATURE:
<223> OTHER INFORMATION: sgRNA sequence

<400> SEQUENCE: 181
augacgagug gacccaggau guuuuagagc uagaaauagc aaguuaaaau aaggcuaguc 60
cguuaucaac uugaaaaagu ggcaccgagu cggugcuuuu 100

<210> SEQ ID NO 182
<211> LENGTH: 100
<212> TYPE: RNA
<213> ORGANISM: Artificial Sequence
<220> FEATURE:
<223> OTHER INFORMATION: sgRNA sequence

<400> SEQUENCE: 182
agaagguggc cgagacccuc guuuuagagc uagaaauagc aaguuaaaau aaggcuaguc 60
cguuaucaac uugaaaaagu ggcaccgagu cggugcuuuu 100

<210> SEQ ID NO 183
<211> LENGTH: 100
<212> TYPE: RNA
<213> ORGANISM: Artificial Sequence
<220> FEATURE:
<223> OTHER INFORMATION: sgRNA sequence

<400> SEQUENCE: 183
ugagggucuc ggccaccuuc guuuuagagc uagaaauagc aaguuaaaau aaggcuaguc 60
cguuaucaac uugaaaaagu ggcaccgagu cggugcuuuu 100

<210> SEQ ID NO 184
<211> LENGTH: 100
<212> TYPE: RNA
<213> ORGANISM: Artificial Sequence
<220> FEATURE:
<223> OTHER INFORMATION: sgRNA sequence

<400> SEQUENCE: 184
agagaucucc cacacccaaa guuuuagagc uagaaauagc aaguuaaaau aaggcuaguc 60
cguuaucaac uugaaaaagu ggcaccgagu cggugcuuuu 100

<210> SEQ ID NO 185
<211> LENGTH: 42
<212> TYPE: RNA
<213> ORGANISM: Homo sapiens

<400> SEQUENCE: 185
ucaggguucu ggauaucugu guuuuagagc uaugcuguuu ug 42

<210> SEQ ID NO 186
<211> LENGTH: 100
<212> TYPE: RNA
<213> ORGANISM: Artificial Sequence
<220> FEATURE:
<223> OTHER INFORMATION: sgRNA sequence

<400> SEQUENCE: 186
cucucagcug guacacggca guuuuagagc uagaaauagc aaguuaaaau aaggcuaguc 60
cguuaucaac uugaaaaagu ggcaccgagu cggugcuuuu 100

<210> SEQ ID NO 187
<211> LENGTH: 100
<212> TYPE: RNA
<213> ORGANISM: Artificial Sequence
<220> FEATURE:
<223> OTHER INFORMATION: sgRNA sequence

<400> SEQUENCE: 187
uucggaaccc aaucacugac guuuuagagc uagaaauagc aaguuaaaau aaggcuaguc 60
cguuaucaac uugaaaaagu ggcaccgagu cggugcuuuu 100

<210> SEQ ID NO 188
<211> LENGTH: 100
<212> TYPE: RNA
<213> ORGANISM: Artificial Sequence
<220> FEATURE:
<223> OTHER INFORMATION: sgRNA sequence

<400> SEQUENCE: 188
uaaacccggc cacuuucagg guuuuagagc uagaaauagc aaguuaaaau aaggcuaguc 60
cguuaucaac uugaaaaagu ggcaccgagu cggugcuuuu 100

<210> SEQ ID NO 189
<211> LENGTH: 100
<212> TYPE: RNA
<213> ORGANISM: Artificial Sequence
<220> FEATURE:
<223> OTHER INFORMATION: sgRNA sequence

<400> SEQUENCE: 189
gauuaaaccc ggccacuuuc guuuuagagc uagaaauagc aaguuaaaau aaggcuaguc 60
cguuaucaac uugaaaaagu ggcaccgagu cggugcuuuu 100

<210> SEQ ID NO 190
<211> LENGTH: 100
<212> TYPE: RNA
<213> ORGANISM: Artificial Sequence
<220> FEATURE:

<223> OTHER INFORMATION: sgRNA sequence

<400> SEQUENCE: 190
cgucaugagc agauuaaacc guuuuagagc uagaaauagc aaguuaaaau aaggcuaguc 60
cguuaucaac uugaaaaagu ggcaccgagu cggugcuuuu 100

<210> SEQ ID NO 191
<211> LENGTH: 100
<212> TYPE: RNA
<213> ORGANISM: Artificial Sequence
<220> FEATURE:
<223> OTHER INFORMATION: sgRNA sequence

<400> SEQUENCE: 191
agagucucuc agcugguaca guuuuagagc uagaaauagc aaguuaaaau aaggcuaguc 60
cguuaucaac uugaaaaagu ggcaccgagu cggugcuuuu 100

<210> SEQ ID NO 192
<211> LENGTH: 100
<212> TYPE: RNA
<213> ORGANISM: Artificial Sequence
<220> FEATURE:
<223> OTHER INFORMATION: sgRNA sequence

<400> SEQUENCE: 192
ucaggguucu ggauaucugu guuuuagagc uagaaauagc aaguuaaaau aaggcuaguc 60
cguuaucaac uugaaaaagu ggcaccgagu cggugcuuuu 100

<210> SEQ ID NO 193
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
1 to 4 are substtuted for phosphorothioate (PS) bonds
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: am
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)

<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substtuted for phosphorothioate (PS) bonds

<400> SEQUENCE: 193
gaguccgagc agaagaagaa guuuuagagc uagaaauagc aaguuaaaau aaggcuaguc 60
cguuaucaac uugaaaaagu ggcaccgagu cggugcuuuu 100

<210> SEQ ID NO 194
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides 1 to 4 are substtuted for phosphorothioate (PS) bonds
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: am
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:

<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substtuted for phosphorothioate (PS) bonds

<400> SEQUENCE: 194
gaguccgagc agaagaagaa guuuuagagc uagaaauagc aaguuaaaau aaggcuaguc 60
cguuaucaac uugaaaaagu ggcaccgagu cggugcuuuu 100

<210> SEQ ID NO 195
<211> LENGTH: 74
<212> TYPE: RNA
<213> ORGANISM: Artificial Sequence
<220> FEATURE:
<223> OTHER INFORMATION: sgRNA sequence

<400> SEQUENCE: 195
aacagcauag caaguuaaaa uaaggcuagu ccguuaucaa cuugaaaaag uggcaccgag 60
ucggugcuuu uuuu 74

<210> SEQ ID NO 196
<211> LENGTH: 100
<212> TYPE: RNA
<213> ORGANISM: Artificial Sequence
<220> FEATURE:
<223> OTHER INFORMATION: sgRNA sequence

<400> SEQUENCE: 196
ggcucucgga gaaugacgag guuuuagagc uagaaauagc aaguuaaaau aaggcuaguc 60
cguuaucaac uugaaaaagu ggcaccgagu cggugcuuuu 100

<210> SEQ ID NO 197
<211> LENGTH: 100
<212> TYPE: RNA
<213> ORGANISM: Artificial Sequence
<220> FEATURE:
<223> OTHER INFORMATION: sgRNA sequence

<400> SEQUENCE: 197
ggccucggcg cugacgaucu guuuuagagc uagaaauagc aaguuaaaau aaggcuaguc 60
cguuaucaac uugaaaaagu ggcaccgagu cggugcuuuu 100

<210> SEQ ID NO 198
<211> LENGTH: 100
<212> TYPE: RNA
<213> ORGANISM: Artificial Sequence -continued
<220> FEATURE:
<223> OTHER INFORMATION: sgRNA sequence

<400> SEQUENCE: 198
augacgagug gacccaggau guuuuagagc uagaaauagc aaguuaaaau aaggcuaguc 60
cguuaucaac uugaaaaagu ggcaccgagu cggugcuuuu 100

<210> SEQ ID NO 199
<211> LENGTH: 100
<212> TYPE: RNA
<213> ORGANISM: Artificial Sequence
<220> FEATURE:
<223> OTHER INFORMATION: sgRNA sequence

<400> SEQUENCE: 199
ugagggucuc ggccaccuuc guuuuagagc uagaaauagc aaguuaaaau aaggcuaguc 60
cguuaucaac uugaaaaagu ggcaccgagu cggugcuuuu 100

<210> SEQ ID NO 200
<211> LENGTH: 100
<212> TYPE: RNA
<213> ORGANISM: Artificial Sequence
<220> FEATURE:
<223> OTHER INFORMATION: sgRNA sequence

<400> SEQUENCE: 200
agagaucucc cacacccaaa guuuuagagc uagaaauagc aaguuaaaau aaggcuaguc 60
cguuaucaac uugaaaaagu ggcaccgagu cggugcuuuu 100

<210> SEQ ID NO 201
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
1 to 4 are substituted for phosphorothioate (PS) bonds
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: am
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:

<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides
97 to 100 are substituted for phosphorothioate (PS) bonds

<400> SEQUENCE: 201
acacggcagg gucaggguuc guuuuagagc uagaaauagc aaguuaaaau aaggcuaguc 60
cguuaucaac uugaaaaagu ggcaccgagu cggugcuuuu 100

<210> SEQ ID NO 202
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
1 to 4 are substituted for phosphorothioate (PS) bonds
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)

```
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides
      97 to 100 are substituted for phosphorothioate (PS) bonds

<400> SEQUENCE: 202

agcugguaca cggcaggguc guuuuagagc uagaaauagc aaguuaaaau aaggcuaguc     60

cguuaucaac uugaaaaagu ggcaccgagu cggugcuuuu                          100


<210> SEQ ID NO 203
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
      1 to 4 are substituted for phosphorothioate (PS) bonds
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
```

<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:

<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substituted for phosphorothioate (PS) bonds

<400> SEQUENCE: 203
cucucagcug guacacggca guuuuagagc uagaaauagc aaguuaaaau aaggcuaguc 60
cguuaucaac uugaaaaagu ggcaccgagu cggugcuuuu 100

<210> SEQ ID NO 204
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides 1 to 4 are substituted for phosphorothioate (PS) bonds
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)

<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides
97 to 100 are substituted for phosphorothioate (PS) bonds

<400> SEQUENCE: 204
ucucucagcu gguacacggc guuuuagagc uagaaauagc aaguuaaaau aaggcuaguc 60
cguuaucaac uugaaaaagu ggcaccgagu cggugcuuuu 100

<210> SEQ ID NO 205
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
1 to 4 are substituted for phosphorothioate (PS) bonds
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:

<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substituted for phosphorothioate (PS) bonds

<400> SEQUENCE: 205
uggauuuaga gucucucagc guuuuagagc uagaaauagc aaguuaaaau aaggcuaguc 60
cguuaucaac uugaaaaagu ggcaccgagu cggugcuuuu 100

<210> SEQ ID NO 206
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides 1 to 4 are substituted for phosphorothioate (PS) bonds
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: am
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)

<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substituted for phosphorothioate (PS) bonds

<400> SEQUENCE: 206
uaggcagaca gacuugucac guuuuagagc uagaaauagc aaguuaaaau aaggcuaguc 60
cguuaucaac uugaaaaagu ggcaccgagu cggugcuuuu 100

<210> SEQ ID NO 207
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides 1 to 4 are substituted for phosphorothioate (PS) bonds
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:

<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substituted for phosphorothioate (PS) bonds

<400> SEQUENCE: 207
ucugugggac aagaggauca guuuuagagc uagaaauagc aaguuaaaau aaggcuaguc 60
cguuaucaac uugaaaaagu ggcaccgagu cggugcuuuu 100

<210> SEQ ID NO 208
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides 1 to 4 are substituted for phosphorothioate (PS) bonds
<220> FEATURE:
<221> NAME/KEY: modified_base
<222> LOCATION: (1)..(1)
<223> OTHER INFORMATION: am
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)

<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides
97 to 100 are substituted for phosphorothioate (PS) bonds

<400> SEQUENCE: 208
aucuguggga caagaggauc guuuuagagc uagaaauagc aaguuaaaau aaggcuaguc 60
cguuaucaac uugaaaaagu ggcaccgagu cggugcuuuu 100

<210> SEQ ID NO 209
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
1 to 4 are substituted for phosphorothioate (PS) bonds
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:

<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides
97 to 100 are substituted for phosphorothioate (PS) bonds

<400> SEQUENCE: 209
cuggauaucu gugggacaag guuuuagagc uagaaauagc aaguuaaaau aaggcuaguc 60
cguuaucaac uugaaaaagu ggcaccgagu cggugcuuuu 100

<210> SEQ ID NO 210
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
1 to 4 are substituted for phosphorothioate (PS) bonds
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)

<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substituted for phosphorothioate (PS) bonds

<400> SEQUENCE: 210
gucaggguuc uggauaucug guuuuagagc uagaaauagc aaguuaaaau aaggcuaguc 60
cguuaucaac uugaaaaagu ggcaccgagu cggugcuuuu 100

<210> SEQ ID NO 211
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides 1 to 4 are substituted for phosphorothioate (PS) bonds
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: am
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:
<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:

<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides 97 to 100 are substituted for phosphorothioate (PS) bonds

<400> SEQUENCE: 211
ucaggguucu ggauaucugu guuuuagagc uagaaauagc aaguuaaaau aaggcuaguc 60
cguuaucaac uugaaaaagu ggcaccgagu cggugcuuuu 100

<210> SEQ ID NO 212
<211> LENGTH: 100
<212> TYPE: RNA
<213> ORGANISM: Artificial Sequence
<220> FEATURE:
<223> OTHER INFORMATION: sgRNA sequence

<400> SEQUENCE: 212
uaggcagaca gacuugucac guuuuagagc uagaaauagc aaguuaaaau aaggcuaguc 60
cguuaucaac uugaaaaagu ggcaccgagu cggugcuuuu 100

<210> SEQ ID NO 213
<211> LENGTH: 20
<212> TYPE: RNA
<213> ORGANISM: Homo sapiens

<400> SEQUENCE: 213
agcugguaca cggcaggguc 20

<210> SEQ ID NO 214
<211> LENGTH: 20
<212> TYPE: RNA
<213> ORGANISM: Homo sapiens

<400> SEQUENCE: 214
uaggcagaca gacuugucac 20

<210> SEQ ID NO 215
<211> LENGTH: 20
<212> TYPE: RNA
<213> ORGANISM: Homo sapiens

<400> SEQUENCE: 215
ucugugggac aagaggauca 20

<210> SEQ ID NO 216
<211> LENGTH: 20
<212> TYPE: RNA
<213> ORGANISM: Homo sapiens

<400> SEQUENCE: 216
aucuguggga caagaggauc 20

<210> SEQ ID NO 217
<211> LENGTH: 20
<212> TYPE: RNA
<213> ORGANISM: Homo sapiens

<400> SEQUENCE: 217
cuggauaucu gugggacaag 20

<210> SEQ ID NO 218
<211> LENGTH: 20
<212> TYPE: RNA
<213> ORGANISM: Homo sapiens

<400> SEQUENCE: 218
gucaggguuc uggauaucug 20

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250
<211> LENGTH: 819
<212> TYPE: DNA
<213> ORGANISM: Homo sapiens

<400> SEQUENCE: 250
atggaaaccc tgctgaaggt gctgagcggc acactgctgt ggcagctgac atgggtccga 60

-continued

```
tctcagcagc ctgtgcagtc tcctcaggcc gtgattctga gagaaggcga ggacgccgtg    120

atcaactgca gcagctctaa ggccctgtac agcgtgcact ggtacagaca gaagcacggc    180

gaggcccctg tgttcctgat gatcctgctg aaaggcggcg agcagaaggg ccacgagaag    240

atcagcgcca gcttcaacga gaagaagcag cagtccagcc tgtacctgac agccagccag    300

ctgagctaca gcggcaccta cttttgtggc accgcctgga tcaacgacta caagctgtct    360

ttcggagccg gcaccacagt gacagtgcgg gccaatattc agaaccccga tcctgccgtg    420

taccagctga gagacagcaa gagcagcgac aagagcgtgt gcctgttcac cgacttcgac    480

agccagacca acgtgtccca gagcaaggac agcgacgtgt acatcaccga taagtgcgtg    540

ctggacatgc ggagcatgga cttcaagagc aacagcgccg tggcctggtc caacaagagc    600

gatttcgcct gcgccaacgc cttcaacaac agcattatcc ccgaggacac attcttccca    660

agtcctgaga gcagctgcga cgtgaagctg gtggaaaaga gcttcgagac agacaccaac    720

ctgaacttcc agaacctgag cgtgatcggc ttcagaatcc tgctgctcaa ggtggccggc    780

ttcaacctgc tgatgaccct gagactgtgg tccagctga                           819


<210> SEQ ID NO 251
<211> LENGTH: 272
<212> TYPE: PRT
<213> ORGANISM: Homo sapiens

<400> SEQUENCE: 251

Met Glu Thr Leu Leu Lys Val Leu Ser Gly Thr Leu Leu Trp Gln Leu
1               5                   10                  15

Thr Trp Val Arg Ser Gln Gln Pro Val Gln Ser Pro Gln Ala Val Ile
            20                  25                  30

Leu Arg Glu Gly Glu Asp Ala Val Ile Asn Cys Ser Ser Ser Lys Ala
        35                  40                  45

Leu Tyr Ser Val His Trp Tyr Arg Gln Lys His Gly Glu Ala Pro Val
    50                  55                  60

Phe Leu Met Ile Leu Leu Lys Gly Gly Glu Gln Lys Gly His Glu Lys
65                  70                  75                  80

Ile Ser Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly Thr Ala
            100                 105                 110

Trp Ile Asn Asp Tyr Lys Leu Ser Phe Gly Ala Gly Thr Thr Val Thr
        115                 120                 125

Val Arg Ala Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240
```

```
Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270


<210> SEQ ID NO 252
<211> LENGTH: 945
<212> TYPE: DNA
<213> ORGANISM: Homo sapiens

<400> SEQUENCE: 252

atgggatctt ggacactgtg ttgcgtgtcc ctgtgcatcc tggtggccaa gcacacagat      60

gccggcgtga tccagtctcc tagacacgaa gtgaccgaga tgggccaaga agtgaccctg     120

cgctgcaagc ctatcagcgg ccacgattac ctgttctggt acagacagac catgatgaga     180

ggcctggaac tgctgatcta cttcaacaac aacgtgccca tcgacgacag cggcatgccc     240

gaggatagat tcagcgccaa gatgcccaac gccagcttca gcaccctgaa gatccagcct     300

agcgagccca gagatagcgc cgtgtacttc tgcgccagca gaaagacagg cggctacagc     360

aatcagcccc agcactttgg agatggcacc cggctgagca tcctggaaga tctgaagaac     420

gtgttcccac ctgaggtggc cgtgttcgag ccttctgagg ccgagatcag ccacacacag     480

aaagccacac tcgtgtgtct ggccaccggc ttctatcccg atcacgtgga actgtcttgg     540

tgggtcaacg gcaaagaggt gcacagcggc gtctgtaccg atcctcagcc tctgaaagag     600

cagcccgctc tgaacgacag cagatactgc ctgagcagca gactgagagt gtccgccacc     660

ttctggcaga accccagaaa ccacttcaga tgccaggtgc agttctacgg cctgagcgag     720

aacgatgagt ggacccagga tagagccaag cctgtgacac agatcgtgtc tgccgaagcc     780

tggggcagag ccgattgtgg ctttaccagc gagagctacc agcagggcgt gctgtctgcc     840

acaatcctgt acgagatcct gctgggcaaa gccactctgt acgccgtgct ggtgtctgcc     900

ctggtgctga tggccatggt caagcggaag gatagcaggg gctga                     945


<210> SEQ ID NO 253
<211> LENGTH: 314
<212> TYPE: PRT
<213> ORGANISM: Homo sapiens

<400> SEQUENCE: 253

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Lys Thr Gly Gly Tyr Ser Asn Gln Pro Gln His Phe Gly Asp
        115                 120                 125

Gly Thr Arg Leu Ser Ile Leu Glu Asp Leu Lys Asn Val Phe Pro Pro
```

```
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Cys
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260
```

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

-continued

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 100
<212> TYPE: RNA
<213> ORGANISM: Artificial Sequence
<220> FEATURE:
<223> OTHER INFORMATION: Modified sgRNA
<220> FEATURE:
<221> NAME/KEY: modified_base
<222> LOCATION: (1)..(4)
<223> OTHER INFORMATION: The 3 phosphodiester bonds between nucleotides
1 to 4 are substtuted for phosphorothioate (PS) bonds
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: am
<220> FEATURE:
<221> NAME/KEY: modified_base
<222> LOCATION: (33)..(33)
<223> OTHER INFORMATION: gm
<220> FEATURE:
<221> NAME/KEY: modified_base
<222> LOCATION: (34)..(36)
<223> OTHER INFORMATION: am
<220> FEATURE:
<221> NAME/KEY: modified_base
<222> LOCATION: (37)..(37)
<223> OTHER INFORMATION: um
<220> FEATURE:
<221> NAME/KEY: modified_base
<222> LOCATION: (38)..(38)
<223> OTHER INFORMATION: am
<220> FEATURE:
<221> NAME/KEY: modified_base
<222> LOCATION: (39)..(39)
<223> OTHER INFORMATION: gm
<220> FEATURE:
<221> NAME/KEY: modified_base
<222> LOCATION: (40)..(40)
<223> OTHER INFORMATION: cm
<220> FEATURE:
<221> NAME/KEY: modified_base
<222> LOCATION: (68)..(69)
<223> OTHER INFORMATION: am
<220> FEATURE:
<221> NAME/KEY: modified_base
<222> LOCATION: (71)..(72)
<223> OTHER INFORMATION: um
<220> FEATURE:
<221> NAME/KEY: modified_base
<222> LOCATION: (73)..(73)
<223> OTHER INFORMATION: gm
<220> FEATURE:
<221> NAME/KEY: modified_base
<222> LOCATION: (74)..(78)
<223> OTHER INFORMATION: am
<220> FEATURE:
<221> NAME/KEY: modified_base
<222> LOCATION: (79)..(79)
<223> OTHER INFORMATION: gm
<220> FEATURE:
<221> NAME/KEY: modified_base
<222> LOCATION: (80)..(80)
<223> OTHER INFORMATION: um
<220> FEATURE:
<221> NAME/KEY: modified_base
<222> LOCATION: (81)..(82)
<223> OTHER INFORMATION: gm
<220> FEATURE:
<221> NAME/KEY: modified_base
<222> LOCATION: (83)..(83)
<223> OTHER INFORMATION: cm
<220> FEATURE:
<221> NAME/KEY: modified_base
<222> LOCATION: (84)..(84)
<223> OTHER INFORMATION: am
<220> FEATURE:
<221> NAME/KEY: modified_base
<222> LOCATION: (85)..(86)
<223> OTHER INFORMATION: cm
<220> FEATURE:
<221> NAME/KEY: modified_base
<222> LOCATION: (87)..(87)
<223> OTHER INFORMATION: gm
<220> FEATURE:
<221> NAME/KEY: modified_base
<222> LOCATION: (88)..(88)
<223> OTHER INFORMATION: am
<220> FEATURE:
<221> NAME/KEY: modified_base
<222> LOCATION: (89)..(89)
<223> OTHER INFORMATION: gm
<220> FEATURE:
<221> NAME/KEY: modified_base
<222> LOCATION: (90)..(90)
<223> OTHER INFORMATION: um
<220> FEATURE:
<221> NAME/KEY: modified_base
<222> LOCATION: (91)..(91)
<223> OTHER INFORMATION: cm
<220> FEATURE:

<221> NAME/KEY: modified_base
<222> LOCATION: (92)..(93)
<223> OTHER INFORMATION: gm
<220> FEATURE:
<221> NAME/KEY: modified_base
<222> LOCATION: (94)..(94)
<223> OTHER INFORMATION: um
<220> FEATURE:
<221> NAME/KEY: modified_base
<222> LOCATION: (95)..(95)
<223> OTHER INFORMATION: gm
<220> FEATURE:
<221> NAME/KEY: modified_base
<222> LOCATION: (96)..(96)
<223> OTHER INFORMATION: cm
<220> FEATURE:
<221> NAME/KEY: modified_base
<222> LOCATION: (97)..(100)
<223> OTHER INFORMATION: um
<220> FEATURE:
<221> NAME/KEY: modified_base
<222> LOCATION: (97)..(100)
<223> OTHER INFORMATION: The 3 phosphodiester bonds between nucleotides
97 to 100 are substtuted for phosphorothioate (PS) bonds

<400> SEQUENCE: 300
nnnnnnnnnn nnnnnnnnnn guuuuagagc uagaaauagc aaguuaaaau aaggcuaguc 60
cguuaucaac uugaaaaagu ggcaccgagu cggugcuuuu 100

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

-continued

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400
<211> LENGTH: 22
<212> TYPE: RNA
<213> ORGANISM: Homo sapiens

<400> SEQUENCE: 400
guuuuagagc uaugcuguuu ug 22

<210> SEQ ID NO 401
<211> LENGTH: 80
<212> TYPE: RNA
<213> ORGANISM: Homo sapiens

<400> SEQUENCE: 401
guuuuagagc uagaaauagc aaguuaaaau aaggcuaguc cguuaucaac uugaaaaagu 60
ggcaccgagu cggugcuuuu 80

<210> SEQ ID NO 402
<211> LENGTH: 76
<212> TYPE: RNA
<213> ORGANISM: Homo sapiens

<400> SEQUENCE: 402
guuuuagagc uagaaauagc aaguuaaaau aaggcuaguc cguuaucaac uugaaaaagu 60
ggcaccgagu cggugc 76

<210> SEQ ID NO 403
<211> LENGTH: 77
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or u

<400> SEQUENCE: 403
nguuuuagag cuagaaauag caaguuaaaa uaaggcuagu ccguuaucaa cuugaaaaag 60
uggcaccgag ucggugc 77

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

-continued

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

-continued

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 608
<212> TYPE: PRT
<213> ORGANISM: Homo sapiens

<400> SEQUENCE: 500

```
Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Lys Thr Gly Gly Tyr Ser Asn Gln Pro Gln His Phe Gly Asp
        115                 120                 125

Gly Thr Arg Leu Ser Ile Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240
```

-continued

Asn Asp Glu Trp Thr Gln Asp Arg Ala Lys Pro Val Thr Gln Ile Val
245 250 255

Ser Ala Glu Ala Trp Gly Arg Ala Asp Cys Gly Phe Thr Ser Glu Ser
260 265 270

Tyr Gln Gln Gly Val Leu Ser Ala Thr Ile Leu Tyr Glu Ile Leu Leu
275 280 285

Gly Lys Ala Thr Leu Tyr Ala Val Leu Val Ser Ala Leu Val Leu Met
290 295 300

Ala Met Val Lys Arg Lys Asp Ser Arg Gly Gly Ser Gly Ala Thr Asn
305 310 315 320

Phe Ser Leu Leu Lys Gln Ala Gly Asp Val Glu Glu Asn Pro Gly Pro
325 330 335

Met Glu Thr Leu Leu Lys Val Leu Ser Gly Thr Leu Leu Trp Gln Leu
340 345 350

Thr Trp Val Arg Ser Gln Gln Pro Val Gln Ser Pro Gln Ala Val Ile
355 360 365

Leu Arg Glu Gly Glu Asp Ala Val Ile Asn Cys Ser Ser Ser Lys Ala
370 375 380

Leu Tyr Ser Val His Trp Tyr Arg Gln Lys His Gly Glu Ala Pro Val
385 390 395 400

Phe Leu Met Ile Leu Leu Lys Gly Gly Glu Gln Lys Gly His Glu Lys
405 410 415

Ile Ser Ala Ser Phe Asn Glu Lys Lys Gln Gln Ser Ser Leu Tyr Leu
420 425 430

Thr Ala Ser Gln Leu Ser Tyr Ser Gly Thr Tyr Phe Cys Gly Thr Ala
435 440 445

Trp Ile Asn Asp Tyr Lys Leu Ser Phe Gly Ala Gly Thr Thr Val Thr
450 455 460

Val Arg Ala Asn Ile Gln Asn Pro Asp Pro Ala Val Tyr Gln Leu Arg
465 470 475 480

Asp Ser Lys Ser Ser Asp Lys Ser Val Cys Leu Phe Thr Asp Phe Asp
485 490 495

Ser Gln Thr Asn Val Ser Gln Ser Lys Asp Ser Asp Val Tyr Ile Thr
500 505 510

Asp Lys Thr Val Leu Asp Met Arg Ser Met Asp Phe Lys Ser Asn Ser
515 520 525

Ala Val Ala Trp Ser Asn Lys Ser Asp Phe Ala Cys Ala Asn Ala Phe
530 535 540

Asn Asn Ser Ile Ile Pro Glu Asp Thr Phe Phe Pro Ser Pro Glu Ser
545 550 555 560

Ser Cys Asp Val Lys Leu Val Glu Lys Ser Phe Glu Thr Asp Thr Asn
565 570 575

Leu Asn Phe Gln Asn Leu Ser Val Ile Gly Phe Arg Ile Leu Leu Leu
580 585 590

Lys Val Ala Gly Phe Asn Leu Leu Met Thr Leu Arg Leu Trp Ser Ser
595 600 605

<210> SEQ ID NO 501
<211> LENGTH: 272
<212> TYPE: PRT
<213> ORGANISM: Homo sapiens

<400> SEQUENCE: 501

Met Glu Thr Leu Leu Lys Val Leu Ser Gly Thr Leu Leu Trp Gln Leu
1 5 10 15

```
Thr Trp Val Arg Ser Gln Gln Pro Val Gln Ser Pro Gln Ala Val Ile
            20                  25                  30

Leu Arg Glu Gly Glu Asp Ala Val Ile Asn Cys Ser Ser Ser Lys Ala
        35                  40                  45

Leu Tyr Ser Val His Trp Tyr Arg Gln Lys His Gly Glu Ala Pro Val
    50                  55                  60

Phe Leu Met Ile Leu Leu Lys Gly Gly Glu Gln Lys Gly His Glu Lys
65                  70                  75                  80

Ile Ser Ala Ser Phe Asn Glu Lys Lys Gln Gln Ser Ser Leu Tyr Leu
                85                  90                  95

Thr Ala Ser Gln Leu Ser Tyr Ser Gly Thr Tyr Phe Cys Gly Thr Ala
            100                 105                 110

Trp Ile Asn Asp Tyr Lys Leu Ser Phe Gly Ala Gly Thr Thr Val Thr
        115                 120                 125

Val Arg Ala Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270


<210> SEQ ID NO 502
<211> LENGTH: 314
<212> TYPE: PRT
<213> ORGANISM: Homo sapiens

<400> SEQUENCE: 502

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Lys Thr Gly Gly Tyr Ser Asn Gln Pro Gln His Phe Gly Asp
```

```
        115                 120                 125

Gly Thr Arg Leu Ser Ile Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310


<210> SEQ ID NO 503
<211> LENGTH: 608
<212> TYPE: PRT
<213> ORGANISM: Homo sapiens

<400> SEQUENCE: 503

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Lys Thr Gly Gly Tyr Ser Asn Gln Pro Gln His Phe Gly Asp
        115                 120                 125

Gly Thr Arg Leu Ser Ile Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175
```

```
Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Glu Thr Leu Leu Lys Val Leu Ser Gly Thr Leu Leu Trp Gln Leu
            340                 345                 350

Thr Trp Val Arg Ser Gln Gln Pro Val Gln Ser Pro Gln Ala Val Ile
        355                 360                 365

Leu Arg Glu Gly Glu Asp Ala Val Ile Asn Cys Ser Ser Ser Lys Ala
    370                 375                 380

Leu Tyr Ser Val His Trp Tyr Arg Gln Lys His Gly Glu Ala Pro Val
385                 390                 395                 400

Phe Leu Met Ile Leu Leu Lys Gly Gly Glu Gln Lys Gly His Glu Lys
                405                 410                 415

Ile Ser Ala Ser Phe Asn Glu Lys Lys Gln Gln Ser Ser Leu Tyr Leu
            420                 425                 430

Thr Ala Ser Gln Leu Ser Tyr Ser Gly Thr Tyr Phe Cys Gly Thr Ala
        435                 440                 445

Trp Ile Asn Asp Tyr Lys Leu Ser Phe Gly Ala Gly Thr Thr Val Thr
    450                 455                 460

Val Arg Ala Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
        515                 520                 525

Ala Val Ala Trp Ser Asn Lys Ser Asp Phe Ala Cys Ala Asn Ala Phe
    530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
```

595 600 605

<210> SEQ ID NO 504
<211> LENGTH: 272
<212> TYPE: PRT
<213> ORGANISM: Homo sapiens

<400> SEQUENCE: 504

Met Glu Thr Leu Leu Lys Val Leu Ser Gly Thr Leu Leu Trp Gln Leu
1 5 10 15

Thr Trp Val Arg Ser Gln Gln Pro Val Gln Ser Pro Gln Ala Val Ile
20 25 30

Leu Arg Glu Gly Glu Asp Ala Val Ile Asn Cys Ser Ser Ser Lys Ala
35 40 45

Leu Tyr Ser Val His Trp Tyr Arg Gln Lys His Gly Glu Ala Pro Val
50 55 60

Phe Leu Met Ile Leu Leu Lys Gly Gly Glu Gln Lys Gly His Glu Lys
65 70 75 80

Ile Ser Ala Ser Phe Asn Glu Lys Lys Gln Gln Ser Ser Leu Tyr Leu
85 90 95

Thr Ala Ser Gln Leu Ser Tyr Ser Gly Thr Tyr Phe Cys Gly Thr Ala
100 105 110

Trp Ile Asn Asp Tyr Lys Leu Ser Phe Gly Ala Gly Thr Thr Val Thr
115 120 125

Val Arg Ala Asn Ile Gln Asn Pro Asp Pro Ala Val Tyr Gln Leu Arg
130 135 140

Asp Ser Lys Ser Ser Asp Lys Ser Val Cys Leu Phe Thr Asp Phe Asp
145 150 155 160

Ser Gln Thr Asn Val Ser Gln Ser Lys Asp Ser Asp Val Tyr Ile Thr
165 170 175

Asp Lys Cys Val Leu Asp Met Arg Ser Met Asp Phe Lys Ser Asn Ser
180 185 190

Ala Val Ala Trp Ser Asn Lys Ser Asp Phe Ala Cys Ala Asn Ala Phe
195 200 205

Asn Asn Ser Ile Ile Pro Glu Asp Thr Phe Phe Pro Ser Pro Glu Ser
210 215 220

Ser Cys Asp Val Lys Leu Val Glu Lys Ser Phe Glu Thr Asp Thr Asn
225 230 235 240

Leu Asn Phe Gln Asn Leu Ser Val Ile Gly Phe Arg Ile Leu Leu Leu
245 250 255

Lys Val Ala Gly Phe Asn Leu Leu Met Thr Leu Arg Leu Trp Ser Ser
260 265 270

<210> SEQ ID NO 505
<211> LENGTH: 314
<212> TYPE: PRT
<213> ORGANISM: Homo sapiens

<400> SEQUENCE: 505

Met Gly Ser Trp Thr Leu Cys Cys Val Ser Leu Cys Ile Leu Val Ala
1 5 10 15

Lys His Thr Asp Ala Gly Val Ile Gln Ser Pro Arg His Glu Val Thr
20 25 30

Glu Met Gly Gln Glu Val Thr Leu Arg Cys Lys Pro Ile Ser Gly His
35 40 45

Asp Tyr Leu Phe Trp Tyr Arg Gln Thr Met Met Arg Gly Leu Glu Leu

```
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Lys Thr Gly Gly Tyr Ser Asn Gln Pro Gln His Phe Gly Asp
        115                 120                 125

Gly Thr Arg Leu Ser Ile Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310


<210> SEQ ID NO 506
<211> LENGTH: 602
<212> TYPE: PRT
<213> ORGANISM: Homo sapiens

<400> SEQUENCE: 506

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110
```

-continued

```
Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Thr Ser Ile
                325                 330                 335

Arg Ala Val Phe Ile Phe Leu Trp Leu Gln Leu Asp Leu Val Asn Gly
            340                 345                 350

Glu Asn Val Glu Gln His Pro Ser Thr Leu Ser Val Gln Glu Gly Asp
        355                 360                 365

Ser Ala Val Ile Lys Cys Thr Tyr Ser Asp Ser Ala Ser Asn Tyr Phe
    370                 375                 380

Pro Trp Tyr Lys Gln Glu Leu Gly Lys Arg Pro Gln Leu Ile Ile Asp
385                 390                 395                 400

Ile Arg Ser Asn Val Gly Glu Lys Lys Asp Gln Arg Ile Ala Val Thr
                405                 410                 415

Leu Asn Lys Thr Ala Lys His Phe Ser Leu His Ile Thr Glu Thr Gln
            420                 425                 430

Pro Glu Asp Ser Ala Val Tyr Phe Cys Ala Ala Thr Glu Asp Leu Thr
        435                 440                 445

Leu Ile Trp Gly Ala Gly Thr Lys Leu Ile Ile Lys Pro Asp Ile Gln
    450                 455                 460

Asn Pro Asp Pro Ala Val Tyr Gln Leu Arg Asp Ser Lys Ser Ser Asp
465                 470                 475                 480

Lys Ser Val Cys Leu Phe Thr Asp Phe Asp Ser Gln Thr Asn Val Ser
                485                 490                 495

Gln Ser Lys Asp Ser Asp Val Tyr Ile Thr Asp Lys Cys Val Leu Asp
            500                 505                 510

Met Arg Ser Met Asp Phe Lys Ser Asn Ser Ala Val Ala Trp Ser Asn
        515                 520                 525

Lys Ser Asp Phe Ala Cys Ala Asn Ala Phe Asn Asn Ser Ile Ile Pro
```

```
    530                 535                 540

Glu Asp Thr Phe Phe Pro Ser Pro Glu Ser Ser Cys Asp Val Lys Leu
545                 550                 555                 560

Val Glu Lys Ser Phe Glu Thr Asp Thr Asn Leu Asn Phe Gln Asn Leu
                565                 570                 575

Ser Val Ile Gly Phe Arg Ile Leu Leu Leu Lys Val Ala Gly Phe Asn
            580                 585                 590

Leu Leu Met Thr Leu Arg Leu Trp Ser Ser
        595                 600


<210> SEQ ID NO 507
<211> LENGTH: 270
<212> TYPE: PRT
<213> ORGANISM: Homo sapiens

<400> SEQUENCE: 507

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Glu Asp Leu Thr Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Cys Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 508
<211> LENGTH: 310
<212> TYPE: PRT
<213> ORGANISM: Homo sapiens
```

<400> SEQUENCE: 508

Met Ser Asn Gln Val Leu Cys Cys Val Val Leu Cys Phe Leu Gly Ala
1 5 10 15

Asn Thr Val Asp Gly Gly Ile Thr Gln Ser Pro Lys Tyr Leu Phe Arg
20 25 30

Lys Glu Gly Gln Asn Val Thr Leu Ser Cys Glu Gln Asn Leu Asn His
35 40 45

Asp Ala Met Tyr Trp Tyr Arg Gln Asp Pro Gly Gln Gly Leu Arg Leu
50 55 60

Ile Tyr Tyr Ser Gln Ile Val Asn Asp Phe Gln Lys Gly Asp Ile Ala
65 70 75 80

Glu Gly Tyr Ser Val Ser Arg Glu Lys Lys Glu Ser Phe Pro Leu Thr
85 90 95

Val Thr Ser Ala Gln Lys Asn Pro Thr Ala Phe Tyr Leu Cys Ala Ser
100 105 110

Ser Pro Gly Ala Leu Tyr Glu Gln Tyr Phe Gly Pro Gly Thr Arg Leu
115 120 125

Thr Val Thr Glu Asp Leu Lys Asn Val Phe Pro Pro Glu Val Ala Val
130 135 140

Phe Glu Pro Ser Glu Ala Glu Ile Ser His Thr Gln Lys Ala Thr Leu
145 150 155 160

Val Cys Leu Ala Thr Gly Phe Tyr Pro Asp His Val Glu Leu Ser Trp
165 170 175

Trp Val Asn Gly Lys Glu Val His Ser Gly Val Cys Thr Asp Pro Gln
180 185 190

Pro Leu Lys Glu Gln Pro Ala Leu Asn Asp Ser Arg Tyr Cys Leu Ser
195 200 205

Ser Arg Leu Arg Val Ser Ala Thr Phe Trp Gln Asn Pro Arg Asn His
210 215 220

Phe Arg Cys Gln Val Gln Phe Tyr Gly Leu Ser Glu Asn Asp Glu Trp
225 230 235 240

Thr Gln Asp Arg Ala Lys Pro Val Thr Gln Ile Val Ser Ala Glu Ala
245 250 255

Trp Gly Arg Ala Asp Cys Gly Phe Thr Ser Glu Ser Tyr Gln Gln Gly
260 265 270

Val Leu Ser Ala Thr Ile Leu Tyr Glu Ile Leu Leu Gly Lys Ala Thr
275 280 285

Leu Tyr Ala Val Leu Val Ser Ala Leu Val Leu Met Ala Met Val Lys
290 295 300

Arg Lys Asp Ser Arg Gly
305 310

<210> SEQ ID NO 509
<211> LENGTH: 612
<212> TYPE: PRT
<213> ORGANISM: Homo sapiens

<400> SEQUENCE: 509

Met Gly Cys Arg Leu Leu Cys Cys Ala Val Leu Cys Leu Leu Gly Ala
1 5 10 15

Gly Glu Leu Val Pro Met Glu Thr Gly Val Thr Gln Thr Pro Arg His
20 25 30

Leu Val Met Gly Met Thr Asn Lys Lys Ser Leu Lys Cys Glu Gln His
35 40 45

```
Leu Gly His Asn Ala Met Tyr Trp Tyr Lys Gln Ser Ala Lys Lys Pro
    50                  55                  60

Leu Glu Leu Met Phe Val Tyr Ser Leu Glu Glu Arg Val Glu Asn Asn
65                  70                  75                  80

Ser Val Pro Ser Arg Phe Ser Pro Glu Cys Pro Asn Ser Ser His Leu
                85                  90                  95

Phe Leu His Leu His Thr Leu Gln Pro Glu Asp Ser Ala Leu Tyr Leu
            100                 105                 110

Cys Ala Ser Ser Gln Asp Tyr Leu Val Ser Asn Glu Lys Leu Phe Phe
        115                 120                 125

Gly Ser Gly Thr Gln Leu Ser Val Leu Glu Asp Leu Lys Asn Val Phe
    130                 135                 140

Pro Pro Glu Val Ala Val Phe Glu Pro Ser Glu Ala Glu Ile Ser His
145                 150                 155                 160

Thr Gln Lys Ala Thr Leu Val Cys Leu Ala Thr Gly Phe Tyr Pro Asp
                165                 170                 175

His Val Glu Leu Ser Trp Trp Val Asn Gly Lys Glu Val His Ser Gly
            180                 185                 190

Val Ser Thr Asp Pro Gln Pro Leu Lys Glu Gln Pro Ala Leu Asn Asp
        195                 200                 205

Ser Arg Tyr Cys Leu Ser Ser Arg Leu Arg Val Ser Ala Thr Phe Trp
    210                 215                 220

Gln Asn Pro Arg Asn His Phe Arg Cys Gln Val Gln Phe Tyr Gly Leu
225                 230                 235                 240

Ser Glu Asn Asp Glu Trp Thr Gln Asp Arg Ala Lys Pro Val Thr Gln
                245                 250                 255

Ile Val Ser Ala Glu Ala Trp Gly Arg Ala Asp Cys Gly Phe Thr Ser
            260                 265                 270

Glu Ser Tyr Gln Gln Gly Val Leu Ser Ala Thr Ile Leu Tyr Glu Ile
        275                 280                 285

Leu Leu Gly Lys Ala Thr Leu Tyr Ala Val Leu Val Ser Ala Leu Val
    290                 295                 300

Leu Met Ala Met Val Lys Arg Lys Asp Ser Arg Gly Gly Ser Gly Ala
305                 310                 315                 320

Thr Asn Phe Ser Leu Leu Lys Gln Ala Gly Asp Val Glu Glu Asn Pro
                325                 330                 335

Gly Pro Met Ile Ser Leu Arg Val Leu Leu Val Ile Leu Trp Leu Gln
            340                 345                 350

Leu Ser Trp Val Trp Ser Gln Arg Lys Glu Val Glu Gln Asp Pro Gly
        355                 360                 365

Pro Phe Asn Val Pro Glu Gly Ala Thr Val Ala Phe Asn Cys Thr Tyr
    370                 375                 380

Ser Asn Ser Ala Ser Gln Ser Phe Phe Trp Tyr Arg Gln Asp Cys Arg
385                 390                 395                 400

Lys Glu Pro Lys Leu Leu Met Ser Val Tyr Ser Ser Gly Asn Glu Asp
                405                 410                 415

Gly Arg Phe Thr Ala Gln Leu Asn Arg Ala Ser Gln Tyr Ile Ser Leu
            420                 425                 430

Leu Ile Arg Asp Ser Lys Leu Ser Asp Ser Ala Thr Tyr Leu Cys Val
        435                 440                 445

Val Asn Leu Leu Ser Asn Gln Gly Gly Lys Leu Ile Phe Gly Gln Gly
    450                 455                 460

Thr Glu Leu Ser Val Lys Pro Asn Ile Gln Asn Pro Asp Pro Ala Val
```

```
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510

Val Tyr Ile Thr Asp Lys Thr Val Leu Asp Met Arg Ser Met Asp Phe
        515                 520                 525

Lys Ser Asn Ser Ala Val Ala Trp Ser Asn Lys Ser Asp Phe Ala Cys
    530                 535                 540

Ala Asn Ala Phe Asn Asn Ser Ile Ile Pro Glu Asp Thr Phe Phe Pro
545                 550                 555                 560

Ser Pro Glu Ser Ser Cys Asp Val Lys Leu Val Glu Lys Ser Phe Glu
                565                 570                 575

Thr Asp Thr Asn Leu Asn Phe Gln Asn Leu Ser Val Ile Gly Phe Arg
            580                 585                 590

Ile Leu Leu Leu Lys Val Ala Gly Phe Asn Leu Leu Met Thr Leu Arg
        595                 600                 605

Leu Trp Ser Ser
    610


<210> SEQ ID NO 510
<211> LENGTH: 274
<212> TYPE: PRT
<213> ORGANISM: Homo sapiens

<400> SEQUENCE: 510

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Leu Leu Ser Asn Gln Gly Gly Lys Leu Ile Phe Gly Gln Gly Thr Glu
        115                 120                 125

Leu Ser Val Lys Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220
```

Glu Ser Ser Cys Asp Val Lys Leu Val Glu Lys Ser Phe Glu Thr Asp
225 230 235 240

Thr Asn Leu Asn Phe Gln Asn Leu Ser Val Ile Gly Phe Arg Ile Leu
245 250 255

Leu Leu Lys Val Ala Gly Phe Asn Leu Leu Met Thr Leu Arg Leu Trp
260 265 270

Ser Ser

<210> SEQ ID NO 511
<211> LENGTH: 316
<212> TYPE: PRT
<213> ORGANISM: Homo sapiens

<400> SEQUENCE: 511

Met Gly Cys Arg Leu Leu Cys Cys Ala Val Leu Cys Leu Leu Gly Ala
1 5 10 15

Gly Glu Leu Val Pro Met Glu Thr Gly Val Thr Gln Thr Pro Arg His
20 25 30

Leu Val Met Gly Met Thr Asn Lys Lys Ser Leu Lys Cys Glu Gln His
35 40 45

Leu Gly His Asn Ala Met Tyr Trp Tyr Lys Gln Ser Ala Lys Lys Pro
50 55 60

Leu Glu Leu Met Phe Val Tyr Ser Leu Glu Glu Arg Val Glu Asn Asn
65 70 75 80

Ser Val Pro Ser Arg Phe Ser Pro Glu Cys Pro Asn Ser Ser His Leu
85 90 95

Phe Leu His Leu His Thr Leu Gln Pro Glu Asp Ser Ala Leu Tyr Leu
100 105 110

Cys Ala Ser Ser Gln Asp Tyr Leu Val Ser Asn Glu Lys Leu Phe Phe
115 120 125

Gly Ser Gly Thr Gln Leu Ser Val Leu Glu Asp Leu Lys Asn Val Phe
130 135 140

Pro Pro Glu Val Ala Val Phe Glu Pro Ser Glu Ala Glu Ile Ser His
145 150 155 160

Thr Gln Lys Ala Thr Leu Val Cys Leu Ala Thr Gly Phe Tyr Pro Asp
165 170 175

His Val Glu Leu Ser Trp Trp Val Asn Gly Lys Glu Val His Ser Gly
180 185 190

Val Ser Thr Asp Pro Gln Pro Leu Lys Glu Gln Pro Ala Leu Asn Asp
195 200 205

Ser Arg Tyr Cys Leu Ser Ser Arg Leu Arg Val Ser Ala Thr Phe Trp
210 215 220

Gln Asn Pro Arg Asn His Phe Arg Cys Gln Val Gln Phe Tyr Gly Leu
225 230 235 240

Ser Glu Asn Asp Glu Trp Thr Gln Asp Arg Ala Lys Pro Val Thr Gln
245 250 255

Ile Val Ser Ala Glu Ala Trp Gly Arg Ala Asp Cys Gly Phe Thr Ser
260 265 270

Glu Ser Tyr Gln Gln Gly Val Leu Ser Ala Thr Ile Leu Tyr Glu Ile
275 280 285

Leu Leu Gly Lys Ala Thr Leu Tyr Ala Val Leu Val Ser Ala Leu Val
290 295 300

Leu Met Ala Met Val Lys Arg Lys Asp Ser Arg Gly
305 310 315

<210> SEQ ID NO 512
<211> LENGTH: 612
<212> TYPE: PRT
<213> ORGANISM: Homo sapiens

<400> SEQUENCE: 512

```
Met Gly Cys Arg Leu Leu Cys Cys Ala Val Leu Cys Leu Leu Gly Ala
1               5                   10                  15

Gly Glu Leu Val Pro Met Glu Thr Gly Val Thr Gln Thr Pro Arg His
            20                  25                  30

Leu Val Met Gly Met Thr Asn Lys Lys Ser Leu Lys Cys Glu Gln His
        35                  40                  45

Leu Gly His Asn Ala Met Tyr Trp Tyr Lys Gln Ser Ala Lys Lys Pro
    50                  55                  60

Leu Glu Leu Met Phe Val Tyr Ser Leu Glu Glu Arg Val Glu Asn Asn
65                  70                  75                  80

Ser Val Pro Ser Arg Phe Ser Pro Glu Cys Pro Asn Ser Ser His Leu
                85                  90                  95

Phe Leu His Leu His Thr Leu Gln Pro Glu Asp Ser Ala Leu Tyr Leu
            100                 105                 110

Cys Ala Ser Ser Gln Asp Tyr Leu Val Ser Asn Glu Lys Leu Phe Phe
        115                 120                 125

Gly Ser Gly Thr Gln Leu Ser Val Leu Glu Asp Leu Lys Asn Val Phe
    130                 135                 140

Pro Pro Glu Val Ala Val Phe Glu Pro Ser Glu Ala Glu Ile Ser His
145                 150                 155                 160

Thr Gln Lys Ala Thr Leu Val Cys Leu Ala Thr Gly Phe Tyr Pro Asp
                165                 170                 175

His Val Glu Leu Ser Trp Trp Val Asn Gly Lys Glu Val His Ser Gly
            180                 185                 190

Val Ser Thr Asp Pro Gln Pro Leu Lys Glu Gln Pro Ala Leu Asn Asp
        195                 200                 205

Ser Arg Tyr Cys Leu Ser Ser Arg Leu Arg Val Ser Ala Thr Phe Trp
    210                 215                 220

Gln Asn Pro Arg Asn His Phe Arg Cys Gln Val Gln Phe Tyr Gly Leu
225                 230                 235                 240

Ser Glu Asn Asp Glu Trp Thr Gln Asp Arg Ala Lys Pro Val Thr Gln
                245                 250                 255

Ile Val Ser Ala Glu Ala Trp Gly Arg Ala Asp Cys Gly Phe Thr Ser
            260                 265                 270

Glu Ser Tyr Gln Gln Gly Val Leu Ser Ala Thr Ile Leu Tyr Glu Ile
        275                 280                 285

Leu Leu Gly Lys Ala Thr Leu Tyr Ala Val Leu Val Ser Ala Leu Val
    290                 295                 300

Leu Met Ala Met Val Lys Arg Lys Asp Ser Arg Gly Gly Ser Gly Ala
305                 310                 315                 320

Thr Asn Phe Ser Leu Leu Lys Gln Ala Gly Asp Val Glu Glu Asn Pro
                325                 330                 335

Gly Pro Met Ile Ser Leu Arg Val Leu Leu Val Ile Leu Trp Leu Gln
            340                 345                 350

Leu Ser Trp Val Trp Ser Gln Arg Lys Glu Val Glu Gln Asp Pro Gly
        355                 360                 365

Pro Phe Asn Val Pro Glu Gly Ala Thr Val Ala Phe Asn Cys Thr Tyr
    370                 375                 380
```

```
Ser Asn Ser Ala Ser Gln Ser Phe Phe Trp Tyr Arg Gln Asp Cys Arg
385                 390                 395                 400

Lys Glu Pro Lys Leu Leu Met Ser Val Tyr Ser Ser Gly Asn Glu Asp
                405                 410                 415

Gly Arg Phe Thr Ala Gln Leu Asn Arg Ala Ser Gln Tyr Ile Ser Leu
            420                 425                 430

Leu Ile Arg Asp Ser Lys Leu Ser Asp Ser Ala Thr Tyr Leu Cys Val
        435                 440                 445

Val Asn Leu Leu Ser Asn Gln Gly Gly Lys Leu Ile Phe Gly Gln Gly
    450                 455                 460

Thr Glu Leu Ser Val Lys Pro Asn Ile Gln Asn Pro Asp Pro Ala Val
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510

Val Tyr Ile Thr Asp Lys Thr Val Leu Asp Met Arg Ser Met Asp Phe
        515                 520                 525

Lys Ser Asn Ser Ala Val Ala Trp Ser Asn Lys Ser Asp Phe Ala Cys
    530                 535                 540

Ala Asn Ala Phe Asn Asn Ser Ile Ile Pro Glu Asp Thr Phe Phe Pro
545                 550                 555                 560

Ser Pro Glu Ser Ser Cys Asp Val Lys Leu Val Glu Lys Ser Phe Glu
                565                 570                 575

Thr Asp Thr Asn Leu Asn Phe Gln Asn Leu Ser Val Ile Gly Phe Arg
            580                 585                 590

Ile Leu Leu Leu Lys Val Ala Gly Phe Asn Leu Leu Met Thr Leu Arg
        595                 600                 605

Leu Trp Ser Ser
    610
```

<210> SEQ ID NO 513
<211> LENGTH: 274
<212> TYPE: PRT
<213> ORGANISM: Homo sapiens

<400> SEQUENCE: 513

```
Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Leu Leu Ser Asn Gln Gly Gly Lys Leu Ile Phe Gly Gln Gly Thr Glu
        115                 120                 125

Leu Ser Val Lys Pro Asn Ile Gln Asn Pro Asp Pro Ala Val Tyr Gln
```

```
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser


<210> SEQ ID NO 514
<211> LENGTH: 316
<212> TYPE: PRT
<213> ORGANISM: Homo sapiens

<400> SEQUENCE: 514

Met Gly Cys Arg Leu Leu Cys Cys Ala Val Leu Cys Leu Leu Gly Ala
1               5                   10                  15

Gly Glu Leu Val Pro Met Glu Thr Gly Val Thr Gln Thr Pro Arg His
            20                  25                  30

Leu Val Met Gly Met Thr Asn Lys Lys Ser Leu Lys Cys Glu Gln His
        35                  40                  45

Leu Gly His Asn Ala Met Tyr Trp Tyr Lys Gln Ser Ala Lys Lys Pro
    50                  55                  60

Leu Glu Leu Met Phe Val Tyr Ser Leu Glu Glu Arg Val Glu Asn Asn
65                  70                  75                  80

Ser Val Pro Ser Arg Phe Ser Pro Glu Cys Pro Asn Ser Ser His Leu
                85                  90                  95

Phe Leu His Leu His Thr Leu Gln Pro Glu Asp Ser Ala Leu Tyr Leu
            100                 105                 110

Cys Ala Ser Ser Gln Asp Tyr Leu Val Ser Asn Glu Lys Leu Phe Phe
        115                 120                 125

Gly Ser Gly Thr Gln Leu Ser Val Leu Glu Asp Leu Lys Asn Val Phe
    130                 135                 140

Pro Pro Glu Val Ala Val Phe Glu Pro Ser Glu Ala Glu Ile Ser His
145                 150                 155                 160

Thr Gln Lys Ala Thr Leu Val Cys Leu Ala Thr Gly Phe Tyr Pro Asp
                165                 170                 175

His Val Glu Leu Ser Trp Trp Val Asn Gly Lys Glu Val His Ser Gly
            180                 185                 190

Val Ser Thr Asp Pro Gln Pro Leu Lys Glu Gln Pro Ala Leu Asn Asp
        195                 200                 205

Ser Arg Tyr Cys Leu Ser Ser Arg Leu Arg Val Ser Ala Thr Phe Trp
    210                 215                 220

Gln Asn Pro Arg Asn His Phe Arg Cys Gln Val Gln Phe Tyr Gly Leu
```

```
225                 230                 235                 240

Ser Glu Asn Asp Glu Trp Thr Gln Asp Arg Ala Lys Pro Val Thr Gln
                245                 250                 255

Ile Val Ser Ala Glu Ala Trp Gly Arg Ala Asp Cys Gly Phe Thr Ser
            260                 265                 270

Glu Ser Tyr Gln Gln Gly Val Leu Ser Ala Thr Ile Leu Tyr Glu Ile
        275                 280                 285

Leu Leu Gly Lys Ala Thr Leu Tyr Ala Val Leu Val Ser Ala Leu Val
    290                 295                 300

Leu Met Ala Met Val Lys Arg Lys Asp Ser Arg Gly
305                 310                 315


<210> SEQ ID NO 515
<211> LENGTH: 614
<212> TYPE: PRT
<213> ORGANISM: Homo sapiens

<400> SEQUENCE: 515

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Arg Gly Gly Leu
        115                 120                 125

Glu Lys Leu Phe Phe Gly Ser Gly Thr Gln Leu Ser Val Leu Glu Asp
    130                 135                 140

Leu Asn Lys Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Phe Pro Asp His Val Glu Leu Ser Trp Trp Val Asn Gly Lys
            180                 185                 190

Glu Val His Ser Gly Val Cys Thr Asp Pro Gln Pro Leu Lys Glu Gln
        195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Val Ser Tyr Gln Gln Gly Val Leu Ser Ala Thr
        275                 280                 285
```

```
Ile Leu Tyr Glu Ile Leu Leu Gly Lys Ala Thr Leu Tyr Ala Val Leu
    290                 295                 300

Val Ser Ala Leu Val Leu Met Ala Met Val Lys Arg Lys Asp Phe Gly
305                 310                 315                 320

Ser Gly Ala Thr Asn Phe Ser Leu Leu Lys Gln Ala Gly Asp Val Glu
                325                 330                 335

Glu Asn Pro Gly Pro Met Ser Leu Ser Ser Leu Leu Lys Val Val Thr
            340                 345                 350

Ala Ser Leu Trp Leu Gly Pro Gly Ile Ala Gln Lys Ile Thr Gln Thr
        355                 360                 365

Gln Pro Gly Met Phe Val Gln Glu Lys Glu Ala Val Thr Leu Asp Cys
    370                 375                 380

Thr Tyr Asp Thr Ser Asp Pro Ser Tyr Gly Leu Phe Trp Tyr Lys Gln
385                 390                 395                 400

Pro Ser Ser Gly Glu Met Ile Phe Leu Ile Tyr Gln Gly Ser Tyr Asp
                405                 410                 415

Gln Gln Asn Ala Thr Glu Gly Arg Tyr Ser Leu Asn Phe Gln Lys Ala
            420                 425                 430

Arg Lys Ser Ala Asn Leu Val Ile Ser Ala Ser Gln Leu Gly Asp Ser
        435                 440                 445

Ala Met Tyr Phe Cys Ala Ile Ser Gly Asn Thr Pro Leu Val Phe Gly
    450                 455                 460

Lys Gly Thr Arg Leu Ser Val Ile Ala Asn Ile Gln Asn Pro Asp Pro
465                 470                 475                 480

Ala Val Tyr Gln Leu Arg Asp Ser Lys Ser Ser Asp Lys Ser Val Cys
                485                 490                 495

Leu Phe Thr Asp Phe Asp Ser Gln Thr Asn Val Ser Gln Ser Lys Asp
            500                 505                 510

Ser Asp Val Tyr Ile Thr Asp Lys Cys Val Leu Asp Met Arg Ser Met
        515                 520                 525

Asp Phe Lys Ser Asn Ser Ala Val Ala Trp Ser Asn Lys Ser Asp Phe
    530                 535                 540

Ala Cys Ala Asn Ala Phe Asn Asn Ser Ile Ile Pro Glu Asp Thr Phe
545                 550                 555                 560

Phe Pro Ser Pro Glu Ser Ser Cys Asp Val Lys Leu Val Glu Lys Ser
                565                 570                 575

Phe Glu Thr Asp Thr Asn Leu Asn Phe Gln Asn Leu Ser Val Ile Gly
            580                 585                 590

Phe Arg Ile Leu Leu Leu Lys Val Ala Gly Phe Asn Leu Leu Met Thr
        595                 600                 605

Leu Arg Leu Trp Ser Ser
    610
```

<210> SEQ ID NO 516
<211> LENGTH: 273
<212> TYPE: PRT
<213> ORGANISM: Homo sapiens

<400> SEQUENCE: 516

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45
```

```
Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Ile Ser Gly Asn Thr Pro Leu Val Phe Gly Lys Gly Thr Arg Leu
        115                 120                 125

Ser Val Ile Ala Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Cys Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
        195                 200                 205

Phe Asn Asn Ser Ile Ile Pro Glu Asp Thr Phe Phe Pro Ser Pro Glu
    210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser


<210> SEQ ID NO 517
<211> LENGTH: 319
<212> TYPE: PRT
<213> ORGANISM: Homo sapiens

<400> SEQUENCE: 517

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
            20                  25                  30

Val Ile Gln Ser Pro Arg His Leu Ile Lys Glu Lys Arg Glu Thr Ala
        35                  40                  45

Thr Leu Lys Cys Tyr Pro Ile Pro Arg His Asp Thr Val Tyr Trp Tyr
    50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Leu Arg Gly Gly Leu
        115                 120                 125

Glu Lys Leu Phe Phe Gly Ser Gly Thr Gln Leu Ser Val Leu Glu Asp
    130                 135                 140
```

Leu Asn Lys Val Phe Pro Pro Glu Val Ala Val Phe Glu Pro Ser Glu
145 150 155 160

Ala Glu Ile Ser His Thr Gln Lys Ala Thr Leu Val Cys Leu Ala Thr
165 170 175

Gly Phe Phe Pro Asp His Val Glu Leu Ser Trp Trp Val Asn Gly Lys
180 185 190

Glu Val His Ser Gly Val Cys Thr Asp Pro Gln Pro Leu Lys Glu Gln
195 200 205

Pro Ala Leu Asn Asp Ser Arg Tyr Cys Leu Ser Ser Arg Leu Arg Val
210 215 220

Ser Ala Thr Phe Trp Gln Asn Pro Arg Asn His Phe Arg Cys Gln Val
225 230 235 240

Gln Phe Tyr Gly Leu Ser Glu Asn Asp Glu Trp Thr Gln Asp Arg Ala
245 250 255

Lys Pro Val Thr Gln Ile Val Ser Ala Glu Ala Trp Gly Arg Ala Asp
260 265 270

Cys Gly Phe Thr Ser Val Ser Tyr Gln Gln Gly Val Leu Ser Ala Thr
275 280 285

Ile Leu Tyr Glu Ile Leu Leu Gly Lys Ala Thr Leu Tyr Ala Val Leu
290 295 300

Val Ser Ala Leu Val Leu Met Ala Met Val Lys Arg Lys Asp Phe
305 310 315

<210> SEQ ID NO 518
<211> LENGTH: 609
<212> TYPE: PRT
<213> ORGANISM: Homo sapiens

<400> SEQUENCE: 518

Met Gly Thr Arg Leu Leu Cys Trp Ala Ala Leu Cys Leu Leu Gly Ala
1 5 10 15

Glu Leu Thr Glu Ala Gly Val Ala Gln Ser Pro Arg Tyr Lys Ile Ile
20 25 30

Glu Lys Arg Gln Ser Val Ala Phe Trp Cys Asn Pro Ile Ser Gly His
35 40 45

Ala Thr Leu Tyr Trp Tyr Gln Gln Ile Leu Gly Gln Gly Pro Lys Leu
50 55 60

Leu Ile Gln Phe Gln Asn Asn Gly Val Val Asp Asp Ser Gln Leu Pro
65 70 75 80

Lys Asp Arg Phe Ser Ala Glu Arg Leu Lys Gly Val Asp Ser Thr Leu
85 90 95

Lys Ile Gln Pro Ala Lys Leu Glu Asp Ser Ala Val Tyr Leu Cys Ala
100 105 110

Ser Ser Leu Tyr Arg Gly Glu Gln Tyr Phe Gly Pro Gly Thr Arg Leu
115 120 125

Thr Val Thr Glu Asp Leu Lys Asn Val Phe Pro Pro Glu Val Ala Val
130 135 140

Phe Glu Pro Ser Glu Ala Glu Ile Ser His Thr Gln Lys Ala Thr Leu
145 150 155 160

Val Cys Leu Ala Thr Gly Phe Tyr Pro Asp His Val Glu Leu Ser Trp
165 170 175

Trp Val Asn Gly Lys Glu Val His Ser Gly Val Cys Thr Asp Pro Gln
180 185 190

Pro Leu Lys Glu Gln Pro Ala Leu Asn Asp Ser Arg Tyr Cys Leu Ser

-continued

```
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Ala Met Leu
                325                 330                 335

Leu Gly Ala Ser Val Leu Ile Leu Trp Leu Gln Pro Asp Trp Val Asn
            340                 345                 350

Ser Gln Gln Lys Asn Asp Asp Gln Gln Val Lys Gln Asn Ser Pro Ser
        355                 360                 365

Leu Ser Val Gln Glu Gly Arg Ile Ser Ile Leu Asn Cys Asp Tyr Thr
    370                 375                 380

Asn Ser Met Phe Asp Tyr Phe Leu Trp Tyr Lys Lys Tyr Pro Ala Glu
385                 390                 395                 400

Gly Pro Thr Phe Leu Ile Ser Ile Ser Ser Ile Lys Asp Lys Asn Glu
                405                 410                 415

Asp Gly Arg Phe Thr Val Phe Leu Asn Lys Ser Ala Lys His Leu Ser
            420                 425                 430

Leu His Ile Val Pro Ser Gln Pro Gly Asp Ser Ala Val Tyr Phe Cys
        435                 440                 445

Ala Ala Arg Gly Gln Gly Asn Leu Ile Phe Gly Lys Gly Thr Lys Leu
    450                 455                 460

Ser Val Lys Pro Asn Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
                485                 490                 495

Asp Ser Gln Thr Asn Val Ser Gln Ser Lys Asp Ser Asp Val Tyr Ile
            500                 505                 510

Thr Asp Lys Cys Val Leu Asp Met Arg Ser Met Asp Phe Lys Ser Asn
        515                 520                 525

Ser Ala Val Ala Trp Ser Asn Lys Ser Asp Phe Ala Cys Ala Asn Ala
    530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
                565                 570                 575

Asn Leu Asn Phe Gln Asn Leu Ser Val Ile Gly Phe Arg Ile Leu Leu
            580                 585                 590

Leu Lys Val Ala Gly Phe Asn Leu Leu Met Thr Leu Arg Leu Trp Ser
        595                 600                 605

Ser
```

<210> SEQ ID NO 519
<211> LENGTH: 277
<212> TYPE: PRT
<213> ORGANISM: Homo sapiens

<400> SEQUENCE: 519

```
Met Ala Met Leu Leu Gly Ala Ser Val Leu Ile Leu Trp Leu Gln Pro
1               5                   10                  15

Asp Trp Val Asn Ser Gln Gln Lys Asn Asp Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Arg Gly Gln Gly Asn Leu Ile Phe Gly Lys
        115                 120                 125

Gly Thr Lys Leu Ser Val Lys Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
        275
```

<210> SEQ ID NO 520
<211> LENGTH: 310
<212> TYPE: PRT
<213> ORGANISM: Homo sapiens

<400> SEQUENCE: 520

```
Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45
```

-continued

```
Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Tyr Arg Gly Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310


<210> SEQ ID NO 521
<211> LENGTH: 641
<212> TYPE: PRT
<213> ORGANISM: Homo sapiens

<400> SEQUENCE: 521

Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110
```

```
Arg Gly Tyr His Arg Leu Asn Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Ile
                325                 330                 335

Ser Leu Arg Val Leu Leu Val Ile Leu Trp Leu Gln Leu Ser Trp Val
            340                 345                 350

Trp Ser Gly Gly Gly Ser Trp Ser His Pro Gln Phe Glu Lys Gly Gly
        355                 360                 365

Gly Ser Gly Gly Gly Ser Gly Gly Ser Ala Trp Ser His Pro Gln Phe
    370                 375                 380

Glu Lys Gln Arg Lys Glu Val Glu Gln Asp Pro Gly Pro Phe Asn Val
385                 390                 395                 400

Pro Glu Gly Ala Thr Val Ala Phe Asn Cys Thr Tyr Ser Asn Ser Ala
                405                 410                 415

Ser Gln Ser Phe Phe Trp Tyr Arg Gln Asp Cys Arg Lys Glu Pro Lys
            420                 425                 430

Leu Leu Met Ser Val Tyr Ser Ser Gly Asn Glu Asp Gly Arg Phe Thr
        435                 440                 445

Ala Gln Leu Asn Arg Ala Ser Gln Tyr Ile Ser Leu Leu Ile Arg Asp
    450                 455                 460

Ser Lys Leu Ser Asp Ser Ala Thr Tyr Leu Cys Val Val Lys Pro Asp
465                 470                 475                 480

Pro Gly Ala Gly Ser Tyr Gln Leu Thr Phe Gly Lys Gly Thr Lys Leu
                485                 490                 495

Ser Val Ile Pro Asn Ile Gln Asn Pro Asp Pro Ala Val Tyr Gln Leu
            500                 505                 510

Arg Asp Ser Lys Ser Ser Asp Lys Ser Val Cys Leu Phe Thr Asp Phe
        515                 520                 525
```

```
Asp Ser Gln Thr Asn Val Ser Gln Ser Lys Asp Ser Asp Val Tyr Ile
    530                 535                 540

Thr Asp Lys Cys Val Leu Asp Met Arg Ser Met Asp Phe Lys Ser Asn
545                 550                 555                 560

Ser Ala Val Ala Trp Ser Asn Lys Ser Asp Phe Ala Cys Ala Asn Ala
                565                 570                 575

Phe Asn Asn Ser Ile Ile Pro Glu Asp Thr Phe Phe Pro Ser Pro Glu
            580                 585                 590

Ser Ser Cys Asp Val Lys Leu Val Glu Lys Ser Phe Glu Thr Asp Thr
        595                 600                 605

Asn Leu Asn Phe Gln Asn Leu Ser Val Ile Gly Phe Arg Ile Leu Leu
    610                 615                 620

Leu Lys Val Ala Gly Phe Asn Leu Leu Met Thr Leu Arg Leu Trp Ser
625                 630                 635                 640

Ser


<210> SEQ ID NO 522
<211> LENGTH: 307
<212> TYPE: PRT
<213> ORGANISM: Homo sapiens

<400> SEQUENCE: 522

Met Ile Ser Leu Arg Val Leu Leu Val Ile Leu Trp Leu Gln Leu Ser
1               5                   10                  15

Trp Val Trp Ser Gly Gly Gly Ser Trp Ser His Pro Gln Phe Glu Lys
            20                  25                  30

Gly Gly Gly Ser Gly Gly Gly Ser Gly Gly Ser Ala Trp Ser His Pro
        35                  40                  45

Gln Phe Glu Lys Gln Arg Lys Glu Val Glu Gln Asp Pro Gly Pro Phe
    50                  55                  60

Asn Val Pro Glu Gly Ala Thr Val Ala Phe Asn Cys Thr Tyr Ser Asn
65                  70                  75                  80

Ser Ala Ser Gln Ser Phe Phe Trp Tyr Arg Gln Asp Cys Arg Lys Glu
                85                  90                  95

Pro Lys Leu Leu Met Ser Val Tyr Ser Ser Gly Asn Glu Asp Gly Arg
            100                 105                 110

Phe Thr Ala Gln Leu Asn Arg Ala Ser Gln Tyr Ile Ser Leu Leu Ile
        115                 120                 125

Arg Asp Ser Lys Leu Ser Asp Ser Ala Thr Tyr Leu Cys Val Val Lys
    130                 135                 140

Pro Asp Pro Gly Ala Gly Ser Tyr Gln Leu Thr Phe Gly Lys Gly Thr
145                 150                 155                 160

Lys Leu Ser Val Ile Pro Asn Ile Gln Asn Pro Asp Pro Ala Val Tyr
                165                 170                 175

Gln Leu Arg Asp Ser Lys Ser Ser Asp Lys Ser Val Cys Leu Phe Thr
            180                 185                 190

Asp Phe Asp Ser Gln Thr Asn Val Ser Gln Ser Lys Asp Ser Asp Val
        195                 200                 205

Tyr Ile Thr Asp Lys Cys Val Leu Asp Met Arg Ser Met Asp Phe Lys
    210                 215                 220

Ser Asn Ser Ala Val Ala Trp Ser Asn Lys Ser Asp Phe Ala Cys Ala
225                 230                 235                 240

Asn Ala Phe Asn Asn Ser Ile Ile Pro Glu Asp Thr Phe Phe Pro Ser
                245                 250                 255
```

```
Pro Glu Ser Ser Cys Asp Val Lys Leu Val Glu Lys Ser Phe Glu Thr
            260                 265                 270

Asp Thr Asn Leu Asn Phe Gln Asn Leu Ser Val Ile Gly Phe Arg Ile
        275                 280                 285

Leu Leu Leu Lys Val Ala Gly Phe Asn Leu Leu Met Thr Leu Arg Leu
    290                 295                 300

Trp Ser Ser
305


<210> SEQ ID NO 523
<211> LENGTH: 312
<212> TYPE: PRT
<213> ORGANISM: Homo sapiens

<400> SEQUENCE: 523

Met Ser Leu Gly Leu Leu Cys Cys Gly Ala Phe Ser Leu Leu Trp Ala
1               5                   10                  15

Gly Pro Val Asn Ala Gly Val Thr Gln Thr Pro Lys Phe Arg Val Leu
            20                  25                  30

Lys Thr Gly Gln Ser Met Thr Leu Leu Cys Ala Gln Asp Met Asn His
        35                  40                  45

Glu Tyr Met Tyr Trp Tyr Arg Gln Asp Pro Gly Met Gly Leu Arg Leu
    50                  55                  60

Ile His Tyr Ser Val Gly Glu Gly Thr Thr Ala Lys Gly Glu Val Pro
65                  70                  75                  80

Asp Gly Tyr Asn Val Ser Arg Leu Lys Lys Gln Asn Phe Leu Leu Gly
                85                  90                  95

Leu Glu Ser Ala Ala Pro Ser Gln Thr Ser Val Tyr Phe Cys Ala Ser
            100                 105                 110

Arg Gly Tyr His Arg Leu Asn Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310
```

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

-continued

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600
<211> LENGTH: 7
<212> TYPE: PRT
<213> ORGANISM: SV40

<400> SEQUENCE: 600

Pro Lys Lys Lys Arg Lys Val
1               5

<210> SEQ ID NO 601
<211> LENGTH: 7
<212> TYPE: PRT
<213> ORGANISM: SV40

<400> SEQUENCE: 601

Pro Lys Lys Lys Arg Arg Val 1 5

<210> SEQ ID NO 602
<211> LENGTH: 16
<212> TYPE: PRT
<213> ORGANISM: Xenopus laevis

<400> SEQUENCE: 602

Lys Arg Pro Ala Ala Thr Lys Lys Ala Gly Gln Ala Lys Lys Lys Lys
1 5 10 15

<210> SEQ ID NO 603
<211> LENGTH: 1183
<212> TYPE: DNA
<213> ORGANISM: Homo sapiens

<400> SEQUENCE: 603
ggctccggtg cccgtcagtg ggcagagcgc acatcgccca cagtccccga gaagttgggg 60
ggaggggtcg gcaattgaac cggtgcctag agaaggtggc gcggggtaaa ctgggaaagt 120
gatgtcgtgt actggctccg cctttttccc gagggtgggg gagaaccgta tataagtgca 180
gtagtcgccg tgaacgttct ttttcgcaac gggtttgccg ccagaacaca ggtaagtgcc 240
gtgtgtggtt cccgcgggcc tggcctcttt acgggttatg gcccttgcgt gccttgaatt 300
acttccacgc ccctggctgc agtacgtgat tcttgatccc gagcttcggg ttggaagtgg 360
gtgggagagt tcgaggcctt gcgcttaagg agccccttcg cctcgtgctt gagttgaggc 420
ctggcttggg cgctggggcc gccgcgtgcg aatctggtgg caccttcgcg cctgtctcgc 480
tgctttcgat aagtctctag ccatttaaaa tttttgatga cctgctgcga cgcttttttt 540
ctggcaagat agtcttgtaa atgcgggcca agatgtgcac actggtattt cggtttttgg 600
ggccgcgggc ggcgacgggg cccgtgcgtc ccagcgcaca tgttcggcga ggcggggcct 660
gcgagcgcgg ccaccgagaa tcggacgggg gtagtctcaa gctggccggc ctgctctggt 720
gcctggcctc gcgccgccgt gtatcgcccc gccctgggcg gcaaggctgg cccggtcggc 780
accagttgcg tgagcggaaa gatggccgct tcccggccct gctgcaggga gctcaaaatg 840
gaggacgcgg cgctcgggag agcgggcggg tgagtcaccc acacaaagga aaagggcctt 900
tccgtcctca gccgtcgctt catgtgactc cacggagtac cgggcgccgt ccaggcacct 960
cgattagttc tcgagctttt ggagtacgtc gtctttaggt tgggggggagg ggttttatgc 1020 gatggagttt ccccacactg agtgggtgga gactgaagtt aggccagctt ggcacttgat 1080
gtaattctcc ttggaatttg ccctttttga gtttggatct tggttcattc tcaagcctca 1140
gacagtggtt caaagttttt ttcttccatt tcaggtgtcg tga 1183

<210> SEQ ID NO 604
<211> LENGTH: 238
<212> TYPE: DNA
<213> ORGANISM: Homo sapiens

<400> SEQUENCE: 604
cgtgaggctc cggtgcccgt cagtgggcag agcgcacatc gcccacagtc cccgagaagt 60
tggggggagg ggtcggcaat tgaaccggtg cctagagaag gtggcgcggg gtaaactggg 120
aaagtgatgt cgtgtactgg ctccgccttt ttcccgaggg tgggggagaa ccgtatataa 180
gtgcagtagt cgccgtgaac gttctttttc gcaacgggtt tgccgccaga acacaggt 238

<210> SEQ ID NO 605

-continued

<211> LENGTH: 457
<212> TYPE: DNA
<213> ORGANISM: Homo sapiens

<400> SEQUENCE: 605
aacagagaaa caggagaata tgggccaaac aggatatctg tggtaagcag ttcctgcccc      60
ggctcagggc caagaacagt tggaacagca gaatatgggc caaacaggat atctgtggta     120
agcagttcct gccccggctc agggccaaga acagatggtc cccagatgcg gtcccgccct     180
cagcagtttc tagagaacca tcagatgttt ccagggtgcc ccaaggacct gaaatgaccc     240
tgtgccttat ttgaactaac caatcagttc gcttctcgct tctgttcgcg cgcttctgct     300
ccccgagctc tatataagca gagctcgttt agtgaaccgt cagatcgcct ggagacgcca     360
tccacgctgt tttgacctcc atagaagaca ccgactctag aggatcgatc ccccgggctg     420
caggaattca agcgagaaga caagggcaga aagcacc                              457

<210> SEQ ID NO 606
<211> LENGTH: 426
<212> TYPE: DNA
<213> ORGANISM: Homo sapiens

<400> SEQUENCE: 606
gatccgaaca gagagacagc agaatatggg ccaaacagga tatctgtggt aagcagttcc      60
tgccccggct cagggccaag aacagttgga acagcagaat atgggccaaa caggatatct     120
gtggtaagca gttcctgccc cggctcaggg ccaagaacag atggtcccca gatgcggtcc     180
cgccctcagc agtttctaga gaaccatcag atgtttccag ggtgccccaa ggacctgaaa     240
tgaccctgtg ccttatttga actaaccaat cagttcgctt ctcgcttctg ttcgcgcgct     300
tctgctcccc gagctctata taagcagagc tcgtttagtg aaccgtcaga tcgcctggag     360
acgccatcca cgctgttttg acctccatag aagacaccga ctctagagga tccaccggtc     420
gccacc                                                               426

<210> SEQ ID NO 607
<211> LENGTH: 500
<212> TYPE: DNA
<213> ORGANISM: Homo sapiens

<400> SEQUENCE: 607
gggtagggga ggcgcttttc ccaaggcagt ctggagcatg cgctttagca gccccgctgg      60
gcacttggcg ctacacaagt ggcctctggc ctcgcacaca ttccacatcc accggtaggc     120
gccaaccggc tccgttcttt ggtggcccct tcgcgccacc ttctactcct cccctagtca     180
ggaagttccc ccccgccccg cagctcgcgt cgtgcaggac gtgacaaatg gaagtagcac     240
gtctcactag tctcgtgcag atggacagca ccgctgagca atggaagcgg gtaggccttt     300
ggggcagcgg ccaatagcag ctttgctcct tcgctttctg ggctcagagg ctgggaaggg     360
gtgggtccgg gggcgggctc aggggcgggc tcaggggcgg ggcgggcgcc cgaaggtcct     420
ccggaggccc ggcattctgc acgcttcaaa agcgcacgtc tgccgcgctg ttctcctctt     480
cctcatctcc gggcctttcg                                                500

<210> SEQ ID NO 608
<211> LENGTH: 54
<212> TYPE: DNA
<213> ORGANISM: Homo sapiens

<400> SEQUENCE: 608
gagggccgcg gcagcctgct gacctgcggc gacgtggagg agaatcccgg cccc 54

<210> SEQ ID NO 609
<211> LENGTH: 22
<212> TYPE: PRT
<213> ORGANISM: Artificial Sequence
<220> FEATURE:
<223> OTHER INFORMATION: Self-cleaving peptide derived from porcine teschovirus-1

<400> SEQUENCE: 609

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 610
<211> LENGTH: 478
<212> TYPE: PRT
<213> ORGANISM: Artificial Sequence
<220> FEATURE:
<223> OTHER INFORMATION: Enhanced Green Fluorescent Protein

<400> SEQUENCE: 610

Met Val Ser Lys Gly Glu Glu Leu Phe Thr Gly Val Val Pro Ile Leu
1 5 10 15

Val Glu Leu Asp Gly Asp Val Asn Gly His Lys Phe Ser Val Ser Gly
20 25 30

Glu Gly Glu Gly Asp Ala Thr Tyr Gly Lys Leu Thr Leu Lys Phe Ile
35 40 45

Cys Thr Thr Gly Lys Leu Pro Val Pro Trp Pro Thr Leu Val Thr Thr
50 55 60

Leu Thr Tyr Gly Val Gln Cys Phe Ser Arg Tyr Pro Asp His Met Lys
65 70 75 80

Gln His Asp Phe Phe Lys Ser Ala Met Pro Glu Gly Tyr Val Gln Glu
85 90 95

Arg Thr Ile Phe Phe Lys Asp Asp Gly Asn Tyr Lys Thr Arg Ala Glu
100 105 110

Val Lys Phe Glu Gly Asp Thr Leu Val Asn Arg Ile Glu Leu Lys Gly
115 120 125

Ile Asp Phe Lys Glu Asp Gly Asn Ile Leu Gly His Lys Leu Glu Tyr
130 135 140

Asn Tyr Asn Ser His Asn Val Tyr Ile Met Ala Asp Lys Gln Lys Asn
145 150 155 160

Gly Ile Lys Val Asn Phe Lys Ile Arg His Asn Ile Glu Asp Gly Ser
165 170 175

Val Gln Leu Ala Asp His Tyr Gln Gln Asn Thr Pro Ile Gly Asp Gly
180 185 190

Pro Val Leu Leu Pro Asp Asn His Tyr Leu Ser Thr Gln Ser Ala Leu
195 200 205

Ser Lys Asp Pro Asn Glu Lys Arg Asp His Met Val Leu Leu Glu Phe
210 215 220

Val Thr Ala Ala Gly Ile Thr Leu Gly Met Asp Glu Leu Tyr Lys Met
225 230 235 240

Val Ser Lys Gly Glu Glu Leu Phe Thr Gly Val Val Pro Ile Leu Val
245 250 255

Glu Leu Asp Gly Asp Val Asn Gly His Lys Phe Ser Val Ser Gly Glu

```
            260                 265                 270

Gly Glu Gly Asp Ala Thr Tyr Gly Lys Leu Thr Leu Lys Phe Ile Cys
        275                 280                 285

Thr Thr Gly Lys Leu Pro Val Pro Trp Pro Thr Leu Val Thr Thr Leu
    290                 295                 300

Thr Tyr Gly Val Gln Cys Phe Ser Arg Tyr Pro Asp His Met Lys Gln
305                 310                 315                 320

His Asp Phe Phe Lys Ser Ala Met Pro Glu Gly Tyr Val Gln Glu Arg
                325                 330                 335

Thr Ile Phe Phe Lys Asp Asp Gly Asn Tyr Lys Thr Arg Ala Glu Val
            340                 345                 350

Lys Phe Glu Gly Asp Thr Leu Val Asn Arg Ile Glu Leu Lys Gly Ile
        355                 360                 365

Asp Phe Lys Glu Asp Gly Asn Ile Leu Gly His Lys Leu Glu Tyr Asn
    370                 375                 380

Tyr Asn Ser His Asn Val Tyr Ile Met Ala Asp Lys Gln Lys Asn Gly
385                 390                 395                 400

Ile Lys Val Asn Phe Lys Ile Arg His Asn Ile Glu Asp Gly Ser Val
                405                 410                 415

Gln Leu Ala Asp His Tyr Gln Gln Asn Thr Pro Ile Gly Asp Gly Pro
            420                 425                 430

Val Leu Leu Pro Asp Asn His Tyr Leu Ser Thr Gln Ser Ala Leu Ser
        435                 440                 445

Lys Asp Pro Asn Glu Lys Arg Asp His Met Val Leu Leu Glu Phe Val
    450                 455                 460

Thr Ala Ala Gly Ile Thr Leu Gly Met Asp Glu Leu Tyr Lys
465                 470                 475
```

<210> SEQ ID NO 611
<211> LENGTH: 35
<212> TYPE: DNA
<213> ORGANISM: SV40

<400> SEQUENCE: 611

```
aataaagcaa tagcatcaca aatttcacaa ataaa                               35
```

<210> SEQ ID NO 612
<211> LENGTH: 276
<212> TYPE: DNA
<213> ORGANISM: Homo sapiens

<400> SEQUENCE: 612

```
cctcgactgt gccttctagt tgccagccat ctgttgtttg cccctccccc gtgccttcct     60

tgaccctgga aggtgccact cccactgtcc tttcctaata aaatgaggaa attgcatcgc    120

attgtctgag taggtgtcat tctattctgg ggggtggggt ggggcaggac agcaaggggg    180

aggattggga agacaatagc aggcatgctg gggatgcggt gggctctatg gcttctgagg    240

cggaaagaac cagctggggc tctagggggt atcccc                              276
```

<210> SEQ ID NO 613
<211> LENGTH: 4612
<212> TYPE: DNA
<213> ORGANISM: Homo sapiens

<400> SEQUENCE: 613

```
ttggccactc cctctctgcg cgctcgctcg ctcactgagg ccgggcgacc aaaggtcgcc     60
```

-continued

```
cgacgcccgg gctttgcccg ggcggcctca gtgagcgagc gagcgcgcag agagggagtg    120
gccaactcca tcactagggg ttcctagatc taatgtgata gatttcccaa cttaatgcca    180
acataccata aacctcccat tctgctaatg cccagcctaa gttggggaga ccactccaga    240
ttccaagatg tacagtttgc tttgctgggc ctttttccca tgcctgcctt tactctgcca    300
gagttatatt gctggggttt tgaagaagat cctattaaat aaaagaataa gcagtattat    360
taagtagccc tgcatttcag gtttccttga gtggcaggcc aggcctggcc gtgaacgttc    420
actgaaatca tggcctcttg gccaagattg atagcttgtg cctgtccctg agtcccagtc    480
catcacgagc agctggtttc taagatgcta tttcccgtat aaagcatgag accgtgactt    540
gccagcccca cagagccccg cccttgtcca tcactggcat ctggactcca gcctgggttg    600
gggcaaagag ggaaatgaga tcatgtccta accctgatcc tcttgtccca cggctccggt    660
gcccgtcagt gggcagagcg cacatcgccc acagtccccg agaagttggg gggaggggtc    720
ggcaattgaa ccggtgccta gagaaggtgg cgcggggtaa actgggaaag tgatgtcgtg    780
tactggctcc gcctttttcc cgagggtggg ggagaaccgt atataagtgc agtagtcgcc    840
gtgaacgttc tttttcgcaa cgggtttgcc gccagaacac aggtaagtgc cgtgtgtggt    900
tcccgcgggc ctggcctctt tacgggttat ggcccttgcg tgccttgaat tacttccacg    960
cccctggctg cagtacgtga ttcttgatcc cgagcttcgg gttggaagtg ggtgggagag   1020
ttcgaggcct tgcgcttaag gagcccttc gcctcgtgct tgagttgagg cctggcttgg   1080
gcgctggggc cgccgcgtgc gaatctggtg gcaccttcgc gcctgtctcg ctgctttcga   1140
taagtctcta gccatttaaa atttttgatg acctgctgcg acgctttttt tctggcaaga   1200
tagtcttgta aatgcgggcc aagatgtgca cactggtatt tcggtttttg gggccgcggg   1260
cggcgacggg gcccgtgcgt cccagcgcac atgttcggcg aggcggggcc tgcgagcgcg   1320
gccaccgaga atcggacggg ggtagtctca agctggccgg cctgctctgg tgcctggcct   1380
cgcgccgccg tgtatcgccc cgccctgggc ggcaaggctg gcccggtcgg caccagttgc   1440
gtgagcggaa agatggccgc ttcccggccc tgctgcaggg agctcaaaat ggaggacgcg   1500
gcgctcggga gagcgggcgg gtgagtcacc cacacaaagg aaaagggcct ttccgtcctc   1560
agccgtcgct tcatgtgact ccacggagta ccgggcgccg tccaggcacc tcgattagtt   1620
ctcgagcttt tggagtacgt cgtctttagg ttggggggag gggttttatg cgatggagtt   1680
tccccacact gagtgggtgg agactgaagt taggccagct tggcacttga tgtaattctc   1740
cttggaattt gccctttttg agtttggatc ttggttcatt ctcaagcctc agacagtggt   1800
tcaaagtttt tttcttccat ttcaggtgtc gtgacggccg gccccgccac catgagcaat   1860
caagtccttt gttgtgttgt cctgtgtttc cttggcgcaa ataccgtcga cggcgggata   1920
actcagtccc ccaaatacct cttcagaaaa gaaggacaaa acgtaacgct ttcctgcgag   1980
cagaatctta accacgacgc catgtactgg tacaggcaag accctggaca aggtcttagg   2040
ctcatatact actctcagat tgtcaatgac ttccaaaaag ggacatagc tgagggctac   2100
tctgtgtccc gagagaagaa ggagtcattt cccctgacag tgacttctgc acaaaaaaat   2160
cccactgcat tttatttgtg tgccagttca ccgggtgcat tgtatgagca atactttggc   2220
cccggcacta gactgacagt tacggaggat ctgaaaaacg tcttcccgcc agaggtggca   2280
gttttcgagc ccagtgaggc tgaaatctct catacccaaa aagcaaccct tgtctgtctc   2340
gccactggat tctatcccga ccacgtcgaa ttgagctggt gggtcaatgg gaaagaggta   2400
catagtgggg tctgtacgga tccacaaccc cttaaggaac aacctgccct taacgattca   2460
```

cgatactgcc tgtcatcacg actcagggta tctgctacct tttggcagaa cccgagaaat 2520
cactttcggt gccaggttca gttttacgga cttagcgaaa atgatgaatg gacacaagac 2580
cgagcaaagc ccgttactca aatagtgagc gcggaagcct gggggcgagc agactgcggc 2640
ttcacctccg aaagttacca gcaaggtgtt ttgtcagcca ccattttgta tgagattttg 2700
ttggggaagg cgacacttta cgcggtactg gtctctgcct tggttcttat ggctatggtc 2760
aagaggaaag attccagggg tggctccggt gccacaaact tctccctgct caagcaggcc 2820
ggagatgtgg aagagaaccc tggccctatg acctctatca gagctgtctt tatatttctc 2880
tggcttcaac ttgatctggt gaatggcgaa aacgtggaac agcacccttc aacgttgagc 2940
gttcaggaag gagattcagc cgtcatcaag tgtacgtatt ccgattccgc gtcaaactac 3000
ttcccgtggt acaaacagga acttggcaag cgcccccagc tcattatcga catcagaagc 3060
aacgtaggag agaagaagga ccaacgcata gctgtgactc tcaacaaaac agctaaacat 3120
ttctccctgc acattacgga aacccaacca gaggattctg ccgtatactt ttgtgctgct 3180
actgaggacc tcactttgat ctggggagcg ggtacgaagc tcataataaa acccgatatc 3240
caaaacccgg acccagcagt ttatcaattg agagatagta agtccagtga caaatcagtt 3300
tgtttgttta cggatttcga tagccagacc aatgtcagtc agtcaaagga cagtgatgta 3360
tacattacag ataaatgtgt acttgacatg cgctcaatgg actttaagtc taactctgct 3420
gtagcttggt ctaacaaaag tgattttgcg tgtgccaacg catttaacaa cagcatcata 3480
cctgaagaca cgttctttcc gagtccagaa agttcctgtg acgtgaaact tgtagaaaag 3540
agtttcgaga ccgacactaa ccttaacttt caaaaccttt cagtgatcgg atttagaatc 3600
ttgctgctca aggtggcagg gttcaatctg ctgatgactc tgcgactgtg gagttcataa 3660
cctcgactgt gccttctagt tgccagccat ctgttgtttg cccctccccc gtgccttcct 3720
tgaccctgga aggtgccact cccactgtcc tttcctaata aaatgaggaa attgcatcgc 3780
attgtctgag taggtgtcat tctattctgg ggggtggggt ggggcaggac agcaaggggg 3840
aggattggga agacaatagc aggcatgctg gggatgcggt gggctctatg gcttctgagg 3900
cggaaagaac cagctggggc tctagggggt atccccacca gctgagagac tctaaatcca 3960
gtgacaagtc tgtctgccta ttcaccgatt ttgattctca aacaaatgtg tcacaaagta 4020
aggattctga tgtgtatatc acagacaaaa ctgtgctaga catgaggtct atggacttca 4080
agagcaacag tgctgtggcc tggagcaaca aatctgactt tgcatgtgca aacgccttca 4140
acaacagcat tattccagaa gacaccttct tccccagccc aggtaagggc agctttggtg 4200
ccttcgcagg ctgtttcctt gcttcaggaa tggccaggtt ctgcccagag ctctggtcaa 4260
tgatgtctaa aactcctctg attggtggtc tcggccttat ccattgccac caaaaccctc 4320
tttttactaa gaaacagtga gccttgttct ggcagtccag agaatgacac gggaaaaaag 4380
cagatgaaga gaaggtggca ggagagggca cgtggcccag cctcagtctc tccaacagat 4440
ctaggaaccc ctagtgatgg agttggccac tccctctctg cgcgctcgct cgctcactga 4500
ggccgcccgg gcaaagcccg ggcgtcgggc gacctttggt cgcccggcct cagtgagcga 4560
gcgagcgcgc agagagggag tggccaaacg cgtggtgtaa tcatggtcat ag 4612

<210> SEQ ID NO 614
<211> LENGTH: 3618
<212> TYPE: DNA
<213> ORGANISM: Homo sapiens

<400> SEQUENCE: 614
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc taatgtgata gatttcccaa cttaatgcca 180
acataccata aacctcccat tctgctaatg cccagcctaa gttggggaga ccactccaga 240
ttccaagatg tacagtttgc tttgctgggc ctttttccca tgcctgcctt tactctgcca 300
gagttatatt gctggggttt tgaagaagat cctattaaat aaaagaataa gcagtattat 360
taagtagccc tgcatttcag gtttccttga gtggcaggcc aggcctggcc gtgaacgttc 420
actgaaatca tggcctcttg gccaagattg atagcttgtg cctgtccctg agtcccagtc 480
catcacgagc agctggtttc taagatgcta tttcccgtat aaagcatgag accgtgactt 540
gccagcccca cagagccccg cccttgtcca tcactggcat ctggactcca gcctgggttg 600
gggcaaagag ggaaatgaga tcatgtccta accctgatcc tcttgtccca ccgtgaggct 660
ccggtgcccg tcagtgggca gagcgcacat cgcccacagt ccccgagaag ttggggggag 720
gggtcggcaa ttgaaccggt gcctagagaa ggtggcgcgg ggtaaactgg gaaagtgatg 780
tcgtgtactg gctccgcctt tttcccgagg gtgggggaga accgtatata agtgcagtag 840
tcgccgtgaa cgttcttttt cgcaacgggt ttgccgccag aacacaggtc gcaccatgag 900
caatcaagtc ctttgttgtg ttgtcctgtg tttccttggc gcaaataccg tcgacggcgg 960
gataactcag tcccccaaat acctcttcag aaaagaagga caaaacgtaa cgctttcctg 1020
cgagcagaat cttaaccacg acgccatgta ctggtacagg caagaccctg gacaaggtct 1080
taggctcata tactactctc agattgtcaa tgacttccaa aaaggggaca tagctgaggg 1140
ctactctgtg tcccgagaga agaaggagtc atttcccctg acagtgactt ctgcacaaaa 1200
aaatcccact gcattttatt tgtgtgccag ttcaccgggt gcattgtatg agcaatactt 1260
tggccccggc actagactga cagttacgga ggatctgaaa aacgtcttcc cgccagaggt 1320
ggcagttttc gagcccagtg aggctgaaat ctctcatacc caaaaagcaa cccttgtctg 1380
tctcgccact ggattctatc ccgaccacgt cgaattgagc tggtgggtca atgggaaaga 1440
ggtacatagt ggggtctgta cggatccaca acccccttaag gaacaacctg cccttaacga 1500
ttcacgatac tgcctgtcat cacgactcag ggtatctgct accttttggc agaacccgag 1560
aaatcacttt cggtgccagg ttcagtttta cggacttagc gaaaatgatg aatggacaca 1620
agaccgagca aagcccgtta ctcaaatagt gagcgcggaa gcctgggggc gagcagactg 1680
cggcttcacc tccgaaagtt accagcaagg tgttttgtca gccaccattt tgtatgagat 1740
tttgttgggg aaggcgacac tttacgcggt actggtctct gccttggttc ttatggctat 1800
ggtcaagagg aaagattcca ggggtggctc cggtgccaca aacttctccc tgctcaagca 1860
ggccggagat gtggaagaga accctggccc tatgacctct atcagagctg tctttatatt 1920
tctctggctt caacttgatc tggtgaatgg cgaaaacgtg gaacagcacc cttcaacgtt 1980
gagcgttcag gaaggagatt cagccgtcat caagtgtacg tattccgatt ccgcgtcaaa 2040
ctacttcccg tggtacaaac aggaacttgg caagcgcccc cagctcatta tcgacatcag 2100
aagcaacgta ggagagaaga aggaccaacg catagctgtg actctcaaca aaacagctaa 2160
acatttctcc ctgcacatta cggaaaccca accagaggat tctgccgtat acttttgtgc 2220
tgctactgag gacctcactt tgatctgggg agcgggtacg aagctcataa taaaacccga 2280
tatccaaaac ccggacccag cagtttatca attgagagat agtaagtcca gtgacaaatc 2340

-continued

```
agtttgtttg tttacggatt tcgatagcca gaccaatgtc agtcagtcaa aggacagtga    2400

tgtatacatt acagataaat gtgtacttga catgcgctca atggacttta agtctaactc    2460

tgctgtagct tggtctaaca aaagtgattt tgcgtgtgcc aacgcattta acaacagcat    2520

catacctgaa gacacgttct ttccgagtcc agaaagttcc tgtgacgtga aacttgtaga    2580

aaagagtttc gagaccgaca ctaaccttaa ctttcaaaac ctttcagtga tcggatttag    2640

aatcttgctg ctcaaggtgg cagggttcaa tctgctgatg actctgcgac tgtggagttc    2700

ataacctcga ctgtgccttc tagttgccag ccatctgttg tttgcccctc ccccgtgcct    2760

tccttgaccc tggaaggtgc cactcccact gtcctttcct aataaaatga ggaaattgca    2820

tcgcattgtc tgagtaggtg tcattctatt ctggggggtg gggtggggca ggacagcaag    2880

ggggaggatt gggaagacaa tagcaggcat gctggggatg cggtgggctc tatggcttct    2940

gaggcggaaa gaaccagctg gggctctagg gggtatcccc accagctgag agactctaaa    3000

tccagtgaca agtctgtctg cctattcacc gattttgatt ctcaaacaaa tgtgtcacaa    3060

agtaaggatt ctgatgtgta tatcacagac aaaactgtgc tagacatgag gtctatggac    3120

ttcaagagca acagtgctgt ggcctggagc aacaaatctg actttgcatg tgcaaacgcc    3180

ttcaacaaca gcattattcc agaagacacc ttcttcccca gcccaggtaa gggcagcttt    3240

ggtgccttcg caggctgttt ccttgcttca ggaatggcca ggttctgccc agagctctgg    3300

tcaatgatgt ctaaaactcc tctgattggt ggtctcggcc ttatccattg ccaccaaaac    3360

cctcttttta ctaagaaaca gtgagccttg ttctggcagt ccagagaatg acacgggaaa    3420

aaagcagatg aagagaaggt ggcaggagag ggcacgtggc ccagcctcag tctctccaac    3480

agatctagga acccctagtg atggagttgg ccactccctc tctgcgcgct cgctcgctca    3540

ctgaggccgc ccgggcaaag cccgggcgtc gggcgacctt tggtcgcccg gcctcagtga    3600

gcgagcgagc gcgcagag                                                  3618
```

<210> SEQ ID NO 615
<211> LENGTH: 3825
<212> TYPE: DNA
<213> ORGANISM: Homo sapiens

<400> SEQUENCE: 615

```
cctgcaggca gctgcgcgct cgctcgctca ctgaggccgc ccgggcaaag cccgggcgtc      60

gggcgacctt tggtcgcccg gcctcagtga gcgagcgagc gcgcagagag ggagtggcca     120

actccatcac taggggttcc tagatctaat gtgatagatt tcccaactta atgccaacat     180

accataaacc tcccattctg ctaatgccca gcctaagttg gggagaccac tccagattcc     240

aagatgtaca gtttgctttg ctgggccttt ttcccatgcc tgcctttact ctgccagagt     300

tatattgctg gggttttgaa gaagatccta ttaaataaaa gaataagcag tattattaag     360

tagccctgca tttcaggttt ccttgagtgg caggccaggc ctggccgtga acgttcactg     420

aaatcatggc ctcttggcca agattgatag cttgtgcctg tccctgagtc ccagtccatc     480

acgagcagct ggtttctaag atgctatttc ccgtataaag catgagaccg tgacttgcca     540

gccccacaga gccccgccct tgtccatcac tggcatctgg actccagcct gggttggggc     600

aaagagggaa atgagatcat gtcctaaccc tgatcctctt gtcccacaac agagaaacag     660

gagaatatgg gccaaacagg atatctgtgg taagcagttc ctgccccggc tcagggccaa     720

gaacagttgg aacagcagaa tatgggccaa acaggatatc tgtggtaagc agttcctgcc     780
```

```
ccggctcagg gccaagaaca gatggtcccc agatgcggtc ccgccctcag cagtttctag    840
agaaccatca gatgtttcca gggtgcccca aggacctgaa atgaccctgt gccttatttg    900
aactaaccaa tcagttcgct tctcgcttct gttcgcgcgc ttctgctccc cgagctctat    960
ataagcagag ctcgtttagt gaaccgtcag atcgcctgga gacgccatcc acgctgtttt   1020
gacctccata gaagacaccg actctagagg atcgatcccc cgggctgcag gaattcaagc   1080
gagaagacaa gggcagaaag caccatgagc aatcaagtcc tttgttgtgt tgtcctgtgt   1140
ttccttggcg caaataccgt cgacggcggg ataactcagt cccccaaata cctcttcaga   1200
aaagaaggac aaaacgtaac gctttcctgc gagcagaatc ttaaccacga cgccatgtac   1260
tggtacaggc aagaccctgg acaaggtctt aggctcatat actactctca gattgtcaat   1320
gacttccaaa aaggggacat agctgagggc tactctgtgt cccgagagaa gaaggagtca   1380
tttcccctga cagtgacttc tgcacaaaaa aatcccactg cattttattt gtgtgccagt   1440
tcaccgggtg cattgtatga gcaatacttt ggccccggca ctagactgac agttacggag   1500
gatctgaaaa acgtcttccc gccagaggtg gcagttttcg agcccagtga ggctgaaatc   1560
tctcataccc aaaaagcaac ccttgtctgt ctcgccactg gattctatcc cgaccacgtc   1620
gaattgagct ggtgggtcaa tgggaaagag gtacatagtg ggtctgtac ggatccacaa   1680
ccccttaagg aacaacctgc ccttaacgat tcacgatact gcctgtcatc acgactcagg   1740
gtatctgcta ccttttggca gaacccgaga aatcactttc ggtgccaggt tcagttttac   1800
ggacttagcg aaaatgatga atggacacaa gaccgagcaa agcccgttac tcaaatagtg   1860
agcgcggaag cctgggggcg agcagactgc ggcttcacct ccgaaagtta ccagcaaggt   1920
gttttgtcag ccaccatttt gtatgagatt ttgttgggga aggcgacact ttacgcggta   1980
ctggtctctg ccttggttct tatggctatg gtcaagagga aagattccag ggtggctcc    2040
ggtgccacaa acttctccct gctcaagcag gccggagatg tggaagagaa ccctggccct   2100
atgacctcta tcagagctgt ctttatattt ctctggcttc aacttgatct ggtgaatggc   2160
gaaaacgtgg aacagcaccc ttcaacgttg agcgttcagg aaggagattc agccgtcatc   2220
aagtgtacgt attccgattc cgcgtcaaac tacttcccgt ggtacaaaca ggaacttggc   2280
aagcgccccc agctcattat cgacatcaga agcaacgtag gagagaagaa ggaccaacgc   2340
atagctgtga ctctcaacaa aacagctaaa catttctccc tgcacattac ggaaacccaa   2400
ccagaggatt ctgccgtata cttttgtgct gctactgagg acctcacttt gatctgggga   2460
gcgggtacga agctcataat aaaacccgat atccaaaacc cggacccagc agtttatcaa   2520
ttgagagata gtaagtccag tgacaaatca gtttgtttgt ttacggattt cgatagccag   2580
accaatgtca gtcagtcaaa ggacagtgat gtatacatta cagataaatg tgtacttgac   2640
atgcgctcaa tggactttaa gtctaactct gctgtagctt ggtctaacaa aagtgatttt   2700
gcgtgtgcca acgcatttaa caacagcatc atacctgaag acacgttctt tccgagtcca   2760
gaaagttcct gtgacgtgaa acttgtagaa aagagtttcg agaccgacac taaccttaac   2820
tttcaaaacc tttcagtgat cggatttaga atcttgctgc tcaaggtggc agggttcaat   2880
ctgctgatga ctctgcgact gtggagttca taacctcgac tgtgccttct agttgccagc   2940
catctgttgt ttgcccctcc cccgtgcctt ccttgaccct ggaaggtgcc actcccactg   3000
tcctttccta ataaaatgag gaaattgcat cgcattgtct gagtaggtgt cattctattc   3060
tggggggtgg ggtggggcag gacagcaagg gggaggattg ggaagacaat agcaggcatg   3120
ctggggatgc ggtgggctct atggcttctg aggcggaaag aaccagctgg ggctctaggg   3180
```

```
ggtatcccca ccagctgaga gactctaaat ccagtgacaa gtctgtctgc ctattcaccg   3240

attttgattc tcaaacaaat gtgtcacaaa gtaaggattc tgatgtgtat atcacagaca   3300

aaactgtgct agacatgagg tctatggact tcaagagcaa cagtgctgtg gcctggagca   3360

acaaatctga ctttgcatgt gcaaacgcct tcaacaacag cattattcca gaagacacct   3420

tcttccccag cccaggtaag ggcagctttg gtgccttcgc aggctgtttc cttgcttcag   3480

gaatggccag gttctgccca gagctctggt caatgatgtc taaaactcct ctgattggtg   3540

gtctcggcct tatccattgc caccaaaacc ctctttttac taagaaacag tgagccttgt   3600

tctggcagtc cagagaatga cacgggaaaa aagcagatga agagaaggtg gcaggagagg   3660

gcacgtggcc cagcctcagt ctctccaaca gatctaggaa cccctagtga tggagttggc   3720

cactccctct ctgcgcgctc gctcgctcac tgaggccggg cgaccaaagg tcgcccgacg   3780

cccgggcggc ctcagtgagc gagcgagcgc gcagctgcct gcagg                   3825
```

<210> SEQ ID NO 616
<211> LENGTH: 3794
<212> TYPE: DNA
<213> ORGANISM: Homo sapiens

<400> SEQUENCE: 616

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tagatctaat gtgatagatt tcccaactta atgccaacat    180

accataaacc tcccattctg ctaatgccca gcctaagttg gggagaccac tccagattcc    240

aagatgtaca gtttgctttg ctgggccttt ttcccatgcc tgcctttact ctgccagagt    300

tatattgctg ggttttgaa gaagatccta ttaaataaaa gaataagcag tattattaag    360

tagccctgca tttcaggttt ccttgagtgg caggccaggc ctggccgtga acgttcactg    420

aaatcatggc ctcttggcca agattgatag cttgtgcctg tccctgagtc ccagtccatc    480

acgagcagct ggtttctaag atgctatttc ccgtataaag catgagaccg tgacttgcca    540

gccccacaga gccccgccct tgtccatcac tggcatctgg actccagcct gggttggggc    600

aaagagggaa atgagatcat gtcctaaccc tgatcctctt gtcccacgat ccgaacagag    660

agacagcaga atatgggcca aacaggatat ctgtggtaag cagttcctgc cccggctcag    720

ggccaagaac agttggaaca gcagaatatg ggccaaacag gatatctgtg gtaagcagtt    780

cctgccccgg ctcagggcca agaacagatg gtccccagat gcggtcccgc cctcagcagt    840

ttctagagaa ccatcagatg tttccagggt gccccaagga cctgaaatga ccctgtgcct    900

tatttgaact aaccaatcag ttcgcttctc gcttctgttc gcgcgcttct gctccccgag    960

ctctatataa gcagagctcg tttagtgaac cgtcagatcg cctggagacg ccatccacgc   1020

tgttttgacc tccatagaag acaccgactc tagaggatcc accggtcgcc accatgagca   1080

atcaagtcct ttgttgtgtt gtcctgtgtt tccttggcgc aaataccgtc gacggcggga   1140

taactcagtc ccccaaatac ctcttcagaa aagaaggaca aaacgtaacg ctttcctgcg   1200

agcagaatct taaccacgac gccatgtact ggtacaggca agaccctgga caaggtctta   1260

ggctcatata ctactctcag attgtcaatg acttccaaaa aggggacata gctgagggct   1320

actctgtgtc ccgagagaag aaggagtcat ttcccctgac agtgacttct gcacaaaaaa   1380

atcccactgc attttatttg tgtgccagtt caccgggtgc attgtatgag caatactttg   1440
```

-continued

```
gccccggcac tagactgaca gttacggagg atctgaaaaa cgtcttcccg ccagaggtgg   1500
cagttttcga gcccagtgag gctgaaatct ctcataccca aaaagcaacc cttgtctgtc   1560
tcgccactgg attctatccc gaccacgtcg aattgagctg gtgggtcaat gggaaagagg   1620
tacatagtgg ggtctgtacg gatccacaac cccttaagga acaacctgcc cttaacgatt   1680
cacgatactg cctgtcatca cgactcaggg tatctgctac cttttggcag aacccgagaa   1740
atcactttcg gtgccaggtt cagttttacg gacttagcga aaatgatgaa tggacacaag   1800
accgagcaaa gcccgttact caaatagtga gcgcggaagc ctgggggcga gcagactgcg   1860
gcttcacctc cgaaagttac cagcaaggtg ttttgtcagc caccattttg tatgagattt   1920
tgttggggaa ggcgacactt tacgcggtac tggtctctgc cttggttctt atggctatgg   1980
tcaagaggaa agattccagg ggtggctccg gtgccacaaa cttctccctg ctcaagcagg   2040
ccggagatgt ggaagagaac cctggcccta tgacctctat cagagctgtc tttatatttc   2100
tctggcttca acttgatctg gtgaatggcg aaaacgtgga acagcaccct tcaacgttga   2160
gcgttcagga aggagattca gccgtcatca agtgtacgta ttccgattcc gcgtcaaact   2220
acttcccgtg gtacaaacag gaacttggca agcgccccca gctcattatc gacatcagaa   2280
gcaacgtagg agagaagaag gaccaacgca tagctgtgac tctcaacaaa acagctaaac   2340
atttctccct gcacattacg gaaacccaac cagaggattc tgccgtatac ttttgtgctg   2400
ctactgagga cctcactttg atctggggag cgggtacgaa gctcataata aaacccgata   2460
tccaaaaccc ggacccagca gtttatcaat tgagagatag taagtccagt gacaaatcag   2520
tttgtttgtt tacggatttc gatagccaga ccaatgtcag tcagtcaaag gacagtgatg   2580
tatacattac agataaatgt gtacttgaca tgcgctcaat ggactttaag tctaactctg   2640
ctgtagcttg gtctaacaaa agtgattttg cgtgtgccaa cgcatttaac aacagcatca   2700
tacctgaaga cacgttcttt ccgagtccag aaagttcctg tgacgtgaaa cttgtagaaa   2760
agagtttcga gaccgacact aaccttaact ttcaaaacct ttcagtgatc ggatttagaa   2820
tcttgctgct caaggtggca gggttcaatc tgctgatgac tctgcgactg tggagttcat   2880
aacctcgact gtgccttcta gttgccagcc atctgttgtt tgcccctccc ccgtgccttc   2940
cttgaccctg gaaggtgcca ctcccactgt cctttcctaa taaaatgagg aaattgcatc   3000
gcattgtctg agtaggtgtc attctattct ggggggtggg gtggggcagg acagcaaggg   3060
ggaggattgg gaagacaata gcaggcatgc tggggatgcg gtgggctcta tggcttctga   3120
ggcggaaaga accagctggg gctctagggg gtatccccac cagctgagag actctaaatc   3180
cagtgacaag tctgtctgcc tattcaccga ttttgattct caaacaaatg tgtcacaaag   3240
taaggattct gatgtgtata tcacagacaa aactgtgcta gacatgaggt ctatggactt   3300
caagagcaac agtgctgtgg cctggagcaa caaatctgac tttgcatgtg caaacgcctt   3360
caacaacagc attattccag aagacacctt cttccccagc ccaggtaagg gcagctttgg   3420
tgccttcgca ggctgtttcc ttgcttcagg aatggccagg ttctgcccag agctctggtc   3480
aatgatgtct aaaactcctc tgattggtgg tctcggcctt atccattgcc accaaaaccc   3540
tctttttact aagaaacagt gagccttgtt ctggcagtcc agagaatgac acgggaaaaa   3600
agcagatgaa gagaaggtgg caggagaggg cacgtggccc agcctcagtc tctccaacag   3660
atctaggaac ccctagtgat ggagttggcc actccctctc tgcgcgctcg ctcgctcact   3720
gaggccgggc gaccaaaggt cgcccgacgc ccgggcggcc tcagtgagcg agcgagcgcg   3780
cagctgcctg cagg                                                     3794
```

<210> SEQ ID NO 617
<211> LENGTH: 3893
<212> TYPE: DNA
<213> ORGANISM: Homo sapiens

<400> SEQUENCE: 617
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct agatctaatg tgatagattt cccaacttaa tgccaacata ccataaacct 180
cccattctgc taatgcccag cctaagttgg ggagaccact ccagattcca agatgtacag 240
tttgctttgc tgggcctttt tcccatgcct gcctttactc tgccagagtt atattgctgg 300
ggttttgaag aagatcctat taaataaaag aataagcagt attattaagt agccctgcat 360
ttcaggtttc cttgagtggc aggccaggcc tggccgtgaa cgttcactga aatcatggcc 420
tcttggccaa gattgatagc ttgtgcctgt ccctgagtcc cagtccatca cgagcagctg 480
gtttctaaga tgctatttcc cgtataaagc atgagaccgt gacttgccag ccccacagag 540
ccccgccctt gtccatcact ggcatctgga ctccagcctg ggttggggca aagagggaaa 600
tgagatcatg tcctaaccct gatcctcttg tcccacgggt aggggaggcg cttttcccaa 660
ggcagtctgg agcatgcgct ttagcagccc cgctgggcac ttggcgctac acaagtggcc 720
tctggcctcg cacacattcc acatccaccg gtaggcgcca accggctccg ttctttggtg 780
gccccttcgc gccaccttct actcctcccc tagtcaggaa gttccccccc gccccgcagc 840
tcgcgtcgtg caggacgtga caaatggaag tagcacgtct cactagtctc gtgcagatgg 900
acagcaccgc tgagcaatgg aagcgggtag gcctttgggg cagcggccaa tagcagcttt 960
gctccttcgc tttctgggct cagaggctgg gaaggggtgg gtccgggggc gggctcaggg 1020
gcgggctcag gggcggggcg ggcgcccgaa ggtcctccgg aggcccggca ttctgcacgc 1080
ttcaaaagcg cacgtctgcc gcgctgttct cctcttcctc atctccgggc ctttcgcgaa 1140
gcaccatgag caatcaagtc ctttgttgtg ttgtcctgtg tttccttggc gcaaataccg 1200
tcgacggcgg gataactcag tcccccaaat acctcttcag aaaagaagga caaaacgtaa 1260
cgctttcctg cgagcagaat cttaaccacg acgccatgta ctggtacagg caagaccctg 1320
gacaaggtct taggctcata tactactctc agattgtcaa tgacttccaa aaaggggaca 1380
tagctgaggg ctactctgtg tcccgagaga agaaggagtc atttcccctg acagtgactt 1440
ctgcacaaaa aaatcccact gcattttatt tgtgtgccag ttcaccgggt gcattgtatg 1500
agcaatactt tggccccggc actagactga cagttacgga ggatctgaaa aacgtcttcc 1560
cgccagaggt ggcagttttc gagcccagtg aggctgaaat ctctcatacc caaaaagcaa 1620
cccttgtctg tctcgccact ggattctatc ccgaccacgt cgaattgagc tggtgggtca 1680
atgggaaaga ggtacatagt ggggtctgta cggatccaca accccttaag gaacaacctg 1740
cccttaacga ttcacgatac tgcctgtcat cacgactcag ggtatctgct accttttggc 1800
agaacccgag aaatcacttt cggtgccagg ttcagtttta cggacttagc gaaaatgatg 1860
aatggacaca agaccgagca aagcccgtta ctcaaatagt gagcgcggaa gcctgggggc 1920
gagcagactg cggcttcacc tccgaaagtt accagcaagg tgttttgtca gccaccattt 1980
tgtatgagat tttgttgggg aaggcgacac tttacgcggt actggtctct gccttggttc 2040
ttatggctat ggtcaagagg aaagattcca ggggtggctc cggtgccaca aacttctccc 2100
tgctcaagca ggccggagat gtggaagaga accctggccc tatgacctct atcagagctg 2160
tctttatatt tctctggctt caacttgatc tggtgaatgg cgaaaacgtg gaacagcacc 2220
cttcaacgtt gagcgttcag gaaggagatt cagccgtcat caagtgtacg tattccgatt 2280
ccgcgtcaaa ctacttcccg tggtacaaac aggaacttgg caagcgcccc cagctcatta 2340
tcgacatcag aagcaacgta ggagagaaga aggaccaacg catagctgtg actctcaaca 2400
aaacagctaa acatttctcc ctgcacatta cggaaaccca accagaggat tctgccgtat 2460
acttttgtgc tgctactgag gacctcactt tgatctgggg agcgggtacg aagctcataa 2520
taaaacccga tatccaaaac ccggacccag cagtttatca attgagagat agtaagtcca 2580
gtgacaaatc agtttgtttg tttacggatt tcgatagcca gaccaatgtc agtcagtcaa 2640
aggacagtga tgtatacatt acagataaat gtgtacttga catgcgctca atggacttta 2700
agtctaactc tgctgtagct tggtctaaca aaagtgattt tgcgtgtgcc aacgcattta 2760
acaacagcat catacctgaa gacacgttct ttccgagtcc agaaagttcc tgtgacgtga 2820
aacttgtaga aaagagtttc gagaccgaca ctaaccttaa ctttcaaaac ctttcagtga 2880
tcggatttag aatcttgctg ctcaaggtgg cagggttcaa tctgctgatg actctgcgac 2940
tgtggagttc ataacctcga ctgtgccttc tagttgccag ccatctgttg tttgcccctc 3000
ccccgtgcct tccttgaccc tggaaggtgc cactcccact gtcctttcct aataaaatga 3060
ggaaattgca tcgcattgtc tgagtaggtg tcattctatt ctggggggtg gggtggggca 3120
ggacagcaag ggggaggatt gggaagacaa tagcaggcat gctggggatg cggtgggctc 3180
tatggcttct gaggcggaaa gaaccagctg gggctctagg gggtatcccc accagctgag 3240
agactctaaa tccagtgaca agtctgtctg cctattcacc gattttgatt ctcaaacaaa 3300
tgtgtcacaa agtaaggatt ctgatgtgta tatcacagac aaaactgtgc tagacatgag 3360
gtctatggac ttcaagagca acagtgctgt ggcctggagc aacaaatctg actttgcatg 3420
tgcaaacgcc ttcaacaaca gcattattcc agaagacacc ttcttcccca gcccaggtaa 3480
gggcagcttt ggtgccttcg caggctgttt ccttgcttca ggaatggcca ggttctgccc 3540
agagctctgg tcaatgatgt ctaaaactcc tctgattggt ggtctcggcc ttatccattg 3600
ccaccaaaac cctcttttta ctaagaaaca gtgagccttg ttctggcagt ccagagaatg 3660
acacgggaaa aaagcagatg aagagaaggt ggcaggagag ggcacgtggc ccagcctcag 3720
tctctccaac agatctagga acccctagtg atggagttgg ccactccctc tctgcgcgct 3780
cgctcgctca ctgaggccgg gcgaccaaag gtcgcccgac gcccgggctt tgcccgggcg 3840
gcctcagtga gcgagcgagc gcgcagctgc ctgcaggaag cttggtgtaa tca 3893

<210> SEQ ID NO 618
<211> LENGTH: 3857
<212> TYPE: DNA
<213> ORGANISM: Homo sapiens

<400> SEQUENCE: 618
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc taatgtgata gatttcccaa cttaatgcca 180
acataccata aacctcccat tctgctaatg cccagcctaa gttggggaga ccactccaga 240
ttccaagatg tacagtttgc tttgctgggc ctttttccca tgcctgcctt tactctgcca 300
gagttatatt gctggggttt tgaagaagat cctattaaat aaaagaataa gcagtattat 360

```
taagtagccc tgcatttcag gtttccttga gtggcaggcc aggcctggcc gtgaacgttc    420
actgaaatca tggcctcttg gccaagattg atagcttgtg cctgtccctg agtcccagtc    480
catcacgagc agctggtttc taagatgcta tttcccgtat aaagcatgag accgtgactt    540
gccagcccca cagagccccg cccttgtcca tcactggcat ctggactcca gcctgggttg    600
gggcaaagag ggaaatgaga tcatgtccta accctgatcc tcttgtccca caacagagaa    660
acaggagaat atgggccaaa caggatatct gtggtaagca gttcctgccc cggctcaggg    720
ccaagaacag ttggaacagc agaatatggg ccaaacagga tatctgtggt aagcagttcc    780
tgccccggct cagggccaag aacagatggt ccccagatgc ggtcccgccc tcagcagttt    840
ctagagaacc atcagatgtt tccagggtgc cccaaggacc tgaaatgacc ctgtgcctta    900
tttgaactaa ccaatcagtt cgcttctcgc ttctgttcgc gcgcttctgc tccccgagct    960
ctatataagc agagctcgtt tagtgaaccg tcagatcgcc tggagacgcc atccacgctg   1020
ttttgacctc catagaagac accgactcta gaggatcgat cccccgggct gcaggaattc   1080
aagcgagaag acaagggcag aaagcaccat gagcaatcaa gtcctttgtt gtgttgtcct   1140
gtgtttcctt ggcgcaaata ccgtcgacgg cgggataact cagtccccca aatacctctt   1200
cagaaaagaa ggacaaaacg taacgctttc ctgcgagcag aatcttaacc acgacgccat   1260
gtactggtac aggcaagacc ctggacaagg tcttaggctc atatactact ctcagattgt   1320
caatgacttc caaaaagggg acatagctga gggctactct gtgtcccgag agaagaagga   1380
gtcatttccc ctgacagtga cttctgcaca aaaaaatccc actgcatttt atttgtgtgc   1440
cagttcaccg ggtgcattgt atgagcaata ctttggcccc ggcactagac tgacagttac   1500
ggaggatctg aaaaacgtct tcccgccaga ggtggcagtt ttcgagccca gtgaggctga   1560
aatctctcat acccaaaaag caacccttgt ctgtctcgcc actggattct atcccgacca   1620
cgtcgaattg agctggtggg tcaatgggaa agaggtacat agtggggtct gtacggatcc   1680
acaacccctt aaggaacaac ctgcccttaa cgattcacga tactgcctgt catcacgact   1740
cagggtatct gctacctttt ggcagaaccc gagaaatcac tttcggtgcc aggttcagtt   1800
ttacggactt agcgaaaatg atgaatggac acaagaccga gcaaagcccg ttactcaaat   1860
agtgagcgcg gaagcctggg ggcgagcaga ctgcggcttc acctccgaaa gttaccagca   1920
aggtgttttg tcagccacca ttttgtatga gattttgttg gggaaggcga cactttacgc   1980
ggtactggtc tctgccttgg ttcttatggc tatggtcaag aggaaagatt ccaggggtgg   2040
ctccggtgcc acaaacttct ccctgctcaa gcaggccgga gatgtggaag agaaccctgg   2100
ccctatgacc tctatcagag ctgtctttat atttctctgg cttcaacttg atctggtgaa   2160
tggcgaaaac gtggaacagc acccttcaac gttgagcgtt caggaaggag attcagccgt   2220
catcaagtgt acgtattccg attccgcgtc aaactacttc ccgtggtaca aacaggaact   2280
tggcaagcgc ccccagctca ttatcgacat cagaagcaac gtaggagaga agaaggacca   2340
acgcatagct gtgactctca acaaaaacagc taaacatttc tccctgcaca ttacggaaac   2400
ccaaccagag gattctgccg tatacttttg tgctgctact gaggacctca ctttgatctg   2460
gggagcgggt acgaagctca taataaaacc cgatatccaa aacccggacc cagcagttta   2520
tcaattgaga gatagtaagt ccagtgacaa atcagtttgt ttgtttacgg atttcgatag   2580
ccagaccaat gtcagtcagt caaaggacag tgatgtatac attacagata aatgtgtact   2640
tgacatgcgc tcaatggact ttaagtctaa ctctgctgta gcttggtcta acaaaagtga   2700
```

ttttgcgtgt gccaacgcat ttaacaacag catcatacct gaagacacgt tctttccgag 2760
tccagaaagt tcctgtgacg tgaaacttgt agaaaagagt ttcgagaccg acactaacct 2820
taactttcaa aacctttcag tgatcggatt tagaatcttg ctgctcaagg tggcagggtt 2880
caatctgctg atgactctgc gactgtggag ttcataacct cgactgtgcc ttctagttgc 2940
cagccatctg ttgtttgccc ctcccccgtg ccttccttga ccctggaagg tgccactccc 3000
actgtccttt cctaataaaa tgaggaaatt gcatcgcatt gtctgagtag gtgtcattct 3060
attctggggg gtggggtggg gcaggacagc aagggggagg attgggaaga caatagcagg 3120
catgctgggg atgcggtggg ctctatggct tctgaggcgg aaagaaccag ctggggctct 3180
agggggtatc cccaccagct gagagactct aaatccagtg acaagtctgt ctgcctattc 3240
accgattttg attctcaaac aaatgtgtca caaagtaagg attctgatgt gtatatcaca 3300
gacaaaactg tgctagacat gaggtctatg gacttcaaga gcaacagtgc tgtggcctgg 3360
agcaacaaat ctgactttgc atgtgcaaac gccttcaaca acagcattat tccagaagac 3420
accttcttcc ccagcccagg taagggcagc tttggtgcct tcgcaggctg tttccttgct 3480
tcaggaatgg ccaggttctg cccagagctc tggtcaatga tgtctaaaac tcctctgatt 3540
ggtggtctcg gccttatcca ttgccaccaa aaccctcttt ttactaagaa acagtgagcc 3600
ttgttctggc agtccagaga atgacacggg aaaaaagcag atgaagagaa ggtggcagga 3660
gagggcacgt ggcccagcct cagtctctcc aacagatcta ggaaccccta gtgatggagt 3720
tggccactcc ctctctgcgc gctcgctcgc tcactgaggc cgcccgggca aagcccgggc 3780
gtcgggcgac ctttggtcgc ccggcctcag tgagcgagcg agcgcgcaga gagggagtgg 3840
ccaaacgcgt ggtgtaa 3857

<210> SEQ ID NO 619
<211> LENGTH: 3891
<212> TYPE: DNA
<213> ORGANISM: Homo sapiens

<400> SEQUENCE: 619
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc taatgtgata gatttcccaa cttaatgcca 180
acataccata aacctcccat tctgctaatg cccagcctaa gttggggaga ccactccaga 240
ttccaagatg tacagtttgc tttgctgggc ctttttccca tgcctgcctt tactctgcca 300
gagttatatt gctggggttt tgaagaagat cctattaaat aaaagaataa gcagtattat 360
taagtagccc tgcatttcag gtttccttga gtggcaggcc aggcctggcc gtgaacgttc 420
actgaaatca tggcctcttg gccaagattg atagcttgtg cctgtccctg agtcccagtc 480
catcacgagc agctggtttc taagatgcta tttcccgtat aaagcatgag accgtgactt 540
gccagcccca cagagccccg cccttgtcca tcactggcat ctggactcca gcctgggttg 600
gggcaaagag ggaaatgaga tcatgtccta accctgatcc tcttgtccca cgggtagggg 660
aggcgctttt cccaaggcag tctggagcat gcgctttagc agccccgctg ggcacttggc 720
gctacacaag tggcctctgg cctcgcacac attccacatc caccggtagg cgccaaccgg 780
ctccgttctt tggtggcccc ttcgcgccac cttctactcc tcccctagtc aggaagttcc 840
cccccgcccc gcagctcgcg tcgtgcagga cgtgacaaat ggaagtagca cgtctcacta 900
gtctcgtgca gatggacagc accgctgagc aatggaagcg ggtaggcctt tggggcagcg 960
gccaatagca gctttgctcc ttcgctttct gggctcagag gctgggaagg ggtgggtccg 1020
ggggcgggct caggggcggg ctcaggggcg gggcgggcgc ccgaaggtcc tccggaggcc 1080
cggcattctg cacgcttcaa aagcgcacgt ctgccgcgct gttctcctct tcctcatctc 1140
cgggcctttc gcgaagcacc atgagcaatc aagtcctttg ttgtgttgtc ctgtgtttcc 1200
ttggcgcaaa taccgtcgac ggcgggataa ctcagtcccc caaatacctc ttcagaaaag 1260
aaggacaaaa cgtaacgctt tcctgcgagc agaatcttaa ccacgacgcc atgtactggt 1320
acaggcaaga ccctggacaa ggtcttaggc tcatatacta ctctcagatt gtcaatgact 1380
tccaaaaagg ggacatagct gagggctact ctgtgtcccg agagaagaag gagtcatttc 1440
ccctgacagt gacttctgca caaaaaaatc ccactgcatt ttatttgtgt gccagttcac 1500
cgggtgcatt gtatgagcaa tactttggcc ccggcactag actgacagtt acggaggatc 1560
tgaaaaacgt cttcccgcca gaggtggcag ttttcgagcc cagtgaggct gaaatctctc 1620
atacccaaaa agcaaccctt gtctgtctcg ccactggatt ctatcccgac cacgtcgaat 1680
tgagctggtg ggtcaatggg aaagaggtac atagtggggt ctgtacggat ccacaacccc 1740
ttaaggaaca acctgccctt aacgattcac gatactgcct gtcatcacga ctcagggtat 1800
ctgctacctt ttggcagaac ccgagaaatc actttcggtg ccaggttcag ttttacggac 1860
ttagcgaaaa tgatgaatgg acacaagacc gagcaaagcc cgttactcaa atagtgagcg 1920
cggaagcctg gggcgagca gactgcggct tcacctccga aagttaccag caaggtgttt 1980
tgtcagccac cattttgtat gagattttgt tggggaaggc gacactttac gcggtactgg 2040
tctctgcctt ggttcttatg gctatggtca agaggaaaga ttccaggggt ggctccggtg 2100
ccacaaactt ctccctgctc aagcaggccg gagatgtgga agagaaccct ggccctatga 2160
cctctatcag agctgtcttt atatttctct ggcttcaact tgatctggtg aatggcgaaa 2220
acgtggaaca gcacccttca acgttgagcg ttcaggaagg agattcagcc gtcatcaagt 2280
gtacgtattc cgattccgcg tcaaactact tcccgtggta caaacaggaa cttggcaagc 2340
gcccccagct cattatcgac atcagaagca acgtaggaga gaagaaggac caacgcatag 2400
ctgtgactct caacaaaaca gctaaacatt tctccctgca cattacggaa acccaaccag 2460
aggattctgc cgtatacttt tgtgctgcta ctgaggacct cactttgatc tggggagcgg 2520
gtacgaagct cataataaaa cccgatatcc aaaacccgga cccagcagtt tatcaattga 2580
gagatagtaa gtccagtgac aaatcagttt gtttgtttac ggatttcgat agccagacca 2640
atgtcagtca gtcaaaggac agtgatgtat acattacaga taaatgtgta cttgacatgc 2700
gctcaatgga ctttaagtct aactctgctg tagcttggtc taacaaaagt gattttgcgt 2760
gtgccaacgc atttaacaac agcatcatac ctgaagacac gttctttccg agtccagaaa 2820
gttcctgtga cgtgaaactt gtagaaaaga gtttcgagac cgacactaac cttaactttc 2880
aaaacctttc agtgatcgga tttagaatct tgctgctcaa ggtggcaggg ttcaatctgc 2940
tgatgactct gcgactgtgg agttcataac ctcgactgtg ccttctagtt gccagccatc 3000
tgttgtttgc ccctcccccg tgccttcctt gaccctggaa ggtgccactc ccactgtcct 3060
ttcctaataa aatgaggaaa ttgcatcgca ttgtctgagt aggtgtcatt ctattctggg 3120
gggtggggtg gggcaggaca gcaaggggga ggattgggaa gacaatagca ggcatgctgg 3180
ggatgcggtg ggctctatgg cttctgaggc ggaaagaacc agctggggct ctagggggta 3240
tccccaccag ctgagagact ctaaatccag tgacaagtct gtctgcctat tcaccgattt 3300
tgattctcaa acaaatgtgt cacaaagtaa ggattctgat gtgtatatca cagacaaaac 3360
tgtgctagac atgaggtcta tggacttcaa gagcaacagt gctgtggcct ggagcaacaa 3420
atctgacttt gcatgtgcaa acgccttcaa caacagcatt attccagaag acaccttctt 3480
ccccagccca ggtaagggca gctttggtgc cttcgcaggc tgtttccttg cttcaggaat 3540
ggccaggttc tgcccagagc tctggtcaat gatgtctaaa actcctctga ttggtggtct 3600
cggccttatc cattgccacc aaaaccctct ttttactaag aaacagtgag ccttgttctg 3660
gcagtccaga gaatgacacg ggaaaaaagc agatgaagag aaggtggcag gagagggcac 3720
gtggcccagc ctcagtctct ccaacagatc taggaacccc tagtgatgga gttggccact 3780
ccctctctgc gcgctcgctc gctcactgag gccgcccggg caaagcccgg gcgtcgggcg 3840
acctttggtc gcccggcctc agtgagcgag cgagcgcgca gagagggagt g 3891

<210> SEQ ID NO 620
<211> LENGTH: 3820
<212> TYPE: DNA
<213> ORGANISM: Homo sapiens

<400> SEQUENCE: 620
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc taatgtgata gatttcccaa cttaatgcca 180
acataccata aacctcccat tctgctaatg cccagcctaa gttggggaga ccactccaga 240
ttccaagatg tacagtttgc tttgctgggc ctttttccca tgcctgcctt tactctgcca 300
gagttatatt gctggggttt tgaagaagat cctattaaat aaaagaataa gcagtattat 360
taagtagccc tgcatttcag gtttccttga gtggcaggcc aggcctggcc gtgaacgttc 420
actgaaatca tggcctcttg gccaagattg atagcttgtg cctgtccctg agtcccagtc 480
catcacgagc agctggtttc taagatgcta tttcccgtat aaagcatgag accgtgactt 540
gccagcccca cagagccccg cccttgtcca tcactggcat ctggactcca gcctgggttg 600
gggcaaagag ggaaatgaga tcatgtccta accctgatcc tcttgtccca cgatccgaac 660
agagagacag cagaatatgg gccaaacagg atatctgtgg taagcagttc ctgccccggc 720
tcagggccaa gaacagttgg aacagcagaa tatgggccaa acaggatatc tgtggtaagc 780
agttcctgcc ccggctcagg gccaagaaca gatggtcccc agatgcggtc ccgccctcag 840
cagtttctag agaaccatca gatgtttcca gggtgcccca aggacctgaa atgaccctgt 900
gccttatttg aactaaccaa tcagttcgct tctcgcttct gttcgcgcgc ttctgctccc 960
cgagctctat ataagcagag ctcgtttagt gaaccgtcag atcgcctgga gacgccatcc 1020
acgctgtttt gacctccata gaagacaccg actctagagg atccaccggt cgccaccatg 1080
agcaatcaag tcctttgttg tgttgtcctg tgtttccttg gcgcaaatac cgtcgacggc 1140
gggataactc agtcccccaa atacctcttc agaaaagaag gacaaaacgt aacgctttcc 1200
tgcgagcaga atcttaacca cgacgccatg tactggtaca ggcaagaccc tggacaaggt 1260
cttaggctca tatactactc tcagattgtc aatgacttcc aaaaagggga catagctgag 1320
ggctactctg tgtcccgaga gaagaaggag tcatttcccc tgacagtgac ttctgcacaa 1380
aaaaatccca ctgcatttta tttgtgtgcc agttcaccgg gtgcattgta tgagcaatac 1440
tttggccccg gcactagact gacagttacg gaggatctga aaaacgtctt cccgccagag 1500
gtggcagttt tcgagcccag tgaggctgaa atctctcata cccaaaaagc aacccttgtc 1560

```
tgtctcgcca ctggattcta tcccgaccac gtcgaattga gctggtgggt caatgggaaa   1620
gaggtacata gtggggtctg tacggatcca caacccctta aggaacaacc tgcccttaac   1680
gattcacgat actgcctgtc atcacgactc agggtatctg ctaccttttg gcagaacccg   1740
agaaatcact ttcggtgcca ggttcagttt tacggactta gcgaaaatga tgaatggaca   1800
caagaccgag caaagcccgt tactcaaata gtgagcgcgg aagcctgggg gcgagcagac   1860
tgcggcttca cctccgaaag ttaccagcaa ggtgttttgt cagccaccat tttgtatgag   1920
attttgttgg ggaaggcgac actttacgcg gtactggtct ctgccttggt tcttatggct   1980
atggtcaaga ggaaagattc caggggtggc tccggtgcca caaacttctc cctgctcaag   2040
caggccggag atgtggaaga gaaccctggc cctatgacct ctatcagagc tgtctttata   2100
tttctctggc ttcaacttga tctggtgaat ggcgaaaacg tggaacagca cccttcaacg   2160
ttgagcgttc aggaaggaga ttcagccgtc atcaagtgta cgtattccga ttccgcgtca   2220
aactacttcc cgtggtacaa acaggaactt ggcaagcgcc cccagctcat tatcgacatc   2280
agaagcaacg taggagagaa gaaggaccaa cgcatagctg tgactctcaa caaaacagct   2340
aaacatttct ccctgcacat tacggaaacc caaccagagg attctgccgt atacttttgt   2400
gctgctactg aggacctcac tttgatctgg ggagcgggta cgaagctcat aataaaaccc   2460
gatatccaaa acccggaccc agcagtttat caattgagag atagtaagtc cagtgacaaa   2520
tcagtttgtt tgtttacgga tttcgatagc cagaccaatg tcagtcagtc aaaggacagt   2580
gatgtataca ttacagataa atgtgtactt gacatgcgct caatggactt taagtctaac   2640
tctgctgtag cttggtctaa caaaagtgat tttgcgtgtg ccaacgcatt taacaacagc   2700
atcataccctg aagacacgtt ctttccgagt ccagaaagtt cctgtgacgt gaaacttgta   2760
gaaaagagtt tcgagaccga cactaacctt aactttcaaa acctttcagt gatcggattt   2820
agaatcttgc tgctcaaggt ggcagggttc aatctgctga tgactctgcg actgtggagt   2880
tcataacctc gactgtgcct tctagttgcc agccatctgt tgtttgcccc tcccccgtgc   2940
cttccttgac cctggaaggt gccactccca ctgtcctttc ctaataaaat gaggaaattg   3000
catcgcattg tctgagtagg tgtcattcta ttctgggggg tggggtgggg caggacagca   3060
agggggagga ttgggaagac aatagcaggc atgctgggga tgcggtgggc tctatggctt   3120
ctgaggcgga aagaaccagc tggggctcta gggggtatcc ccaccagctg agagactcta   3180
aatccagtga caagtctgtc tgcctattca ccgattttga ttctcaaaca aatgtgtcac   3240
aaagtaagga ttctgatgtg tatatcacag acaaaactgt gctagacatg aggtctatgg   3300
acttcaagag caacagtgct gtggcctgga gcaacaaatc tgactttgca tgtgcaaacg   3360
ccttcaacaa cagcattatt ccagaagaca ccttcttccc cagcccaggt aagggcagct   3420
ttggtgcctt cgcaggctgt ttccttgctt caggaatggc caggttctgc ccagagctct   3480
ggtcaatgat gtctaaaact cctctgattg gtggtctcgg ccttatccat tgccaccaaa   3540
accctctttt tactaagaaa cagtgagcct tgttctggca gtccagagaa tgacacggga   3600
aaaaagcaga tgaagagaag gtggcaggag agggcacgtg gcccagcctc agtctctcca   3660
acagatctag gaacccctag tgatggagtt ggccactccc tctctgcgcg ctcgctcgct   3720
cactgaggcc gcccgggcaa agcccgggcg tcgggcgacc tttggtcgcc cggcctcagt   3780
gagcgagcga gcgcgcagag agggagtggc caaacgcgtg                          3820
```

<210> SEQ ID NO 621

<211> LENGTH: 3638
<212> TYPE: DNA
<213> ORGANISM: Homo sapiens

<400> SEQUENCE: 621
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tcaatgagag agcaatctcc tggtaatgtg 180
atagatttcc caacttaatg ccaacatacc ataaacctcc cattctgcta atgcccagcc 240
taagttgggg agaccactcc agattccaag atgtacagtt tgctttgctg ggcctttttc 300
ccatgcctgc ctttactctg ccagagttat attgctgggg ttttgaagaa gatcctatta 360
aataaaagaa taagcagtat tattaagtag ccctgcattt caggtttcct tgagtggcag 420
gccaggcctg gccgtgaacg ttcactgaaa tcatggcctc ttggccaaga ttgatagctt 480
gtgcctgtcc ctgagtccca gtccatcacg agcagctggt ttctaagatg ctatttcccg 540
tataaagcat gagaccgtga cttgccagcc ccacagagcc ccgcccttgt ccatcactgg 600
catctggact ccagcctggg ttggggcaaa gagggaaatg agatcatgtc cgagtaattc 660
atacaaaagg actcgcccct gccttgggga atcccaggga ccgtcgttaa actcccacta 720
acgtagaacc cagagatcgc tgcgttcccg ccccctcacc cgcccgctct cgtcatcact 780
gaggtggaga agagcatgcg tgaggctccg gtgcccgtca gtgggcagag cgcacatcgc 840
ccacagtccc cgagaagttg gggggagggg tcggcaattg aaccggtgcc tagagaaggt 900
ggcgcggggt aaactgggaa agtgatgtcg tgtactggct ccgccttttt cccgagggtg 960
ggggagaacc gtatataagt gcagtagtcg ccgtgaacgt tctttttcgc aacgggtttg 1020
ccgccagaac acaggtaagt gccgtgtgtg gttcccgcgg gcctggcctc tttacgggtt 1080
atggcccttg cgtgccttga attacttcca cgcccctggc tgcagtacgt gattcttgat 1140
cccgagcttc gggttggaag tgggtgggag agttcgaggc cttgcgctta aggagcccct 1200
tcgcctcgtg cttgagttga ggcctggctt gggcgctggg gccgccgcgt gcgaatctgg 1260
tggcaccttc gcgcctgtct cgctgctttc gataagtctc tagccattta aaatttttga 1320
tgacctgctg cgacgctttt tttctggcaa gatagtcttg taaatgcggg ccaacatctg 1380
cacactggta tttcggtttt tggggccgcg ggcggcgacg gggcccgtgc gtcccagcgc 1440
acatgttcgg cgaggcgggg cctgcgagcg cggccaccga gaatcggacg ggggtagtct 1500
caagctggcc ggcctgctct ggtgcctggc ctcgcgccgc cgtgtatcgc cccgccctgg 1560
gcggcaaggc tggcccggtc ggcaccagtt gcgtgagcgg aaagatggcc gcttcccggc 1620
cctgctgcag ggagctcaaa atggaggacg cggcgctcgg gagagcgggc gggtgagtca 1680
cccacacaaa ggaaaagggc ctttccgtcc tcagccgtcg cttcatgtga ctccacggag 1740
taccgggcgc cgtccaggca cctcgattag ttctcgagct tttggagtac gtcgtcttta 1800
ggttgggggg aggggtttta tgcgatggag tttccccaca ctgagtgggt ggagactgaa 1860
gttaggccag cttggcactt gatgtaattc tccttggaat ttgccctttt tgagtttgga 1920
tcttggttca ttctcaagcc tcagacagtg gttcaaagtt tttttcttcc atttcaggtg 1980
tcgtgacacc ggtcgccacc atggtgagca agggcgagga gctgttcacc ggggtggtgc 2040
ccatcctggt cgagctggac ggcgacgtaa acggccacaa gttcagcgtg tccggcgagg 2100
gcgagggcga tgccacctac ggcaagctga ccctgaagtt catctgcacc accggcaagc 2160
tgcccgtgcc ctggcccacc ctcgtgacca ccctgaccta cggcgtgcag tgcttcagcc 2220
gctaccccga ccacatgaag cagcacgact tcttcaagtc cgccatgccc gaaggctacg 2280
tccaggagcg caccatcttc ttcaaggacg acggcaacta caagacccgc gccgaggtga 2340
agttcgaggg cgacaccctg gtgaaccgca tcgagctgaa gggcatcgac ttcaaggagg 2400
acggcaacat cctggggcac aagctggagt acaactacaa cagccacaac gtctatatca 2460
tggccgacaa gcagaagaac ggcatcaagg tgaacttcaa gatccgccac aacatcgagg 2520
acggcagcgt gcagctcgcc gaccactacc agcagaacac ccccatcggc gacggccccg 2580
tgctgctgcc cgacaaccac tacctgagca cccagtccgc cctgagcaaa gaccccaacg 2640
agaagcgcga tcacatggtc ctgctggagt tcgtgaccgc cgccgggatc actctcggca 2700
tggacgagct gtacaagtaa tagcggccgc gactctagat cataatcagc cataccacat 2760
ttgtagaggt tttacttgct ttaaaaaacc tcccacacct ccccctgaac ctgaaacata 2820
aaatgaatgc aattgttgtt gttaacttgt ttattgcagc ttataatggt tacaaataaa 2880
gcaatagcat cacaaatttc acaaataaag catttttttc actgcattct agttgtggtt 2940
tgtccaaact catcaatgta tcttaaggcg ttgacaagtc tgtctgccta ttcaccgatt 3000
ttgattctca aacaaatgtg tcacaaagta aggattctga tgtgtatatc acagacaaaa 3060
ctgtgctaga catgaggtct atggacttca agagcaacag tgctgtggcc tggagcaaca 3120
aatctgactt tgcatgtgca aacgccttca acaacagcat tattccagaa gacaccttct 3180
tccccagccc aggtaagggc agctttggtg ccttcgcagg ctgtttcctt gcttcaggaa 3240
tggccaggtt ctgcccagag ctctggtcaa tgatgtctaa aactcctctg attggtggtc 3300
tcggccttat ccattgccac caaaaccctc tttttactaa gaaacagtga gccttgttct 3360
ggcagtccag agaatgacac gggaaaaaag cagatgaaga gaaggtggca ggagagggca 3420
cgtggcccag cctcagtctc tccaactgag ttcctgcctg cctgcctttg cagatctagg 3480
aacccctagt gatggagttg gccactccct ctctgcgcgc tcgctcgctc actgaggccg 3540
cccgggcaaa gcccgggcgt cgggcgacct ttggtcgccc ggcctcagtg agcgagcgag 3600
cgcgcagaga gggagtggcc aaacgcgtgg tgtaatca 3638

<210> SEQ ID NO 622
<211> LENGTH: 2382
<212> TYPE: DNA
<213> ORGANISM: Homo sapiens

<400> SEQUENCE: 622
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc ttgccaacat accataaacc tcccattctg 180
ctaatgccca gcctaagttg gggagaccac tccagattcc aagatgtaca gtttgctttg 240
ctgggccttt ttcccatgcc tgcctttact ctgccagagt tatattgctg gggttttgaa 300
gaagatccta ttaaataaaa gaataagcag tattattaag tagccctgca tttcaggttt 360
ccttgagtgg caggccaggc ctggccgtga acgttcactg aaatcatggc ctcttggcca 420
agattgatag cttgtgcctg tccctgagtc ccagtccatc acgagcagct ggtttctaag 480
atgctatttc ccgtataaag catgagaccg tgacttgcca gccccacaga gccccgccct 540
tgtccatcac tggcatctgg actccagcct gggttggggc aaagagggaa atgagatcat 600
gtcctaaccc tgatcctctt gtcccacaga tatccagaac cctgaccctg ccgagggccg 660

```
cggcagcctg ctgacctgcg gcgacgtgga ggagaatccc ggccccatgg tgagcaaggg    720

cgaggagctg ttcaccgggg tggtgcccat cctggtcgag ctggacggcg acgtaaacgg    780

ccacaagttc agcgtgtccg gcgagggcga gggcgatgcc acctacggca agctgaccct    840

gaagttcatc tgcaccaccg gcaagctgcc cgtgccctgg cccaccctcg tgaccaccct    900

gacctacggc gtgcagtgct tcagccgcta ccccgaccac atgaagcagc acgacttctt    960

caagtccgcc atgcccgaag gctacgtcca ggagcgcacc atcttcttca aggacgacgg   1020

caactacaag acccgcgccg aggtgaagtt cgagggcgac accctggtga accgcatcga   1080

gctgaagggc atcgacttca aggaggacgg caacatcctg gggcacaagc tggagtacaa   1140

ctacaacagc cacaacgtct atatcatggc cgacaagcag aagaacggca tcaaggtgaa   1200

cttcaagatc cgccacaaca tcgaggacgg cagcgtgcag ctcgccgacc actaccagca   1260

gaacaccccc atcggcgacg gccccgtgct gctgcccgac aaccactacc tgagcaccca   1320

gtccgccctg agcaaagacc ccaacgagaa gcgcgatcac atggtcctgc tggagttcgt   1380

gaccgccgcc gggatcactc tcggcatgga cgagctgtac aagtaacctc gactgtgcct   1440

tctagttgcc agccatctgt tgtttgcccc tcccccgtgc cttccttgac cctggaaggt   1500

gccactccca ctgtcctttc ctaataaaat gaggaaattg catcgcattg tctgagtagg   1560

tgtcattcta ttctgggggg tggggtgggg caggacagca agggggagga ttgggaagac   1620

aatagcaggc atgctgggga tgcggtgggc tctatggctt ctgaggcgga aagaaccagc   1680

tggggctcta ggggtatcc ccactagtcg tgtaccagct gagagactct aaatccagtg    1740

acaagtctgt ctgcctattc accgattttg attctcaaac aaatgtgtca caaagtaagg   1800

attctgatgt gtatatcaca gacaaaactg tgctagacat gaggtctatg gacttcaaga   1860

gcaacagtgc tgtggcctgg agcaacaaat ctgactttgc atgtgcaaac gccttcaaca   1920

acagcattat tccagaagac accttcttcc ccagcccagg taagggcagc tttggtgcct   1980

tcgcaggctg tttccttgct tcaggaatgg ccaggttctg cccagagctc tggtcaatga   2040

tgtctaaaac tcctctgatt ggtggtctcg gccttatcca ttgccaccaa aaccctcttt   2100

ttactaagaa acagtgagcc ttgttctggc agtccagaga atgacacggg aaaaaagcag   2160

atgaagagaa ggtggcagga gagggcacgt ggcccagcct cagtctctag atctaggaac   2220

ccctagtgat ggagttggcc actccctctc tgcgcgctcg ctcgctcact gaggccgccc   2280

gggcaaagcc cgggcgtcgg gcgacctttg gtcgcccggc ctcagtgagc gagcgagcgc   2340

gcagagaggg agtggccaag aattctctgg ccgtcgtttt ac                      2382
```

<210> SEQ ID NO 623
<211> LENGTH: 4618
<212> TYPE: DNA
<213> ORGANISM: Homo sapiens

<400> SEQUENCE: 623

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctagatc ttgccaacat accataaacc tcccattctg    180

ctaatgccca gcctaagttg gggagaccac tccagattcc aagatgtaca gtttgctttg    240

ctgggccttt ttcccatgcc tgcctttact ctgccagagt tatattgctg gggttttgaa    300

gaagatccta ttaaataaaa gaataagcag tattattaag tagccctgca tttcaggttt    360

ccttgagtgg caggccaggc ctggccgtga acgttcactg aaatcatggc ctcttggcca    420
```

```
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg cggctccggt    660
gcccgtcagt gggcagagcg cacatcgccc acagtccccg agaagttggg gggaggggtc    720
ggcaattgaa ccggtgccta gagaaggtgg cgcggggtaa actgggaaag tgatgtcgtg    780
tactggctcc gcctttttcc cgagggtggg ggagaaccgt atataagtgc agtagtcgcc    840
gtgaacgttc tttttcgcaa cgggtttgcc gccagaacac aggtaagtgc cgtgtgtggt    900
tcccgcgggc ctggcctctt tacgggttat ggcccttgcg tgccttgaat tacttccacg    960
cccctggctg cagtacgtga ttcttgatcc cgagcttcgg gttggaagtg ggtgggagag   1020
ttcgaggcct tgcgcttaag gagccccttc gcctcgtgct tgagttgagg cctggcttgg   1080
gcgctggggc cgccgcgtgc gaatctggtg gcaccttcgc gcctgtctcg ctgctttcga   1140
taagtctcta gccatttaaa atttttgatg acctgctgcg acgctttttt tctggcaaga   1200
tagtcttgta aatgcgggcc aagatgtgca cactggtatt tcggtttttg gggccgcggg   1260
cggcgacggg gcccgtgcgt cccagcgcac atgttcggcg aggcggggcc tgcgagcgcg   1320
gccaccgaga atcggacggg ggtagtctca agctggccgg cctgctctgg tgcctggcct   1380
cgcgccgccg tgtatcgccc cgccctgggc ggcaaggctg gcccggtcgg caccagttgc   1440
gtgagcggaa agatggccgc ttcccggccc tgctgcaggg agctcaaaat ggaggacgcg   1500
gcgctcggga gagcgggcgg gtgagtcacc cacacaaagg aaaagggcct ttccgtcctc   1560
agccgtcgct tcatgtgact ccacggagta ccgggcgccg tccaggcacc tcgattagtt   1620
ctcgagcttt tggagtacgt cgtctttagg ttggggggag gggttttatg cgatggagtt   1680
tccccacact gagtgggtgg agactgaagt taggccagct tggcacttga tgtaattctc   1740
cttggaattt gccctttttg agtttggatc ttggttcatt ctcaagcctc agacagtggt   1800
tcaaagtttt tttcttccat ttcaggtgtc gtgatgcggc cgccaccatg ggatcttgga   1860
cactgtgttg cgtgtccctg tgcatcctgg tggccaagca cacagatgcc ggcgtgatcc   1920
agtctcctag acacgaagtg accgagatgg gccaagaagt gaccctgcgc tgcaagccta   1980
tcagcggcca cgattacctg ttctggtaca gacagaccat gatgagaggc ctggaactgc   2040
tgatctactt caacaacaac gtgcccatcg acgacagcgg catgcccgag gatagattca   2100
gcgccaagat gcccaacgcc agcttcagca ccctgaagat ccagcctagc gagcccagag   2160
atagcgccgt gtacttctgc gccagcagaa agacaggcgg ctacagcaat cagccccagc   2220
actttggaga tggcacccgg ctgagcatcc tggaagatct gaagaacgtg ttcccacctg   2280
aggtggccgt gttcgagcct tctgaggccg agatcagcca cacacagaaa gccacactcg   2340
tgtgtctggc caccggcttc tatcccgatc acgtggaact gtcttggtgg gtcaacggca   2400
aagaggtgca cagcggcgtc agcaccgatc ctcagcctct gaaagagcag cccgctctga   2460
acgacagcag atactgcctg agcagcagac tgagagtgtc cgccaccttc tggcagaacc   2520
ccagaaacca cttcagatgc caggtgcagt tctacggcct gagcgagaac gatgagtgga   2580
cccaggatag agccaagcct gtgacacaga tcgtgtctgc cgaagcctgg ggcagagccg   2640
attgtggctt taccagcgag agctaccagc agggcgtgct gtctgccaca atcctgtacg   2700
agatcctgct gggcaaagcc actctgtacg ccgtgctggt gtctgccctg gtgctgatgg   2760
```

ccatggtcaa gcggaaggat agcaggggcg gctccggtgc cacaaacttc tccctgctca 2820
agcaggccgg agatgtggaa gagaaccctg gccctatgga aaccctgctg aaggtgctga 2880
gcggcacact gctgtggcag ctgacatggg tccgatctca gcagcctgtg cagtctcctc 2940
aggccgtgat tctgagagaa ggcgaggacg ccgtgatcaa ctgcagcagc tctaaggccc 3000
tgtacagcgt gcactggtac agacagaagc acggcgaggc ccctgtgttc ctgatgatcc 3060
tgctgaaagg cggcgagcag aagggccacg agaagatcag cgccagcttc aacgagaaga 3120
agcagcagtc cagcctgtac ctgacagcca gccagctgag ctacagcggc acctactttt 3180
gtggcaccgc ctggatcaac gactacaagc tgtctttcgg agccggcacc acagtgacag 3240
tgcgggccaa tattcagaac cccgatcctg ccgtgtacca gctgagagac agcaagagca 3300
gcgacaagag cgtgtgcctg ttcaccgact tcgacagcca gaccaacgtg tcccagagca 3360
aggacagcga cgtgtacatc accgataaga ctgtgctgga catgcggagc atggacttca 3420
agagcaacag cgccgtggcc tggtccaaca agagcgattt cgcctgcgcc aacgccttca 3480
acaacagcat tatccccgag gacacattct tcccaagtcc tgagagcagc tgcgacgtga 3540
agctggtgga aaagagcttc gagacagaca ccaacctgaa cttccagaac ctgagcgtga 3600
tcggcttcag aatcctgctg ctcaaggtgg ccggcttcaa cctgctgatg accctgagac 3660
tgtggtccag ctaacctcga ctgtgccttc tagttgccag ccatctgttg tttgcccctc 3720
ccccgtgcct tccttgaccc tggaaggtgc cactcccact gtcctttcct aataaaatga 3780
ggaaattgca tcgcattgtc tgagtaggtg tcattctatt ctggggggtg gggtggggca 3840
ggacagcaag ggggaggatt gggaagacaa tagcaggcat gctggggatg cggtgggctc 3900
tatggcttct gaggcggaaa gaaccagctg gggctctagg gggtatcccc actagtcgtg 3960
taccagctga gagactctaa atccagtgac aagtctgtct gcctattcac cgattttgat 4020
tctcaaacaa atgtgtcaca aagtaaggat tctgatgtgt atatcacaga caaaactgtg 4080
ctagacatga ggtctatgga cttcaagagc aacagtgctg tggcctggag caacaaatct 4140
gactttgcat gtgcaaacgc cttcaacaac agcattattc cagaagacac cttcttcccc 4200
agcccaggta agggcagctt tggtgccttc gcaggctgtt tccttgcttc aggaatggcc 4260
aggttctgcc cagagctctg gtcaatgatg tctaaaactc ctctgattgg tggtctcggc 4320
cttatccatt gccaccaaaa ccctcttttt actaagaaac agtgagcctt gttctggcag 4380
tccagagaat gacacgggaa aaaagcagat gaagagaagg tggcaggaga gggcacgtgg 4440
cccagcctca gtctctagat ctaggaaccc ctagtgatgg agttggccac tccctctctg 4500
cgcgctcgct cgctcactga ggccgcccgg gcaaagcccg ggcgtcgggc gacctttggt 4560
cgcccggcct cagtgagcga gcgagcgcgc agagagggag tggccaagaa ttctctgg 4618

<210> SEQ ID NO 624
<211> LENGTH: 4587
<212> TYPE: DNA
<213> ORGANISM: Homo sapiens

<400> SEQUENCE: 624
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc ttgccaacat accataaacc tcccattctg 180
ctaatgccca gcctaagttg gggagaccac tccagattcc aagatgtaca gtttgctttg 240
ctgggccttt ttcccatgcc tgcctttact ctgccagagt tatattgctg ggttttgaa 300

```
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg cggctccggt    660
gcccgtcagt gggcagagcg cacatcgccc acagtccccg agaagttggg gggaggggtc    720
ggcaattgaa ccggtgccta gagaaggtgg cgcggggtaa actgggaaag tgatgtcgtg    780
tactggctcc gcctttttcc cgagggtggg ggagaaccgt atataagtgc agtagtcgcc    840
gtgaacgttc tttttcgcaa cgggtttgcc gccagaacac aggtaagtgc cgtgtgtggt    900
tcccgcgggc ctggcctctt tacgggttat ggcccttgcg tgccttgaat tacttccacg    960
cccctggctg cagtacgtga ttcttgatcc cgagcttcgg gttggaagtg ggtgggagag   1020
ttcgaggcct tgcgcttaag gagccccttc gcctcgtgct tgagttgagg cctggcttgg   1080
gcgctggggc cgccgcgtgc gaatctggtg gcaccttcgc gcctgtctcg ctgctttcga   1140
taagtctcta gccatttaaa atttttgatg acctgctgcg acgctttttt tctggcaaga   1200
tagtcttgta aatgcgggcc aagatgtgca cactggtatt tcggtttttg gggccgcggg   1260
cggcgacggg gcccgtgcgt cccagcgcac atgttcggcg aggcggggcc tgcgagcgcg   1320
gccaccgaga atcggacggg ggtagtctca agctggccgg cctgctctgg tgcctggcct   1380
cgcgccgccg tgtatcgccc cgccctgggc ggcaaggctg gcccggtcgg caccagttgc   1440
gtgagcggaa agatggccgc ttcccggccc tgctgcaggg agctcaaaat ggaggacgcg   1500
gcgctcggga gagcgggcgg gtgagtcacc cacacaaagg aaaagggcct ttccgtcctc   1560
agccgtcgct tcatgtgact ccacggagta ccgggcgccg tccaggcacc tcgattagtt   1620
ctcgagcttt tggagtacgt cgtctttagg ttggggggag gggttttatg cgatggagtt   1680
tccccacact gagtgggtgg agactgaagt taggccagct tggcacttga tgtaattctc   1740
cttggaattt gccctttttg agtttggatc ttggttcatt ctcaagcctc agacagtggt   1800
tcaaagtttt tttcttccat ttcaggtgtc gtgacggccg gccccgccac catgagcaat   1860
caagtccttt gttgtgttgt cctgtgtttc cttggcgcaa ataccgtcga cggcgggata   1920
actcagtccc ccaaatacct cttcagaaaa gaaggacaaa acgtaacgct ttcctgcgag   1980
cagaatctta accacgacgc catgtactgg tacaggcaag accctggaca aggtcttagg   2040
ctcatatact actctcagat tgtcaatgac ttccaaaaag ggacatagc tgagggctac    2100
tctgtgtccc gagagaagaa ggagtcattt cccctgacag tgacttctgc acaaaaaaat   2160
cccactgcat tttatttgtg tgccagttca ccgggtgcat tgtatgagca atactttggc   2220
cccggcacta gactgacagt tacggaggat ctgaaaaacg tcttcccgcc agaggtggca   2280
gttttcgagc ccagtgaggc tgaaatctct catacccaaa aagcaaccct tgtctgtctc   2340
gccactggat tctatcccga ccacgtcgaa ttgagctggt gggtcaatgg gaaagaggta   2400
catagtgggg tctgtacgga tccacaaccc cttaaggaac aacctgccct taacgattca   2460
cgatactgcc tgtcatcacg actcagggta tctgctacct tttggcagaa cccgagaaat   2520
cactttcggt gccaggttca gttttacgga cttagcgaaa atgatgaatg gacacaagac   2580
cgagcaaagc ccgttactca aatagtgagc gcggaagcct gggggcgagc agactgcggc   2640
```

ttcacctccg aaagttacca gcaaggtgtt ttgtcagcca ccattttgta tgagattttg 2700
ttggggaagg cgacacttta cgcggtactg gtctctgcct tggttcttat ggctatggtc 2760
aagaggaaag attccagggg tggctccggt gccacaaact tctccctgct caagcaggcc 2820
ggagatgtgg aagagaaccc tggccctatg acctctatca gagctgtctt tatatttctc 2880
tggcttcaac ttgatctggt gaatggcgaa aacgtggaac agcacccttc aacgttgagc 2940
gttcaggaag gagattcagc cgtcatcaag tgtacgtatt ccgattccgc gtcaaactac 3000
ttcccgtggt acaaacagga acttggcaag cgcccccagc tcattatcga catcagaagc 3060
aacgtaggag agaagaagga ccaacgcata gctgtgactc tcaacaaaac agctaaacat 3120
ttctccctgc acattacgga aacccaacca gaggattctg ccgtatactt ttgtgctgct 3180
actgaggacc tcactttgat ctggggagcg ggtacgaagc tcataataaa acccgatatc 3240
caaaacccgg acccagcagt ttatcaattg agagatagta agtccagtga caaatcagtt 3300
tgtttgttta cggatttcga tagccagacc aatgtcagtc agtcaaagga cagtgatgta 3360
tacattacag ataaatgtgt acttgacatg cgctcaatgg actttaagtc taactctgct 3420
gtagcttggt ctaacaaaag tgattttgcg tgtgccaacg catttaacaa cagcatcata 3480
cctgaagaca cgttctttcc gagtccagaa agttcctgtg acgtgaaact tgtagaaaag 3540
agtttcgaga ccgacactaa ccttaacttt caaaaccttt cagtgatcgg atttagaatc 3600
ttgctgctca aggtggcagg gttcaatctg ctgatgactc tgcgactgtg gagttcataa 3660
cctcgactgt gccttctagt tgccagccat ctgttgtttg cccctccccc gtgccttcct 3720
tgaccctgga aggtgccact cccactgtcc tttcctaata aaatgaggaa attgcatcgc 3780
attgtctgag taggtgtcat tctattctgg ggggtggggt ggggcaggac agcaaggggg 3840
aggattggga agacaatagc aggcatgctg gggatgcggt gggctctatg gcttctgagg 3900
cggaaagaac cagctggggc tctagggggt atcccccgtg taccagctga gagactctaa 3960
atccagtgac aagtctgtct gcctattcac cgattttgat tctcaaacaa atgtgtcaca 4020
aagtaaggat tctgatgtgt atatcacaga caaaactgtg ctagacatga ggtctatgga 4080
cttcaagagc aacagtgctg tggcctggag caacaaatct gactttgcat gtgcaaacgc 4140
cttcaacaac agcattattc cagaagacac cttcttcccc agcccaggta agggcagctt 4200
tggtgccttc gcaggctgtt tccttgcttc aggaatggcc aggttctgcc cagagctctg 4260
gtcaatgatg tctaaaactc ctctgattgg tggtctcggc cttatccatt gccaccaaaa 4320
ccctcttttt actaagaaac agtgagcctt gttctggcag tccagagaat gacacgggaa 4380
aaaagcagat gaagagaagg tggcaggaga gggcacgtgg cccagcctca gtctctagat 4440
ctaggaaccc ctagtgatgg agttggccac tccctctctg cgcgctcgct cgctcactga 4500
ggccgcccgg gcaaagcccg ggcgtcgggc gacctttggt cgcccggcct cagtgagcga 4560
gcgagcgcgc agagagggag tggccaa 4587

<210> SEQ ID NO 625
<211> LENGTH: 4630
<212> TYPE: DNA
<213> ORGANISM: Homo sapiens

<400> SEQUENCE: 625
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc ttgccaacat accataaacc tcccattctg 180

-continued

```
ctaatgccca gcctaagttg gggagaccac tccagattcc aagatgtaca gtttgctttg    240
ctgggccttt ttcccatgcc tgcctttact ctgccagagt tatattgctg ggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg cggctccggt    660
gcccgtcagt gggcagagcg cacatcgccc acagtccccg agaagttggg gggaggggtc    720
ggcaattgaa ccggtgccta gagaaggtgg cgcggggtaa actgggaaag tgatgtcgtg    780
tactggctcc gcctttttcc cgagggtggg ggagaaccgt atataagtgc agtagtcgcc    840
gtgaacgttc tttttcgcaa cgggtttgcc gccagaacac aggtaagtgc cgtgtgtggt    900
tcccgcgggc ctggcctctt tacgggttat ggcccttgcg tgccttgaat tacttccacg    960
cccctggctg cagtacgtga ttcttgatcc cgagcttcgg gttggaagtg ggtgggagag   1020
ttcgaggcct tgcgcttaag gagccccttc gcctcgtgct tgagttgagg cctggcttgg   1080
gcgctggggc cgccgcgtgc gaatctggtg gcaccttcgc gcctgtctcg ctgctttcga   1140
taagtctcta gccatttaaa atttttgatg acctgctgcg acgctttttt tctggcaaga   1200
tagtcttgta aatgcgggcc aagatgtgca cactggtatt tcggtttttg gggccgcggg   1260
cggcgacggg gcccgtgcgt cccagcgcac atgttcggcg aggcggggcc tgcgagcgcg   1320
gccaccgaga atcggacggg ggtagtctca agctggccgg cctgctctgg tgcctggcct   1380
cgcgccgccg tgtatcgccc cgccctgggc ggcaaggctg gcccggtcgg caccagttgc   1440
gtgagcggaa agatggccgc ttcccggccc tgctgcaggg agctcaaaat ggaggacgcg   1500
gcgctcggga gagcgggcgg gtgagtcacc cacacaaagg aaaagggcct ttccgtcctc   1560
agccgtcgct tcatgtgact ccacggagta ccgggcgccg tccaggcacc tcgattagtt   1620
ctcgagcttt tggagtacgt cgtctttagg ttggggggag gggttttatg cgatggagtt   1680
tccccacact gagtgggtgg agactgaagt taggccagct tggcacttga tgtaattctc   1740
cttggaattt gccctttttg agtttggatc ttggttcatt ctcaagcctc agacagtggt   1800
tcaaagtttt tttcttccat ttcaggtgtc gtgatgcggc cgccaccatg ggatcttgga   1860
cactgtgttg cgtgtccctg tgcatcctgg tggccaagca cacagatgcc ggcgtgatcc   1920
agtctcctag acacgaagtg accgagatgg gccaagaagt gaccctgcgc tgcaagccta   1980
tcagcggcca cgattacctg ttctggtaca gacagaccat gatgagaggc ctggaactgc   2040
tgatctactt caacaacaac gtgcccatcg acgacagcgg catgcccgag gatagattca   2100
gcgccaagat gcccaacgcc agcttcagca ccctgaagat ccagcctagc gagcccagag   2160
atagcgccgt gtacttctgc gccagcagaa agacaggcgg ctacagcaat cagccccagc   2220
actttggaga tggcacccgg ctgagcatcc tggaagatct gaagaacgtg ttcccacctg   2280
aggtggccgt gttcgagcct tctgaggccg agatcagcca cacacagaaa gccacactcg   2340
tgtgtctggc caccggcttc tatcccgatc acgtggaact gtcttggtgg gtcaacggca   2400
aagaggtgca cagcggcgtc tgtaccgatc ctcagcctct gaaagagcag cccgctctga   2460
acgacagcag atactgcctg agcagcagac tgagagtgtc cgccaccttc tggcagaacc   2520
```

```
ccagaaacca cttcagatgc caggtgcagt tctacggcct gagcgagaac gatgagtgga   2580
cccaggatag agccaagcct gtgacacaga tcgtgtctgc cgaagcctgg ggcagagccg   2640
attgtggctt taccagcgag agctaccagc agggcgtgct gtctgccaca atcctgtacg   2700
agatcctgct gggcaaagcc actctgtacg ccgtgctggt gtctgccctg gtgctgatgg   2760
ccatggtcaa gcggaaggat agcaggggcg gctccggtgc cacaaacttc tccctgctca   2820
agcaggccgg agatgtggaa gagaaccctg gccctatgga aaccctgctg aaggtgctga   2880
gcggcacact gctgtggcag ctgacatggg tccgatctca gcagcctgtg cagtctcctc   2940
aggccgtgat tctgagagaa ggcgaggacg ccgtgatcaa ctgcagcagc tctaaggccc   3000
tgtacagcgt gcactggtac agacagaagc acggcgaggc ccctgtgttc ctgatgatcc   3060
tgctgaaagg cggcgagcag aagggccacg agaagatcag cgccagcttc aacgagaaga   3120
agcagcagtc cagcctgtac ctgacagcca gccagctgag ctacagcggc acctactttt   3180
gtggcaccgc ctggatcaac gactacaagc tgtctttcgg agccggcacc acagtgacag   3240
tgcgggccaa tattcagaac cccgatcctg ccgtgtacca gctgagagac agcaagagca   3300
gcgacaagag cgtgtgcctg ttcaccgact tcgacagcca gaccaacgtg tcccagagca   3360
aggacagcga cgtgtacatc accgataagt gcgtgctgga catgcggagc atggacttca   3420
agagcaacag cgccgtggcc tggtccaaca agagcgattt cgcctgcgcc aacgccttca   3480
acaacagcat tatccccgag gacacattct tcccaagtcc tgagagcagc tgcgacgtga   3540
agctggtgga aaagagcttc gagacagaca ccaacctgaa cttccagaac ctgagcgtga   3600
tcggcttcag aatcctgctg ctcaaggtgg ccggcttcaa cctgctgatg accctgagac   3660
tgtggtccag ctaacctcga ctgtgccttc tagttgccag ccatctgttg tttgcccctc   3720
ccccgtgcct tccttgaccc tggaaggtgc cactcccact gtcctttcct aataaaatga   3780
ggaaattgca tcgcattgtc tgagtaggtg tcattctatt ctggggggtg gggtggggca   3840
ggacagcaag ggggaggatt gggaagacaa tagcaggcat gctggggatg cggtgggctc   3900
tatggcttct gaggcggaaa gaaccagctg gggctctagg gggtatcccc actagtcgtg   3960
taccagctga gagactctaa atccagtgac aagtctgtct gcctattcac cgattttgat   4020
tctcaaacaa atgtgtcaca aagtaaggat tctgatgtgt atatcacaga caaaactgtg   4080
ctagacatga ggtctatgga cttcaagagc aacagtgctg tggcctggag caacaaatct   4140
gactttgcat gtgcaaacgc cttcaacaac agcattattc cagaagacac cttcttcccc   4200
agcccaggta agggcagctt tggtgccttc gcaggctgtt tccttgcttc aggaatggcc   4260
aggttctgcc cagagctctg gtcaatgatg tctaaaactc ctctgattgg tggtctcggc   4320
cttatccatt gccaccaaaa ccctcttttt actaagaaac agtgagcctt gttctggcag   4380
tccagagaat gacacgggaa aaaagcagat gaagagaagg tggcaggaga gggcacgtgg   4440
cccagcctca gtctctagat ctaggaaccc ctagtgatgg agttggccac tccctctctg   4500
cgcgctcgct cgctcactga ggccgcccgg gcaaagcccg ggcgtcgggc gacctttggt   4560
cgcccggcct cagtgagcga gcgagcgcgc agagagggag tggccaagaa ttctctggcc   4620
gtcgttttac                                                          4630
```

<210> SEQ ID NO 626
<211> LENGTH: 4654
<212> TYPE: DNA
<213> ORGANISM: Homo sapiens

<400> SEQUENCE: 626

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctagatc ttgccaacat accataaacc tcccattctg    180
ctaatgccca gcctaagttg ggagaccac tccagattcc aagatgtaca gtttgctttg    240
ctgggccttt ttcccatgcc tgcctttact ctgccagagt tatattgctg gggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg cggctccggt    660
gcccgtcagt gggcagagcg cacatcgccc acagtccccg agaagttggg gggaggggtc    720
ggcaattgaa ccggtgccta gagaaggtgg cgcggggtaa actgggaaag tgatgtcgtg    780
tactggctcc gcctttttcc cgagggtggg ggagaaccgt atataagtgc agtagtcgcc    840
gtgaacgttc tttttcgcaa cgggtttgcc gccagaacac aggtaagtgc cgtgtgtggt    900
tcccgcgggc ctggcctctt tacgggttat ggcccttgcg tgccttgaat tacttccacg    960
cccctggctg cagtacgtga ttcttgatcc cgagcttcgg gttggaagtg ggtgggagag   1020
ttcgaggcct tgcgcttaag gagccccttc gcctcgtgct tgagttgagg cctggcttgg   1080
gcgctggggc cgccgcgtgc gaatctggtg gcaccttcgc gcctgtctcg ctgctttcga   1140
taagtctcta gccatttaaa atttttgatg acctgctgcg acgctttttt tctggcaaga   1200
tagtcttgta aatgcgggcc aagatgtgca cactggtatt tcggtttttg gggccgcggg   1260
cggcgacggg gcccgtgcgt cccagcgcac atgttcggcg aggcggggcc tgcgagcgcg   1320
gccaccgaga atcggacggg ggtagtctca agctggccgg cctgctctgg tgcctggcct   1380
cgcgccgccg tgtatcgccc cgccctgggc ggcaaggctg gcccggtcgg caccagttgc   1440
gtgagcggaa agatggccgc ttcccggccc tgctgcaggg agctcaaaat ggaggacgcg   1500
gcgctcggga gagcgggcgg gtgagtcacc cacacaaagg aaaagggcct ttccgtcctc   1560
agccgtcgct tcatgtgact ccacggagta ccgggcgccg tccaggcacc tcgattagtt   1620
ctcgagcttt tggagtacgt cgtctttagg ttgggggggag gggttttatg cgatggagtt   1680
tccccacact gagtgggtgg agactgaagt taggccagct tggcacttga tgtaattctc   1740
cttggaattt gccctttttg agtttggatc ttggttcatt ctcaagcctc agacagtggt   1800
tcaaagtttt tttcttccat ttcaggtgtc gtgatgcggc cgccaccatg ctgagccccg   1860
atctgcctga cagcgcctgg aacaccagac tgctgtgcca cgtgatgctg tgcctgctgg   1920
gagccgtgtc tgtggctgct ggcgtgatcc agagccccag acacctgatc aaagagaaga   1980
gagagacagc caccctgaag tgctacccca tccccaggca cgacaccgtg tactggtatc   2040
agcagggccc aggccaggac ccccagttcc tgatcagctt ctacgagaag atgcagagcg   2100
acaagggcag catccccgac agattcagcg cccagcagtt cagcgactac cacagcgagc   2160
tgaacatgag cagcctggaa ctgggcgaca gcgccctgta cttctgtgcc agctctctga   2220
gaggcggcct ggaaaagctg ttcttcggca gcggcaccca gctgagcgtg ctggaagacc   2280
tgaacaaggt gttcccccca gaggtggccg tgttcgagcc ttctgaggcc gaaatctccc   2340
```

-continued

```
acacccagaa agccaccctc gtgtgcctgg ccaccggctt tttccccgac cacgtggaac   2400
tgtcttggtg ggtcaacggc aaagaggtgc actccggcgt gtgcaccgat ccccagcctc   2460
tgaaagaaca gcccgccctg aacgacagcc ggtactgcct gagcagcaga ctgagagtgt   2520
ccgccacctt ctggcagaac ccccggaacc acttcagatg ccaggtgcag ttctacggcc   2580
tgagcgagaa cgacgagtgg acccaggaca gagccaagcc cgtgacacag atcgtgtctg   2640
ccgaagcctg gggcagagcc gattgcggct ttacctccgt gtcctatcag cagggcgtgc   2700
tgagcgccac aatcctgtac gagatcctgc tgggcaaggc caccctgtac gccgtgctgg   2760
tgtctgccct ggtgctgatg gccatggtca agcggaagga cttcggttcc ggagccacga   2820
acttctctct gttaaagcaa gcaggagacg tggaagaaaa ccccggtccc atgagcctga   2880
gcagcctgct gaaagtcgtg accgccagcc tgtggctggg acctggaatc gcccagaaga   2940
tcacccagac ccagcccggc atgttcgtgc aggaaaaaga agccgtgacc ctggactgca   3000
cctacgacac cagcgaccct agctacggcc tgttctggta caagcagccc agcagcggcg   3060
agatgatctt cctgatctac cagggcagct acgaccagca gaacgccacc gagggccggt   3120
acagcctgaa cttccagaag gcccggaagt ccgccaacct cgtgatcagc gccagccagc   3180
tgggcgacag cgccatgtac ttttgcgcca tcagcggcaa cacccccctg gtgtttggca   3240
agggcacccg gctgagcgtg atcgccaaca tccagaaccc cgaccccgca gtgtaccagc   3300
tgcgggacag caagagcagc gacaagagcg tgtgcctgtt caccgacttc gacagccaga   3360
ccaacgtgtc ccagagcaag gacagcgacg tgtacatcac cgataagtgc gtgctggaca   3420
tgcggagcat ggacttcaag agcaacagcg ccgtggcctg gtccaacaag agcgacttcg   3480
cctgcgccaa cgccttcaac aacagcatta tccccgagga cacattcttc ccaagccccg   3540
agagcagctg cgacgtgaag ctggtggaaa agagcttcga gacagacacc aacctgaact   3600
tccagaacct cagcgtgatc ggcttccgga tcctgctgct gaaggtggcc ggcttcaacc   3660
tgctgatgac cctgcggctg tggtccagct aatcgatcct cgactgtgcc ttctagttgc   3720
cagccatctg ttgtttgccc ctcccccgtg ccttccttga ccctggaagg tgccactccc   3780
actgtccttt cctaataaaa tgaggaaatt gcatcgcatt gtctgagtag gtgtcattct   3840
attctggggg gtggggtggg gcaggacagc aagggggagg attgggaaga caatagcagg   3900
catgctgggg atgcggtggg ctctatggct tctgaggcgg aaagaaccag ctggggctct   3960
agggggtatc cccactagtc gtgtaccagc tgagagactc taaatccagt gacaagtctg   4020
tctgcctatt caccgatttt gattctcaaa caaatgtgtc acaaagtaag gattctgatg   4080
tgtatatcac agacaaaact gtgctagaca tgaggtctat ggacttcaag agcaacagtg   4140
ctgtggcctg gagcaacaaa tctgactttg catgtgcaaa cgccttcaac aacagcatta   4200
ttccagaaga caccttcttc cccagcccag gtaagggcag ctttggtgcc ttcgcaggct   4260
gtttccttgc ttcaggaatg gccaggttct gcccagagct ctggtcaatg atgtctaaaa   4320
ctcctctgat tggtggtctc ggccttatcc attgccacca aaaccctctt tttactaaga   4380
aacagtgagc cttgttctgg cagtccagag aatgacacgg gaaaaaagca gatgaagaga   4440
aggtggcagg agagggcacg tggcccagcc tcagtctcta gatctaggaa cccctagtga   4500
tggagttggc cactccctct ctgcgcgctc gctcgctcac tgaggccgcc cgggcaaagc   4560
ccgggcgtcg ggcgaccttt ggtcgcccgg cctcagtgag cgagcgagcg cgcagagagg   4620
gagtggccaa gaattctctg gccgtcgttt taca                               4654
```

<210> SEQ ID NO 627
<211> LENGTH: 4638
<212> TYPE: DNA
<213> ORGANISM: Homo sapiens

<400> SEQUENCE: 627

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcctagatc ttgccaacat accataaacc tcccattctg    180
ctaatgccca gcctaagttg gggagaccac tccagattcc aagatgtaca gtttgctttg    240
ctgggccttt ttcccatgcc tgcctttact ctgccagagt tatattgctg ggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg cggctccggt    660
gcccgtcagt gggcagagcg cacatcgccc acagtccccg agaagttggg gggaggggtc    720
ggcaattgaa ccggtgccta gagaaggtgg cgcggggtaa actgggaaag tgatgtcgtg    780
tactggctcc gcctttttcc cgagggtggg ggagaaccgt atataagtgc agtagtcgcc    840
gtgaacgttc tttttcgcaa cgggtttgcc gccagaacac aggtaagtgc cgtgtgtggt    900
tcccgcgggc ctggcctctt tacgggttat ggcccttgcg tgccttgaat tacttccacg    960
cccctggctg cagtacgtga ttcttgatcc cgagcttcgg gttggaagtg ggtgggagag   1020
ttcgaggcct tgcgcttaag gagccccttc gcctcgtgct tgagttgagg cctggcttgg   1080
gcgctggggc cgccgcgtgc gaatctggtg gcaccttcgc gcctgtctcg ctgctttcga   1140
taagtctcta gccatttaaa atttttgatg acctgctgcg acgctttttt tctggcaaga   1200
tagtcttgta aatgcgggcc aagatgtgca cactggtatt tcggtttttg gggccgcggg   1260
cggcgacggg gcccgtgcgt cccagcgcac atgttcggcg aggcggggcc tgcgagcgcg   1320
gccaccgaga atcggacggg ggtagtctca agctggccgg cctgctctgg tgcctggcct   1380
cgcgccgccg tgtatcgccc cgccctgggc ggcaaggctg gcccggtcgg caccagttgc   1440
gtgagcggaa agatggccgc ttcccggccc tgctgcaggg agctcaaaat ggaggacgcg   1500
gcgctcggga gagcgggcgg gtgagtcacc cacacaaagg aaaagggcct ttccgtcctc   1560
agccgtcgct tcatgtgact ccacggagta ccgggcgccg tccaggcacc tcgattagtt   1620
ctcgagcttt tggagtacgt cgtctttagg ttggggggag gggttttatg cgatggagtt   1680
tccccacact gagtgggtgg agactgaagt taggccagct tggcacttga tgtaattctc   1740
cttggaattt gccctttttg agtttggatc ttggttcatt ctcaagcctc agacagtggt   1800
tcaaagtttt tttcttccat ttcaggtgtc gtgatgcggc cgccaccatg ggcaccagac   1860
tgctgtgttg ggccgctctg tgtctgctgg gagccgaact gactgaagct ggcgtggccc   1920
agagcccccg gtacaagatc atcgagaagc ggcagagcgt ggccttctgg tgcaacccta   1980
tcagcggaca cgccaccctg tactggtatc agcagatcct gggccagggc cccaagctgc   2040
tgattcagtt ccagaacaac ggcgtggtgg acgacagcca gctgcccaag gatagattca   2100
gcgccgagcg gctgaagggc gtggacagca cactgaagat ccagcccgcc aagctggaag   2160
```

atagcgccgt gtacctgtgc gccagcagcc tgtatagagg cgagcagtac ttcggccctg 2220
gcacccggct gaccgtgacc gaggatctga agaacgtgtt ccccccagag gtggccgtgt 2280
tcgagcctag cgaggccgag atcagccaca cccagaaagc caccctcgtg tgcctggcca 2340
ccggctttta ccccgaccac gtggaactgt cttggtgggt caacggcaaa gaggtgcaca 2400
gcggcgtctg caccgacccc cagcccctga aagagcagcc cgccctgaac gacagccggt 2460
actgtctgag cagcagactg agagtgtccg ccaccttctg gcagaacccc cggaaccact 2520
tcagatgcca ggtgcagttc tacggcctga gcgagaacga cgagtggacc caggaccggg 2580
ccaagcccgt gacccagatc gtgtctgctg aggcctgggg cagagccgat tgcggcttca 2640
ccagcgagag ctaccagcag ggcgtgctga gcgccaccat cctgtacgag atcctgctgg 2700
gcaaggccac cctgtacgcc gtgctggtgt ccgccctggt gctgatggcc atggtcaagc 2760
ggaaggacag ccggggcggt tccggagcca cgaacttctc tctgttaaag caagcaggag 2820
acgtggaaga aaaccccggt cccatggcta tgctgctggg cgcctctgtg ctgatcctgt 2880
ggctgcagcc cgactgggtc aacagccagc agaagaacga cgaccagcaa gtgaagcaga 2940
acagccccag cctgagcgtg caggaaggcc ggatcagcat cctgaactgc gactacacca 3000
actctatgtt cgactacttc ctgtggtaca agaagtaccc cgccgagggc cccaccttcc 3060
tgatctccat cagcagcatc aaggacaaga acgaggacgg ccggttcacc gtgtttctga 3120
acaagagcgc caagcacctg agcctgcaca tcgtgcctag ccagcctggc gatagcgccg 3180
tgtacttctg tgccgccaga ggccagggca acctgatctt tggcaagggc accaagctga 3240
gcgtgaagcc caacatccag aaccccgacc ccgcagtgta ccagctgcgg gacagcaaga 3300
gcagcgacaa gagcgtgtgc ctgttcaccg acttcgacag ccagaccaac gtgtcccaga 3360
gcaaggacag cgacgtgtac atcaccgata agtgcgtgct ggacatgcgg agcatggact 3420
tcaagagcaa cagcgccgtg gcctggtcca acaagagcga cttcgcctgc gccaacgcct 3480
tcaacaacag cattatcccc gaggacacat tcttcccaag ccccgagagc agctgcgacg 3540
tgaagctggt ggaaaagagc ttcgagacag acaccaacct gaacttccag aacctcagcg 3600
tgatcggctt ccggatcctg ctgctgaagg tggccggctt caacctgctg atgaccctgc 3660
ggctgtggtc cagctaatcg atcctcgact gtgccttcta gttgccagcc atctgttgtt 3720
tgcccctccc ccgtgccttc cttgaccctg gaaggtgcca ctcccactgt cctttcctaa 3780
taaaatgagg aaattgcatc gcattgtctg agtaggtgtc attctattct ggggggtggg 3840
gtggggcagg acagcaaggg ggaggattgg gaagacaata gcaggcatgc tggggatgcg 3900
gtgggctcta tggcttctga ggcggaaaga accagctggg gctctagggg gtatccccac 3960
tagtcgtgta ccagctgaga gactctaaat ccagtgacaa gtctgtctgc ctattcaccg 4020
attttgattc tcaaacaaat gtgtcacaaa gtaaggattc tgatgtgtat atcacagaca 4080
aaactgtgct agacatgagg tctatggact tcaagagcaa cagtgctgtg gcctggagca 4140
acaaatctga ctttgcatgt gcaaacgcct tcaacaacag cattattcca gaagacacct 4200
tcttccccag cccaggtaag ggcagctttg gtgccttcgc aggctgtttc cttgcttcag 4260
gaatggccag gttctgccca gagctctggt caatgatgtc taaaactcct ctgattggtg 4320
gtctcggcct tatccattgc caccaaaacc ctctttttac taagaaacag tgagccttgt 4380
tctggcagtc cagagaatga cacgggaaaa aagcagatga agagaaggtg gcaggagagg 4440
gcacgtggcc cagcctcagt ctctagatct aggaacccct agtgatggag ttggccactc 4500
cctctctgcg cgctcgctcg ctcactgagg ccgcccgggc aaagcccggg cgtcgggcga 4560
cctttggtcg cccggcctca gtgagcgagc gagcgcgcag agagggagtg gccaagaatt 4620
ctctggccgt cgttttac 4638

<210> SEQ ID NO 628
<211> LENGTH: 4737
<212> TYPE: DNA
<213> ORGANISM: Homo sapiens

<400> SEQUENCE: 628
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc ttgccaacat accataaacc tcccattctg 180
ctaatgccca gcctaagttg gggagaccac tccagattcc aagatgtaca gtttgctttg 240
ctgggccttt ttcccatgcc tgcctttact ctgccagagt tatattgctg gggttttgaa 300
gaagatccta ttaaataaaa gaataagcag tattattaag tagccctgca tttcaggttt 360
ccttgagtgg caggccaggc ctggccgtga acgttcactg aaatcatggc ctcttggcca 420
agattgatag cttgtgcctg tccctgagtc ccagtccatc acgagcagct ggtttctaag 480
atgctatttc ccgtataaag catgagaccg tgacttgcca gccccacaga gccccgccct 540
tgtccatcac tggcatctgg actccagcct gggttggggc aaagagggaa atgagatcat 600
gtcctaaccc tgatcctctt gtcccacaga tatccagaac cctgaccctg cggctccggt 660
gcccgtcagt gggcagagcg cacatcgccc acagtccccg agaagttggg gggaggggtc 720
ggcaattgaa ccggtgccta gagaaggtgg cgcggggtaa actgggaaag tgatgtcgtg 780
tactggctcc gcctttttcc cgagggtggg ggagaaccgt atataagtgc agtagtcgcc 840
gtgaacgttc tttttcgcaa cgggtttgcc gccagaacac aggtaagtgc cgtgtgtggt 900
tcccgcgggc ctggcctctt tacgggttat ggcccttgcg tgccttgaat tacttccacg 960
cccctggctg cagtacgtga ttcttgatcc cgagcttcgg gttggaagtg ggtgggagag 1020
ttcgaggcct tgcgcttaag gagccccttc gcctcgtgct tgagttgagg cctggcttgg 1080
gcgctggggc cgccgcgtgc gaatctggtg gcaccttcgc gcctgtctcg ctgctttcga 1140
taagtctcta gccatttaaa atttttgatg acctgctgcg acgctttttt tctggcaaga 1200
tagtcttgta aatgcgggcc aagatgtgca cactggtatt tcggtttttg gggccgcggg 1260
cggcgacggg gcccgtgcgt cccagcgcac atgttcggcg aggcggggcc tgcgagcgcg 1320
gccaccgaga atcggacggg ggtagtctca agctggccgg cctgctctgg tgcctggcct 1380
cgcgccgccg tgtatcgccc cgccctgggc ggcaaggctg gcccggtcgg caccagttgc 1440
gtgagcggaa agatggccgc ttcccggccc tgctgcaggg agctcaaaat ggaggacgcg 1500
gcgctcggga gagcgggcgg gtgagtcacc cacacaaagg aaaagggcct ttccgtcctc 1560
agccgtcgct tcatgtgact ccacggagta ccgggcgccg tccaggcacc tcgattagtt 1620
ctcgagcttt tggagtacgt cgtctttagg ttgggggggag gggttttatg cgatggagtt 1680
tccccacact gagtgggtgg agactgaagt taggccagct tggcacttga tgtaattctc 1740
cttggaattt gccctttttg agtttggatc ttggttcatt ctcaagcctc agacagtggt 1800
tcaaagtttt tttcttccat ttcaggtgtc gtgatgcggc cgccaccatg tctctgggcc 1860
tgctgtgctg tggcgccttc tctctgctgt gggccggacc tgtgaatgcc ggcgtgaccc 1920
agacccccaa gttccgggtg ctgaaaaccg gccagagcat gaccctgctg tgtgcccagg 1980

```
acatgaacca cgagtacatg tattggtaca gacaggaccc cggcatgggc ctgcggctga   2040
tccactattc tgtgggcgag ggcaccaccg ccaagggcga agtgcctgat ggctacaacg   2100
tgtcccggct gaagaagcag aacttcctgc tgggcctgga aagcgccgct cctagccaga   2160
ccagcgtgta cttctgtgcc agccggggct accaccggct gaacaacgag cagttcttcg   2220
gccctggcac ccggctgacc gtgctggaag acctgaagaa cgtgttcccc ccagaggtgg   2280
ccgtgttcga gcctagcgag gccgagatca gccacaccca gaaagccacc ctcgtgtgcc   2340
tggccaccgg cttttacccc gaccacgtgg aactgtcttg gtgggtcaac ggcaaagagg   2400
tgcacagcgg cgtctgcacc gacccccagc ccctgaaaga gcagcccgcc ctgaacgaca   2460
gccggtactg tctgagcagc agactgagag tgtccgccac cttctggcag aacccccgga   2520
accacttcag atgccaggtg cagttctacg gcctgagcga gaacgacgag tggacccagg   2580
accgggccaa gcccgtgacc cagatcgtgt ctgctgaggc ctggggcaga gccgattgcg   2640
gcttcaccag cgagagctac cagcagggcg tgctgagcgc caccatcctg tacgagatcc   2700
tgctgggcaa ggccaccctg tacgccgtgc tggtgtccgc cctggtgctg atggccatgg   2760
tcaagcggaa ggacagccgg ggcggttccg gagccacgaa cttctctctg ttaaagcaag   2820
caggagacgt ggaagaaaac cccggtccca tgatcagcct gcgggtgctg ctcgtgatcc   2880
tgtggctgca gctgagctgg gtgtggtccg gaggtgggtc atggtcccat ccgcaattcg   2940
aaaagggagg tgggtcaggt ggaggaagcg gcggatccgc gtggtcacat cctcagttcg   3000
aaaagcagcg gaaagaggtg gaacaggacc ctggcccctt caacgtgcca gagggcgcca   3060
ccgtggcctt caactgcacc tacagcaaca gcgccagcca gagcttcttc tggtacagac   3120
aggactgccg gaaagaaccc aagctgctga tgagcgtgta cagcagcggc aacgaggacg   3180
gcagattcac cgcccagctg aacagagcct cccagtacat ctccctgctg atccgggaca   3240
gcaagctgag cgacagcgcc acctacctgt gcgtcgtgaa gcctgatcct ggcgccggaa   3300
gctaccagct gacctttggc aagggcacca agctgtccgt gatccccaac atccagaacc   3360
ccgaccccgc agtgtaccag ctgcgggaca gcaagagcag cgacaagagc gtgtgcctgt   3420
tcaccgactt cgacagccag accaacgtgt cccagagcaa ggacagcgac gtgtacatca   3480
ccgataagtg cgtgctggac atgcggagca tggacttcaa gagcaacagc gccgtggcct   3540
ggtccaacaa gagcgacttc gcctgcgcca acgccttcaa caacagcatt atccccgagg   3600
acacattctt cccaagcccc gagagcagct gcgacgtgaa gctggtggaa aagagcttcg   3660
agacagacac caacctgaac ttccagaacc tcagcgtgat cggcttccgg atcctgctgc   3720
tgaaggtggc cggcttcaac ctgctgatga ccctgcggct gtggtccagc taatcgatcc   3780
tcgactgtgc cttctagttg ccagccatct gttgtttgcc cctcccccgt gccttccttg   3840
accctggaag gtgccactcc cactgtcctt tcctaataaa atgaggaaat tgcatcgcat   3900
tgtctgagta ggtgtcattc tattctgggg ggtggggtgg ggcaggacag caagggggag   3960
gattgggaag acaatagcag gcatgctggg gatgcggtgg gctctatggc ttctgaggcg   4020
gaaagaacca gctggggctc tagggggtat ccccactagt cgtgtaccag ctgagagact   4080
ctaaatccag tgacaagtct gtctgcctat tcaccgattt tgattctcaa acaaatgtgt   4140
cacaaagtaa ggattctgat gtgtatatca cagacaaaac tgtgctagac atgaggtcta   4200
tggacttcaa gagcaacagt gctgtggcct ggagcaacaa atctgacttt gcatgtgcaa   4260
acgccttcaa caacagcatt attccagaag acaccttctt ccccagccca ggtaagggca   4320
gctttggtgc cttcgcaggc tgtttccttg cttcaggaat ggccaggttc tgcccagagc   4380
```

tctggtcaat gatgtctaaa actcctctga ttggtggtct cggccttatc cattgccacc 4440
aaaaccctct ttttactaag aaacagtgag ccttgttctg gcagtccaga gaatgacacg 4500
ggaaaaaagc agatgaagag aaggtggcag gagagggcac gtggcccagc ctcagtctct 4560
agatctagga acccctagtg atggagttgg ccactccctc tctgcgcgct cgctcgctca 4620
ctgaggccgc ccgggcaaag cccgggcgtc gggcgacctt tggtcgcccg gcctcagtga 4680
gcgagcgagc gcgcagagag ggagtggcca agaattctct ggccgtcgtt ttacaac 4737

<210> SEQ ID NO 629
<211> LENGTH: 4646
<212> TYPE: DNA
<213> ORGANISM: Homo sapiens

<400> SEQUENCE: 629
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc ttgccaacat accataaacc tcccattctg 180
ctaatgccca gcctaagttg gggagaccac tccagattcc aagatgtaca gtttgctttg 240
ctgggccttt ttcccatgcc tgcctttact ctgccagagt tatattgctg gggttttgaa 300
gaagatccta ttaaataaaa gaataagcag tattattaag tagccctgca tttcaggttt 360
ccttgagtgg caggccaggc ctggccgtga acgttcactg aaatcatggc ctcttggcca 420
agattgatag cttgtgcctg tccctgagtc ccagtccatc acgagcagct ggtttctaag 480
atgctatttc ccgtataaag catgagaccg tgacttgcca gccccacaga gccccgccct 540
tgtccatcac tggcatctgg actccagcct gggttggggc aaagagggaa atgagatcat 600
gtcctaaccc tgatcctctt gtcccacaga tatccagaac cctgaccctg cggctccggt 660
gcccgtcagt gggcagagcg cacatcgccc acagtccccg agaagttggg gggaggggtc 720
ggcaattgaa ccggtgccta gagaaggtgg cgcggggtaa actgggaaag tgatgtcgtg 780
tactggctcc gcctttttcc cgagggtggg ggagaaccgt atataagtgc agtagtcgcc 840
gtgaacgttc tttttcgcaa cgggtttgcc gccagaacac aggtaagtgc cgtgtgtggt 900
tcccgcgggc ctggcctctt tacgggttat ggcccttgcg tgccttgaat tacttccacg 960
cccctggctg cagtacgtga ttcttgatcc cgagcttcgg gttggaagtg ggtgggagag 1020
ttcgaggcct tgcgcttaag gagccccttc gcctcgtgct tgagttgagg cctggcttgg 1080
gcgctggggc cgccgcgtgc gaatctggtg gcaccttcgc gcctgtctcg ctgctttcga 1140
taagtctcta gccatttaaa atttttgatg acctgctgcg acgctttttt tctggcaaga 1200
tagtcttgta aatgcgggcc aagatgtgca cactggtatt tcggtttttg gggccgcggg 1260
cggcgacggg gcccgtgcgt cccagcgcac atgttcggcg aggcggggcc tgcgagcgcg 1320
gccaccgaga atcggacggg ggtagtctca agctggccgg cctgctctgg tgcctggcct 1380
cgcgccgccg tgtatcgccc cgccctgggc ggcaaggctg gcccggtcgg caccagttgc 1440
gtgagcggaa agatggccgc ttcccggccc tgctgcaggg agctcaaaat ggaggacgcg 1500
gcgctcggga gagcgggcgg gtgagtcacc cacacaaagg aaaagggcct ttccgtcctc 1560
agccgtcgct tcatgtgact ccacggagta ccgggcgccg tccaggcacc tcgattagtt 1620
ctcgagcttt tggagtacgt cgtctttagg ttggggggag gggttttatg cgatggagtt 1680
tccccacact gagtgggtgg agactgaagt taggccagct tggcacttga tgtaattctc 1740

-continued

```
cttggaattt gccctttttg agtttggatc ttggttcatt ctcaagcctc agacagtggt   1800
tcaaagtttt tttcttccat ttcaggtgtc gtgatgcggc cgccaccatg ggatgtagac   1860
ttctgtgttg cgccgtgctg tgtctgcttg gagctggcga actggtgcct atggaaaccg   1920
gcgtgaccca gacacctaga cacctggtca tgggcatgac aaacaagaaa agcctgaagt   1980
gcgagcagca cctgggccac aatgccatgt actggtacaa gcagagcgcc aagaaacccc   2040
tggaactgat gttcgtgtac agcctggaag agagggtcga gaacaacagc gtgcccagca   2100
gattcagccc tgagtgccct aatagcagcc acctgtttct gcatctgcac accctgcagc   2160
ctgaggactc tgccctgtat ctgtgtgcca gcagccagga ctacctggtg tccaacgaga   2220
agctgttctt cggcagcggc acacagctga gcgtgctgga agatctgaag aacgtgttcc   2280
cacctgaggt ggccgtgttc gagccttctg aggccgagat cagccacaca cagaaagcca   2340
cactcgtgtg tctggccacc ggcttctatc ccgatcacgt ggaactgtct tggtgggtca   2400
acggcaaaga ggtgcacagc ggcgtcagca ccgatcctca gcctctgaaa gagcagcccg   2460
ctctgaacga cagcagatac tgcctgagca gcagactgag agtgtccgcc accttctggc   2520
agaaccccag aaaccacttc agatgccagg tgcagttcta cggcctgagc gagaacgatg   2580
agtggaccca ggatagagcc aagcctgtga cacagatcgt gtctgccgaa gcctggggca   2640
gagccgattg tggctttacc agcgagagct accagcaggg cgtgctgtct gccacaatcc   2700
tgtacgagat cctgctggga aaagccactc tgtacgctgt gctggtgtcc gctctggtgc   2760
tgatggccat ggtcaagcgg aaggatagca ggggcggctc cggtgccaca aacttctccc   2820
tgctcaagca ggccggagat gtggaagaga accctggccc tatgatcagc ctgagagtgc   2880
tgctggtcat cctgtggctg cagctgtctt gggtctggtc ccagcggaaa gaggtggaac   2940
aggaccccgg acctttcaat gtgcctgaag gcgccaccgt ggccttcaac tgcacctaca   3000
gcaatagcgc cagccagagc ttcttctggt acagacagga ctgccggaaa gaacccaagc   3060
tgctgatgag cgtgtacagc agcggcaacg aggacggcag attcacagcc cagctgaaca   3120
gagccagcca gtacatcagc ctgctgatcc gggatagcaa gctgagcgat agcgccacct   3180
acctgtgcgt ggtcaacctg ctgtctaatc aaggcggcaa gctgatcttc ggccagggca   3240
cagagctgag cgtgaagccc aacattcaga accccgatcc tgccgtgtac cagctgagag   3300
acagcaagag cagcgacaag agcgtgtgcc tgttcaccga cttcgacagc cagaccaacg   3360
tgtcccagag caaggacagc gacgtgtaca tcaccgataa gaccgtgctg gacatgcgga   3420
gcatggactt caagagcaac agcgccgtgg cctggtccaa caagagcgat ttcgcctgcg   3480
ccaacgcctt caacaacagc attatccccg aggacacatt cttcccaagt cctgagagca   3540
gctgcgacgt gaagctggtg gaaaagagct tcgagacaga caccaacctg aacttccaga   3600
acctgtccgt gatcggcttc cggatcctgc tgctgaaagt ggccggcttc aacctcctga   3660
tgaccctgag actgtggtcc agctaacctc gactgtgcct tctagttgcc agccatctgt   3720
tgtttgcccc tcccccgtgc cttccttgac cctggaaggt gccactccca ctgtcctttc   3780
ctaataaaat gaggaaattg catcgcattg tctgagtagg tgtcattcta ttctgggggg   3840
tggggtgggg caggacagca agggggagga ttgggaagac aatagcaggc atgctgggga   3900
tgcggtgggc tctatggctt ctgaggcgga aagaaccagc tggggctcta gggggtatcc   3960
ccactagtcg tgtaccagct gagagactct aaatccagtg acaagtctgt ctgcctattc   4020
accgattttg attctcaaac aaatgtgtca caaagtaagg attctgatgt gtatatcaca   4080
gacaaaactg tgctagacat gaggtctatg gacttcaaga gcaacagtgc tgtggcctgg   4140
```

```
agcaacaaat ctgactttgc atgtgcaaac gccttcaaca acagcattat tccagaagac   4200

accttcttcc ccagcccagg taagggcagc tttggtgcct tcgcaggctg tttccttgct   4260

tcaggaatgg ccaggttctg cccagagctc tggtcaatga tgtctaaaac tcctctgatt   4320

ggtggtctcg gccttatcca ttgccaccaa aaccctcttt ttactaagaa acagtgagcc   4380

ttgttctggc agtccagaga atgacacggg aaaaaagcag atgaagagaa ggtggcagga   4440

gagggcacgt ggcccagcct cagtctctag atctaggaac ccctagtgat ggagttggcc   4500

actccctctc tgcgcgctcg ctcgctcact gaggccgccc gggcaaagcc cgggcgtcgg   4560

gcgacctttg gtcgcccggc ctcagtgagc gagcgagcgc gcagagaggg agtggccaag   4620

aattctctgg ccgtcgtttt acaacg                                         4646
```

<210> SEQ ID NO 630
<211> LENGTH: 3448
<212> TYPE: DNA
<213> ORGANISM: Homo sapiens

<400> SEQUENCE: 630

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctagatc ttgccaacat accataaacc tcccattctg    180

ctaatgccca gcctaagttg gggagaccac tccagattcc aagatgtaca gtttgctttg    240

ctgggccttt ttcccatgcc tgcctttact ctgccagagt tatattgctg ggttttgaa    300

gaagatccta ttaaataaaa gaataagcag tattattaag tagccctgca tttcaggttt    360

ccttgagtgg caggccaggc ctggccgtga acgttcactg aaatcatggc ctcttggcca    420

agattgatag cttgtgcctg tccctgagtc ccagtccatc acgagcagct ggtttctaag    480

atgctatttc ccgtataaag catgagaccg tgacttgcca gccccacaga gccccgccct    540

tgtccatcac tggcatctgg actccagcct gggttggggc aaagagggaa atgagatcat    600

gtcctaaccc tgatcctctt gtcccacaga tatccagaac cctgaccctg ccgagggccg    660

cggcagcctg ctgacctgcg gcgacgtgga ggagaatccc ggccccatga gcaatcaagt    720

cctttgttgt gttgtcctgt gtttccttgg cgcaaatacc gtcgacggcg ggataactca    780

gtcccccaaa tacctcttca gaaaagaagg acaaaacgta acgctttcct gcgagcagaa    840

tcttaaccac gacgccatgt actggtacag gcaagaccct ggacaaggtc ttaggctcat    900

atactactct cagattgtca atgacttcca aaaaggggac atagctgagg gctactctgt    960

gtcccgagag aagaaggagt catttcccct gacagtgact tctgcacaaa aaaatcccac   1020

tgcattttat ttgtgtgcca gttcaccggg tgcattgtat gagcaatact ttggccccgg   1080

cactagactg acagttacgg aggatctgaa aaacgtcttc ccgccagagg tggcagtttt   1140

cgagcccagt gaggctgaaa tctctcatac ccaaaaagca acccttgtct gtctcgccac   1200

tggattctat cccgaccacg tcgaattgag ctggtgggtc aatgggaaag aggtacatag   1260

tggggtctgt acggatccac aaccccttaa ggaacaacct gcccttaacg attcacgata   1320

ctgcctgtca tcacgactca gggtatctgc taccttttgg cagaacccga gaaatcactt   1380

tcggtgccag gttcagtttt acggacttag cgaaaatgat gaatggacac aagaccgagc   1440

aaagcccgtt actcaaatag tgagcgcgga agcctggggg cgagcagact gcggcttcac   1500

ctccgaaagt taccagcaag gtgttttgtc agccaccatt ttgtatgaga ttttgttggg   1560
```

gaaggcgaca ctttacgcgg tactggtctc tgccttggtt cttatggcta tggtcaagag 1620
gaaagattcc aggggtggct ccggtgccac aaacttctcc ctgctcaagc aggccggaga 1680
tgtggaagag aaccctggcc ctatgacctc tatcagagct gtctttatat ttctctggct 1740
tcaacttgat ctggtgaatg gcgaaaacgt ggaacagcac ccttcaacgt tgagcgttca 1800
ggaaggagat tcagccgtca tcaagtgtac gtattccgat tccgcgtcaa actacttccc 1860
gtggtacaaa caggaacttg gcaagcgccc ccagctcatt atcgacatca gaagcaacgt 1920
aggagagaag aaggaccaac gcatagctgt gactctcaac aaaacagcta aacatttctc 1980
cctgcacatt acggaaaccc aaccagagga ttctgccgta tacttttgtg ctgctactga 2040
ggacctcact ttgatctggg gagcgggtac gaagctcata ataaaacccg atatccaaaa 2100
cccggaccca gcagtttatc aattgagaga tagtaagtcc agtgacaaat cagtttgttt 2160
gtttacggat ttcgatagcc agaccaatgt cagtcagtca aaggacagtg atgtatacat 2220
tacagataaa tgtgtacttg acatgcgctc aatggacttt aagtctaact ctgctgtagc 2280
ttggtctaac aaaagtgatt ttgcgtgtgc caacgcattt aacaacagca tcatacctga 2340
agacacgttc tttccgagtc cagaaagttc ctgtgacgtg aaacttgtag aaaagagttt 2400
cgagaccgac actaacctta actttcaaaa cctttcagtg atcggattta gaatcttgct 2460
gctcaaggtg gcagggttca atctgctgat gactctgcga ctgtggagtt cataacctcg 2520
actgtgcctt ctagttgcca gccatctgtt gtttgcccct cccccgtgcc ttccttgacc 2580
ctggaaggtg ccactcccac tgtcctttcc taataaaatg aggaaattgc atcgcattgt 2640
ctgagtaggt gtcattctat tctggggggt ggggtggggc aggacagcaa gggggaggat 2700
tgggaagaca atagcaggca tgctggggat gcggtgggct ctatggcttc tgaggcggaa 2760
agaaccagct ggggctctag ggggtatccc cactagtcgt gtaccagctg agagactcta 2820
aatccagtga caagtctgtc tgcctattca ccgattttga ttctcaaaca aatgtgtcac 2880
aaagtaagga ttctgatgtg tatatcacag acaaaactgt gctagacatg aggtctatgg 2940
acttcaagag caacagtgct gtggcctgga gcaacaaatc tgactttgca tgtgcaaacg 3000
ccttcaacaa cagcattatt ccagaagaca ccttcttccc cagcccaggt aagggcagct 3060
ttggtgcctt cgcaggctgt ttccttgctt caggaatggc caggttctgc ccagagctct 3120
ggtcaatgat gtctaaaact cctctgattg gtggtctcgg ccttatccat tgccaccaaa 3180
accctctttt tactaagaaa cagtgagcct tgttctggca gtccagagaa tgacacggga 3240
aaaaagcaga tgaagagaag gtggcaggag agggcacgtg gcccagcctc agtctctaga 3300
tctaggaacc cctagtgatg gagttggcca ctccctctct gcgcgctcgc tcgctcactg 3360
aggccgcccg ggcaaagccc gggcgtcggg cgacctttgg tcgcccggcc tcagtgagcg 3420
agcgagcgcg cagagaggga gtggccaa 3448

<210> SEQ ID NO 631
<211> LENGTH: 3478
<212> TYPE: DNA
<213> ORGANISM: Homo sapiens

<400> SEQUENCE: 631
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc ttgccaacat accataaacc tcccattctg 180
ctaatgccca gcctaagttg gggagaccac tccagattcc aagatgtaca gtttgctttg 240

-continued

```
ctgggccttt ttcccatgcc tgcctttact ctgccagagt tatattgctg ggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttggggc aaagagggaa atgagatcat    600
gtcctaaccc tgatcctctt gtcccacaga tatccagaac cctgaccctg ccgagggccg    660
cggcagcctg ctgacctgcg gcgacgtgga ggagaatccc ggccccatgg gatgtagact    720
tctgtgttgc gccgtgctgt gtctgcttgg agctggcgaa ctggtgccta tggaaaccgg    780
cgtgacccag acacctagac acctggtcat gggcatgaca aacaagaaaa gcctgaagtg    840
cgagcagcac ctgggccaca atgccatgta ctggtacaag cagagcgcca agaaacccct    900
ggaactgatg ttcgtgtaca gcctggaaga gagggtcgag aacaacagcg tgcccagcag    960
attcagccct gagtgcccta atagcagcca cctgtttctg catctgcaca ccctgcagcc   1020
tgaggactct gccctgtatc tgtgtgccag cagccaggac tacctggtgt ccaacgagaa   1080
gctgttcttc ggcagcggca cacagctgag cgtgctggaa gatctgaaga acgtgttccc   1140
acctgaggtg gccgtgttcg agccttctga ggccgagatc agccacacac agaaagccac   1200
actcgtgtgt ctggccaccg gcttctatcc cgatcacgtg gaactgtctt ggtgggtcaa   1260
cggcaaagag gtgcacagcg gcgtcagcac cgatcctcag cctctgaaag agcagcccgc   1320
tctgaacgac agcagatact gcctgagcag cagactgaga gtgtccgcca ccttctggca   1380
gaaccccaga aaccacttca gatgccaggt gcagttctac ggcctgagcg agaacgatga   1440
gtggacccag gatagagcca agcctgtgac acagatcgtg tctgccgaag cctggggcag   1500
agccgattgt ggctttacca gcgagagcta ccagcagggc gtgctgtctg ccacaatcct   1560
gtacgagatc ctgctgggaa aagccactct gtacgctgtg ctggtgtccg ctctggtgct   1620
gatggccatg gtcaagcgga aggatagcag gggcggctcc ggtgccacaa acttctccct   1680
gctcaagcag gccggagatg tggaagagaa ccctggccct atgatcagcc tgagagtgct   1740
gctggtcatc ctgtggctgc agctgtcttg ggtctggtcc cagcggaaag aggtggaaca   1800
ggaccccgga cctttcaatg tgcctgaagg cgccaccgtg gccttcaact gcacctacag   1860
caatagcgcc agccagagct tcttctggta cagacaggac tgccggaaag aacccaagct   1920
gctgatgagc gtgtacagca gcggcaacga ggacggcaga ttcacagccc agctgaacag   1980
agccagccag tacatcagcc tgctgatccg ggatagcaag ctgagcgata gcgccaccta   2040
cctgtgcgtg gtcaacctgc tgtctaatca aggcggcaag ctgatcttcg gccagggcac   2100
agagctgagc gtgaagccca acattcagaa ccccgatcct gccgtgtacc agctgagaga   2160
cagcaagagc agcgacaaga gcgtgtgcct gttcaccgac ttcgacagcc agaccaacgt   2220
gtcccagagc aaggacagcg acgtgtacat caccgataag accgtgctgg acatgcggag   2280
catggacttc aagagcaaca gcgccgtggc ctggtccaac aagagcgatt tcgcctgcgc   2340
caacgccttc aacaacagca ttatccccga ggacacattc ttcccaagtc ctgagagcag   2400
ctgcgacgtg aagctggtgg aaaagagctt cgagacagac accaacctga acttccagaa   2460
cctgtccgtg atcggcttcc ggatcctgct gctgaaagtg gccggcttca acctcctgat   2520
gaccctgaga ctgtggtcca gctaacctcg actgtgcctt ctagttgcca gccatctgtt   2580
```

gtttgcccct cccccgtgcc ttccttgacc ctggaaggtg ccactcccac tgtcctttcc 2640
taataaaatg aggaaattgc atcgcattgt ctgagtaggt gtcattctat tctggggggt 2700
ggggtggggc aggacagcaa gggggaggat tgggaagaca atagcaggca tgctggggat 2760
gcggtgggct ctatggcttc tgaggcggaa agaaccagct ggggctctag ggggtatccc 2820
cactagtcgt gtaccagctg agagactcta aatccagtga caagtctgtc tgcctattca 2880
ccgattttga ttctcaaaca aatgtgtcac aaagtaagga ttctgatgtg tatatcacag 2940
acaaaactgt gctagacatg aggtctatgg acttcaagag caacagtgct gtggcctgga 3000
gcaacaaatc tgactttgca tgtgcaaacg ccttcaacaa cagcattatt ccagaagaca 3060
ccttcttccc cagcccaggt aagggcagct ttggtgcctt cgcaggctgt ttccttgctt 3120
caggaatggc caggttctgc ccagagctct ggtcaatgat gtctaaaact cctctgattg 3180
gtggtctcgg ccttatccat tgccaccaaa accctctttt tactaagaaa cagtgagcct 3240
tgttctggca gtccagagaa tgacacggga aaaaagcaga tgaagagaag gtggcaggag 3300
agggcacgtg gcccagcctc agtctctaga tctaggaacc cctagtgatg gagttggcca 3360
ctccctctct gcgcgctcgc tcgctcactg aggccgcccg ggcaaagccc gggcgtcggg 3420
cgacctttgg tcgcccggcc tcagtgagcg agcgagcgcg cagagaggga gtggccaa 3478

<210> SEQ ID NO 632
<211> LENGTH: 3466
<212> TYPE: DNA
<213> ORGANISM: Homo sapiens

<400> SEQUENCE: 632
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc ttgccaacat accataaacc tcccattctg 180
ctaatgccca gcctaagttg gggagaccac tccagattcc aagatgtaca gtttgctttg 240
ctgggccttt ttcccatgcc tgcctttact ctgccagagt tatattgctg gggttttgaa 300
gaagatccta ttaaataaaa gaataagcag tattattaag tagccctgca tttcaggttt 360
ccttgagtgg caggccaggc ctggccgtga acgttcactg aaatcatggc ctcttggcca 420
agattgatag cttgtgcctg tccctgagtc ccagtccatc acgagcagct ggtttctaag 480
atgctatttc ccgtataaag catgagaccg tgacttgcca gccccacaga gccccgccct 540
tgtccatcac tggcatctgg actccagcct gggttggggc aaagagggaa atgagatcat 600
gtcctaaccc tgatcctctt gtcccacaga tatccagaac cctgaccctg ccgagggccg 660
cggcagcctg ctgacctgcg gcgacgtgga ggagaatccc ggccccatgg gatcttggac 720
actgtgttgc gtgtccctgt gcatcctggt ggccaagcac acagatgccg gcgtgatcca 780
gtctcctaga cacgaagtga ccgagatggg ccaagaagtg accctgcgct gcaagcctat 840
cagcggccac gattacctgt tctggtacag acagaccatg atgagaggcc tggaactgct 900
gatctacttc aacaacaacg tgcccatcga cgacagcggc atgcccgagg atagattcag 960
cgccaagatg cccaacgcca gcttcagcac cctgaagatc cagcctagcg agcccagaga 1020
tagcgccgtg tacttctgcg ccagcagaaa gacaggcggc tacagcaatc agccccagca 1080
ctttggagat ggcacccggc tgagcatcct ggaagatctg aagaacgtgt tcccacctga 1140
ggtggccgtg ttcgagcctt ctgaggccga gatcagccac acacagaaag ccacactcgt 1200
gtgtctggcc accggcttct atcccgatca cgtggaactg tcttggtggg tcaacggcaa 1260

-continued agaggtgcac agcggcgtca gcaccgatcc tcagcctctg aaagagcagc ccgctctgaa 1320
cgacagcaga tactgcctga gcagcagact gagagtgtcc gccaccttct ggcagaaccc 1380
cagaaaccac ttcagatgcc aggtgcagtt ctacggcctg agcgagaacg atgagtggac 1440
ccaggataga gccaagcctg tgacacagat cgtgtctgcc gaagcctggg gcagagccga 1500
ttgtggcttt accagcgaga gctaccagca gggcgtgctg tctgccacaa tcctgtacga 1560
gatcctgctg ggcaaagcca ctctgtacgc cgtgctggtg tctgccctgg tgctgatggc 1620
catggtcaag cggaaggata gcaggggcgg ctccggtgcc acaaacttct ccctgctcaa 1680
gcaggccgga gatgtggaag agaaccctgg ccctatggaa accctgctga aggtgctgag 1740
cggcacactg ctgtggcagc tgacatgggt ccgatctcag cagcctgtgc agtctcctca 1800
ggccgtgatt ctgagagaag gcgaggacgc cgtgatcaac tgcagcagct ctaaggccct 1860
gtacagcgtg cactggtaca gacagaagca cggcgaggcc cctgtgttcc tgatgatcct 1920
gctgaaaggc ggcgagcaga agggccacga gaagatcagc gccagcttca acgagaagaa 1980
gcagcagtcc agcctgtacc tgacagccag ccagctgagc tacagcggca cctacttttg 2040
tggcaccgcc tggatcaacg actacaagct gtctttcgga gccggcacca cagtgacagt 2100
gcgggccaat attcagaacc ccgatcctgc cgtgtaccag ctgagagaca gcaagagcag 2160
cgacaagagc gtgtgcctgt tcaccgactt cgacagccag accaacgtgt cccagagcaa 2220
ggacagcgac gtgtacatca ccgataagac tgtgctggac atgcggagca tggacttcaa 2280
gagcaacagc gccgtggcct ggtccaacaa gagcgatttc gcctgcgcca acgccttcaa 2340
caacagcatt atccccgagg acacattctt cccaagtcct gagagcagct gcgacgtgaa 2400
gctggtggaa aagagcttcg agacagacac caacctgaac ttccagaacc tgagcgtgat 2460
cggcttcaga atcctgctgc tcaaggtggc cggcttcaac ctgctgatga ccctgagact 2520
gtggtccagc taacctcgac tgtgccttct agttgccagc catctgttgt ttgcccctcc 2580
cccgtgcctt ccttgaccct ggaaggtgcc actcccactg tcctttccta ataaaatgag 2640
gaaattgcat cgcattgtct gagtaggtgt cattctattc tggggggtgg ggtggggcag 2700
gacagcaagg gggaggattg ggaagacaat agcaggcatg ctggggatgc ggtgggctct 2760
atggcttctg aggcggaaag aaccagctgg ggctctaggg ggtatcccca ctagtcgtgt 2820
accagctgag agactctaaa tccagtgaca agtctgtctg cctattcacc gattttgatt 2880
ctcaaacaaa tgtgtcacaa agtaaggatt ctgatgtgta tatcacagac aaaactgtgc 2940
tagacatgag gtctatggac ttcaagagca acagtgctgt ggcctggagc aacaaatctg 3000
actttgcatg tgcaaacgcc ttcaacaaca gcattattcc agaagacacc ttcttcccca 3060
gcccaggtaa gggcagcttt ggtgccttcg caggctgttt ccttgcttca ggaatggcca 3120
ggttctgccc agagctctgg tcaatgatgt ctaaaactcc tctgattggt ggtctcggcc 3180
ttatccattg ccaccaaaac cctcttttta ctaagaaaca gtgagccttg ttctggcagt 3240
ccagagaatg acacgggaaa aaagcagatg aagagaaggt ggcaggagag ggcacgtggc 3300
ccagcctcag tctctagatc taggaacccc tagtgatgga gttggccact ccctctctgc 3360
gcgctcgctc gctcactgag gccgcccggg caaagcccgg gcgtcgggcg acctttggtc 3420
gcccggcctc agtgagcgag cgagcgcgca gagagggagt ggccaa 3466